(12) United States Patent
Jiang et al.

(10) Patent No.: US 6,965,033 B2
(45) Date of Patent: Nov. 15, 2005

(54) BISAMIDATE PHOSPHONATE PRODRUGS

(75) Inventors: Tao Jiang, San Diego, CA (US); Srinivas Rao Kasibhatla, San Diego, CA (US); K. Raja Reddy, San Diego, CA (US)

(73) Assignee: Metabasis Therapeutics, Inc., San Diego, CA (US)

( * ) Notice: Subject to any disclaimer, the term of this patent is extended or adjusted under 35 U.S.C. 154(b) by 0 days.

(21) Appl. No.: 09/747,182

(22) Filed: Dec. 22, 2000

(65) Prior Publication Data

US 2002/0173490 A1 Nov. 21, 2002

Related U.S. Application Data

(60) Provisional application No. 60/171,862, filed on Dec. 22, 1999.

(51) Int. Cl.[7] .............................. C07F 9/24; C07F 9/44; A61P 3/10
(52) U.S. Cl. ........................ 548/119; 548/103; 514/91; 514/92; 514/93; 514/94
(58) Field of Search ................................ 514/114, 118, 514/218, 377, 370, 91, 92, 93, 94; 548/112, 111, 117, 119, 190, 233, 103, 412; 544/133, 139

(56) References Cited

U.S. PATENT DOCUMENTS

| | | | |
|---|---|---|---|
| 5,658,889 A | 8/1997 | Gruber et al. | |
| 5,798,340 A | 8/1998 | Bischofberger et al. | ...... 514/45 |
| 6,054,587 A | 4/2000 | Reddy et al. | |
| 6,110,903 A | 8/2000 | Kasibhatla et al. | |
| 6,284,748 B1 | 9/2001 | Dang et al. | |
| 6,294,672 B1 | 9/2001 | Reddy et al. | |
| 6,399,782 B1 | 6/2002 | Kasibhatla et al. | |
| 6,489,476 B1 | 12/2002 | Dang et al. | |

FOREIGN PATENT DOCUMENTS

| | | |
|---|---|---|
| WO | 91/19721 | 12/1991 |
| WO | 9119721 | * 12/1991 |
| WO | 95/07920 | 3/1995 |
| WO | 9507920 | * 3/1995 |
| WO | 98/39342 | 9/1998 |
| WO | 98/39343 | 9/1998 |
| WO | 98/39344 | 9/1998 |
| WO | WO 99/45016 A2 | 9/1999 |
| WO | WO 99/47549 A1 | 9/1999 |
| WO | 00/14095 | 3/2000 |
| WO | 0014095 | * 3/2000 |
| WO | WO 00/38666 A2 | 7/2000 |

OTHER PUBLICATIONS

Alimov, P. I. Fedorova, O. N., CA59: 9782d "Preparation of amides on N–phosphorylated amino carboxylic acids", Online, Chemical Abstracts, Columbus, OH, retrieved Apr. 25, 2003.*

Benzaria, et al., "Synthesis in Vitro Antiviral Evaluation, and Stability Studies of Bis(S–acyl–2–thioethyl) Ester Derivatives of 9–[2–(Phosphonomethoxy) ethyl]adenine (PMEA) as Potential PMEA Prodrugs with Improved Oral Bioavailability," *J. Med. Chem.* 39:4958–4965 (1996).

de Lombaert, et al., "N–Phosphonomethyl Dipeptides and Their Phosphonate Prodrugs, and New Generation of Neutral Endopeptidase (NEP, EC 3.4.24.11) Inhibitors," *J. Med. Chem.* 37:498–511 (1994).

Egron, et al., "Synthesis and Anti–HIV Activity of Some S–Acyl–2–Thioethyl (SATE) Phosphoramidate Derivatives of 3'–Azido–2',3'—Dideoxythymidine, " *Nucleosides & Nucleotides* 18(4 &5) 981–982 (1999).

Farquar, et al., "Biologically Reversible Phosphate–Protective Group," *J. Pharm. Sci.* 72: 324 (1983).

Freeman, et al., "Prodrug Design for Phosphates and Phosphonates," *Progress in Med. Chem.* 34: 112–147 (1997).

Khamnei, et al., "Neighboring Group Catalysis in the Design of Nucleotide Prodrugs," *J. Med. Chem.* 39:4109–4115 (1996).

Mitchell, et al., "Bioreversible Protection for the Phospho Group: Bioactivation of the Di(4–acyloxybenzyl) and Mono (4–acyloxybenzyl) Phophoesters of Methylphosphonate and Phosphonoacetate," *J. Chem. Soc. Perkin Trans.* 2345–2353 (1992).

Puech, et al., "Intracellular delivery of nucleoside monophosphates through a reductase–mediated activation process," *Antiviral Research* 22:155–174 (1993).

Serafinowska, et al. "Synthesis and in Vivo Evaluation of Prodrugs of 9–[2–(Phosphonomethoxy)ethoxy]adenine," *J. Med Chem* ., 38:1372–1379 (1995).

Siddiqui, et al., "The Presence of Substituents on the Aryl Moiety of the Aryl Phophoramidate Derivative of d4T Enhances Anti–HIV Efficacy in Cell Culture: A Structure–Activity Relationship," *J. Med. Chem.* 42:393–399 (1999).

Starrett, et al., "Synthesis, Oral Bioavailability Determination, and in Vitro Evaluation of Prodrugs of the Antiviral Agent 9–[2–(Phosphonomethoxy) ethyl]adenine (PMEA), "*J. Med. Chem.* 37:1857–1864 (1994).

* cited by examiner

Primary Examiner—Thomas C. McKenzie
(74) Attorney, Agent, or Firm—Paul, Hastings, Janofsky & Walker LLP

(57) ABSTRACT

Novel bisamidate phosphonate prodrugs of FBPase inhibitors of the Formula IA:

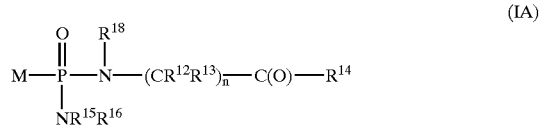

and their use in the treatment of diabetes and other conditions associated with elevated blood glucose.

55 Claims, No Drawings

BISAMIDATE PHOSPHONATE PRODRUGS

RELATED APPLICATION

This application claims the benefit of priority to U.S. Ser. No. 60/171,862 filed Dec. 22, 1999, which is incorporated by reference in its entirety.

FIELD OF THE INVENTION

The present invention is directed towards novel prodrugs, to their preparation, to their use for the oral delivery of Fructose-1,6-bisphosphatase inhibitors (FBPase), and to their use in the treatment of diabetes and other diseases where the inhibition of gluconeogenesis, control of blood glucose levels, reduction in glycogen storage, or reduction in insulin levels is beneficial.

BACKGROUND OF THE INVENTION

Organic compounds that are charged at physiological pH frequently exhibit limited oral bioavailability, cell penetration, and tissue distribution (e.g. CNS). These properties are attributed to the failure of ionic compounds to cross cell membranes by passive diffusion. One strategy to circumvent this problem is to prepare lipophilic prodrugs which are capable of crossing cell membranes and subsequently undergoing a transformation to generate the charged compound. The transformation could result from either chemical instability or an enzyme-catalyzed reaction.

A large number of structurally-diverse prodrugs are described for phosphonic acids. Freeman and Ross in *Progress in Medicinal Chemistry* 34: 112–147 (1997). The most commonly used prodrug class is the acyloxyalkyl ester, which was first used as a prodrug strategy for carboxylic acids and then applied to phosphates in 1983 by Farquhar et al. *J. Pharm. Sci.* 72: 324 (1983). Subsequently, the acyloxyalkyl ester was used to deliver phosphonic acids across cell membranes and to enhance oral bioavailability. A close variant of the acyloxyalkyl ester strategy, the alkoxycarbonyloxyalkyl ester, is also reported to enhance oral bioavailability.

Much less success has been achieved with other classes of phosphonate prodrugs. Aryl esters, especially phenyl esters, are reported in a few cases to enhance oral bioavailability. DeLambert et al., *J. Med. Chem.* 37: 498 (1994). Phenyl esters containing a carboxylic ester ortho to the phosphate have also been described. Khamnei and Torrence, *J. Med. Chem.* 39:4109–4115 (1996). Benzyl esters are reported to generate the parent phosphonic acid. In some cases using substituents at the ortho- or para-position can accelerate the hydrolysis. Benzyl analogs with an acylated phenol or an alkylated phenol can generate the phenolic compound through the action of enzymes, e.g. esterases, oxidases, etc., which in turn undergoes cleavage at the benzylic C—O bond to generate the phosphoric acid and the quinone methide intermediate. Examples of this class of prodrugs are described by Mitchell et al., *J. Chem. Soc. Perkin Trans.* I 2345 (1992); Brook, et al. WO 91/19721. Still other benzylic prodrugs have been described containing a carboxylic ester-containing group attached to the benzylic methylene. Glazier et al. WO 91/19721. Thio-containing prodrugs are reported to be useful for the intracellular delivery of phosphonate drugs. These proesters contain an ethylthio group in which the thiol group is either esterified with an acyl group or combined with another thiol group to form a disulfide. Desterification or reduction of the disulfide generates the free thio intermediate which subsequently breaks down to the phosphoric acid and episulfide. Puech et al., *Antiviral Res.,* 22: 155–174 (1993); Benzaria, et al.,*J. Med. Chem.* 39: 4958 (1996). Cyclic phosphonate esters have also been described as prodrugs of phosphorus-containing compounds.

Some phosphoramidates are also known prodrugs of phosphonates, but they have shown poor oral bioavailability. In some cases the phosphoramidates were very unstable under acidic conditions which was reported as a potential explanation for their poor oral bioavailability (*J. Med. Chem.,* 37: 1857–1864 (1994)). Similarly, poor oral bioavailability was reported for a bisamidate of a PMEA analog (*J. Med. Chem.,* 38: 1372–1379 (1995)). Another PMEA prodrug consists of a mono glycine ester amidate and a phenyl ester (WO 95/07920).

Although numerous phosphoric acid prodrug strategies are reported to achieve high intracellular delivery of phosphoric acids, few are known to result in good oral bioavailability. In some cases, the prodrugs are unstable to the gastrointestinal tract environment (low pH, esterase activity). In other cases the prodrugs are too stable and are therefore poorly transformed in vivo to the parent drug.

WO 98/39344, WO 98/39343, WO 98/139342, and WO 00/14095 describe compounds containing phosphoric acids and esters that inhibit fructose-1,6-bisphosphatase.

The entire disclosures of the publication and references referred to above and hereafter in this specification are incorporated herein by reference and are not admitted to be prior art.

SUMMARY OF THE INVENTION

The present invention is directed towards novel bisamidate phosphonates that are potent FBPase inhibitors. In one aspect these compounds possess superior oral bioavailability compared to the corresponding phosphonic acids. In another aspect, the present invention is directed to the in vitro and in vivo FBPase inhibitory activity of these compounds. Another aspect of the present invention is directed to the clinical use of these FBPase inhibitors as a method of treatment or prevention of diseases responsive to inhibition of gluconeogenesis and in diseases responsive to lowered blood glucose levels.

In another aspect, the compounds are also useful in treating or preventing excess glycogen storage diseases and diseases such as cardiovascular diseases including atherosclerosis, myocardial ischemic injury, and diseases such as metabolic disorders such as hypercholesterolemia, hyperlipidemia which are exacerbated by hyperinsulinema and hyperglycemia.

The invention also comprises the novel compounds and methods of using them as specified below in formulae I, X, and XI. Also included in the scope of the present invention are standard salts and prodrugs of the compounds of formulae I, X, and XI.

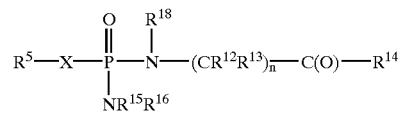

Formula I

Formula X

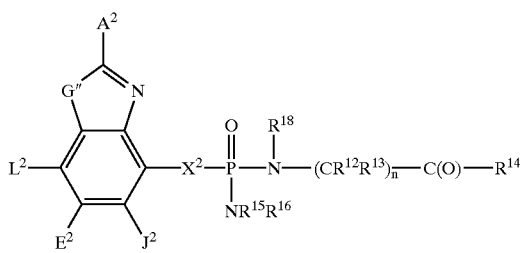

Formula XI

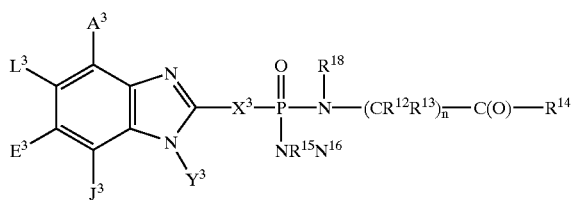

Since these compounds may have asymmetric centers, the present invention is directed not only to racemic mixtures of these compounds, but also to individual stereoisomers. The present invention also includes pharmaceutically acceptable and/or useful salts of the compounds of formulae I, X, and XI, including acid addition salts. The present inventions also encompass standard prodrugs of compounds of formulae I, X, and XI.

DETAILED DESCRIPTION OF THE INVENTION

Definitions

In accordance with the present invention and as used herein, the following terms are defined with the following meanings, unless explicitly stated otherwise.

X, X", $X^2$ and $X^3$ group nomenclature as used herein in formulae I and XI describes the group attached to the phosphonate and ends with the group attached to the heteroaromatic ring. For example, when X is alkylamino, the following structure is intended:

(heteroaromatic ring)-NR-alk-P(O)(NR$^{15}$R$^{16}$)(NR$^{18}$—(CR$^{12}$R$^{13}$)$_n$—(C(O)—R$^{14}$)

Likewise, A, B, C, D, E, A", B", C", D", E", $A^2$, $L^2$, $E^2$, $J^2$, $A^3$, $L^3$, $E^3$, and $J^3$ groups and other substituents of the heteroaromatic ring are described in such a way that the term ends with the group attached to the heteroaromatic ring. Generally, substituents are named such that the term ends with the group at the point of attachment. A hyphen before or after a term indicates a point of attachment. For example, "-alkyl-" refers to divalent alkyl or alkylene.

The term "aryl" refers to aromatic groups which have 5–14 ring atoms and at least one ring having a conjugated pi electron system and includes carbocyclic aryl, heterocyclic aryl and biaryl groups, all of which may be optionally substituted. Suitable aryl groups include phenyl and furan-2,5-diyl.

Carbocyclic aryl groups are groups wherein the ring atoms on the aromatic ring are carbon atoms. Carbocyclic aryl groups include monocyclic carbocyclic aryl groups and polycyclic or fused compounds such as optionally substituted naphthyl groups.

Heterocyclic aryl or heteroaryl groups are groups having from 1 to 4 heteroatoms as ring atoms in the aromatic ring and the remainder of the ring atoms being carbon atoms. Suitable heteroatoms include oxygen, sulfur, nitrogen, and selenium. Suitable heteroaryl groups include furanyl, thienyl, pyridyl, pyrrolyl, N-lower alkyl pyrrolyl, pyridyl-N-oxide, pyrimidyl, pyrazinyl, imidazolyl, and the like, all optionally substituted.

The term "annulation" or "annulated" refers to the formation of an additional cyclic moiety onto an existing aryl or heteroaryl group. It is a form of optional substitution on an aryl or heteroaryl group. The newly formed ring may be carbocyclic or heterocyclic, saturated or unsaturated, and contains 2–9 new atoms of which 0–3 may be heteroatoms taken from the group of N, O, and S. The annulation may incorporate atoms from the X group as part of the newly formed ring. For example, the phrase "together $L^2$ and $E^2$ form an annulated cyclic group", includes

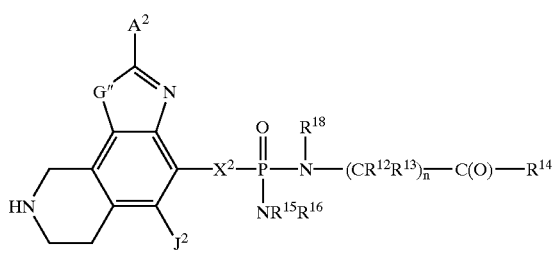

The term "biaryl" represents aryl groups containing more than one aromatic ring including both fused ring systems and aryl groups substituted with other aryl groups. Such groups may be optionally substituted. Suitable biaryl groups include naphthyl and biphenyl.

The term "alicyclic" means compounds which combine the properties of aliphatic and cyclic compounds. Such cyclic compounds include but are not limited to, aromatic, cycloalkyl and bridged cycloalkyl compounds. The cyclic compound includes heterocycles. Cyclohexenylethyl and cyclohexylethyl are suitable alicyclic groups. Such groups may be optionally substituted.

The term "optionally substituted" or "substituted" includes groups substituted by one to four substituents, independently selected from lower alkyl, lower aryl, lower aralkyl, lower alicyclic, hydroxy, lower alkoxy, lower aryloxy, perhaloalkoxy, aralkoxy, heteroaryl, heterocyclic alkyl, heteroaryloxy, heteroarylalkyl, heteroaralkoxy, azido, amino, guanidino, amidino, halo, lower alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, aralkylamino, phosphono, sulfonyl, -carboxamidoalkylaryl, -carboxamidoaryl, hydroxyalkyl, haloalkyl, alkylaminoalkylcarboxy-, aminocarboxamidoalkyl-, cyano, lower alkoxyalkyl, lower perhaloalkyl, and arylalkyloxyalkyl. "Substituted aryl" and "substituted heteroaryl" refer to aryl and heteroaryl groups substituted with 1–2; 1–3; or 1–4 substituents. In one aspect, suitable substituents of aryl groups include lower alkyl, lower alkoxy, lower perhaloalkyl, halo, hydroxy, and amino. "Substituted" when describing an $R^5$ group does not include annulation.

The term "aralkyl" refers to an alkyl group substituted with an aryl group. Suitable aralkyl groups include benzyl, picolyl, and the like, and may be optionally substituted. The term "-aralkyl-" refers to a divalent group -aryl-alkylene-. "Heteroarylalkyl" refers to an alkylene group substituted with a heteroaryl group.

The term "-alkylaryl-" refers to the group -alk-aryl- where "alk" is an alkylene group. "Lower -alkylaryl-" refers to such groups where alkylene is lower alkylene.

The term "lower" referred to herein in connection with organic radicals or compounds respectively defines such as with up to and including 10, or up to and including 6, or one to four carbon atoms. Such groups may be straight chain, branched, or cyclic.

The terms "arylamino" (a), and "aralkylamino" (b), respectively, refer to the group —NRR' wherein respectively, (a) R is aryl and R' is hydrogen, alkyl, aralkyl or aryl, and (b) R is aralkyl and R' is hydrogen or aralkyl, aryl, alkyl.

The term "acyl" refers to —C(O)R where R is alkyl and aryl.

The term "carboxy esters" refers to —C(O)OR where R is alkyl, aryl, aralkyl, and alicyclic, all optionally substituted.

The term "carboxyl" refers to —C(O)OH.

The term "oxo" refers to =O in an alkyl group.

The term "amino" refers to —NRR$^1$ where R and R$^1$ are independently selected from hydrogen, alkyl, aryl, aralkyl and alicyclic, all except H are optionally substituted; and R and R$^1$ can form a cyclic ring system.

The term "carbonylamino" and "-carbonylamino-" refers to RCONR— and —CONR—, respectively, where each R is independently hydrogen or alkyl.

The term "halogen" or "halo" refers to —F, —Cl, —Br and —I.

The term "-oxyalkylamino-" refers to —O-alk-NR—, where "alk" is an alkylene group and R is H or alkyl.

The term "-alkylaminoalkylcarboxy-" refers to the group -alk-NR-alk-C(O)—O where "alk" is an alkylene group, and R is a H or lower alkyl.

The term "-alkylaminocarbonyl-" refers to the group -alk-NR—C(O)— where "alk" is an alkylene group, and R is a H or lower alkyl.

The term "-oxyalkyl-" refers to the group —O-alk- where "alk" is an alkylene group.

The term "-alkylcarboxyalkyl-" refers to the group -alk-C(O)—O-alk- where each alk is independently an alkylene group.

The term "alkyl" refers to saturated aliphatic groups including straight-chain, branched chain and cyclic groups. Alkyl groups may be optionally substituted. Suitable alkyl groups include methyl, isopropyl, and cyclopropyl.

The term "cyclic alkyl" or "cycloalkyl" refers to alkyl groups that are cyclic groups of 3 to 6; or 3 to 10 atoms. Suitable cyclic groups include norbomyl and cyclopropyl. Such groups may be substituted.

The term "heterocyclic" and "heterocyclic alkyl" refer to cyclic groups of 3 to 6; or 3 to 10 atoms, containing at least one heteroatom. In one aspect, these groups contain 1 to 3 heteroatoms. Suitable heteroatoms include oxygen, sulfur, and nitrogen. Heterocyclic groups may be attached through a nitrogen or through a carbon atom in the ring. Suitable heterocyclic groups include pyrrolidinyl, morpholino, morpholinoethyl, and pyridyl. Such groups may be substituted.

The term "phosphono" refers to —PO$_3$R$_2$, where R is selected from the group consisting of —H, alkyl, aryl, aralkyl, and alicyclic.

The term "sulphonyl" or "sulfonyl" refers to —SO$_3$R, where R is H, alkyl, aryl, aralkyl, and alicyclic.

The term "alkenyl" refers to unsaturated groups which contain at least one carbon-carbon double bond and includes straight-chain, branched-chain and cyclic groups. Alkenyl groups may be optionally substituted. Suitable alkenyl groups include allyl. "1-alkenyl" refers to alkenyl groups where the double bond is between the first and second carbon atom. If the 1-alkenyl group is attached to another group, e.g. it is a W substituent attached to the cyclic phosph(oramid)ate, it is attached at the first carbon.

The term "alkynyl" refers to unsaturated groups which contain at least one carbon-carbon triple bond and includes straight-chain, branched-chain and cyclic groups. Alkynyl groups may be optionally substituted. Suitable alkynyl groups include ethynyl. "1-alkynyl" refers to alkynyl groups where the triple bond is between the first and second carbon atom. If the 1-alkynyl group is attached to another group, it is attached at the first carbon.

The term "alkylene" refers to a divalent straight chain, branched chain or cyclic saturated aliphatic group.

The term "-cycloalkylene-COOR$^3$" refers to a divalent cyclic alkyl group or heterocyclic group containing 4 to 6 atoms in the ring, with 0–1 heteroatoms selected from O, N, and S. The cyclic alkyl or heterocyclic group is substituted with —COOR$^3$.

The term "acyloxy" refers to the ester group —O—C(O)R, where R is H, alkyl, alkenyl, alkynyl, aryl, aralkyl, or alicyclic.

The term "aminoalkyl-" refers to the group NR$_2$-alk- wherein "alk" is an alkylene group and R is selected from H, alkyl, aryl, aralkyl, and alicyclic.

The term "-alkyl(hydroxy)-" refers to an —OH off the alkyl chain. When this term is an X group, the —OH is at the position $\alpha$ to the phosphorus atom.

The term "alkylaminoalkyl-" refers to the group alkyl-NR-alk- wherein each "alk" is an independently selected alkylene, and R is H or lower alkyl. "Lower alkylaminoalkyl-" refers to groups where each alkylene group is lower alkylene.

The term "arylaminoalkyl-" refers to the group aryl-NR-alk- wherein "alk" is an alkylene group and R is H, alkyl, aryl, aralkyl, and alicyclic. In "lower arylaminoalkyl-", the alkylene group is lower alkylene.

The term "alkylaminoaryl-" refers to the group alkyl-NR-aryl- wherein "aryl" is a divalent group and R is H, alkyl, aralkyl, and alicyclic. In "lower alkylaminoaryl-", the alkylene group is lower alkyl.

The term "alkyloxyaryl-" refers to an aryl group substituted with an alkyloxy group. In "lower alkyloxyaryl-", the alkyl group is lower alkyl.

The term "aryloxyalkyl-" refers to an alkyl group substituted with an aryloxy group.

The term "aralkyloxyalkyl-" refers to the group aryl-alk-O-alk- wherein "alk" is an alkylene group. "Lower aralkyloxyalkyl-" refers to such groups where the alkylene groups are lower alkylene.

The term "-alkoxy-" or "-alkyloxy-" refers to the group -alk-O— wherein "alk" is an alkylene group. The term "alkoxy-" refers to the group alkyl-O—.

The term "-alkoxyalkyl-" or "-alkyloxyalkyl-" refer to the group -alk-O-alk- wherein each "alk" is an independently selected alkylene group. In "lower -alkoxyalkyl-", each alkylene is lower alkylene.

The terms "alkylthio-" and "-alkylthio-" refer to the groups alkyl-S—, and -alk-S—, respectively, wherein "alk" is alkylene group.

The term "-alkylthioalkyl-" refers to the group -alk-S-alk- wherein each "alk" is an independently selected alkylene group. In "lower-alkylthioalkyl" each alkylene is lower alkylene.

The term "alkoxycarbonyloxy-" refers to alkyl-O—C(O)—O—.

The term "aryloxycarbonyloxy-" refers to aryl-O—C(O)—O—.

The term "alkylthiocarbonyloxy-" refers to alkyl-S—C(O)—O—.

The term "-alkoxycarbonylamino-" refers to -alk-O—C(O)—NR$^1$—, where "alk" is alkylene and R$^1$, includes —H, alkyl, aryl, alicyclic, and aralkyl.

The term "-alkylaminocarbonylamino" refers to -alk-NR$^1$—C(O)—NR$^1$—, where "alk" is alkylene and R$^1$ is independently selected from H, alkyl, aryl, aralkyl, and alicyclic.

The terms "amido" or "carboxamido" refer to NR$_2$—C(O)— and RC(O)—NR$^1$—, where R and R$^1$ include H, alkyl, aryl, aralkyl, and alicyclic. The term does not include urea, —NR—C(O)—NR—.

The terms "carboxamidoalkylaryl" and "carboxamidoaryl" refers to an aryl-alk-NR$^1$—C(O)—, and ar-NR$^1$—C(O)-alk-, respectively, where "ar" is aryl, and "alk" is alkylene, R$^1$ and R include H, alkyl, aryl, aralkyl, and alicyclic.

The term "-alkylcarboxamido-" or "-alkylcarbonylamino-" refers to the group -alk-C(O)N(R)— wherein "alk" is an alkylene group and R is H or lower alkyl.

The term "-alkylaminocarbonyl-" refers to the group -alk-NR—C(O)— wherein "alk" is an alkylene group and R is H or lower alkyl.

The term "aminocarboxamidoalkyl-" refers to the group NR$_2$—C(O)—N(R)-alk- wherein R is an alkyl group or H and "alk" is an alkylene group. "Lower aminocarboxamidoalkyl-" refers to such groups wherein "alk" is lower alkylene.

The term "thiocarbonate" refers to —O—C(S)—O— either in a chain or in a cyclic group.

The term "hydroxyalkyl" refers to an alkyl group substituted with one —OH.

The term "haloalkyl" refers to an alkyl group substituted with one halo, selected from the group I, Cl, Br, F.

The term "cyano" refers to —C≡N.

The term "nitro" refers to —NO$_2$.

The term "acylalkyl" refers to an alkyl-C(O)-alk-, where "alk" is alkylene.

The term "heteroarylalkyl" refers to an alkyl group substituted with a heteroaryl group.

The term "-1,1-dihaloalkyl-" refers to an X group where the 1 position and therefore halogens are α to the phosphorus atom.

The term "perhalo" refers to groups wherein every C—H bond has been replaced with a C-halo bond on an aliphatic or aryl group. Suitable perhaloalkyl groups include —CF$_3$ and —CFCl$_2$.

The term "guanidino" refers to both —NR—C(NR)—NR$_2$ as well as —N=C(NR$_2$)$_2$ where each R group is independently selected from the group of —H, alkyl, alkenyl, alkynyl, aryl, and alicyclic, all except —H are optionally substituted.

The term "bidentate" refers to an alkyl group that is attached by its terminal ends to the same atom to form a cyclic group. For example, propylene amine contains a bidentate propylene group.

The term "naturally occurring amino acid" refers to alpha amino acids containing at least one hydrogen at the alpha carbon and when the alpha carbon is chiral, it has S absolute configuration.

The term "amidino" refers to —C(NR)—NR$_2$ where each R group is independently selected from the group of —H, alkyl, alkenyl, alkynyl, aryl, and alicyclic, all except —H are optionally substituted.

The term "pharmaceutically acceptable salt" includes salts of compounds of formula IA and its prodrugs derived from the combination of a compound of this invention and an organic or inorganic acid or base. Suitable acids include hydrochloric acid, hydrobromic acid, acetic acid, trifluoroacetic acid, methanesulfonic acid, p-toluenesulfonic acid and maleic acid.

The term "prodrug" as used herein refers to any compound that when administered to a biological system generates the "drug" substance (a biologically active compound) as a result of spontaneous chemical reaction(s), enzyme catalyzed chemical reaction(s), and/or metabolic chemical reaction(s). Standard prodrugs are formed using groups attached to functionality, e.g. HO—, HS—, HOOC—, R$_2$N—, associated with the FBPase inhibitor, that cleave in vivo. Standard prodrugs include, but are not limited to, carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. The groups illustrated are exemplary, not exhaustive, and one skilled in the art could prepare other known varieties of prodrugs. Such prodrugs of the compounds of formulae I, X, and XI, fall within the scope of the present invention. Prodrugs must undergo some form of a chemical transformation to produce the compound that is biologically active or is a precursor of the biologically active compound. In some cases, the prodrug is biologically active usually less than the drug itself, and serves to improve efficacy or safety through improved oral bioavailability, pharmacodynamic half-life, etc.

Phosphoramidate derivatives have been explored as phosphate prodrugs (e.g. McGuigan et al., *J. Med. Chem.*, 1999, 42: 393 and references cited therein) and phosphonate prodrugs (Bischofberger, et al., U.S. Pat. No. 5,798,340 and references cited therein) as shown in Formulae G and H.

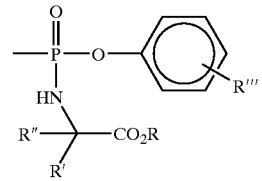

Formula G

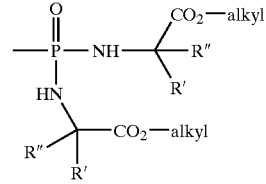

Formula H

Cyclic phosphoramidates have also been studied as phosphonate prodrugs because of their speculated higher stability compared to non-cyclic phosphoramidates (e.g. Starrett et al., *J. Med. Chem.*, 1994, 37:1857).

Another type of nucleotide prodrug was reported as the combination of S-acyl-2-thioethyl ester and phosphoramidate (Egron et al., *Nucleosides & Nucleotides*, 1999,18, 981) as shown in Formula J.

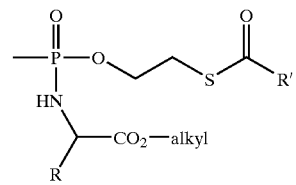

Formula J

The term "enhancing" refers to increasing or improving a specific property.

The term "enhanced oral bioavailability" refers to an increase of at least 50% of the absorption of the dose of the parent drug or prodrug (not of this invention) from the gastrointestinal tract. In one aspect, this increase is at least 100%. Measurement of oral bioavailability usually refers to measurements of the prodrug, drug, or drug metabolite in blood, tissues, or urine following oral administration, compared to measurements following systemic administration.

The term "parent drug" refers to any compound which delivers the same biologically active compound. The parent drug form is M-P(O)(OH)$_2$ and standard prodrugs, such as esters.

The term "drug metabolite" refers to any compound produced in vivo or in vitro from the parent drug, which can include the biologically active drug.

The term "pharmacodynamic half-life" refers to the time after administration of the drug or prodrug to observe a diminution of one half of the measured pharmacological response. In one aspect, the half-life is enhanced when the half-life is increased by at least 50%.

The term "biologically active drug or agent" refers to the chemical entity that produces a biological effect. Thus, active drugs or agents include compounds which as M-P(O)(OH)$_2$ are biologically active.

The term "inhibitor of fructose-1,6-bisphosphatase" refers to chemical entities M-PO$_3$H$_2$ that have an IC$_{50}$ of equal to or less than 50 µM on human liver FBPase.

The term "therapeutically effective amount" refers to an amount that has any beneficial effect in treating a disease or condition.

Compounds

Suitable alkyl groups include groups having from 1 to about 20 carbon atoms. Suitable aryl groups include groups having from 1 to about 20 carbon atoms. Suitable aralkyl groups include groups having from 2 to about 21 carbon atoms. Suitable acyloxy groups include groups having from 1 to about 20 carbon atoms. Suitable alkylene groups include groups having from 1 to about 20 carbon atoms. Suitable alicyclic groups include groups having 3 to about 20 carbon atoms. Suitable heteroaryl groups include groups having from 1 to about 20 carbon atoms and from 1 to 4 heteroatoms, independently selected from nitrogen, oxygen, phosphorous, and sulfur. Suitable heteroalicyclic groups include groups having from 2 to about twenty carbon atoms and from 1 to 5 heteroatoms, independently selected from nitrogen, oxygen, phosphorous, and sulfur.

One aspect of the invention is directed to the compound of formula IA

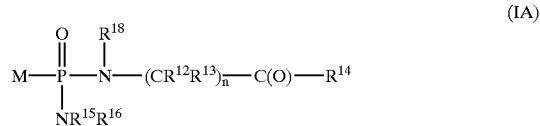

(IA)

wherein compounds of formula IA are converted in vivo or in vitro to M-PO$_3$H$_2$ which is an inhibitor of fructose-1,6-bisphosphatase and n is an integer from 1 to 3;

$R^2$ is selected from the group of —H and —$R^3$.

$R^3$ is selected from the group consisting of alkyl, aryl, alicyclic, and aralkyl;

each $R^{12}$ and $R^{13}$ is independently selected from the group consisting of H, lower alkyl, lower aryl, lower aralkyl, all optionally substituted, or $R^{12}$ and $R^{13}$ together are connected via 2–6 atoms, optionally including 1–2 heteroatoms selected from the group consisting of O, N and S, to form a cyclic group;

each $R^{14}$ is independently selected from the group consisting of —OR$^{17}$, —N(R$^{17}$)$_2$, —NHR$^{17}$, —NR$^2$OR$^{19}$ and —SR$^{17}$;

$R^{15}$ is selected from the group consisting of —H, lower alkyl, lower aryl, lower aralkyl, or together with $R^{16}$ is connected via 2–6 atoms, optionally including 1 heteroatom selected from the group consisting of O, N, and S;

$R^{16}$ is selected from the group consisting of —(CR$^{12}$R$^{13}$)$_n$— —C(O)—R$^{14}$, —H, lower alkyl, lower aryl, lower aralkyl, or together with $R^{15}$ is connected via 2–6 atoms, optionally including 1 heteroatom selected from the group consisting of O, N, and S;

each $R^{17}$ is independently selected from the group consisting of lower alkyl, lower aryl, and lower aralkyl, all optionally substituted, or together $R^{17}$ and $R^{17}$ on N is connected via 2–6 atoms, optionally including 1 heteroatom selected from the group consisting of O, N, and S;

$R^{18}$ is independently selected from the group consisting of H, lower alkyl, aryl, aralkyl, or together with $R^{12}$ is connected via 1–4 carbon atoms to form a cyclic group;

each $R^{19}$ is independently selected from the group consisting of —H, lower alkyl, lower aryl, lower alicyclic, lower aralkyl, and COR$^3$;

and pharmaceutically acceptable salts thereof.

Such compounds converted to M-PO$_3$H$_2$ include compounds that have an IC$_{50}$ on isolated human liver FBPase enzyme of less than or equal to 10 µM. Alternatively, the IC$_{50}$ is less than or equal to 1 µM. Such compounds may also bind to the AMP site of FBPase.

In one aspect, M is $R^5$—X—, wherein $R^5$ is selected from the group consisting of:

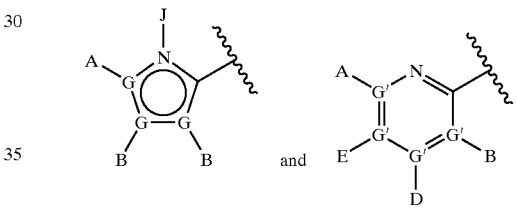

wherein:

each G is independently selected from the group consisting of C, N, O, S, and Se, and wherein only one G may be O, S, or Se, and at most one G is N;

each G' is independently selected from the group consisting of C and N and wherein no more than two G' groups are N;

A is selected from the group consisting of —H, —NR$^4_2$, —CONR$^4_2$, —CO$_2$R$^3$, halo, —S(O)R$^3$, —SO$_2$R$^3$, alkyl, alkenyl, alkynyl, perhaloalkyl, haloalkyl, aryl, —CH$_2$OH, —CH$_2$NR$^4_2$, —CH$_2$CN, —CN, —C(S)NH$_2$, —OR$^2$, —SR$^2$, —N$_3$, —NHC(S)NR$^4_2$, —NHAc, and null;

each B and D are independently selected from the group consisting of —H, alkyl, alkenyl, alkynyl, aryl, alicyclic, aralkyl, alkoxyalkyl, —C(O)R$^{11}$, —C(O)SR$^3$, —SO$_2$R$^{11}$, —S(O)R$^3$, —CN, —NR$^9_2$, —OR$^3$, —SR$^3$, perhaloalkyl, halo, —NO$_2$, and null, all except —H, —CN, perhaloalkyl, —NO$_2$, and halo are optionally substituted;

E is selected from the group consisting of —H, alkyl, alkenyl, alkynyl, aryl, alicyclic, alkoxyalkyl, —C(O)OR$^3$, —CONR$^4_2$, —CN, —NR$^9_2$, —NO$_2$, —OR$^3$, —SR$^3$, perhaloalkyl, halo, and null, all except —H, —CN, perhaloalkyl, and halo are optionally substituted;

J is selected from the group consisting of —H and null;

X is an optionally substituted linking group that links $R^5$ to the phosphorus atom via 2–4 atoms, including 0–1 heteroatoms selected from N, O, and S, except that if X is urea or carbamate there is 2 heteroatoms, measured by the shortest path between $R^5$ and the phosphorus atom, and wherein the atom attached to the phosphorus is a carbon atom, and wherein X is selected from the group consisting of -alkyl(hydroxy)-, -alkynyl-, -heteroaryl-, -carbonylalkyl-, -1,1-dihaloalkyl-, -alkoxyalkyl-, -alkyloxy-, -alkylthioalkyl-, -alkylthio-, -alkylaminocarbonyl-, -alkylcarbonylamino-, -alkoxycarbonyl-, -carbonyloxyalkyl-, -alkoxycarbonylamino-, and -alkylaminocarbonylamino-, all optionally substituted; with the proviso that X is not substituted with —COOR$^2$, —SO$_3$H, or —PO$_3$R$^2{}_2$;

R$^2$ is selected from the group consisting of R$^3$ and —H;

R$^3$ is selected from the group consisting of alkyl, aryl, alicyclic, and aralkyl;

each R$^4$ is independently selected from the group consisting of —H, and alkyl, or together R$^4$ and R$^4$ form a cyclic alkyl group;

each R$^9$ is independently selected from the group consisting of —H, alkyl, aryl, aralkyl, and alicyclic, or together R$^9$ and R$^9$ form a cyclic alkyl group;

R$^{11}$ is selected from the group consisting of alkyl, aryl, —NR$^2{}_2$, and —OR$^2$;

and with the proviso that:

1) when G' is N, then the respective A, B, D, or E is null;
2) at least one of A and B, or A, B, D, and E is not selected from the group consisting of —H or null;
3) when G is N, then the respective A or B is not halogen or a group directly bonded to G via a heteroatom;

and pharmaceutically acceptable salts thereof.

In one aspect, the following additional provisos may apply:

4) when R$^5$ is a six-membered ring, then X is not any 2 atom linker, an optionally substituted-alkyloxy-, or an optionally substituted-alkylthio-;
5) when X is not a -heteroaryl- group, then R$^5$ is not substituted with two or more aryl groups.

In one aspect of the present invention, compounds of formula IA have an IC$_{50}$ of ≦50 µM on glucose production in isolated rat hepatocytes.

In one aspect, compounds of formula IA can be selected from those compounds where M is attached to

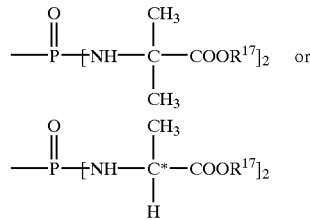

wherein R$^{17}$ is selected from the group consisting of ethyl, i-propyl, n-propyl and neopentyl and wherein C* has S stereochemistry.

In thiazoles where A" is —NH$_2$, X is furan-2,5-diyl, B" is —S(CH$_2$)$_2$CH$_3$; or where A" is —NH$_2$, D is furan-2,5-diyl, B" is —CH$_2$—CH(CH$_3$)$_2$, then M may be attached to

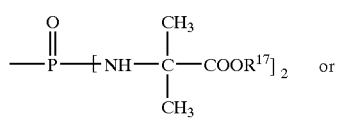

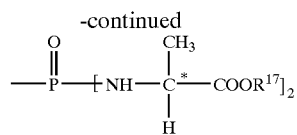

wherein R$^{17}$ is selected from the group consisting of ethyl, i-propyl, n-propyl and neopentyl and wherein C* has S stereochemistry.

In one aspect, the compounds of formula IA can be selected from:

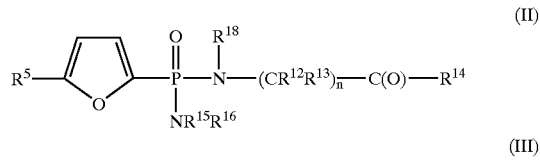

(II)

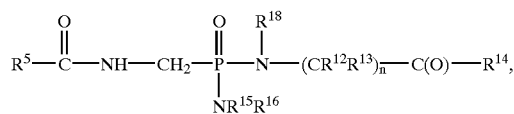

(III)

and

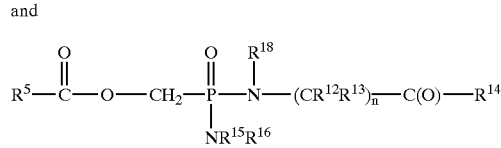

Within such a group, compounds of formula IA may be compounds of formulae II or IV:

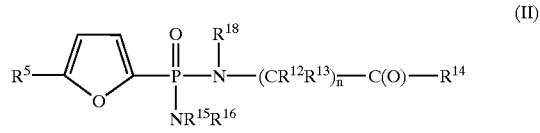

(II)

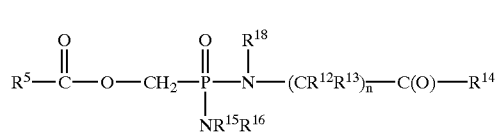

(IV)

In one aspect, compounds are of Formula IA wherein M is

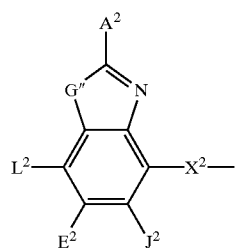

wherein:

G" is selected from the group consisting of —O— and —S—;

A$^2$ is selected from the group consisting of —H, —NR$^4{}_2$, —NHAc, —OR$^2$, —SR$^2$, —C(O)NR$^4{}_2$, halo, —COR$^{11}$, —CN, perhaloalkyl, C1–C6 alkyl, C2–C6 alkenyl, and C2–C6 alkynyl;

L$^2$, E$^2$, and J$^2$ are selected from the group consisting of —NR$^4{}_2$, —NHAc, —NO$_2$, —H, —OR$^2$, —SR$^2$, —C(O)

$NR^4{}_2$, halo, $—COR^{11}$, $—SO_2R^3$, guanidinyl, amidinyl, aryl, aralkyl, alkyloxyalkyl, —SCN, $—NHSO_2R^3$, $—SO_2NR^4{}_2$, —CN, $—S(O)R^3$, perhaloacyl, perhaloalkyl, perhaloalkoxy, C1–C6 alkyl(OH), C1–C6 alkyl(SH), C1–C6 alkyl, C2–C6 alkenyl, C2–C6 alkynyl, heteroaryl, and lower alicyclic, or together $L^2$ and $E^2$ or $E^2$ and $J^2$ form an annulated cyclic group;

$X^2$ is selected from the group consisting of $—CR^2{}_2—$, $—CF_2—$, $—CR^2{}_2—O—$, $—CR^2{}_2—S—$, $—C(O)—O—$, $—C(O)—S—$, $—C(S)—O—$, $—CH_2—C(O)—O—$ and $—CR^2{}_2—NR^{20}—$, and wherein in the atom attached to the phosphorus is a carbon atom; with the proviso that $X^2$ is not substituted with $—COOR^2$, $—SO_3H$, or $—PO_3R^2{}_2$;

$R^2$ is selected from the group consisting of $R^3$ and —H;

$R^3$ is selected from the group consisting of alkyl, aryl, alicyclic, and aralkyl;

each $R^4$ is independently selected from the group consisting of —H, and alkyl, or together $R^4$ and $R^4$ form a cyclic alkyl group;

$R^{11}$ is selected from the group consisting of alkyl, aryl, $—NR^2{}_2$, and $—OR^2$;

$R^{20}$ is selected from the group consisting of lower alkyl, —H, and $—COR^2$; and pharmaceutically acceptable salts thereof.

In one aspect, the bisphosphoramidate portion of the compounds of the invention,

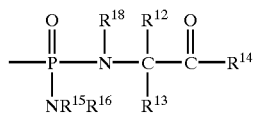

may be selected from the group consisting of

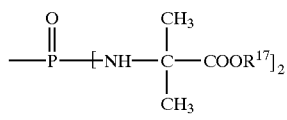

and

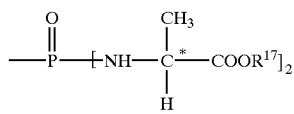

wherein $R^{17}$ is selected from the group consisting of ethyl, i-propyl, n-propyl, n-butyl and neopentyl. In another aspect, C* has S stereochemistry.

Alternatively, such compounds may be of the formula:

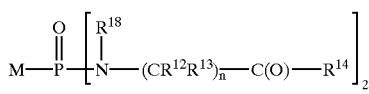

In one aspect of the invention, M is

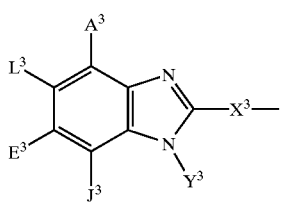

wherein:

$A^3$, $E^3$, and $L^3$ are selected from the group consisting of $—NR^8{}_2$, $—NO_2$, —H, $—OR^7$, $—SR^7$, $—C(O)NR^4{}_2$, halo, $—COR^{11}$, $—SO_2R^3$, guanidine, amidine, $—NHSO_2R^3$, $—SO_2NR^4{}_2$, —CN, sulfoxide, perhaloacyl, perhaloalkyl, perhaloalkoxy, C1–C5 alkyl, C2–C5 alkenyl, C2–C5 alkynyl, and lower alicyclic, or together $A^3$ and $L^3$ form a cyclic group, or together $L^3$ and $E^3$ form a cyclic group, or together $E^3$ and $J^3$ form a cyclic group including aryl, cyclic alkyl, and heterocyclic;

$J^3$ is selected from the group consisting of $—NR^8{}_2$, $—NO_2$, —H, $—OR^7$, $—SR^7$, $—C(O)NR^4{}_2$, halo, $—C(O)R^{11}$, —CN, sulfonyl, sulfoxide, perhaloalkyl, hydroxyalkyl, perhaloalkoxy, alkyl, haloalkyl, aminoalkyl, alkenyl, alkynyl; alicyclic, aryl, and aralkyl, or together with $Y^3$ forms a cyclic group including aryl, cyclic alkyl and heterocyclic alkyl;

$X^3$ is selected from the group consisting of —alkyl (hydroxy)-, -alkyl-, -alkynyl-, -aryl-, -carbonylalkyl-, -1,1-dihaloalkyl-, -alkoxyalkyl-, -alkyloxy-, -alkylthioalkyl-, -alkylthio-, -alkylaminocarbonyl-, -alkylcarbonylamino-, -alicyclic-, -aralkyl-, -alkylaryl-, -alkoxycarbonyl-, -carbonyloxyalkyl-, -alkoxycarbonylamino-, and -alkylaminocarbonylamino-, all optionally substituted; with the proviso that $X^3$ is not substituted with $—COOR^2$, $—SO_3H$, or $—PO_3R^2{}_2$;

$Y^3$ is selected from the group consisting of —H, alkyl, alkenyl, alkynyl, aryl, alicyclic, aralkyl, aryloxyalkyl, alkoxyalkyl, $—C(O)R^3$, $—S(O)_2R^3$, $—C(O)—R^{11}$, $—CONHR^3$, $—NR^2{}_2$, and $—OR^3$, all except H are optionally substituted;

$R^2$ is selected from the group consisting of $R^3$ and —H;

$R^3$ is selected from the group consisting of alkyl, aryl, alicyclic, and aralkyl;

each $R^4$ is independently selected from the group consisting of —H, and alkyl, or together $R^4$ and $R^4$ form a cyclic alkyl group;

$R^7$ is independently selected from the group consisting of —H, lower alkyl, lower alicyclic, lower aralkyl, lower aryl, and $—C(O)R^{10}$;

$R^8$ is independently selected from the group consisting of —H, lower alkyl, lower aralkyl, lower aryl, lower alicyclic, $—C(O)R^{10}$, or together they form a bidentate alkyl;

each $R^9$ is independently selected from the group consisting of —H, -alkyl, aralkyl, and alicyclic, or together $R^9$ and $R^9$ form a cyclic alkyl group;

$R^{10}$ is selected from the group consisting of —H, lower alkyl, $—NH_2$, lower aryl, and lower perhaloalkyl;

$R^{11}$ is selected from the group consisting of alkyl, aryl, $—NR^2{}_2$, and $—OR^2$; and pharmaceutically acceptable salts thereof.

In one aspect, the following provisos may apply:

a) when $X^3$ is alkyl or alkene, then $A^3$ is $—N(R^8{}_2)$;

b) $X^3$ is not alkylamine and alkylaminoalkyl substituted with phosphonic esters and acids; and c) $A^3$, $L^3$, $E^3$, $J^3$, and $Y^3$ together may only form 0–2 cyclic groups.

In the following table, the inventors contemplate any combination of the following Markush groups and those described above for the various variables.

TABLE A

Table of Markush Groups by Variable

| | Markush Group A | Markush Group B | Markush Group C | Markush Group D |
|---|---|---|---|---|
| $R^2$ | $R^3$ and —H | —H, lower alkyl, lower alicyclic and lower aralkyl | —H, C1–C4 alkyl, C2–C7 alicyclic, C4–C6 aryl, and C5–C7 aralkyl, wherein said alicyclic, aryl, aralkyl may be optionally substituted with 1–2 heteroatoms | |
| $R^3$ | alykl, aryl, alicyclic, and aralkyl | lower alkyl, lower aryl, lower alicyclic and lower aralkyl | C1–C4 alkyl, C2–C7 alicyclic, C4–C6 aryl, and C5–C7 aralkyl, wherein said alicyclic, aryl, aralkyl may be optionally substituted with 1–2 heteroatoms | |
| $R^4$ | —H, and C1–C4 alkyl, or $R^4$ and $R^4$ are connected by 4–5 atoms to form a cyclic group | —H, and C1–C2 alkyl | | |
| $R^5$ | pyrrolyl, imidazolyl, oxazolyl, thiazolyl, isothiazolyl, | pyrrolyl, imidazolyl, isothiazolyl, 1,2,4-thiadiazolyl, | (thiazole structure with A″, B″) | (thiazole structure with A″, B″) |
| | 1,2,4-thiadiazolyl, pyrazolyl, isoxazolyl, 1,2,3-oxadiazolyl, | pyrazolyl, isoxazolyl, 1,2,3-oxadiazolyl, 1,2,4-oxadiazolyl, | (oxazole structure with A″, B″) | (oxazole structure with A″, B″) |
| | 1,2,4-oxadiazolyl, 1,2,5-oxadiazolyl, | 1,2,5-oxadiazolyl, 1,3,4-oxadiazolyl, | (pyrazine structure with A″, E″, B″, D″) | (pyridine structure with A″, E″, B″, D″) |
| | 1,3,4-oxadiazolyl, 1,2,4-thiadiazolyl, 1,3,4-thiadiazolyl, | 1,2,4-thiadiazolyl, 1,3,4-thiadiazolyl, pyridinyl, pyrimidinyl, | (pyridine structure with A″, E″, B″, D″) | (pyrazine structure with A″, E″, B″, N) |
| | pyridinyl, pyrimidinyl, pyrazinyl, pyridazinyl, 1,3,5-triazinyl, 1,2,4-triazinyl, and 1,3-selenazolyl, all of which contain at least one substituent | pyrazinyl, pyridazinyl, 1,3,5-triazinyl, 1,2,4-triazinyl, and 1,3-selenazolyl, all of which contain at least one substituent | (pyrimidine structure with A″, B″, D″) | (pyrimidine structure with A″, B″, D″) |

TABLE A-continued

Table of Markush Groups by Variable

| | Markush Group A | Markush Group B | Markush Group C | Markush Group D |
|---|---|---|---|---|
| | | thiazolyl, oxazolyl, and selenazolyl | 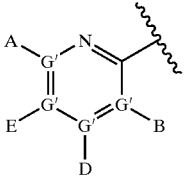 | 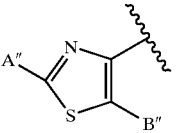 |
| $R^7$ | —H, lower alkyl, lower alicyclic, lower aralkyl, lower aryl, and $C(O)R^{10}$ | —H, $C(O)R^{10}$, C1–C4 alkyl, C2–C7 alicyclic, C4–C6 aryl, and C5–C7 aralkyl, wherein said alicyclic, aryl, aralkyl may be optionally substituted with 1–2 heteroatoms | | |
| $R^8$ | —H, lower alkyl, lower alicyclic, lower aralkyl, lower aryl, and $C(O)R^{10}$; or | H, $C(O)R^{10}$, C1–C4 alkyl, C2–C7 alicyclic, C4–C6 aryl, and C5–C7 aralkyl, wherein said alicyclic, aryl, aralkyl may be optionally substituted with 1–2 heteroatoms; or | | |
| | together $R^8$ and $R^8$ form a bidentate alkyl | together $R^8$ and $R^8$ form a C2–C5 bidentate alkyl | | |
| $R^9$ | —H, lower alkyl, lower aralkyl, and lower alicyclic; or | —H, C1–C4 alkyl, C5–C7 aralkyl, and C2–C7 alicyclic, wherein said alicyclic, and aralkyl may be optionally substituted with 1–2 heteroatoms; or | | |
| | together $R^9$ and $R^9$ form a cyclic alkyl group | together $R^9$ and $R^9$ form a C2–C6 cyclic alkyl | | |
| $R^{10}$ | —H, —$NH_2$, lower alkyl, lower aryl, and lower perhaloalkyl | —H, —$NH_2$, C1–C4 alkyl, C4–C6 aryl, and C1–C4 perhaloalkyl, wherein said aryl, may be optionally substituted with 1–2 heteroatoms | | |
| $R^{11}$ | —$NR_2^2$, —$OR^2$, lower alkyl, and lower aryl | —$NR_2^2$, —$OR^2$, C1–C4 alkyl, and C4–C6 aryl, wherein said aryl may be optionally substituted with 1–2 heteroatoms | | |

TABLE A-continued

Table of Markush Groups by Variable

|  | Markush Group A | Markush Group B | Markush Group C | Markush Group D | | |
| --- | --- | --- | --- | --- | --- | --- |
| $R^{12}$ | —H, lower alkyl, lower perhaloalkyl, lower aryl, optionally substituted with —$OR^{19}$, —$NR_2^{19}$, —$SR^{19}$, —C(O)—$NR^{21}R^3$, halo, —$CO_2R^2$, 3-indolyl, 4-imidazolyl, or guanidinyl; or | —H, C1–C6 alkyl, -lower alkoxyalkyl, alkylthioalkyl, phenyl, and benzyl, or | —H, C1–C4 alkyl, and benzyl; or | —H, lower alkyl, lower perhaloalkyl optionally substituted with —$OR^{19}$, —$NR_2^{19}$, —$SR^{19}$, —C(O)—N-$R^2R^3$, halogen, —$CO_2R^2$, 3-indolyl, 4-imidazolyl, or guanidinyl; or | —H, C1–C4 alkyl, —$CH_2$—O—$C(CH_3)_3$, phenyl, aryl, and benzyl; or | —H and methyl, methyl H |
|  | together $R^{12}$ and $R^{13}$ are connected via 2–5 carbon atoms to form a cycloalkyl group | $R^{12}$ and $R^{13}$ are connected via 2–5 carbon atoms to form a cycloalkyl group | $R^{12}$ and $R^{13}$ are connected via 2–5 carbon atoms to form a cycloalkyl group | $R^{12}$ and $R^{13}$ are connected via 2 or 4 carbon atoms to form a cyclopropyl or cyclopentyl group | $R^{12}$ and $R^{13}$ are connected via 4 carbon atoms to form cyclopentyl group | |
| $R^{13}$ | —H, lower alkyl, lower perhaloalkyl, lower aralkyl, lower aryl, optionally substituted with —$OR^{19}$, —$NR_2^{19}$, —$SR^{19}$, —C(O)—$NR^2$-$R^3$, halogen, —$CO_2R^2$, 3-indolyl, 4-imidazolyl, or guanidinyl; or | —H, C1–C6 alkyl, -lower alkoxyalkyl, lower alkylthioalkyl, phenyl, and benzyl, or | —H, C1–C4 alkyl, phenyl, and benzyl; or | —H, lower alkyl, lower perhaloalkyl, and lower aryl, optionally substituted with —$OR^{19}$, $NR_2^{19}$, $SR^{19}$, $C(O)NR^2R^3$, halogen, —$CO_2R^2$, 3-indolyl, 4-imidazolyl, or guanidinyl; or | —H, C1–C4 alkyl, —$CH_2$—O—$C(CH_3)_3$, phenyl, and benzyl; or | —H, methyl, i-propyl, and benzyl, |
|  | together $R^{12}$ and $R^{13}$ are connected via 2–5 carbon atoms to form a cycloalkyl group | $R^{12}$ and $R^{13}$ are connected via 2–5 carbon atoms to form a cycloalkyl group | $R^{12}$ and $R^{13}$ are connected via 2–5 carbon atoms to form a cycloalkyl group | $R^{12}$ and $R^{13}$ are connected via 2 or 4 carbon atoms to form a cyclopropyl or cyclopentyl group | $R^{12}$ and $R^{13}$ are connected via 4 carbon atoms to form cyclopentyl group | |
| $R^{14}$ | —$OR^{17}$, —$SR^{17}$ and —$NR^2OR^{19}$ | —$OR^{17}$ | | | | |
| $R^{15}$ | —H, lower alkyl, lower aryl, and lower aralkyl, or | —H, and C1–C6 alkyl, or | —H and C1–C3 alkyl | —H, methyl, ethyl, and propyl | | |
|  | together $R^{15}$ and $R^{16}$ are connected via 2–6 atoms, optionally including 1 heteroatom selected from the group consisting of O, N, and S | together $R^{15}$ and $R^{16}$ are connected via 2–6 atoms, optionally including 1 heteroatom selected from the group consisting of, O, N, and S | —$NR^{15}R^{16}$ is a cyclic amine | $NR^{15}R^{16}$ is morpholinyl and pyrrolidinyl | | |

TABLE A-continued

Table of Markush Groups by Variable

| | Markush Group A | Markush Group B | Markush Group C | Markush Group D |
|---|---|---|---|---|
| $R^{16}$ | —H, lower alkyl, lower aryl, and lower arylalkyl, or together $R^{15}$ and $R^{16}$ are connected via 2–6 atoms, optionally including 1 heteroatom selected from the group consisting of O, N, and S | —H, and C1–C6 alkyl, or together $R^{15}$ and $R^{16}$ are connected via 2–6 atoms, optionally including 1 heteroatom selected from the group consisting of, O, N, and S | —H and C1–C3 alkyl<br><br>—$NR^{15}R^{16}$ is a cyclic amine<br><br>—H, C1–C6 alkyl and —$(CR^{12}R^{13})_n$—C(O)—$R^{14}$ or<br><br>together $R^{15}$ and $R^{16}$ are connected via 2–6 atoms, optionally including 1 heteroatom selected from the group consisting of, O, N, and S | —$(CR^{12}R^{13})_n$—C(O)—$R^{14}$<br><br>$NR^{15}R^{16}$ is morpholinyl and pyrrolidinyl |
| $R^{17}$ | C1–C7 alkyl, phenyl, indolyl, 3,4-(methylenedioxy)phenyl and benzyl, wherein said phenyl, indolyl,3,4-(methylenedioxy)-phenyl and benzyl may be optionally substituted with 1–3 groups selected from the group consisting of —$CO_2R^2$, —$OR^3$, halo, —$NHC(O)R^3$, and lower alkyl | methyl, ethyl, i-propyl n-propyl, t-butyl isobutyl neopentyl, cyclopentyl and unsubstituted benzyl | methyl, ethyl, i-propyl, n-propyl, t-butyl, cyclopentyl, neopentyl, phenyl and benzyl | ethyl, n-propyl, i-propyl, and neopentyl<br><br>ethyl, i-propyl, n-propyl, n-butyl, and neopentyl<br><br>ethyl |
| $R^{18}$ | —H, C1–C6 alkyl and benzyl | —H and C1–C6 alkyl | —H and methyl | —H |
| $R^{19}$ | —H, —$COR^3$, lower alkyl, lower aryl, lower alicyclic, and lower aralkyl | —H, —$COR^3$, C1–C4 alkyl, C4–C6 aryl, C2–C7 alicyclic, and C5–C7 aralkyl | | |
| $R^{20}$ | —H, —$COR^2$, and lower alkyl | —H, —$COR^2$, and C1–C4 alkyl | | |
| A | —H, —$NR_2^4$, —$CONR_2^4$, —$CO_2R^3$, halo, C1–C6 alkyl, C2–C6 alkenyl, C2–C6 alkynyl, C1–C6 perhaloalkyl, C1–C6 haloalkyl, aryl, —$CH_2OH$, —$CH_2NR_2^4$, $CH_2CN$, —CN, —$C(S)NH_2$, —$OR^2$, —$SR^2$, —$N_3$, —$NHC(S)NR_2^4$, —NHAc, and null | | | |
| B | —H, alkyl, alkenyl, alkynyl, aryl, heteroaryl, alicyclic, aralkyl, alkoxyalkyl, —$C(O)R^{11}$, —$C(O)SR^3$, $SO_2R^{11}$, —$S(O)R^3$, —CN, —$NR_2^9$, —$OR^3$, —$SR^3$, perhaloalkyl, halo, and null, all except —H, —CN, perhalo-alkyl, and halo are optionally substituted | | | |
| D | —H, alkyl, alkenyl, alkynyl, aryl, heteroaryl, alicyclic, aralkyl, alkoxyalkyl, —$C(O)R^{11}$, —$C(O)SR^3$, $SO_2R^{11}$, —$S(O)R^3$, —CN, —$NR_2^2$, —$OR^3$, —$SR^3$, perhaloalkyl, halo, and null, all except —H, —CN, perhalo-alkyl, and halo are optionally substituted | | | |
| E | —H, C1–C6 alkyl, C2–C6 alkenyl, C2–C6 alkynyl, aryl, C4–C6 alicyclic, alkoxyalkyl, —$C(O)OR^3$, —$CONR_2^4$, —CN, —$NR_2^9$, —$SR^3$, C1–C6 perhaloalkyl, halo, and null, all except —H, —CN, perhaloalkyl, and halo are optionally substituted | | | |

TABLE A-continued

Table of Markush Groups by Variable

| | Markush Group A | Markush Group B | Markush Group C | Markush Group D |
|---|---|---|---|---|
| X | -heteroaryl-, -alkylcarbonyl-amino-, -alkyl-, aminocarbonyl-, and -alkoxycarbonyl- | -heteroaryl-, -alkylamino-carbonyl-, and -alkoxy-carbonyl-, all optionally substituted | methylenoxycarbonyl and furan-2,5-diyl | furan-2,5-diyl |
| | -heteroaryl-, -alkoxyalkyl-alkylcarbonyl-amino-, -alkyl-aminocarbonyl-, -alkoxyalkyl and -alkoxy-carbonyl- | -heteroaryl- and -alkoxy-carbonyl- | | methylenoxycarbonyl |
| G' | C, and N | | | |
| A" | —H, —NR$_2^4$, —CONR$_2^4$, —CO$_2$R$^3$, halo, C1–C6 alkyl, C2–C6 alkenyl, C2–C6 alkynyl, C1–C6 perhaloalkyl, C1–C6 haloalkyl, aryl, —CH$_2$OH, —CH$_2$NR$_2^4$, —CH$_2$CN, —CN, —C(S)NH$_2$, —OR$^2$, —SR$^2$, —N$_3$, —NHC(S)NR$_2^4$, and —NHAc | —NH$_2$, —CONH$_2$, halo, —CH$_3$, —CF$_3$, —CH$_2$-halo, —CN, —OCH$_3$, —SCH$_3$, and —H | —H, —NH$_2$, —Cl, —Br, and —CH$_3$ | —NH$_2$ |
| B" | —H, alykl, alkenyl, alkynyl, aryl, heteroaryl, alicyclic, aralkyl, alkoxyalkyl, —C(O)R$^{11}$, —C(O)SR$^3$, —SO$_2$R$^{11}$, —S(O)R$^3$, —CN, —NR$_2^9$, —OR$^3$, —SR$^3$, perhaloalkyl, and halo, all except —H, —CN, perhaloalkyl, and halo are optionally substituted | —H, —C(O)R$^{11}$, —C(O)SR$^3$, alkyl, aryl, heteroaryl, alicyclic, halo, —CN, —SR$^3$, OR$^3$ and —NR$_2^9$ | —H, —C(O)OR$^3$, —C(O)SR$^3$, C1–C6 alkyl, alicyclic, aryl, heteroaryl, and —SR$^3$<br><br>—S(CH$_2$)$_2$CH$_3$, —CH$_2$—CH(CH$_3$)$_2$, —COOEt, —SMe, —CH(CH$_3$)$_2$ cyclopropyl and n-propyl | —S(CH$_2$)$_2$CH$_3$<br><br>—SMe<br><br>—CH(CH$_3$)$_2$<br><br>—CH$_2$—CH(CH$_3$)$_2$<br>—COOEt |
| D" | —H, alkyl, alkenyl, alkynyl, aryl, heteroaryl, alicyclic, aralkyl, alkoxyalkyl, —C(O)R$^{11}$, —C(O)SR$^3$, —SO$_2$R$^{11}$, —CN, —S(O)R$^3$, —NR$_2^9$, —OR$^3$, —SR$^3$, perhaloalkyl, and halo, all except —H, —CN, perhaloalkyl, and halo are optionally substituted | —H, —C(O)R$^{11}$, —C(O)SR$^3$, alkyl, aryl, heteroaryl, alicyclic, halo, —NR$_2^9$, and —SR$^3$ | —H, —C(O)OR$^3$, lower alkyl, alicyclic, and halo | —H |
| E" | —H, C1–C6 alkyl, C2–C6 alkenyl, C2–C6 alkynyl, aryl, C4–C6 alicyclic, alkoxyalkyl, —C(O)OR$^3$, —CONR$_2^4$, —CN, —NR$_2^9$, —OR$^3$, —SR$^3$, C1–C6 | —H, C1–C6 alkyl, lower alicyclic, halo, —CN, —C(O)OR$^3$, —SR$^3$, and —CONR$_2^4$ | —H, C1–C6 alkyl, lower alicyclic, halo, —CN, —C(O)OR$^3$, and —SR$^3$<br><br>H, —Br, and —Cl | —H |

TABLE A-continued

Table of Markush Groups by Variable

| | Markush Group A | Markush Group B | Markush Group C | Markush Group D | | |
|---|---|---|---|---|---|---|
| | perhaloalkyl, and halo, all except H, —CN, perhaloalkyl, and halo are optionally substituted | | | | | |
| G" | —S— | | | | | |
| A² | —H, —NR₂⁴, —CN, —NHAc, halogen, —OR³, perhaloalkyl, —C(O)—NR₂⁴, C1–C6 alkyl, C2–C6 alkenyl, C2–C6 alkynyl | —H, —NR₂⁴, halogen, and C1–C5 alkyl, | —NH₂, —H, halo, and C1–C5 alkyl | —H, —NH₂, —Cl, —Br and —CH₃ | —NH₂ | |
| E² | —H, —NR₂⁴, —NO₂, —NHAc, —S—C≡N, —CN, halogen, —OR³, hydroxy, lower alkoxymethylene, -alkyl(OH), aryl, alkyloxycarbonyl, —CO(OH), —SR³, —SH, lower perhaloalkyl, heteroaryl, lower alicyclic and C1–C6 alkyl, or together L² and E² form an annulated cyclic group | —H, —NR₂⁴, —S—C≡N, —C(O)OH, halogen, lower alkoxy, lower alkylthio, hydroxy, lower alkyl(hydroxy), lower alkoxymethylene, lower aryl, lower heteroaryl, and C1–C5 alkyl, or together L² and E² form an annulated cyclic group | —H, —NR₂⁴, —S—C≡N, —CN, —C(O)OH, lower alkoxy, lower alkylthio, C1–C5 alkyl, lower alkyl(hydroxy), lower aryl, and halogen, or together L² and E² form an annulated cyclic group containing an additional 4 carbon atoms | —H, —SCN, halogen, —CN, C1–C6 alkyl, C1–C6 alkoxy, or | H, lower alkyl, halogen, —SCN, —OR³, lower alkyloxy, carbonyl, lower alkyloxy, —CN, lower alkylthio, or together L² and E² form a cyclic group including aryl, cyclic alkyl, heteroaryl, or heterocyclic alkyl | —SCN, C1–C6 alkyl, C1–C6 alkoxy, C1–C6 alkylthio, and —Br Me OMe OEt —(O)—CH₂—CH—CH—(CH₃)₂ |
| J² | —H, —NR₂⁴, —NO₂, —NHAc, —S—C≡N, —CN, halogen, —OR³, hydroxy, lower alkoxymethylene, -alkyl(OH), aryl, alkyloxycarbonyl, —CO(OH), —SR³, —SH, lower perhaloalkyl, heteroaryl, lower alicyclic and C1–C6 alkyl | —H, —NR₂⁴, —S—C≡N, —C(O)OH, halogen, lower alkoxy, lower alkylthio, hydroxy, lower alkyl(hydroxy), lower alkoxymethylene, lower aryl, lower heteroaryl, and C1–C5 alkyl | —H, halo, and C1–C5 alkyl | H, Cl, and —CH₃ | —H | |
| L² | —H, —NR₂⁴, —NO₂, —NHAc, —S—C≡N, —CN, halogen, —OR³, hydroxy, lower alkoxymethylene, -alkyl(OH), aryl, alkyloxycarbonyl, —CO(OH), —SR³, —SH, lower perhaloalkyl, heteroaryl, lower alicyclic and C1–C6 alkyl, or | —H, —NR₂⁴, —S—C≡N, —C(O)OH, halogen, lower alkoxy, lower alkylthio, hydroxy, lower alkyl(hydroxy), lower alkoxymethylene, lower aryl, lower heteroaryl, and C1–C5 alkyl; or | —H, —NR₂⁴, —S—C≡N, —CN, —C(O)OH, lower alkoxy, lower alkylthio, C1–C5 alkyl, lower alkyl-(hydroxy), lower aryl, and halogen, or | —H, —CN, —SCN, C1–C6 alkyl, halogen, and lower alkoxy, or | —H, —CN, —SCN, lower alkyl, alicyclic, aryl, halogen, lower alkyloxy, hydroxy, and alkenylene, OH, or | —H, methyl, ethyl, propyl, —SCN and —Cl |

TABLE A-continued

Table of Markush Groups by Variable

| | Markush Group A | Markush Group B | Markush Group C | Markush Group D |
|---|---|---|---|---|
| | together $L^2$ and $E^2$ form an annulated cyclic group | together $L^2$ and $E^2$ form an annulated cyclic group | together $L^2$ and $E^2$ form an annulated cyclic group containing an additional 4 carbon atoms | together $L^2$ and $E^2$ form a cyclic group including aryl, cyclic alkyl, heteroaryl, or heterocyclic alkyl |
| $X^2$ | —$CR_2^2$—, —$CF_2$—, —$CR_2^2$—O—, —$CR_2^2$—S—, —C(O)—O—, —C(O)—S—, —C(S)—O—, —$CH_2$—C(O)—O— and —$CR_2^2$—$NR^{20}$— | —$CH_2$—O— and —$CH_2$—S— | —$CH_2O$— | |
| $A^3$ | —H, —$NR_2^8$, —$NO_2$, hydroxy, halogen, —$OR^7$, alkylaminocarbonyl, —$SR^7$, lower perhaloalkyl, and C1–C5 alkyl | —H, —$NH_2$, —F, and —$CH_3$ | —$NH_2$ | |
| $E^3$ | —H, —$NR_2^8$, —$NO_2$, hydroxy, halogen, —$OR^7$, alkylaminocarbonyl, —$SR^7$, lower perhaloalkyl, and C1–C5 alkyl, or together $E^3$ and $J^3$ together form a cyclic group | —H and —Cl | —H | |
| $J^3$ | —H, halogen, lower alkyl, lower hydroxyalkyl, —$NR_2^8$, lower $R_2^8$N-alkyl, lower haloalkyl, lower perhaloalkyl, lower alkenyl, lower alkynyl, lower aryl, heterocyclic, and alicyclic or together $E^3$ and $J^3$ together form a cyclic group | —H, halo, C1–C5 hydroxyalkyl, C1–C5 haloalkyl, $R_2^8$N-C1–C5 alkyl, C1–C5 alicyclic, and C1–C5 alkyl | -ethyl<br><br>-N,N-dimethylaminopropyl | |
| $L^3$ | —H, —$NR_2^8$, —$NO_2$, hydroxy, halogen, —$OR^7$, alkylaminocarbonyl, —$SR^7$, lower perhaloalkyl, and C1–C5 alkyl | —H, —F, —$OCH_3$, —Cl, and —$CH_3$ | —F | |
| $Y^3$ | alicyclic and lower alkyl | lower alkyl | -i-butyl | |
| $X^3$ | -heteroaryl-, -alkylcarbonylamino-, -alkylaminocarbonyl-, and -alkoxycarbonyl- | —$CH_2OCH_2$, -methyleneoxycarbonyl- and -furan-2,5-diyl- | -furan-2,5-diyl- | |
| n | 1, 2 | 1 | | |

Compounds of formula IA may have oral bioavailability of at least 5% and some may have oral bio availability of at least 10%.

The prodrugs of the present invention may have two isomeric forms around the phosphorus. In one aspect, the compounds of the invention are not chiral at the phosphorus. In another aspect, there is no chiral center in the amino groups attached to the phosphorus. The prodrugs of the present invention may have isomers at the carbon substituted with $R^{12}$ and $R^{13}$. The invention contemplates mixtures of isomers as well as individual stereoisomers. For instance, when n is 1, and $R^{12}$ is H, the carbon attached to $R^{12}$ and $R^{13}$ can have R stereochemistry. In another aspect, when n is 1 and $R^{12}$ is —H, the carbon attached to $R^{12}$ and $R^{13}$ can have S stereochemistry.

The present invention includes compounds designated in Table 1 as defined in the following formulae: formula i, formula ii, and formula iii.

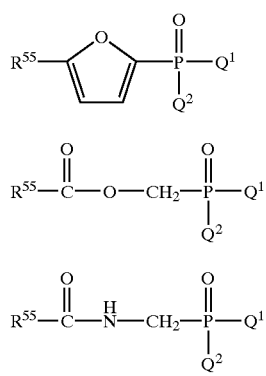

Formula i

Formula ii

Formula iii

In the above formulae i, ii, and iii, $R^{55}$ may be substituted by A and B. The compounds of formulae i, ii, and iii are listed in Table 1 by designated numbers assigned to $R^{55}$, A, B, $Q^1$, and $Q^2$ in the above formulae i, ii, and iii according to the following convention:

$Q^1.Q^2.R^{55}.B.A$. For each moiety, structures assigned to a number shown in the following tables for $R^{55}$, A, B, $Q^1$ and $Q^2$.

Variable $R^{55}$ is divided into two groups, each listing four different structures.

Compounds named in Table 1 of formulae i, ii, and iii wherein the $R^{55}$ moieties are assigned the following numbers:

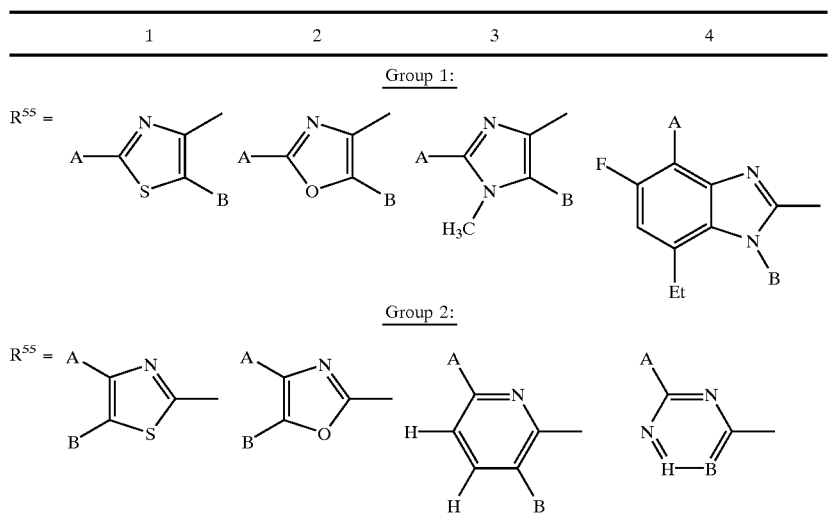

Variable A moieties are assigned the following numbers:

| | 1 | 2 | 3 | 4 |
|---|---|---|---|---|
| A = | $NH_2$ | H | Me | Cl |

Variable B moieties are assigned the following numbers:

| | 1 | 2 | 3 | 4 | 5 | 6 | 7 | 8 |
|---|---|---|---|---|---|---|---|---|
| B= | —$SCH_3$ | -iBu | -cPr | —S-nPr | —SEt | -iPr | -nPr | —$CH_2cPr$ |

Variables $Q^1$ and $Q^2$ are divided into three groups, each listing eight different substituents.

$Q^1$ and $Q^2$ moieties are assigned the following numbers:
Group 1:
$Q^1$ and $Q^2$
1. —NH—$CH_2$—$C(O)R^{14}$
2. —NH—$CH(CH_3)$—$C(O)R^{14}$
3. —NH—$C(CH_3)_2$—$C(O)R^{14}$
4. —NH—$C(CH_3)_2CH_2$—$C(O)R^{14}$
5. —NH—$CH(CH_3)_2)$)—$C(O)R^{14}$
6. —NH—$CH(CH_2(CH(CH_3)_2))$—$C(O)R^{14}$
7. —NH—$CH(CH_2CH_2SCH_3)$—$C(O)R^{14}$
8. —NH—$CH(CH_2SCH_2Ph)$—$C(O)R^{14}$
Group 2:
$Q^1$ and $Q^2$
1. —NH—$CH_2CH_2$—$C(O)R^{14}$
2. —NH—$CH(CH_2CH_2COR^{14})$—$C(O)R^{14}$
3. —NH—$CH(CH_2COR^{14})$—$C(O)R^{14}$
4. —NH—$CH(CH_2CONH_2)$—$C(O)R^{14}$
5. —NH—$CH(COR^{14})CH_2$—$C(O)R^{14}$
6. —NH—$CH(CH_2OR^{21})$—$C(O)R^{14}$

7. —NH—CH(CH$_2$CH$_2$COR$^{14}$)—C(O)R$^{14}$
8. —NH—CH(CH$_2$OH)—C(O)R$^{14}$

Group 3:

Q$^1$ and Q$^2$

1. —NH—CH(CH$_2$—C$_6$H$_5$OH)—C(O)R$^{14}$
2. —NH—C(c-propyl)—C(O)R$^{14}$
3. —NH—C(c-pentyl)—C(O)R$^{14}$
4. —NH—C(c-hexyl)—C(O)R$^{14}$
5. —NH—CH(CH$_2$Ph)—C(O)R$^{14}$
6. —N(CH$_3$)—CH$_2$—C(O)R$^{14}$ 7. 

8. —NR$^{22}$R$^{23}$ where R$^{14}$ is selected from the groups consisting of OMe, OEt, OBn, O-iPr, O-neopentyl, O-tBu, O-nPr, OPh, —N(Me)$_2$, oxyethylene-N-morpholino, SMe, SEt; R$^{21}$ is methyl, ethyl, benzyl, and propyl; R$^{22}$ is H, Me, Et, Bn, Pr and Ph; and R$^{23}$ is Me, Et, Bn, Pr and Ph; or R$^{22}$ and R$^{23}$ is morpholinyl and pyrrolidinyl.

Thus, the compound 3.3.1.2.1 in Group 1 corresponds to the structure below for formula i:

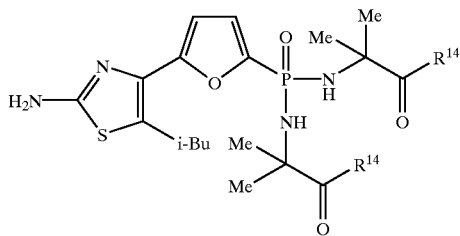

and when R$^{14}$ is ethoxy the structure would be:

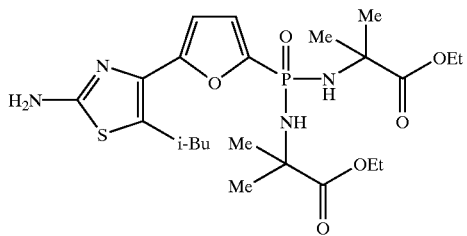

The numbers designated in Table 1 also refer to benzothiazole and benzoxazole compounds of formula X. These compounds are shown in formulae iv and v.

Formula iv

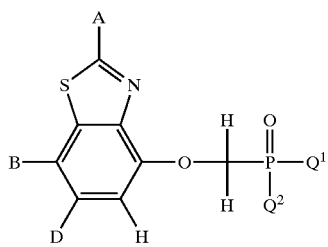

Formula v

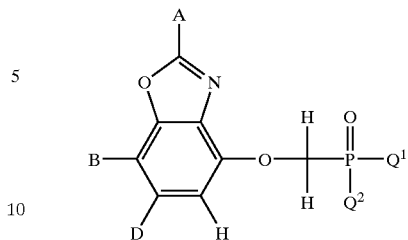

The compounds of formulae iv and formula v are listed in Table 1 by designated numbers assigned to A, B, D, Q$^1$, and Q$^2$ in the above formulae iv and v according to the following convention: Q$^1$.Q$^2$.A.B.D. For each moiety, structures assigned to a number shown in the following tables for A, B, D, Q$^1$ and Q$^2$.

Variables Q$^1$ and Q$^2$ are divided into three groups, each listing eight different substituents.

Group 1:

Q$^1$ and Q$^2$ moieties are assigned the following numbers:

Q$^1$ and Q$^2$

1. —NH—CH$_2$—C(O)R$^{14}$
2. —NH—CH(CH$_3$)—C(O)R$^{14}$
3. —NH—C(CH$_3$)$_2$—C(O)R$^{14}$
4. —NH—C(CH$_3$)$_2$CH$_2$—C(O)R$^{14}$
5. —NH—CH(CH(CH$_3$)$_2$))—C(O)R$^{14}$
6. —NH—CH(CH$_2$(CH(CH$_3$)$_2$)))—C(O)R$^{14}$
7. —NH—CH(CH$_2$CH$_2$SCH$_3$)—C(O)R$^{14}$
8. —NH—CH(CH$_2$SCH$_2$Ph)—C(O)R$^{14}$

Group 2:

Q$^1$ and Q$^2$

1. —NH—CH$_2$CH$_2$—C(O)R$^{14}$
2. —NH—CH(CH$_2$CH$_2$COR$^{14}$)—C(O)R$^{14}$
3. —NH—CH(CH$_2$COR$^{14}$)—C(O)R$^{14}$
4. —NH—CH(CH$_2$CONH$_2$)—C(O)R$^{14}$
5. —NH—CH(COR$^{14}$)CH$_2$—C(O)R$^{14}$
6. —NH—CH(CH$_2$OR$^{21}$)—C(O)R$^{14}$
7. —NH—CH(CH$_2$CH$_2$COR$^{14}$)—C(O)R$^{14}$
8. —NH—CH(CH$_2$OH)—C(O)R$^{14}$

Group 3:

Q$^1$ and Q$^2$

1. —NH—CH(CH$_2$—C$_6$H$_5$OH)—C(O)R$^{14}$
2. —NH—C(c-propyl)—C(O)R$^{14}$
3. —NH—C(c-pentyl)—C(O)R$^{14}$
4. —NH—C(c-hexyl)—C(O)R$^{14}$
5. —NH—CH(CH$_2$Ph)—C(O)R$^{14}$
6. —N(CH$_3$)—CH$_2$—C(O)R$^{14}$ 7. 

8. —NR$^{22}$R$^{23}$

Variable B is divided into three groups, each listing eight different substituents.

Group 1:

B moieties are assigned the following numbers:

| | 1 | 2 | 3 | 4 | 5 | 6 | 7 | 8 |
|---|---|---|---|---|---|---|---|---|
| B= | H | Me | Et | nPr | Br | iPr | SCN | cPr |

Group 2:

| | 1 | 2 | 3 | 4 | 5 | 6 | 7 | 8 |
|---|---|---|---|---|---|---|---|---|
| B= | CN | F | OMe | OEt | SMe | SEt | 2-furanyl | C(O)OEt |

Group 3:

| | 1 | 2 | 3 | 4 | 5 | 6 | 7 | 8 |
|---|---|---|---|---|---|---|---|---|
| B= | B & D are connected to form cyclohexyl ring | B & D are connected to form phenyl ring | B & D are connected to form furanyl ring (O attached at B) | B & D are connected to form furanyl ring (O attached at D) | B & D are connected to form cyclohexyl ring | B & D are connected to form phenyl ring | B & D are connected to form furanyl ring (O attached at B) | B & D are connected to form furanyl ring (O attached at D) |

Group 3 for Variable B can only be combined with Group 3 variable for D.

Variable D is Divided into nine groups, each listing four different substituents.

| | 1 | 2 | 3 | 4 |
|---|---|---|---|---|
| Group 1: | | | | |
| D= | H | Me | Et | SCN |

Group 2:
Variable D is replaced with the moieties assigned in the following numbers:

| | 1 | 2 | 3 | 4 |
|---|---|---|---|---|
| D = | SMe | SEt | CH$_2$OMe | OMe |
| Group 3. | | | | |
| D= | null | null | null | null |
| Group 4: | | | | |
| D= | Pr | O-Et | O-Pr | O-isopropyl |
| Group 5: | | | | |
| D= | O-Bu | O-isobutyl | O-cyclopropyl | O-pentyl |
| Group 6: | | | | |
| D= | O-neopentyl | O-cyclopentyl | O-cyclohexyl | O-benzyl |
| Group 7: | | | | |
| D= | S-Pr | S-isopropyl | S-Bu | S-isobutyl |
| Group 8: | | | | |
| D= | S-cyclopropyl | S-pentyl | S-neopentyl | S-cyclopentyl |
| Group 9: | | | | |
| D= | cyclohexyl | S-benzyl | OCH$_2$OCH$_3$ | OCH$_2$SCH$_3$ |

Compounds named in Table 1 of formulae iv and v wherein the A moieties are assigned the following numbers:

| | 1 | 2 | 3 | 4 |
|---|---|---|---|---|
| A= | NH$_2$ | H | Me | Cl | where $R^{14}$ is selected from the groups consisting of OMe, OEt, OBn, O-tBu, O-nPr, OPh, O-neopentyl, —N(Me)$_2$, oxyethylene-N-morpholino, SMe, SEt; $R^{21}$ is methyl, ethyl, benzyl, and propyl; $R^{22}$ is H, Me, Et, Bn, Pr, and Ph; and $R^{23}$ is Me, Et, Bn, Pr and Ph; or $R^{22}$ and $R^{23}$ is morpholinyl and pyrrolidinyl.

Thus, the compound 2.2.1.7.4 from Group 1 for B, D, $Q^1$ and $Q^2$ corresponds to the structure below for formula iv

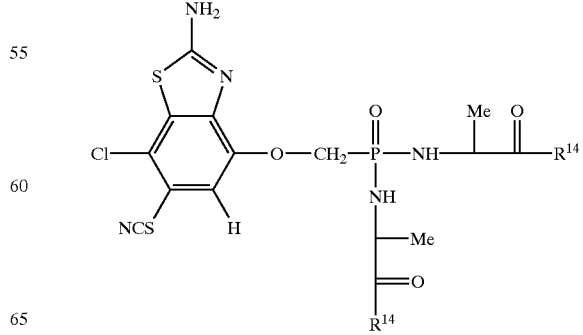

and when R¹⁴ is ethoxy the structure would be
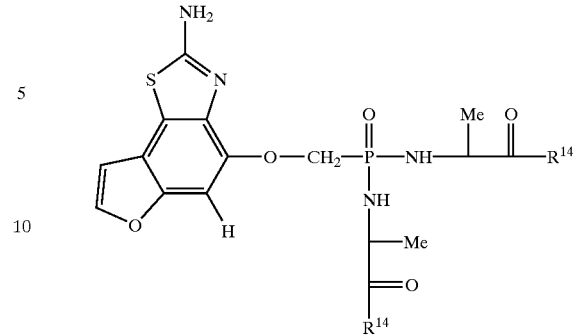
and when R¹⁴ is ethoxy the structure would be
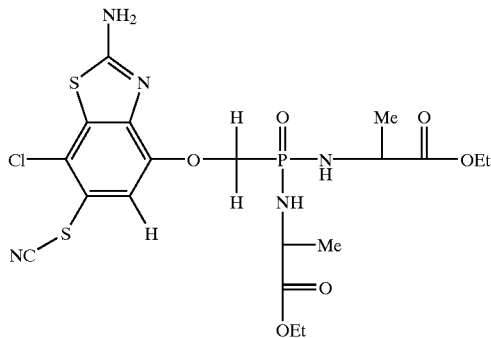
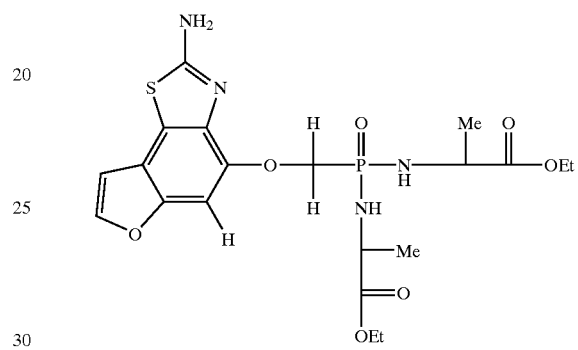
Similarly, in group 3 for variable B, the compound 2.2.1.7.4 corresponds to the structure below for formula iv
TABLE 1
| | | | | | | | |
|---|---|---|---|---|---|---|---|
| 1.1.1.1.1 | 1.1.1.1.2 | 1.1.1.1.3 | 1.1.1.1.4 | 1.1.1.2.1 | 1.1.1.2.2 | 1.1.1.2.3 | 1.1.1.2.4 |
| 1.1.1.3.1 | 1.1.1.3.2 | 1.1.1.3.3 | 1.1.1.3.4 | 1.1.1.4.1 | 1.1.1.4.2 | 1.1.1.4.3 | 1.1.1.4.4 |
| 1.1.1.5.1 | 1.1.1.5.2 | 1.1.1.5.3 | 1.1.1.5.4 | 1.1.1.6.1 | 1.1.1.6.2 | 1.1.1.6.3 | 1.1.1.6.4 |
| 1.1.1.7.1 | 1.1.1.7.2 | 1.1.1.7.3 | 1.1.1.7.4 | 1.1.1.8.1 | 1.1.1.8.2 | 1.1.1.8.3 | 1.1.1.8.4 |
| 1.1.2.1.1 | 1.1.2.1.2 | 1.1.2.1.3 | 1.1.2.1.4 | 1.1.2.2.1 | 1.1.2.2.2 | 1.1.2.2.3 | 1.1.2.2.4 |
| 1.1.2.3.1 | 1.1.2.3.2 | 1.1.2.3.3 | 1.1.2.3.4 | 1.1.2.4.1 | 1.1.2.4.2 | 1.1.2.4.3 | 1.1.2.4.4 |
| 1.1.2.5.1 | 1.1.2.5.2 | 1.1.2.5.3 | 1.1.2.5.4 | 1.1.2.6.1 | 1.1.2.6.2 | 1.1.2.6.3 | 1.1.2.6.4 |
| 1.1.2.7.1 | 1.1.2.7.2 | 1.1.2.7.3 | 1.1.2.7.4 | 1.1.2.8.1 | 1.1.2.8.2 | 1.1.2.8.3 | 1.1.2.8.4 |
| 1.1.3.1.1 | 1.1.3.1.2 | 1.1.3.1.3 | 1.1.3.1.4 | 1.1.3.2.1 | 1.1.3.2.2 | 1.1.3.2.3 | 1.1.3.2.4 |
| 1.1.3.3.1 | 1.1.3.3.2 | 1.1.3.3.3 | 1.1.3.3.4 | 1.1.3.4.1 | 1.1.3.4.2 | 1.1.3.4.3 | 1.1.3.4.4 |
| 1.1.3.5.1 | 1.1.3.5.2 | 1.1.3.5.3 | 1.1.3.5.4 | 1.1.3.6.1 | 1.1.3.6.2 | 1.1.3.6.3 | 1.1.3.6.4 |
| 1.1.3.7.1 | 1.1.3.7.2 | 1.1.3.7.3 | 1.1.3.7.4 | 1.1.3.8.1 | 1.1.3.8.2 | 1.1.3.8.3 | 1.1.3.8.4 |
| 1.1.4.1.1 | 1.1.4.1.2 | 1.1.4.1.3 | 1.1.4.1.4 | 1.1.4.2.1 | 1.1.4.2.2 | 1.1.4.2.3 | 1.1.4.2.4 |
| 1.1.4.3.1 | 1.1.4.3.2 | 1.1.4.3.3 | 1.1.4.3.4 | 1.1.4.4.1 | 1.1.4.4.2 | 1.1.4.4.3 | 1.1.4.4.4 |
| 1.1.4.5.1 | 1.1.4.5.2 | 1.1.4.5.3 | 1.1.4.5.4 | 1.1.4.6.1 | 1.1.4.6.2 | 1.1.4.6.3 | 1.1.4.6.4 |
| 1.1.4.7.1 | 1.1.4.7.2 | 1.1.4.7.3 | 1.1.4.7.4 | 1.1.4.8.1 | 1.1.4.8.2 | 1.1.4.8.3 | 1.1.4.8.4 |
| 1.2.1.1.1 | 1.2.1.1.2 | 1.2.1.1.3 | 1.2.1.1.4 | 1.2.1.2.1 | 1.2.1.2.2 | 1.2.1.2.3 | 1.2.1.2.4 |
| 1.2.1.3.1 | 1.2.1.3.2 | 1.2.1.3.3 | 1.2.1.3.4 | 1.2.1.4.1 | 1.2.1.4.2 | 1.2.1.4.3 | 1.2.1.4.4 |
| 1.2.1.5.1 | 1.2.1.5.2 | 1.2.1.5.3 | 1.2.1.5.4 | 1.2.1.6.1 | 1.2.1.6.2 | 1.2.1.6.3 | 1.2.1.6.4 |
| 1.2.1.7.1 | 1.2.1.7.2 | 1.2.1.7.3 | 1.2.1.7.4 | 1.2.1.8.1 | 1.2.1.8.2 | 1.2.1.8.3 | 1.2.1.8.4 |
| 1.2.2.1.1 | 1.2.2.1.2 | 1.2.2.1.3 | 1.2.2.1.4 | 1.2.2.2.1 | 1.2.2.2.2 | 1.2.2.2.3 | 1.2.2.2.4 |
| 1.2.2.3.1 | 1.2.2.3.2 | 1.2.2.3.3 | 1.2.2.3.4 | 1.2.2.4.1 | 1.2.2.4.2 | 1.2.2.4.3 | 1.2.2.4.4 |
| 1.2.2.5.1 | 1.2.2.5.2 | 1.2.2.5.3 | 1.2.2.5.4 | 1.2.2.6.1 | 1.2.2.6.2 | 1.2.2.6.3 | 1.2.2.6.4 |
| 1.2.2.7.1 | 1.2.2.7.2 | 1.2.2.7.3 | 1.2.2.7.4 | 1.2.2.8.1 | 1.2.2.8.2 | 1.2.2.8.3 | 1.2.2.8.4 |
| 1.2.3.1.1 | 1.2.3.1.2 | 1.2.3.1.3 | 1.2.3.1.4 | 1.2.3.2.1 | 1.2.3.2.2 | 1.2.3.2.3 | 1.2.3.2.4 |
| 1.2.3.3.1 | 1.2.3.3.2 | 1.2.3.3.3 | 1.2.3.3.4 | 1.2.3.4.1 | 1.2.3.4.2 | 1.2.3.4.3 | 1.2.3.4.4 |
| 1.2.3.5.1 | 1.2.3.5.2 | 1.2.3.5.3 | 1.2.3.5.4 | 1.2.3.6.1 | 1.2.3.6.2 | 1.2.3.6.3 | 1.2.3.6.4 |
| 1.2.3.7.1 | 1.2.3.7.2 | 1.2.3.7.3 | 1.2.3.7.4 | 1.2.3.8.1 | 1.2.3.8.2 | 1.2.3.8.3 | 1.2.3.8.4 |
| 1.2.4.1.1 | 1.2.4.1.2 | 1.2.4.1.3 | 1.2.4.1.4 | 1.2.4.2.1 | 1.2.4.2.2 | 1.2.4.2.3 | 1.2.4.2.4 |
| 1.2.4.3.1 | 1.2.4.3.2 | 1.2.4.3.3 | 1.2.4.3.4 | 1.2.4.4.1 | 1.2.4.4.2 | 1.2.4.4.3 | 1.2.4.4.4 |
| 1.2.4.5.1 | 1.2.4.5.2 | 1.2.4.5.3 | 1.2.4.5.4 | 1.2.4.6.1 | 1.2.4.6.2 | 1.2.4.6.3 | 1.2.4.6.4 |
| 1.2.4.7.1 | 1.2.4.7.2 | 1.2.4.7.3 | 1.2.4.7.4 | 1.2.4.8.1 | 1.2.4.8.2 | 1.2.4.8.3 | 1.2.4.8.4 |
| 1.3.1.1.1 | 1.3.1.1.2 | 1.3.1.1.3 | 1.3.1.1.4 | 1.3.1.2.1 | 1.3.1.2.2 | 1.3.1.2.3 | 1.3.1.2.4 |
| 1.3.1.3.1 | 1.3.1.3.2 | 1.3.1.3.3 | 1.3.1.3.4 | 1.3.1.4.1 | 1.3.1.4.2 | 1.3.1.4.3 | 1.3.1.4.4 |
| 1.3.1.5.1 | 1.3.1.5.2 | 1.3.1.5.3 | 1.3.1.5.4 | 1.3.1.6.1 | 1.3.1.6.2 | 1.3.1.6.3 | 1.3.1.6.4 |
| 1.3.1.7.1 | 1.3.1.7.2 | 1.3.1.7.3 | 1.3.1.7.4 | 1.3.1.8.1 | 1.3.1.8.2 | 1.3.1.8.3 | 1.3.1.8.4 |
| 1.3.2.1.1 | 1.3.2.1.2 | 1.3.2.1.3 | 1.3.2.1.4 | 1.3.2.2.1 | 1.3.2.2.2 | 1.3.2.2.3 | 1.3.2.2.4 |
| 1.3.2.3.1 | 1.3.2.3.2 | 1.3.2.3.3 | 1.3.2.3.4 | 1.3.2.4.1 | 1.3.2.4.2 | 1.3.2.4.3 | 1.3.2.4.4 |

TABLE 1-continued

| | | | | | | | |
|---|---|---|---|---|---|---|---|
| 1.3.2.5.1 | 1.3.2.5.2 | 1.3.2.5.3 | 1.3.2.5.4 | 1.3.2.6.1 | 1.3.2.6.2 | 1.3.2.6.3 | 1.3.2.6.4 |
| 1.3.2.7.1 | 1.3.2.7.2 | 1.3.2.7.3 | 1.3.2.7.4 | 1.3.2.8.1 | 1.3.2.8.2 | 1.3.2.8.3 | 1.3.2.8.4 |
| 1.3.3.1.1 | 1.3.3.1.2 | 1.3.3.1.3 | 1.3.3.1.4 | 1.3.3.2.1 | 1.3.3.2.2 | 1.3.3.2.3 | 1.3.3.2.4 |
| 1.3.3.3.1 | 1.3.3.3.2 | 1.3.3.3.3 | 1.3.3.3.4 | 1.3.3.4.1 | 1.3.3.4.2 | 1.3.3.4.3 | 1.3.3.4.4 |
| 1.3.3.5.1 | 1.3.3.5.2 | 1.3.3.5.3 | 1.3.3.5.4 | 1.3.3.6.1 | 1.3.3.6.2 | 1.3.3.6.3 | 1.3.3.6.4 |
| 1.3.3.7.1 | 1.3.3.7.2 | 1.3.3.7.3 | 1.3.3.7.4 | 1.3.3.8.1 | 1.3.3.8.2 | 1.3.3.8.3 | 1.3.3.8.4 |
| 1.3.4.1.1 | 1.3.4.1.2 | 1.3.4.1.3 | 1.3.4.1.4 | 1.3.4.2.1 | 1.3.4.2.2 | 1.3.4.2.3 | 1.3.4.2.4 |
| 1.3.4.3.1 | 1.3.4.3.2 | 1.3.4.3.3 | 1.3.4.3.4 | 1.3.4.4.1 | 1.3.4.4.2 | 1.3.4.4.3 | 1.3.4.4.4 |
| 1.3.4.5.1 | 1.3.4.5.2 | 1.3.4.5.3 | 1.3.4.5.4 | 1.3.4.6.1 | 1.3.4.6.2 | 1.3.4.6.3 | 1.3.4.6.4 |
| 1.3.4.7.1 | 1.3.4.7.2 | 1.3.4.7.3 | 1.3.4.7.4 | 1.3.4.8.1 | 1.3.4.8.2 | 1.3.4.8.3 | 1.3.4.8.4 |
| 1.4.1.1.1 | 1.4.1.1.2 | 1.4.1.1.3 | 1.4.1.1.4 | 1.4.1.2.1 | 1.4.1.2.2 | 1.4.1.2.3 | 1.4.1.2.4 |
| 1.4.1.3.1 | 1.4.1.3.2 | 1.4.1.3.3 | 1.4.1.3.4 | 1.4.1.4.1 | 1.4.1.4.2 | 1.4.1.4.3 | 1.4.1.4.4 |
| 1.4.1.5.1 | 1.4.1.5.2 | 1.4.1.5.3 | 1.4.1.5.4 | 1.4.1.6.1 | 1.4.1.6.2 | 1.4.1.6.3 | 1.4.1.6.4 |
| 1.4.1.7.1 | 1.4.1.7.2 | 1.4.1.7.3 | 1.4.1.7.4 | 1.4.1.8.1 | 1.4.1.8.2 | 1.4.1.8.3 | 1.4.1.8.4 |
| 1.4.2.1.1 | 1.4.2.1.2 | 1.4.2.1.3 | 1.4.2.1.4 | 1.4.2.2.1 | 1.4.2.2.2 | 1.4.2.2.3 | 1.4.2.2.4 |
| 1.4.2.3.1 | 1.4.2.3.2 | 1.4.2.3.3 | 1.4.2.3.4 | 1.4.2.4.1 | 1.4.2.4.2 | 1.4.2.4.3 | 1.4.2.4.4 |
| 1.4.2.5.1 | 1.4.2.5.2 | 1.4.2.5.3 | 1.4.2.5.4 | 1.4.2.6.1 | 1.4.2.6.2 | 1.4.2.6.3 | 1.4.2.6.4 |
| 1.4.2.7.1 | 1.4.2.7.2 | 1.4.2.7.3 | 1.4.2.7.4 | 1.4.2.8.1 | 1.4.2.8.2 | 1.4.2.8.3 | 1.4.2.8.4 |
| 1.4.3.1.1 | 1.4.3.1.2 | 1.4.3.1.3 | 1.4.3.1.4 | 1.4.3.2.1 | 1.4.3.2.2 | 1.4.3.2.3 | 1.4.3.2.4 |
| 1.4.3.3.1 | 1.4.3.3.2 | 1.4.3.3.3 | 1.4.3.3.4 | 1.4.3.4.1 | 1.4.3.4.2 | 1.4.3.4.3 | 1.4.3.4.4 |
| 1.4.3.5.1 | 1.4.3.5.2 | 1.4.3.5.3 | 1.4.3.5.4 | 1.4.3.6.1 | 1.4.3.6.2 | 1.4.3.6.3 | 1.4.3.6.4 |
| 1.4.3.7.1 | 1.4.3.7.2 | 1.4.3.7.3 | 1.4.3.7.4 | 1.4.3.8.1 | 1.4.3.8.2 | 1.4.3.8.3 | 1.4.3.8.4 |
| 1.4.4.1.1 | 1.4.4.1.2 | 1.4.4.1.3 | 1.4.4.1.4 | 1.4.4.2.1 | 1.4.4.2.2 | 1.4.4.2.3 | 1.4.4.2.4 |
| 1.4.4.3.1 | 1.4.4.3.2 | 1.4.4.3.3 | 1.4.4.3.4 | 1.4.4.4.1 | 1.4.4.4.2 | 1.4.4.4.3 | 1.4.4.4.4 |
| 1.4.4.5.1 | 1.4.4.5.2 | 1.4.4.5.3 | 1.4.4.5.4 | 1.4.4.6.1 | 1.4.4.6.2 | 1.4.4.6.3 | 1.4.4.6.4 |
| 1.4.4.7.1 | 1.4.4.7.2 | 1.4.4.7.3 | 1.4.4.7.4 | 1.4.4.8.1 | 1.4.4.8.2 | 1.4.4.8.3 | 1.4.4.8.4 |
| 1.5.1.1.1 | 1.5.1.1.2 | 1.5.1.1.3 | 1.5.1.1.4 | 1.5.1.2.1 | 1.5.1.2.2 | 1.5.1.2.3 | 1.5.1.2.4 |
| 1.5.1.3.1 | 1.5.1.3.2 | 1.5.1.3.3 | 1.5.1.3.4 | 1.5.1.4.1 | 1.5.1.4.2 | 1.5.1.4.3 | 1.5.1.4.4 |
| 1.5.1.5.1 | 1.5.1.5.2 | 1.5.1.5.3 | 1.5.1.5.4 | 1.5.1.6.1 | 1.5.1.6.2 | 1.5.1.6.3 | 1.5.1.6.4 |
| 1.5.1.7.1 | 1.5.1.7.2 | 1.5.1.7.3 | 1.5.1.7.4 | 1.5.1.8.1 | 1.5.1.8.2 | 1.5.1.8.3 | 1.5.1.8.4 |
| 1.5.2.1.1 | 1.5.2.1.2 | 1.5.2.1.3 | 1.5.2.1.4 | 1.5.2.2.1 | 1.5.2.2.2 | 1.5.2.2.3 | 1.5.2.2.4 |
| 1.5.2.3.1 | 1.5.2.3.2 | 1.5.2.3.3 | 1.5.2.3.4 | 1.5.2.4.1 | 1.5.2.4.2 | 1.5.2.4.3 | 1.5.2.4.4 |
| 1.5.2.5.1 | 1.5.2.5.2 | 1.5.2.5.3 | 1.5.2.5.4 | 1.5.2.6.1 | 1.5.2.6.2 | 1.5.2.6.3 | 1.5.2.6.4 |
| 1.5.2.7.1 | 1.5.2.7.2 | 1.5.2.7.3 | 1.5.2.7.4 | 1.5.2.8.1 | 1.5.2.8.2 | 1.5.2.8.3 | 1.5.2.8.4 |
| 1.5.3.1.1 | 1.5.3.1.2 | 1.5.3.1.3 | 1.5.3.1.4 | 1.5.3.2.1 | 1.5.3.2.2 | 1.5.3.2.3 | 1.5.3.2.4 |
| 1.5.3.3.1 | 1.5.3.3.2 | 1.5.3.3.3 | 1.5.3.3.4 | 1.5.3.4.1 | 1.5.3.4.2 | 1.5.3.4.3 | 1.5.3.4.4 |
| 1.5.3.5.1 | 1.5.3.5.2 | 1.5.3.5.3 | 1.5.3.5.4 | 1.5.3.6.1 | 1.5.3.6.2 | 1.5.3.6.3 | 1.5.3.6.4 |
| 1.5.3.7.1 | 1.5.3.7.2 | 1.5.3.7.3 | 1.5.3.7.4 | 1.5.3.8.1 | 1.5.3.8.2 | 1.5.3.8.3 | 1.5.3.8.4 |
| 1.5.4.1.1 | 1.5.4.1.2 | 1.5.4.1.3 | 1.5.4.1.4 | 1.5.4.2.1 | 1.5.4.2.2 | 1.5.4.2.3 | 1.5.4.2.4 |
| 1.5.4.3.1 | 1.5.4.3.2 | 1.5.4.3.3 | 1.5.4.3.4 | 1.5.4.4.1 | 1.5.4.4.2 | 1.5.4.4.3 | 1.5.4.4.4 |
| 1.5.4.5.1 | 1.5.4.5.2 | 1.5.4.5.3 | 1.5.4.5.4 | 1.5.4.6.1 | 1.5.4.6.2 | 1.5.4.6.3 | 1.5.4.6.4 |
| 1.5.4.7.1 | 1.5.4.7.2 | 1.5.4.7.3 | 1.5.4.7.4 | 1.5.4.8.1 | 1.5.4.8.2 | 1.5.4.8.3 | 1.5.4.8.4 |
| 1.6.1.1.1 | 1.6.1.1.2 | 1.6.1.1.3 | 1.6.1.1.4 | 1.6.1.2.1 | 1.6.1.2.2 | 1.6.1.2.3 | 1.6.1.2.4 |
| 1.6.1.3.1 | 1.6.1.3.2 | 1.6.1.3.3 | 1.6.1.3.4 | 1.6.1.4.1 | 1.6.1.4.2 | 1.6.1.4.3 | 1.6.1.4.4 |
| 1.6.1.5.1 | 1.6.1.5.2 | 1.6.1.5.3 | 1.6.1.5.4 | 1.6.1.6.1 | 1.6.1.6.2 | 1.6.1.6.3 | 1.6.1.6.4 |
| 1.6.1.7.1 | 1.6.1.7.2 | 1.6.1.7.3 | 1.6.1.7.4 | 1.6.1.8.1 | 1.6.1.8.2 | 1.6.1.8.3 | 1.6.1.8.4 |
| 1.6.2.1.1 | 1.6.2.1.2 | 1.6.2.1.3 | 1.6.2.1.4 | 1.6.2.2.1 | 1.6.2.2.2 | 1.6.2.2.3 | 1.6.2.2.4 |
| 1.6.2.3.1 | 1.6.2.3.2 | 1.6.2.3.3 | 1.6.2.3.4 | 1.6.2.4.1 | 1.6.2.4.2 | 1.6.2.4.3 | 1.6.2.4.4 |
| 1.6.2.5.1 | 1.6.2.5.2 | 1.6.2.5.3 | 1.6.2.5.4 | 1.6.2.6.1 | 1.6.2.6.2 | 1.6.2.6.3 | 1.6.2.6.4 |
| 1.6.2.7.1 | 1.6.2.7.2 | 1.6.2.7.3 | 1.6.2.7.4 | 1.6.2.8.1 | 1.6.2.8.2 | 1.6.2.8.3 | 1.6.2.8.4 |
| 1.6.3.1.1 | 1.6.3.1.2 | 1.6.3.1.3 | 1.6.3.1.4 | 1.6.3.2.1 | 1.6.3.2.2 | 1.6.3.2.3 | 1.6.3.2.4 |
| 1.6.3.3.1 | 1.6.3.3.2 | 1.6.3.3.3 | 1.6.3.3.4 | 1.6.3.4.1 | 1.6.3.4.2 | 1.6.3.4.3 | 1.6.3.4.4 |
| 1.6.3.5.1 | 1.6.3.5.2 | 1.6.3.5.3 | 1.6.3.5.4 | 1.6.3.6.1 | 1.6.3.6.2 | 1.6.3.6.3 | 1.6.3.6.4 |
| 1.6.3.7.1 | 1.6.3.7.2 | 1.6.3.7.3 | 1.6.3.7.4 | 1.6.3.8.1 | 1.6.3.8.2 | 1.6.3.8.3 | 1.6.3.8.4 |
| 1.6.4.1.1 | 1.6.4.1.2 | 1.6.4.1.3 | 1.6.4.1.4 | 1.6.4.2.1 | 1.6.4.2.2 | 1.6.4.2.3 | 1.6.4.2.4 |
| 1.6.4.3.1 | 1.6.4.3.2 | 1.6.4.3.3 | 1.6.4.3.4 | 1.6.4.4.1 | 1.6.4.4.2 | 1.6.4.4.3 | 1.6.4.4.4 |
| 1.6.4.5.1 | 1.6.4.5.2 | 1.6.4.5.3 | 1.6.4.5.4 | 1.6.4.6.1 | 1.6.4.6.2 | 1.6.4.6.3 | 1.6.4.6.4 |
| 1.6.4.7.1 | 1.6.4.7.2 | 1.6.4.7.3 | 1.6.4.7.4 | 1.6.4.8.1 | 1.6.4.8.2 | 1.6.4.8.3 | 1.6.4.8.4 |
| 1.7.1.1.1 | 1.7.1.1.2 | 1.7.1.1.3 | 1.7.1.1.4 | 1.7.1.2.1 | 1.7.1.2.2 | 1.7.1.2.3 | 1.7.1.2.4 |
| 1.7.1.3.1 | 1.7.1.3.2 | 1.7.1.3.3 | 1.7.1.3.4 | 1.7.1.4.1 | 1.7.1.4.2 | 1.7.1.4.3 | 1.7.1.4.4 |
| 1.7.1.5.1 | 1.7.1.5.2 | 1.7.1.5.3 | 1.7.1.5.4 | 1.7.1.6.1 | 1.7.1.6.2 | 1.7.1.6.3 | 1.7.1.6.4 |
| 1.7.1.7.1 | 1.7.1.7.2 | 1.7.1.7.3 | 1.7.1.7.4 | 1.7.1.8.1 | 1.7.1.8.2 | 1.7.1.8.3 | 1.7.1.8.4 |
| 1.7.2.1.1 | 1.7.2.1.2 | 1.7.2.1.3 | 1.7.2.1.4 | 1.7.2.2.1 | 1.7.2.2.2 | 1.7.2.2.3 | 1.7.2.2.4 |
| 1.7.2.3.1 | 1.7.2.3.2 | 1.7.2.3.3 | 1.7.2.3.4 | 1.7.2.4.1 | 1.7.2.4.2 | 1.7.2.4.3 | 1.7.2.4.4 |
| 1.7.2.5.1 | 1.7.2.5.2 | 1.7.2.5.3 | 1.7.2.5.4 | 1.7.2.6.1 | 1.7.2.6.2 | 1.7.2.6.3 | 1.7.2.6.4 |
| 1.7.2.7.1 | 1.7.2.7.2 | 1.7.2.7.3 | 1.7.2.7.4 | 1.7.2.8.1 | 1.7.2.8.2 | 1.7.2.8.3 | 1.7.2.8.4 |
| 1.7.3.1.1 | 1.7.3.1.2 | 1.7.3.1.3 | 1.7.3.1.4 | 1.7.3.2.1 | 1.7.3.2.2 | 1.7.3.2.3 | 1.7.3.2.4 |
| 1.7.3.3.1 | 1.7.3.3.2 | 1.7.3.3.3 | 1.7.3.3.4 | 1.7.3.4.1 | 1.7.3.4.2 | 1.7.3.4.3 | 1.7.3.4.4 |
| 1.7.3.5.1 | 1.7.3.5.2 | 1.7.3.5.3 | 1.7.3.5.4 | 1.7.3.6.1 | 1.7.3.6.2 | 1.7.3.6.3 | 1.7.3.6.4 |
| 1.7.3.7.1 | 1.7.3.7.2 | 1.7.3.7.3 | 1.7.3.7.4 | 1.7.3.8.1 | 1.7.3.8.2 | 1.7.3.8.3 | 1.7.3.8.4 |
| 1.7.4.1.1 | 1.7.4.1.2 | 1.7.4.1.3 | 1.7.4.1.4 | 1.7.4.2.1 | 1.7.4.2.2 | 1.7.4.2.3 | 1.7.4.2.4 |
| 1.7.4.3.1 | 1.7.4.3.2 | 1.7.4.3.3 | 1.7.4.3.4 | 1.7.4.4.1 | 1.7.4.4.2 | 1.7.4.4.3 | 1.7.4.4.4 |
| 1.7.4.5.1 | 1.7.4.5.2 | 1.7.4.5.3 | 1.7.4.5.4 | 1.7.4.6.1 | 1.7.4.6.2 | 1.7.4.6.3 | 1.7.4.6.4 |
| 1.7.4.7.1 | 1.7.4.7.2 | 1.7.4.7.3 | 1.7.4.7.4 | 1.7.4.8.1 | 1.7.4.8.2 | 1.7.4.8.3 | 1.7.4.8.4 |
| 1.8.1.1.1 | 1.8.1.1.2 | 1.8.1.1.3 | 1.8.1.1.4 | 1.8.1.2.1 | 1.8.1.2.2 | 1.8.1.2.3 | 1.8.1.2.4 |
| 1.8.1.3.1 | 1.8.1.3.2 | 1.8.1.3.3 | 1.8.1.3.4 | 1.8.1.4.1 | 1.8.1.4.2 | 1.8.1.4.3 | 1.8.1.4.4 |
| 1.8.1.5.1 | 1.8.1.5.2 | 1.8.1.5.3 | 1.8.1.5.4 | 1.8.1.6.1 | 1.8.1.6.2 | 1.8.1.6.3 | 1.8.1.6.4 |
| 1.8.1.7.1 | 1.8.1.7.2 | 1.8.1.7.3 | 1.8.1.7.4 | 1.8.1.8.1 | 1.8.1.8.2 | 1.8.1.8.3 | 1.8.1.8.4 |
| 1.8.2.1.1 | 1.8.2.1.2 | 1.8.2.1.3 | 1.8.2.1.4 | 1.8.2.2.1 | 1.8.2.2.2 | 1.8.2.2.3 | 1.8.2.2.4 |

TABLE 1-continued

| | | | | | | | |
|---|---|---|---|---|---|---|---|
| 1.8.2.3.1 | 1.8.2.3.2 | 1.8.2.3.3 | 1.8.2.3.4 | 1.8.2.4.1 | 1.8.2.4.2 | 1.8.2.4.3 | 1.8.2.4.4 |
| 1.8.2.5.1 | 1.8.2.5.2 | 1.8.2.5.3 | 1.8.2.5.4 | 1.8.2.6.1 | 1.8.2.6.2 | 1.8.2.6.3 | 1.8.2.6.4 |
| 1.8.2.7.1 | 1.8.2.7.2 | 1.8.2.7.3 | 1.8.2.7.4 | 1.8.2.8.1 | 1.8.2.8.2 | 1.8.2.8.3 | 1.8.2.8.4 |
| 1.8.3.1.1 | 1.8.3.1.2 | 1.8.3.1.3 | 1.8.3.1.4 | 1.8.3.2.1 | 1.8.3.2.2 | 1.8.3.2.3 | 1.8.3.2.4 |
| 1.8.3.3.1 | 1.8.3.3.2 | 1.8.3.3.3 | 1.8.3.3.4 | 1.8.3.4.1 | 1.8.3.4.2 | 1.8.3.4.3 | 1.8.3.4.4 |
| 1.8.3.5.1 | 1.8.3.5.2 | 1.8.3.5.3 | 1.8.3.5.4 | 1.8.3.6.1 | 1.8.3.6.2 | 1.8.3.6.3 | 1.8.3.6.4 |
| 1.8.3.7.1 | 1.8.3.7.2 | 1.8.3.7.3 | 1.8.3.7.4 | 1.8.3.8.1 | 1.8.3.8.2 | 1.8.3.8.3 | 1.8.3.8.4 |
| 1.8.4.1.1 | 1.8.4.1.2 | 1.8.4.1.3 | 1.8.4.1.4 | 1.8.4.2.1 | 1.8.4.2.2 | 1.8.4.2.3 | 1.8.4.2.4 |
| 1.8.4.3.1 | 1.8.4.3.2 | 1.8.4.3.3 | 1.8.4.3.4 | 1.8.4.4.1 | 1.8.4.4.2 | 1.8.4.4.3 | 1.8.4.4.4 |
| 1.8.4.5.1 | 1.8.4.5.2 | 1.8.4.5.3 | 1.8.4.5.4 | 1.8.4.6.1 | 1.8.4.6.2 | 1.8.4.6.3 | 1.8.4.6.4 |
| 1.8.4.7.1 | 1.8.4.7.2 | 1.8.4.7.3 | 1.8.4.7.4 | 1.8.4.8.1 | 1.8.4.8.2 | 1.8.4.8.3 | 1.8.4.8.4 |
| 2.1.1.1.1 | 2.1.1.1.2 | 2.1.1.1.3 | 2.1.1.1.4 | 2.1.1.2.1 | 2.1.1.2.2 | 2.1.1.2.3 | 2.1.1.2.4 |
| 2.1.1.3.1 | 2.1.1.3.2 | 2.1.1.3.3 | 2.1.1.3.4 | 2.1.1.4.1 | 2.1.1.4.2 | 2.1.1.4.3 | 2.1.1.4.4 |
| 2.1.1.5.1 | 2.1.1.5.2 | 2.1.1.5.3 | 2.1.1.5.4 | 2.1.1.6.1 | 2.1.1.6.2 | 2.1.1.6.3 | 2.1.1.6.4 |
| 2.1.1.7.1 | 2.1.1.7.2 | 2.1.1.7.3 | 2.1.1.7.4 | 2.1.1.8.1 | 2.1.1.8.2 | 2.1.1.8.3 | 2.1.1.8.4 |
| 2.1.2.1.1 | 2.1.2.1.2 | 2.1.2.1.3 | 2.1.2.1.4 | 2.1.2.2.1 | 2.1.2.2.2 | 2.1.2.2.3 | 2.1.2.2.4 |
| 2.1.2.3.1 | 2.1.2.3.2 | 2.1.2.3.3 | 2.1.2.3.4 | 2.1.2.4.1 | 2.1.2.4.2 | 2.1.2.4.3 | 2.1.2.4.4 |
| 2.1.2.5.1 | 2.1.2.5.2 | 2.1.2.5.3 | 2.1.2.5.4 | 2.1.2.6.1 | 2.1.2.6.2 | 2.1.2.6.3 | 2.1.2.6.4 |
| 2.1.2.7.1 | 2.1.2.7.2 | 2.1.2.7.3 | 2.1.2.7.4 | 2.1.2.8.1 | 2.1.2.8.2 | 2.1.2.8.3 | 2.1.2.8.4 |
| 2.1.3.1.1 | 2.1.3.1.2 | 2.1.3.1.3 | 2.1.3.1.4 | 2.1.3.2.1 | 2.1.3.2.2 | 2.1.3.2.3 | 2.1.3.2.4 |
| 2.1.3.3.1 | 2.1.3.3.2 | 2.1.3.3.3 | 2.1.3.3.4 | 2.1.3.4.1 | 2.1.3.4.2 | 2.1.3.4.3 | 2.1.3.4.4 |
| 2.1.3.5.1 | 2.1.3.5.2 | 2.1.3.5.3 | 2.1.3.5.4 | 2.1.3.6.1 | 2.1.3.6.2 | 2.1.3.6.3 | 2.1.3.6.4 |
| 2.1.3.7.1 | 2.1.3.7.2 | 2.1.3.7.3 | 2.1.3.7.4 | 2.1.3.8.1 | 2.1.3.8.2 | 2.1.3.8.3 | 2.1.3.8.4 |
| 2.1.4.1.1 | 2.1.4.1.2 | 2.1.4.1.3 | 2.1.4.1.4 | 2.1.4.2.1 | 2.1.4.2.2 | 2.1.4.2.3 | 2.1.4.2.4 |
| 2.1.4.3.1 | 2.1.4.3.2 | 2.1.4.3.3 | 2.1.4.3.4 | 2.1.4.4.1 | 2.1.4.4.2 | 2.1.4.4.3 | 2.1.4.4.4 |
| 2.1.4.5.1 | 2.1.4.5.2 | 2.1.4.5.3 | 2.1.4.5.4 | 2.1.4.6.1 | 2.1.4.6.2 | 2.1.4.6.3 | 2.1.4.6.4 |
| 2.1.4.7.1 | 2.1.4.7.2 | 2.1.4.7.3 | 2.1.4.7.4 | 2.1.4.8.1 | 2.1.4.8.2 | 2.1.4.8.3 | 2.1.4.8.4 |
| 2.2.1.1.1 | 2.2.1.1.2 | 2.2.1.1.3 | 2.2.1.1.4 | 2.2.1.2.1 | 2.2.1.2.2 | 2.2.1.2.3 | 2.2.1.2.4 |
| 2.2.1.3.1 | 2.2.1.3.2 | 2.2.1.3.3 | 2.2.1.3.4 | 2.2.1.4.1 | 2.2.1.4.2 | 2.2.1.4.3 | 2.2.1.4.4 |
| 2.2.1.5.1 | 2.2.1.5.2 | 2.2.1.5.3 | 2.2.1.5.4 | 2.2.1.6.1 | 2.2.1.6.2 | 2.2.1.6.3 | 2.2.1.6.4 |
| 2.2.1.7.1 | 2.2.1.7.2 | 2.2.1.7.3 | 2.2.1.7.4 | 2.2.1.8.1 | 2.2.1.8.2 | 2.2.1.8.3 | 2.2.1.8.4 |
| 2.2.2.1.1 | 2.2.2.1.2 | 2.2.2.1.3 | 2.2.2.1.4 | 2.2.2.2.1 | 2.2.2.2.2 | 2.2.2.2.3 | 2.2.2.2.4 |
| 2.2.2.3.1 | 2.2.2.3.2 | 2.2.2.3.3 | 2.2.2.3.4 | 2.2.2.4.1 | 2.2.2.4.2 | 2.2.2.4.3 | 2.2.2.4.4 |
| 2.2.2.5.1 | 2.2.2.5.2 | 2.2.2.5.3 | 2.2.2.5.4 | 2.2.2.6.1 | 2.2.2.6.2 | 2.2.2.6.3 | 2.2.2.6.4 |
| 2.2.2.7.1 | 2.2.2.7.2 | 2.2.2.7.3 | 2.2.2.7.4 | 2.2.2.8.1 | 2.2.2.8.2 | 2.2.2.8.3 | 2.2.2.8.4 |
| 2.2.3.1.1 | 2.2.3.1.2 | 2.2.3.1.3 | 2.2.3.1.4 | 2.2.3.2.1 | 2.2.3.2.2 | 2.2.3.2.3 | 2.2.3.2.4 |
| 2.2.3.3.1 | 2.2.3.3.2 | 2.2.3.3.3 | 2.2.3.3.4 | 2.2.3.4.1 | 2.2.3.4.2 | 2.2.3.4.3 | 2.2.3.4.4 |
| 2.2.3.5.1 | 2.2.3.5.2 | 2.2.3.5.3 | 2.2.3.5.4 | 2.2.3.6.1 | 2.2.3.6.2 | 2.2.3.6.3 | 2.2.3.6.4 |
| 2.2.3.7.1 | 2.2.3.7.2 | 2.2.3.7.3 | 2.2.3.7.4 | 2.2.3.8.1 | 2.2.3.8.2 | 2.2.3.8.3 | 2.2.3.8.4 |
| 2.2.4.1.1 | 2.2.4.1.2 | 2.2.4.1.3 | 2.2.4.1.4 | 2.2.4.2.1 | 2.2.4.2.2 | 2.2.4.2.3 | 2.2.4.2.4 |
| 2.2.4.3.1 | 2.2.4.3.2 | 2.2.4.3.3 | 2.2.4.3.4 | 2.2.4.4.1 | 2.2.4.4.2 | 2.2.4.4.3 | 2.2.4.4.4 |
| 2.2.4.5.1 | 2.2.4.5.2 | 2.2.4.5.3 | 2.2.4.5.4 | 2.2.4.6.1 | 2.2.4.6.2 | 2.2.4.6.3 | 2.2.4.6.4 |
| 2.2.4.7.1 | 2.2.4.7.2 | 2.2.4.7.3 | 2.2.4.7.4 | 2.2.4.8.1 | 2.2.4.8.2 | 2.2.4.8.3 | 2.2.4.8.4 |
| 2.3.1.1.1 | 2.3.1.1.2 | 2.3.1.1.3 | 2.3.1.1.4 | 2.3.1.2.1 | 2.3.1.2.2 | 2.3.1.2.3 | 2.3.1.2.4 |
| 2.3.1.3.1 | 2.3.1.3.2 | 2.3.1.3.3 | 2.3.1.3.4 | 2.3.1.4.1 | 2.3.1.4.2 | 2.3.1.4.3 | 2.3.1.4.4 |
| 2.3.1.5.1 | 2.3.1.5.2 | 2.3.1.5.3 | 2.3.1.5.4 | 2.3.1.6.1 | 2.3.1.6.2 | 2.3.1.6.3 | 2.3.1.6.4 |
| 2.3.1.7.1 | 2.3.1.7.2 | 2.3.1.7.3 | 2.3.1.7.4 | 2.3.1.8.1 | 2.3.1.8.2 | 2.3.1.8.3 | 2.3.1.8.4 |
| 2.3.2.1.1 | 2.3.2.1.2 | 2.3.2.1.3 | 2.3.2.1.4 | 2.3.2.2.1 | 2.3.2.2.2 | 2.3.2.2.3 | 2.3.2.2.4 |
| 2.3.2.3.1 | 2.3.2.3.2 | 2.3.2.3.3 | 2.3.2.3.4 | 2.3.2.4.1 | 2.3.2.4.2 | 2.3.2.4.3 | 2.3.2.4.4 |
| 2.3.2.5.1 | 2.3.2.5.2 | 2.3.2.5.3 | 2.3.2.5.4 | 2.3.2.6.1 | 2.3.2.6.2 | 2.3.2.6.3 | 2.3.2.6.4 |
| 2.3.2.7.1 | 2.3.2.7.2 | 2.3.2.7.3 | 2.3.2.7.4 | 2.3.2.8.1 | 2.3.2.8.2 | 2.3.2.8.3 | 2.3.2.8.4 |
| 2.3.3.1.1 | 2.3.3.1.2 | 2.3.3.1.3 | 2.3.3.1.4 | 2.3.3.2.1 | 2.3.3.2.2 | 2.3.3.2.3 | 2.3.3.2.4 |
| 2.3.3.3.1 | 2.3.3.3.2 | 2.3.3.3.3 | 2.3.3.3.4 | 2.3.3.4.1 | 2.3.3.4.2 | 2.3.3.4.3 | 2.3.3.4.4 |
| 2.3.3.5.1 | 2.3.3.5.2 | 2.3.3.5.3 | 2.3.3.5.4 | 2.3.3.6.1 | 2.3.3.6.2 | 2.3.3.6.3 | 2.3.3.6.4 |
| 2.3.3.7.1 | 2.3.3.7.2 | 2.3.3.7.3 | 2.3.3.7.4 | 2.3.3.8.1 | 2.3.3.8.2 | 2.3.3.8.3 | 2.3.3.8.4 |
| 2.3.4.1.1 | 2.3.4.1.2 | 2.3.4.1.3 | 2.3.4.1.4 | 2.3.4.2.1 | 2.3.4.2.2 | 2.3.4.2.3 | 2.3.4.2.4 |
| 2.3.4.3.1 | 2.3.4.3.2 | 2.3.4.3.3 | 2.3.4.3.4 | 2.3.4.4.1 | 2.3.4.4.2 | 2.3.4.4.3 | 2.3.4.4.4 |
| 2.3.4.5.1 | 2.3.4.5.2 | 2.3.4.5.3 | 2.3.4.5.4 | 2.3.4.6.1 | 2.3.4.6.2 | 2.3.4.6.3 | 2.3.4.6.4 |
| 2.3.4.7.1 | 2.3.4.7.2 | 2.3.4.7.3 | 2.3.4.7.4 | 2.3.4.8.1 | 2.3.4.8.2 | 2.3.4.8.3 | 2.3.4.8.4 |
| 2.4.1.1.1 | 2.4.1.1.2 | 2.4.1.1.3 | 2.4.1.1.4 | 2.4.1.2.1 | 2.4.1.2.2 | 2.4.1.2.3 | 2.4.1.2.4 |
| 2.4.1.3.1 | 2.4.1.3.2 | 2.4.1.3.3 | 2.4.1.3.4 | 2.4.1.4.1 | 2.4.1.4.2 | 2.4.1.4.3 | 2.4.1.4.4 |
| 2.4.1.5.1 | 2.4.1.5.2 | 2.4.1.5.3 | 2.4.1.5.4 | 2.4.1.6.1 | 2.4.1.6.2 | 2.4.1.6.3 | 2.4.1.6.4 |
| 2.4.1.7.1 | 2.4.1.7.2 | 2.4.1.7.3 | 2.4.1.7.4 | 2.4.1.8.1 | 2.4.1.8.2 | 2.4.1.8.3 | 2.4.1.8.4 |
| 2.4.2.1.1 | 2.4.2.1.2 | 2.4.2.1.3 | 2.4.2.1.4 | 2.4.2.2.1 | 2.4.2.2.2 | 2.4.2.2.3 | 2.4.2.2.4 |
| 2.4.2.3.1 | 2.4.2.3.2 | 2.4.2.3.3 | 2.4.2.3.4 | 2.4.2.4.1 | 2.4.2.4.2 | 2.4.2.4.3 | 2.4.2.4.4 |
| 2.4.2.5.1 | 2.4.2.5.2 | 2.4.2.5.3 | 2.4.2.5.4 | 2.4.2.6.1 | 2.4.2.6.2 | 2.4.2.6.3 | 2.4.2.6.4 |
| 2.4.2.7.1 | 2.4.2.7.2 | 2.4.2.7.3 | 2.4.2.7.4 | 2.4.2.8.1 | 2.4.2.8.2 | 2.4.2.8.3 | 2.4.2.8.4 |
| 2.4.3.1.1 | 2.4.3.1.2 | 2.4.3.1.3 | 2.4.3.1.4 | 2.4.3.2.1 | 2.4.3.2.2 | 2.4.3.2.3 | 2.4.3.2.4 |
| 2.4.3.3.1 | 2.4.3.3.2 | 2.4.3.3.3 | 2.4.3.3.4 | 2.4.3.4.1 | 2.4.3.4.2 | 2.4.3.4.3 | 2.4.3.4.4 |
| 2.4.3.5.1 | 2.4.3.5.2 | 2.4.3.5.3 | 2.4.3.5.4 | 2.4.3.6.1 | 2.4.3.6.2 | 2.4.3.6.3 | 2.4.3.6.4 |
| 2.4.3.7.1 | 2.4.3.7.2 | 2.4.3.7.3 | 2.4.3.7.4 | 2.4.3.8.1 | 2.4.3.8.2 | 2.4.3.8.3 | 2.4.3.8.4 |
| 2.4.4.1.1 | 2.4.4.1.2 | 2.4.4.1.3 | 2.4.4.1.4 | 2.4.4.2.1 | 2.4.4.2.2 | 2.4.4.2.3 | 2.4.4.2.4 |
| 2.4.4.3.1 | 2.4.4.3.2 | 2.4.4.3.3 | 2.4.4.3.4 | 2.4.4.4.1 | 2.4.4.4.2 | 2.4.4.4.3 | 2.4.4.4.4 |
| 2.4.4.5.1 | 2.4.4.5.2 | 2.4.4.5.3 | 2.4.4.5.4 | 2.4.4.6.1 | 2.4.4.6.2 | 2.4.4.6.3 | 2.4.4.6.4 |
| 2.4.4.7.1 | 2.4.4.7.2 | 2.4.4.7.3 | 2.4.4.7.4 | 2.4.4.8.1 | 2.4.4.8.2 | 2.4.4.8.3 | 2.4.4.8.4 |
| 2.5.1.1.1 | 2.5.1.1.2 | 2.5.1.1.3 | 2.5.1.1.4 | 2.5.1.2.1 | 2.5.1.2.2 | 2.5.1.2.3 | 2.5.1.2.4 |
| 2.5.1.3.1 | 2.5.1.3.2 | 2.5.1.3.3 | 2.5.1.3.4 | 2.5.1.4.1 | 2.5.1.4.2 | 2.5.1.4.3 | 2.5.1.4.4 |
| 2.5.1.5.1 | 2.5.1.5.2 | 2.5.1.5.3 | 2.5.1.5.4 | 2.5.1.6.1 | 2.5.1.6.2 | 2.5.1.6.3 | 2.5.1.6.4 |
| 2.5.1.7.1 | 2.5.1.7.2 | 2.5.1.7.3 | 2.5.1.7.4 | 2.5.1.8.1 | 2.5.1.8.2 | 2.5.1.8.3 | 2.5.1.8.4 |

TABLE 1-continued

| | | | | | | | |
|---|---|---|---|---|---|---|---|
| 2.5.2.1.1 | 2.5.2.1.2 | 2.5.2.1.3 | 2.5.2.1.4 | 2.5.2.2.1 | 2.5.2.2.2 | 2.5.2.2.3 | 2.5.2.2.4 |
| 2.5.2.3.1 | 2.5.2.3.2 | 2.5.2.3.3 | 2.5.2.3.4 | 2.5.2.4.1 | 2.5.2.4.2 | 2.5.2.4.3 | 2.5.2.4.4 |
| 2.5.2.5.1 | 2.5.2.5.2 | 2.5.2.5.3 | 2.5.2.5.4 | 2.5.2.6.1 | 2.5.2.6.2 | 2.5.2.6.3 | 2.5.2.6.4 |
| 2.5.2.7.1 | 2.5.2.7.2 | 2.5.2.7.3 | 2.5.2.7.4 | 2.5.2.8.1 | 2.5.2.8.2 | 2.5.2.8.3 | 2.5.2.8.4 |
| 2.5.3.1.1 | 2.5.3.1.2 | 2.5.3.1.3 | 2.5.3.1.4 | 2.5.3.2.1 | 2.5.3.2.2 | 2.5.3.2.3 | 2.5.3.2.4 |
| 2.5.3.3.1 | 2.5.3.3.2 | 2.5.3.3.3 | 2.5.3.3.4 | 2.5.3.4.1 | 2.5.3.4.2 | 2.5.3.4.3 | 2.5.3.4.4 |
| 2.5.3.5.1 | 2.5.3.5.2 | 2.5.3.5.3 | 2.5.3.5.4 | 2.5.3.6.1 | 2.5.3.6.2 | 2.5.3.6.3 | 2.5.3.6.4 |
| 2.5.3.7.1 | 2.5.3.7.2 | 2.5.3.7.3 | 2.5.3.7.4 | 2.5.3.8.1 | 2.5.3.8.2 | 2.5.3.8.3 | 2.5.3.8.4 |
| 2.5.4.1.1 | 2.5.4.1.2 | 2.5.4.1.3 | 2.5.4.1.4 | 2.5.4.2.1 | 2.5.4.2.2 | 2.5.4.2.3 | 2.5.4.2.4 |
| 2.5.4.3.1 | 2.5.4.3.2 | 2.5.4.3.3 | 2.5.4.3.4 | 2.5.4.4.1 | 2.5.4.4.2 | 2.5.4.4.3 | 2.5.4.4.4 |
| 2.5.4.5.1 | 2.5.4.5.2 | 2.5.4.5.3 | 2.5.4.5.4 | 2.5.4.6.1 | 2.5.4.6.2 | 2.5.4.6.3 | 2.5.4.6.4 |
| 2.5.4.7.1 | 2.5.4.7.2 | 2.5.4.7.3 | 2.5.4.7.4 | 2.5.4.8.1 | 2.5.4.8.2 | 2.5.4.8.3 | 2.5.4.8.4 |
| 2.6.1.1.1 | 2.6.1.1.2 | 2.6.1.1.3 | 2.6.1.1.4 | 2.6.1.2.1 | 2.6.1.2.2 | 2.6.1.2.3 | 2.6.1.2.4 |
| 2.6.1.3.1 | 2.6.1.3.2 | 2.6.1.3.3 | 2.6.1.3.4 | 2.6.1.4.1 | 2.6.1.4.2 | 2.6.1.4.3 | 2.6.1.4.4 |
| 2.6.1.5.1 | 2.6.1.5.2 | 2.6.1.5.3 | 2.6.1.5.4 | 2.6.1.6.1 | 2.6.1.6.2 | 2.6.1.6.3 | 2.6.1.6.4 |
| 2.6.1.7.1 | 2.6.1.7.2 | 2.6.1.7.3 | 2.6.1.7.4 | 2.6.1.8.1 | 2.6.1.8.2 | 2.6.1.8.3 | 2.6.1.8.4 |
| 2.6.2.1.1 | 2.6.2.1.2 | 2.6.2.1.3 | 2.6.2.1.4 | 2.6.2.2.1 | 2.6.2.2.2 | 2.6.2.2.3 | 2.6.2.2.4 |
| 2.6.2.3.1 | 2.6.2.3.2 | 2.6.2.3.3 | 2.6.2.3.4 | 2.6.2.4.1 | 2.6.2.4.2 | 2.6.2.4.3 | 2.6.2.4.4 |
| 2.6.2.5.1 | 2.6.2.5.2 | 2.6.2.5.3 | 2.6.2.5.4 | 2.6.2.6.1 | 2.6.2.6.2 | 2.6.2.6.3 | 2.6.2.6.4 |
| 2.6.2.7.1 | 2.6.2.7.2 | 2.6.2.7.3 | 2.6.2.7.4 | 2.6.2.8.1 | 2.6.2.8.2 | 2.6.2.8.3 | 2.6.2.8.4 |
| 2.6.3.1.1 | 2.6.3.1.2 | 2.6.3.1.3 | 2.6.3.1.4 | 2.6.3.2.1 | 2.6.3.2.2 | 2.6.3.2.3 | 2.6.3.2.4 |
| 2.6.3.3.1 | 2.6.3.3.2 | 2.6.3.3.3 | 2.6.3.3.4 | 2.6.3.4.1 | 2.6.3.4.2 | 2.6.3.4.3 | 2.6.3.4.4 |
| 2.6.3.5.1 | 2.6.3.5.2 | 2.6.3.5.3 | 2.6.3.5.4 | 2.6.3.6.1 | 2.6.3.6.2 | 2.6.3.6.3 | 2.6.3.6.4 |
| 2.6.3.7.1 | 2.6.3.7.2 | 2.6.3.7.3 | 2.6.3.7.4 | 2.6.3.8.1 | 2.6.3.8.2 | 2.6.3.8.3 | 2.6.3.8.4 |
| 2.6.4.1.1 | 2.6.4.1.2 | 2.6.4.1.3 | 2.6.4.1.4 | 2.6.4.2.1 | 2.6.4.2.2 | 2.6.4.2.3 | 2.6.4.2.4 |
| 2.6.4.3.1 | 2.6.4.3.2 | 2.6.4.3.3 | 2.6.4.3.4 | 2.6.4.4.1 | 2.6.4.4.2 | 2.6.4.4.3 | 2.6.4.4.4 |
| 2.6.4.5.1 | 2.6.4.5.2 | 2.6.4.5.3 | 2.6.4.5.4 | 2.6.4.6.1 | 2.6.4.6.2 | 2.6.4.6.3 | 2.6.4.6.4 |
| 2.6.4.7.1 | 2.6.4.7.2 | 2.6.4.7.3 | 2.6.4.7.4 | 2.6.4.8.1 | 2.6.4.8.2 | 2.6.4.8.3 | 2.6.4.8.4 |
| 2.7.1.1.1 | 2.7.1.1.2 | 2.7.1.1.3 | 2.7.1.1.4 | 2.7.1.2.1 | 2.7.1.2.2 | 2.7.1.2.3 | 2.7.1.2.4 |
| 2.7.1.3.1 | 2.7.1.3.2 | 2.7.1.3.3 | 2.7.1.3.4 | 2.7.1.4.1 | 2.7.1.4.2 | 2.7.1.4.3 | 2.7.1.4.4 |
| 2.7.1.5.1 | 2.7.1.5.2 | 2.7.1.5.3 | 2.7.1.5.4 | 2.7.1.6.1 | 2.7.1.6.2 | 2.7.1.6.3 | 2.7.1.6.4 |
| 2.7.1.7.1 | 2.7.1.7.2 | 2.7.1.7.3 | 2.7.1.7.4 | 2.7.1.8.1 | 2.7.1.8.2 | 2.7.1.8.3 | 2.7.1.8.4 |
| 2.7.2.1.1 | 2.7.2.1.2 | 2.7.2.1.3 | 2.7.2.1.4 | 2.7.2.2.1 | 2.7.2.2.2 | 2.7.2.2.3 | 2.7.2.2.4 |
| 2.7.2.3.1 | 2.7.2.3.2 | 2.7.2.3.3 | 2.7.2.3.4 | 2.7.2.4.1 | 2.7.2.4.2 | 2.7.2.4.3 | 2.7.2.4.4 |
| 2.7.2.5.1 | 2.7.2.5.2 | 2.7.2.5.3 | 2.7.2.5.4 | 2.7.2.6.1 | 2.7.2.6.2 | 2.7.2.6.3 | 2.7.2.6.4 |
| 2.7.2.7.1 | 2.7.2.7.2 | 2.7.2.7.3 | 2.7.2.7.4 | 2.7.2.8.1 | 2.7.2.8.2 | 2.7.2.8.3 | 2.7.2.8.4 |
| 2.7.3.1.1 | 2.7.3.1.2 | 2.7.3.1.3 | 2.7.3.1.4 | 2.7.3.2.1 | 2.7.3.2.2 | 2.7.3.2.3 | 2.7.3.2.4 |
| 2.7.3.3.1 | 2.7.3.3.2 | 2.7.3.3.3 | 2.7.3.3.4 | 2.7.3.4.1 | 2.7.3.4.2 | 2.7.3.4.3 | 2.7.3.4.4 |
| 2.7.3.5.1 | 2.7.3.5.2 | 2.7.3.5.3 | 2.7.3.5.4 | 2.7.3.6.1 | 2.7.3.6.2 | 2.7.3.6.3 | 2.7.3.6.4 |
| 2.7.3.7.1 | 2.7.3.7.2 | 2.7.3.7.3 | 2.7.3.7.4 | 2.7.3.8.1 | 2.7.3.8.2 | 2.7.3.8.3 | 2.7.3.8.4 |
| 2.7.4.1.1 | 2.7.4.1.2 | 2.7.4.1.3 | 2.7.4.1.4 | 2.7.4.2.1 | 2.7.4.2.2 | 2.7.4.2.3 | 2.7.4.2.4 |
| 2.7.4.3.1 | 2.7.4.3.2 | 2.7.4.3.3 | 2.7.4.3.4 | 2.7.4.4.1 | 2.7.4.4.2 | 2.7.4.4.3 | 2.7.4.4.4 |
| 2.7.4.5.1 | 2.7.4.5.2 | 2.7.4.5.3 | 2.7.4.5.4 | 2.7.4.6.1 | 2.7.4.6.2 | 2.7.4.6.3 | 2.7.4.6.4 |
| 2.7.4.7.1 | 2.7.4.7.2 | 2.7.4.7.3 | 2.7.4.7.4 | 2.7.4.8.1 | 2.7.4.8.2 | 2.7.4.8.3 | 2.7.4.8.4 |
| 2.8.1.1.1 | 2.8.1.1.2 | 2.8.1.1.3 | 2.8.1.1.4 | 2.8.1.2.1 | 2.8.1.2.2 | 2.8.1.2.3 | 2.8.1.2.4 |
| 2.8.1.3.1 | 2.8.1.3.2 | 2.8.1.3.3 | 2.8.1.3.4 | 2.8.1.4.1 | 2.8.1.4.2 | 2.8.1.4.3 | 2.8.1.4.4 |
| 2.8.1.5.1 | 2.8.1.5.2 | 2.8.1.5.3 | 2.8.1.5.4 | 2.8.1.6.1 | 2.8.1.6.2 | 2.8.1.6.3 | 2.8.1.6.4 |
| 2.8.1.7.1 | 2.8.1.7.2 | 2.8.1.7.3 | 2.8.1.7.4 | 2.8.1.8.1 | 2.8.1.8.2 | 2.8.1.8.3 | 2.8.1.8.4 |
| 2.8.2.1.1 | 2.8.2.1.2 | 2.8.2.1.3 | 2.8.2.1.4 | 2.8.2.2.1 | 2.8.2.2.2 | 2.8.2.2.3 | 2.8.2.2.4 |
| 2.8.2.3.1 | 2.8.2.3.2 | 2.8.2.3.3 | 2.8.2.3.4 | 2.8.2.4.1 | 2.8.2.4.2 | 2.8.2.4.3 | 2.8.2.4.4 |
| 2.8.2.5.1 | 2.8.2.5.2 | 2.8.2.5.3 | 2.8.2.5.4 | 2.8.2.6.1 | 2.8.2.6.2 | 2.8.2.6.3 | 2.8.2.6.4 |
| 2.8.2.7.1 | 2.8.2.7.2 | 2.8.2.7.3 | 2.8.2.7.4 | 2.8.2.8.1 | 2.8.2.8.2 | 2.8.2.8.3 | 2.8.2.8.4 |
| 2.8.3.1.1 | 2.8.3.1.2 | 2.8.3.1.3 | 2.8.3.1.4 | 2.8.3.2.1 | 2.8.3.2.2 | 2.8.3.2.3 | 2.8.3.2.4 |
| 2.8.3.3.1 | 2.8.3.3.2 | 2.8.3.3.3 | 2.8.3.3.4 | 2.8.3.4.1 | 2.8.3.4.2 | 2.8.3.4.3 | 2.8.3.4.4 |
| 2.8.3.5.1 | 2.8.3.5.2 | 2.8.3.5.3 | 2.8.3.5.4 | 2.8.3.6.1 | 2.8.3.6.2 | 2.8.3.6.3 | 2.8.3.6.4 |
| 2.8.3.7.1 | 2.8.3.7.2 | 2.8.3.7.3 | 2.8.3.7.4 | 2.8.3.8.1 | 2.8.3.8.2 | 2.8.3.8.3 | 2.8.3.8.4 |
| 2.8.4.1.1 | 2.8.4.1.2 | 2.8.4.1.3 | 2.8.4.1.4 | 2.8.4.2.1 | 2.8.4.2.2 | 2.8.4.2.3 | 2.8.4.2.4 |
| 2.8.4.3.1 | 2.8.4.3.2 | 2.8.4.3.3 | 2.8.4.3.4 | 2.8.4.4.1 | 2.8.4.4.2 | 2.8.4.4.3 | 2.8.4.4.4 |
| 2.8.4.5.1 | 2.8.4.5.2 | 2.8.4.5.3 | 2.8.4.5.4 | 2.8.4.6.1 | 2.8.4.6.2 | 2.8.4.6.3 | 2.8.4.6.4 |
| 2.8.4.7.1 | 2.8.4.7.2 | 2.8.4.7.3 | 2.8.4.7.4 | 2.8.4.8.1 | 2.8.4.8.2 | 2.8.4.8.3 | 2.8.4.8.4 |
| 3.1.1.1.1 | 3.1.1.1.2 | 3.1.1.1.3 | 3.1.1.1.4 | 3.1.1.2.1 | 3.1.1.2.2 | 3.1.1.2.3 | 3.1.1.2.4 |
| 3.1.1.3.1 | 3.1.1.3.2 | 3.1.1.3.3 | 3.1.1.3.4 | 3.1.1.4.1 | 3.1.1.4.2 | 3.1.1.4.3 | 3.1.1.4.4 |
| 3.1.1.5.1 | 3.1.1.5.2 | 3.1.1.5.3 | 3.1.1.5.4 | 3.1.1.6.1 | 3.1.1.6.2 | 3.1.1.6.3 | 3.1.1.6.4 |
| 3.1.1.7.1 | 3.1.1.7.2 | 3.1.1.7.3 | 3.1.1.7.4 | 3.1.1.8.1 | 3.1.1.8.2 | 3.1.1.8.3 | 3.1.1.8.4 |
| 3.1.2.1.1 | 3.1.2.1.2 | 3.1.2.1.3 | 3.1.2.1.4 | 3.1.2.2.1 | 3.1.2.2.2 | 3.1.2.2.3 | 3.1.2.2.4 |
| 3.1.2.3.1 | 3.1.2.3.2 | 3.1.2.3.3 | 3.1.2.3.4 | 3.1.2.4.1 | 3.1.2.4.2 | 3.1.2.4.3 | 3.1.2.4.4 |
| 3.1.2.5.1 | 3.1.2.5.2 | 3.1.2.5.3 | 3.1.2.5.4 | 3.1.2.6.1 | 3.1.2.6.2 | 3.1.2.6.3 | 3.1.2.6.4 |
| 3.1.2.7.1 | 3.1.2.7.2 | 3.1.2.7.3 | 3.1.2.7.4 | 3.1.2.8.1 | 3.1.2.8.2 | 3.1.2.8.3 | 3.1.2.8.4 |
| 3.1.3.1.1 | 3.1.3.1.2 | 3.1.3.1.3 | 3.1.3.1.4 | 3.1.3.2.1 | 3.1.3.2.2 | 3.1.3.2.3 | 3.1.3.2.4 |
| 3.1.3.3.1 | 3.1.3.3.2 | 3.1.3.3.3 | 3.1.3.3.4 | 3.1.3.4.1 | 3.1.3.4.2 | 3.1.3.4.3 | 3.1.3.4.4 |
| 3.1.3.5.1 | 3.1.3.5.2 | 3.1.3.5.3 | 3.1.3.5.4 | 3.1.3.6.1 | 3.1.3.6.2 | 3.1.3.6.3 | 3.1.3.6.4 |
| 3.1.3.7.1 | 3.1.3.7.2 | 3.1.3.7.3 | 3.1.3.7.4 | 3.1.3.8.1 | 3.1.3.8.2 | 3.1.3.8.3 | 3.1.3.8.4 |
| 3.1.4.1.1 | 3.1.4.1.2 | 3.1.4.1.3 | 3.1.4.1.4 | 3.1.4.2.1 | 3.1.4.2.2 | 3.1.4.2.3 | 3.1.4.2.4 |
| 3.1.4.3.1 | 3.1.4.3.2 | 3.1.4.3.3 | 3.1.4.3.4 | 3.1.4.4.1 | 3.1.4.4.2 | 3.1.4.4.3 | 3.1.4.4.4 |
| 3.1.4.5.1 | 3.1.4.5.2 | 3.1.4.5.3 | 3.1.4.5.4 | 3.1.4.6.1 | 3.1.4.6.2 | 3.1.4.6.3 | 3.1.4.6.4 |
| 3.1.4.7.1 | 3.1.4.7.2 | 3.1.4.7.3 | 3.1.4.7.4 | 3.1.4.8.1 | 3.1.4.8.2 | 3.1.4.8.3 | 3.1.4.8.4 |
| 3.2.1.1.1 | 3.2.1.1.2 | 3.2.1.1.3 | 3.2.1.1.4 | 3.2.1.2.1 | 3.2.1.2.2 | 3.2.1.2.3 | 3.2.1.2.4 |
| 3.2.1.3.1 | 3.2.1.3.2 | 3.2.1.3.3 | 3.2.1.3.4 | 3.2.1.4.1 | 3.2.1.4.2 | 3.2.1.4.3 | 3.2.1.4.4 |
| 3.2.1.5.1 | 3.2.1.5.2 | 3.2.1.5.3 | 3.2.1.5.4 | 3.2.1.6.1 | 3.2.1.6.2 | 3.2.1.6.3 | 3.2.1.6.4 |

TABLE 1-continued

| | | | | | | | |
|---|---|---|---|---|---|---|---|
| 3.2.1.7.1 | 3.2.1.7.2 | 3.2.1.7.3 | 3.2.1.7.4 | 3.2.1.8.1 | 3.2.1.8.2 | 3.2.1.8.3 | 3.2.1.8.4 |
| 3.2.2.1.1 | 3.2.2.1.2 | 3.2.2.1.3 | 3.2.2.1.4 | 3.2.2.2.1 | 3.2.2.2.2 | 3.2.2.2.3 | 3.2.2.2.4 |
| 3.2.2.3.1 | 3.2.2.3.2 | 3.2.2.3.3 | 3.2.2.3.4 | 3.2.2.4.1 | 3.2.2.4.2 | 3.2.2.4.3 | 3.2.2.4.4 |
| 3.2.2.5.1 | 3.2.2.5.2 | 3.2.2.5.3 | 3.2.2.5.4 | 3.2.2.6.1 | 3.2.2.6.2 | 3.2.2.6.3 | 3.2.2.6.4 |
| 3.2.2.7.1 | 3.2.2.7.2 | 3.2.2.7.3 | 3.2.2.7.4 | 3.2.2.8.1 | 3.2.2.8.2 | 3.2.2.8.3 | 3.2.2.8.4 |
| 3.2.3.1.1 | 3.2.3.1.2 | 3.2.3.1.3 | 3.2.3.1.4 | 3.2.3.2.1 | 3.2.3.2.2 | 3.2.3.2.3 | 3.2.3.2.4 |
| 3.2.3.3.1 | 3.2.3.3.2 | 3.2.3.3.3 | 3.2.3.3.4 | 3.2.3.4.1 | 3.2.3.4.2 | 3.2.3.4.3 | 3.2.3.4.4 |
| 3.2.3.5.1 | 3.2.3.5.2 | 3.2.3.5.3 | 3.2.3.5.4 | 3.2.3.6.1 | 3.2.3.6.2 | 3.2.3.6.3 | 3.2.3.6.4 |
| 3.2.3.7.1 | 3.2.3.7.2 | 3.2.3.7.3 | 3.2.3.7.4 | 3.2.3.8.1 | 3.2.3.8.2 | 3.2.3.8.3 | 3.2.3.8.4 |
| 3.2.4.1.1 | 3.2.4.1.2 | 3.2.4.1.3 | 3.2.4.1.4 | 3.2.4.2.1 | 3.2.4.2.2 | 3.2.4.2.3 | 3.2.4.2.4 |
| 3.2.4.3.1 | 3.2.4.3.2 | 3.2.4.3.3 | 3.2.4.3.4 | 3.2.4.4.1 | 3.2.4.4.2 | 3.2.4.4.3 | 3.2.4.4.4 |
| 3.2.4.5.1 | 3.2.4.5.2 | 3.2.4.5.3 | 3.2.4.5.4 | 3.2.4.6.1 | 3.2.4.6.2 | 3.2.4.6.3 | 3.2.4.6.4 |
| 3.2.4.7.1 | 3.2.4.7.2 | 3.2.4.7.3 | 3.2.4.7.4 | 3.2.4.8.1 | 3.2.4.8.2 | 3.2.4.8.3 | 3.2.4.8.4 |
| 3.3.1.1.1 | 3.3.1.1.2 | 3.3.1.1.3 | 3.3.1.1.4 | 3.3.1.2.1 | 3.3.1.2.2 | 3.3.1.2.3 | 3.3.1.2.4 |
| 3.3.1.3.1 | 3.3.1.3.2 | 3.3.1.3.3 | 3.3.1.3.4 | 3.3.1.4.1 | 3.3.1.4.2 | 3.3.1.4.3 | 3.3.1.4.4 |
| 3.3.1.5.1 | 3.3.1.5.2 | 3.3.1.5.3 | 3.3.1.5.4 | 3.3.1.6.1 | 3.3.1.6.2 | 3.3.1.6.3 | 3.3.1.6.4 |
| 3.3.1.7.1 | 3.3.1.7.2 | 3.3.1.7.3 | 3.3.1.7.4 | 3.3.1.8.1 | 3.3.1.8.2 | 3.3.1.8.3 | 3.3.1.8.4 |
| 3.3.2.1.1 | 3.3.2.1.2 | 3.3.2.1.3 | 3.3.2.1.4 | 3.3.2.2.1 | 3.3.2.2.2 | 3.3.2.2.3 | 3.3.2.2.4 |
| 3.3.2.3.1 | 3.3.2.3.2 | 3.3.2.3.3 | 3.3.2.3.4 | 3.3.2.4.1 | 3.3.2.4.2 | 3.3.2.4.3 | 3.3.2.4.4 |
| 3.3.2.5.1 | 3.3.2.5.2 | 3.3.2.5.3 | 3.3.2.5.4 | 3.3.2.6.1 | 3.3.2.6.2 | 3.3.2.6.3 | 3.3.2.6.4 |
| 3.3.2.7.1 | 3.3.2.7.2 | 3.3.2.7.3 | 3.3.2.7.4 | 3.3.2.8.1 | 3.3.2.8.2 | 3.3.2.8.3 | 3.3.2.8.4 |
| 3.3.3.1.1 | 3.3.3.1.2 | 3.3.3.1.3 | 3.3.3.1.4 | 3.3.3.2.1 | 3.3.3.2.2 | 3.3.3.2.3 | 3.3.3.2.4 |
| 3.3.3.3.1 | 3.3.3.3.2 | 3.3.3.3.3 | 3.3.3.3.4 | 3.3.3.4.1 | 3.3.3.4.2 | 3.3.3.4.3 | 3.3.3.4.4 |
| 3.3.3.5.1 | 3.3.3.5.2 | 3.3.3.5.3 | 3.3.3.5.4 | 3.3.3.6.1 | 3.3.3.6.2 | 3.3.3.6.3 | 3.3.3.6.4 |
| 3.3.3.7.1 | 3.3.3.7.2 | 3.3.3.7.3 | 3.3.3.7.4 | 3.3.3.8.1 | 3.3.3.8.2 | 3.3.3.8.3 | 3.3.3.8.4 |
| 3.3.4.1.1 | 3.3.4.1.2 | 3.3.4.1.3 | 3.3.4.1.4 | 3.3.4.2.1 | 3.3.4.2.2 | 3.3.4.2.3 | 3.3.4.2.4 |
| 3.3.4.3.1 | 3.3.4.3.2 | 3.3.4.3.3 | 3.3.4.3.4 | 3.3.4.4.1 | 3.3.4.4.2 | 3.3.4.4.3 | 3.3.4.4.4 |
| 3.3.4.5.1 | 3.3.4.5.2 | 3.3.4.5.3 | 3.3.4.5.4 | 3.3.4.6.1 | 3.3.4.6.2 | 3.3.4.6.3 | 3.3.4.6.4 |
| 3.3.4.7.1 | 3.3.4.7.2 | 3.3.4.7.3 | 3.3.4.7.4 | 3.3.4.8.1 | 3.3.4.8.2 | 3.3.4.8.3 | 3.3.4.8.4 |
| 3.4.1.1.1 | 3.4.1.1.2 | 3.4.1.1.3 | 3.4.1.1.4 | 3.4.1.2.1 | 3.4.1.2.2 | 3.4.1.2.3 | 3.4.1.2.4 |
| 3.4.1.3.1 | 3.4.1.3.2 | 3.4.1.3.3 | 3.4.1.3.4 | 3.4.1.4.1 | 3.4.1.4.2 | 3.4.1.4.3 | 3.4.1.4.4 |
| 3.4.1.5.1 | 3.4.1.5.2 | 3.4.1.5.3 | 3.4.1.5.4 | 3.4.1.6.1 | 3.4.1.6.2 | 3.4.1.6.3 | 3.4.1.6.4 |
| 3.4.1.7.1 | 3.4.1.7.2 | 3.4.1.7.3 | 3.4.1.7.4 | 3.4.1.8.1 | 3.4.1.8.2 | 3.4.1.8.3 | 3.4.1.8.4 |
| 3.4.2.1.1 | 3.4.2.1.2 | 3.4.2.1.3 | 3.4.2.1.4 | 3.4.2.2.1 | 3.4.2.2.2 | 3.4.2.2.3 | 3.4.2.2.4 |
| 3.4.2.3.1 | 3.4.2.3.2 | 3.4.2.3.3 | 3.4.2.3.4 | 3.4.2.4.1 | 3.4.2.4.2 | 3.4.2.4.3 | 3.4.2.4.4 |
| 3.4.2.5.1 | 3.4.2.5.2 | 3.4.2.5.3 | 3.4.2.5.4 | 3.4.2.6.1 | 3.4.2.6.2 | 3.4.2.6.3 | 3.4.2.6.4 |
| 3.4.2.7.1 | 3.4.2.7.2 | 3.4.2.7.3 | 3.4.2.7.4 | 3.4.2.8.1 | 3.4.2.8.2 | 3.4.2.8.3 | 3.4.2.8.4 |
| 3.4.3.1.1 | 3.4.3.1.2 | 3.4.3.1.3 | 3.4.3.1.4 | 3.4.3.2.1 | 3.4.3.2.2 | 3.4.3.2.3 | 3.4.3.2.4 |
| 3.4.3.3.1 | 3.4.3.3.2 | 3.4.3.3.3 | 3.4.3.3.4 | 3.4.3.4.1 | 3.4.3.4.2 | 3.4.3.4.3 | 3.4.3.4.4 |
| 3.4.3.5.1 | 3.4.3.5.2 | 3.4.3.5.3 | 3.4.3.5.4 | 3.4.3.6.1 | 3.4.3.6.2 | 3.4.3.6.3 | 3.4.3.6.4 |
| 3.4.3.7.1 | 3.4.3.7.2 | 3.4.3.7.3 | 3.4.3.7.4 | 3.4.3.8.1 | 3.4.3.8.2 | 3.4.3.8.3 | 3.4.3.8.4 |
| 3.4.4.1.1 | 3.4.4.1.2 | 3.4.4.1.3 | 3.4.4.1.4 | 3.4.4.2.1 | 3.4.4.2.2 | 3.4.4.2.3 | 3.4.4.2.4 |
| 3.4.4.3.1 | 3.4.4.3.2 | 3.4.4.3.3 | 3.4.4.3.4 | 3.4.4.4.1 | 3.4.4.4.2 | 3.4.4.4.3 | 3.4.4.4.4 |
| 3.4.4.5.1 | 3.4.4.5.2 | 3.4.4.5.3 | 3.4.4.5.4 | 3.4.4.6.1 | 3.4.4.6.2 | 3.4.4.6.3 | 3.4.4.6.4 |
| 3.4.4.7.1 | 3.4.4.7.2 | 3.4.4.7.3 | 3.4.4.7.4 | 3.4.4.8.1 | 3.4.4.8.2 | 3.4.4.8.3 | 3.4.4.8.4 |
| 3.5.1.1.1 | 3.5.1.1.2 | 3.5.1.1.3 | 3.5.1.1.4 | 3.5.1.2.1 | 3.5.1.2.2 | 3.5.1.2.3 | 3.5.1.2.4 |
| 3.5.1.3.1 | 3.5.1.3.2 | 3.5.1.3.3 | 3.5.1.3.4 | 3.5.1.4.1 | 3.5.1.4.2 | 3.5.1.4.3 | 3.5.1.4.4 |
| 3.5.1.5.1 | 3.5.1.5.2 | 3.5.1.5.3 | 3.5.1.5.4 | 3.5.1.6.1 | 3.5.1.6.2 | 3.5.1.6.3 | 3.5.1.6.4 |
| 3.5.1.7.1 | 3.5.1.7.2 | 3.5.1.7.3 | 3.5.1.7.4 | 3.5.1.8.1 | 3.5.1.8.2 | 3.5.1.8.3 | 3.5.1.8.4 |
| 3.5.2.1.1 | 3.5.2.1.2 | 3.5.2.1.3 | 3.5.2.1.4 | 3.5.2.2.1 | 3.5.2.2.2 | 3.5.2.2.3 | 3.5.2.2.4 |
| 3.5.2.3.1 | 3.5.2.3.2 | 3.5.2.3.3 | 3.5.2.3.4 | 3.5.2.4.1 | 3.5.2.4.2 | 3.5.2.4.3 | 3.5.2.4.4 |
| 3.5.2.5.1 | 3.5.2.5.2 | 3.5.2.5.3 | 3.5.2.5.4 | 3.5.2.6.1 | 3.5.2.6.2 | 3.5.2.6.3 | 3.5.2.6.4 |
| 3.5.2.7.1 | 3.5.2.7.2 | 3.5.2.7.3 | 3.5.2.7.4 | 3.5.2.8.1 | 3.5.2.8.2 | 3.5.2.8.3 | 3.5.2.8.4 |
| 3.5.3.1.1 | 3.5.3.1.2 | 3.5.3.1.3 | 3.5.3.1.4 | 3.5.3.2.1 | 3.5.3.2.2 | 3.5.3.2.3 | 3.5.3.2.4 |
| 3.5.3.3.1 | 3.5.3.3.2 | 3.5.3.3.3 | 3.5.3.3.4 | 3.5.3.4.1 | 3.5.3.4.2 | 3.5.3.4.3 | 3.5.3.4.4 |
| 3.5.3.5.1 | 3.5.3.5.2 | 3.5.3.5.3 | 3.5.3.5.4 | 3.5.3.6.1 | 3.5.3.6.2 | 3.5.3.6.3 | 3.5.3.6.4 |
| 3.5.3.7.1 | 3.5.3.7.2 | 3.5.3.7.3 | 3.5.3.7.4 | 3.5.3.8.1 | 3.5.3.8.2 | 3.5.3.8.3 | 3.5.3.8.4 |
| 3.5.4.1.1 | 3.5.4.1.2 | 3.5.4.1.3 | 3.5.4.1.4 | 3.5.4.2.1 | 3.5.4.2.2 | 3.5.4.2.3 | 3.5.4.2.4 |
| 3.5.4.3.1 | 3.5.4.3.2 | 3.5.4.3.3 | 3.5.4.3.4 | 3.5.4.4.1 | 3.5.4.4.2 | 3.5.4.4.3 | 3.5.4.4.4 |
| 3.5.4.5.1 | 3.5.4.5.2 | 3.5.4.5.3 | 3.5.4.5.4 | 3.5.4.6.1 | 3.5.4.6.2 | 3.5.4.6.3 | 3.5.4.6.4 |
| 3.5.4.7.1 | 3.5.4.7.2 | 3.5.4.7.3 | 3.5.4.7.4 | 3.5.4.8.1 | 3.5.4.8.2 | 3.5.4.8.3 | 3.5.4.8.4 |
| 3.6.1.1.1 | 3.6.1.1.2 | 3.6.1.1.3 | 3.6.1.1.4 | 3.6.1.2.1 | 3.6.1.2.2 | 3.6.1.2.3 | 3.6.1.2.4 |
| 3.6.1.3.1 | 3.6.1.3.2 | 3.6.1.3.3 | 3.6.1.3.4 | 3.6.1.4.1 | 3.6.1.4.2 | 3.6.1.4.3 | 3.6.1.4.4 |
| 3.6.1.5.1 | 3.6.1.5.2 | 3.6.1.5.3 | 3.6.1.5.4 | 3.6.1.6.1 | 3.6.1.6.2 | 3.6.1.6.3 | 3.6.1.6.4 |
| 3.6.1.7.1 | 3.6.1.7.2 | 3.6.1.7.3 | 3.6.1.7.4 | 3.6.1.8.1 | 3.6.1.8.2 | 3.6.1.8.3 | 3.6.1.8.4 |
| 3.6.2.1.1 | 3.6.2.1.2 | 3.6.2.1.3 | 3.6.2.1.4 | 3.6.2.2.1 | 3.6.2.2.2 | 3.6.2.2.3 | 3.6.2.2.4 |
| 3.6.2.3.1 | 3.6.2.3.2 | 3.6.2.3.3 | 3.6.2.3.4 | 3.6.2.4.1 | 3.6.2.4.2 | 3.6.2.4.3 | 3.6.2.4.4 |
| 3.6.2.5.1 | 3.6.2.5.2 | 3.6.2.5.3 | 3.6.2.5.4 | 3.6.2.6.1 | 3.6.2.6.2 | 3.6.2.6.3 | 3.6.2.6.4 |
| 3.6.2.7.1 | 3.6.2.7.2 | 3.6.2.7.3 | 3.6.2.7.4 | 3.6.2.8.1 | 3.6.2.8.2 | 3.6.2.8.3 | 3.6.2.8.4 |
| 3.6.3.1.1 | 3.6.3.1.2 | 3.6.3.1.3 | 3.6.3.1.4 | 3.6.3.2.1 | 3.6.3.2.2 | 3.6.3.2.3 | 3.6.3.2.4 |
| 3.6.3.3.1 | 3.6.3.3.2 | 3.6.3.3.3 | 3.6.3.3.4 | 3.6.3.4.1 | 3.6.3.4.2 | 3.6.3.4.3 | 3.6.3.4.4 |
| 3.6.3.5.1 | 3.6.3.5.2 | 3.6.3.5.3 | 3.6.3.5.4 | 3.6.3.6.1 | 3.6.3.6.2 | 3.6.3.6.3 | 3.6.3.6.4 |
| 3.6.3.7.1 | 3.6.3.7.2 | 3.6.3.7.3 | 3.6.3.7.4 | 3.6.3.8.1 | 3.6.3.8.2 | 3.6.3.8.3 | 3.6.3.8.4 |
| 3.6.4.1.1 | 3.6.4.1.2 | 3.6.4.1.3 | 3.6.4.1.4 | 3.6.4.2.1 | 3.6.4.2.2 | 3.6.4.2.3 | 3.6.4.2.4 |
| 3.6.4.3.1 | 3.6.4.3.2 | 3.6.4.3.3 | 3.6.4.3.4 | 3.6.4.4.1 | 3.6.4.4.2 | 3.6.4.4.3 | 3.6.4.4.4 |
| 3.6.4.5.1 | 3.6.4.5.2 | 3.6.4.5.3 | 3.6.4.5.4 | 3.6.4.6.1 | 3.6.4.6.2 | 3.6.4.6.3 | 3.6.4.6.4 |
| 3.6.4.7.1 | 3.6.4.7.2 | 3.6.4.7.3 | 3.6.4.7.4 | 3.6.4.8.1 | 3.6.4.8.2 | 3.6.4.8.3 | 3.6.4.8.4 |
| 3.7.1.1.1 | 3.7.1.1.2 | 3.7.1.1.3 | 3.7.1.1.4 | 3.7.1.2.1 | 3.7.1.2.2 | 3.7.1.2.3 | 3.7.1.2.4 |
| 3.7.1.3.1 | 3.7.1.3.2 | 3.7.1.3.3 | 3.7.1.3.4 | 3.7.1.4.1 | 3.7.1.4.2 | 3.7.1.4.3 | 3.7.1.4.4 |

TABLE 1-continued

| | | | | | | | |
|---|---|---|---|---|---|---|---|
| 3.7.1.5.1 | 3.7.1.5.2 | 3.7.1.5.3 | 3.7.1.5.4 | 3.7.1.6.1 | 3.7.1.6.2 | 3.7.1.6.3 | 3.7.1.6.4 |
| 3.7.1.7.1 | 3.7.1.7.2 | 3.7.1.7.3 | 3.7.1.7.4 | 3.7.1.8.1 | 3.7.1.8.2 | 3.7.1.8.3 | 3.7.1.8.4 |
| 3.7.2.1.1 | 3.7.2.1.2 | 3.7.2.1.3 | 3.7.2.1.4 | 3.7.2.2.1 | 3.7.2.2.2 | 3.7.2.2.3 | 3.7.2.2.4 |
| 3.7.2.3.1 | 3.7.2.3.2 | 3.7.2.3.3 | 3.7.2.3.4 | 3.7.2.4.1 | 3.7.2.4.2 | 3.7.2.4.3 | 3.7.2.4.4 |
| 3.7.2.5.1 | 3.7.2.5.2 | 3.7.2.5.3 | 3.7.2.5.4 | 3.7.2.6.1 | 3.7.2.6.2 | 3.7.2.6.3 | 3.7.2.6.4 |
| 3.7.2.7.1 | 3.7.2.7.2 | 3.7.2.7.3 | 3.7.2.7.4 | 3.7.2.8.1 | 3.7.2.8.2 | 3.7.2.8.3 | 3.7.2.8.4 |
| 3.7.3.1.1 | 3.7.3.1.2 | 3.7.3.1.3 | 3.7.3.1.4 | 3.7.3.2.1 | 3.7.3.2.2 | 3.7.3.2.3 | 3.7.3.2.4 |
| 3.7.3.3.1 | 3.7.3.3.2 | 3.7.3.3.3 | 3.7.3.3.4 | 3.7.3.4.1 | 3.7.3.4.2 | 3.7.3.4.3 | 3.7.3.4.4 |
| 3.7.3.5.1 | 3.7.3.5.2 | 3.7.3.5.3 | 3.7.3.5.4 | 3.7.3.6.1 | 3.7.3.6.2 | 3.7.3.6.3 | 3.7.3.6.4 |
| 3.7.3.7.1 | 3.7.3.7.2 | 3.7.3.7.3 | 3.7.3.7.4 | 3.7.3.8.1 | 3.7.3.8.2 | 3.7.3.8.3 | 3.7.3.8.4 |
| 3.7.4.1.1 | 3.7.4.1.2 | 3.7.4.1.3 | 3.7.4.1.4 | 3.7.4.2.1 | 3.7.4.2.2 | 3.7.4.2.3 | 3.7.4.2.4 |
| 3.7.4.3.1 | 3.7.4.3.2 | 3.7.4.3.3 | 3.7.4.3.4 | 3.7.4.4.1 | 3.7.4.4.2 | 3.7.4.4.3 | 3.7.4.4.4 |
| 3.7.4.5.1 | 3.7.4.5.2 | 3.7.4.5.3 | 3.7.4.5.4 | 3.7.4.6.1 | 3.7.4.6.2 | 3.7.4.6.3 | 3.7.4.6.4 |
| 3.7.4.7.1 | 3.7.4.7.2 | 3.7.4.7.3 | 3.7.4.7.4 | 3.7.4.8.1 | 3.7.4.8.2 | 3.7.4.8.3 | 3.7.4.8.4 |
| 3.8.1.1.1 | 3.8.1.1.2 | 3.8.1.1.3 | 3.8.1.1.4 | 3.8.1.2.1 | 3.8.1.2.2 | 3.8.1.2.3 | 3.8.1.2.4 |
| 3.8.1.3.1 | 3.8.1.3.2 | 3.8.1.3.3 | 3.8.1.3.4 | 3.8.1.4.1 | 3.8.1.4.2 | 3.8.1.4.3 | 3.8.1.4.4 |
| 3.8.1.5.1 | 3.8.1.5.2 | 3.8.1.5.3 | 3.8.1.5.4 | 3.8.1.6.1 | 3.8.1.6.2 | 3.8.1.6.3 | 3.8.1.6.4 |
| 3.8.1.7.1 | 3.8.1.7.2 | 3.8.1.7.3 | 3.8.1.7.4 | 3.8.1.8.1 | 3.8.1.8.2 | 3.8.1.8.3 | 3.8.1.8.4 |
| 3.8.2.1.1 | 3.8.2.1.2 | 3.8.2.1.3 | 3.8.2.1.4 | 3.8.2.2.1 | 3.8.2.2.2 | 3.8.2.2.3 | 3.8.2.2.4 |
| 3.8.2.3.1 | 3.8.2.3.2 | 3.8.2.3.3 | 3.8.2.3.4 | 3.8.2.4.1 | 3.8.2.4.2 | 3.8.2.4.3 | 3.8.2.4.4 |
| 3.8.2.5.1 | 3.8.2.5.2 | 3.8.2.5.3 | 3.8.2.5.4 | 3.8.2.6.1 | 3.8.2.6.2 | 3.8.2.6.3 | 3.8.2.6.4 |
| 3.8.2.7.1 | 3.8.2.7.2 | 3.8.2.7.3 | 3.8.2.7.4 | 3.8.2.8.1 | 3.8.2.8.2 | 3.8.2.8.3 | 3.8.2.8.4 |
| 3.8.3.1.1 | 3.8.3.1.2 | 3.8.3.1.3 | 3.8.3.1.4 | 3.8.3.2.1 | 3.8.3.2.2 | 3.8.3.2.3 | 3.8.3.2.4 |
| 3.8.3.3.1 | 3.8.3.3.2 | 3.8.3.3.3 | 3.8.3.3.4 | 3.8.3.4.1 | 3.8.3.4.2 | 3.8.3.4.3 | 3.8.3.4.4 |
| 3.8.3.5.1 | 3.8.3.5.2 | 3.8.3.5.3 | 3.8.3.5.4 | 3.8.3.6.1 | 3.8.3.6.2 | 3.8.3.6.3 | 3.8.3.6.4 |
| 3.8.3.7.1 | 3.8.3.7.2 | 3.8.3.7.3 | 3.8.3.7.4 | 3.8.3.8.1 | 3.8.3.8.2 | 3.8.3.8.3 | 3.8.3.8.4 |
| 3.8.4.1.1 | 3.8.4.1.2 | 3.8.4.1.3 | 3.8.4.1.4 | 3.8.4.2.1 | 3.8.4.2.2 | 3.8.4.2.3 | 3.8.4.2.4 |
| 3.8.4.3.1 | 3.8.4.3.2 | 3.8.4.3.3 | 3.8.4.3.4 | 3.8.4.4.1 | 3.8.4.4.2 | 3.8.4.4.3 | 3.8.4.4.4 |
| 3.8.4.5.1 | 3.8.4.5.2 | 3.8.4.5.3 | 3.8.4.5.4 | 3.8.4.6.1 | 3.8.4.6.2 | 3.8.4.6.3 | 3.8.4.6.4 |
| 3.8.4.7.1 | 3.8.4.7.2 | 3.8.4.7.3 | 3.8.4.7.4 | 3.8.4.8.1 | 3.8.4.8.2 | 3.8.4.8.3 | 3.8.4.8.4 |
| 4.1.1.1.1 | 4.1.1.1.2 | 4.1.1.1.3 | 4.1.1.1.4 | 4.1.1.2.1 | 4.1.1.2.2 | 4.1.1.2.3 | 4.1.1.2.4 |
| 4.1.1.3.1 | 4.1.1.3.2 | 4.1.1.3.3 | 4.1.1.3.4 | 4.1.1.4.1 | 4.1.1.4.2 | 4.1.1.4.3 | 4.1.1.4.4 |
| 4.1.1.5.1 | 4.1.1.5.2 | 4.1.1.5.3 | 4.1.1.5.4 | 4.1.1.6.1 | 4.1.1.6.2 | 4.1.1.6.3 | 4.1.1.6.4 |
| 4.1.1.7.1 | 4.1.1.7.2 | 4.1.1.7.3 | 4.1.1.7.4 | 4.1.1.8.1 | 4.1.1.8.2 | 4.1.1.8.3 | 4.1.1.8.4 |
| 4.1.2.1.1 | 4.1.2.1.2 | 4.1.2.1.3 | 4.1.2.1.4 | 4.1.2.2.1 | 4.1.2.2.2 | 4.1.2.2.3 | 4.1.2.2.4 |
| 4.1.2.3.1 | 4.1.2.3.2 | 4.1.2.3.3 | 4.1.2.3.4 | 4.1.2.4.1 | 4.1.2.4.2 | 4.1.2.4.3 | 4.1.2.4.4 |
| 4.1.2.5.1 | 4.1.2.5.2 | 4.1.2.5.3 | 4.1.2.5.4 | 4.1.2.6.1 | 4.1.2.6.2 | 4.1.2.6.3 | 4.1.2.6.4 |
| 4.1.2.7.1 | 4.1.2.7.2 | 4.1.2.7.3 | 4.1.2.7.4 | 4.1.2.8.1 | 4.1.2.8.2 | 4.1.2.8.3 | 4.1.2.8.4 |
| 4.1.3.1.1 | 4.1.3.1.2 | 4.1.3.1.3 | 4.1.3.1.4 | 4.1.3.2.1 | 4.1.3.2.2 | 4.1.3.2.3 | 4.1.3.2.4 |
| 4.1.3.3.1 | 4.1.3.3.2 | 4.1.3.3.3 | 4.1.3.3.4 | 4.1.3.4.1 | 4.1.3.4.2 | 4.1.3.4.3 | 4.1.3.4.4 |
| 4.1.3.5.1 | 4.1.3.5.2 | 4.1.3.5.3 | 4.1.3.5.4 | 4.1.3.6.1 | 4.1.3.6.2 | 4.1.3.6.3 | 4.1.3.6.4 |
| 4.1.3.7.1 | 4.1.3.7.2 | 4.1.3.7.3 | 4.1.3.7.4 | 4.1.3.8.1 | 4.1.3.8.2 | 4.1.3.8.3 | 4.1.3.8.4 |
| 4.1.4.1.1 | 4.1.4.1.2 | 4.1.4.1.3 | 4.1.4.1.4 | 4.1.4.2.1 | 4.1.4.2.2 | 4.1.4.2.3 | 4.1.4.2.4 |
| 4.1.4.3.1 | 4.1.4.3.2 | 4.1.4.3.3 | 4.1.4.3.4 | 4.1.4.4.1 | 4.1.4.4.2 | 4.1.4.4.3 | 4.1.4.4.4 |
| 4.1.4.5.1 | 4.1.4.5.2 | 4.1.4.5.3 | 4.1.4.5.4 | 4.1.4.6.1 | 4.1.4.6.2 | 4.1.4.6.3 | 4.1.4.6.4 |
| 4.1.4.7.1 | 4.1.4.7.2 | 4.1.4.7.3 | 4.1.4.7.4 | 4.1.4.8.1 | 4.1.4.8.2 | 4.1.4.8.3 | 4.1.4.8.4 |
| 4.2.1.1.1 | 4.2.1.1.2 | 4.2.1.1.3 | 4.2.1.1.4 | 4.2.1.2.1 | 4.2.1.2.2 | 4.2.1.2.3 | 4.2.1.2.4 |
| 4.2.1.3.1 | 4.2.1.3.2 | 4.2.1.3.3 | 4.2.1.3.4 | 4.2.1.4.1 | 4.2.1.4.2 | 4.2.1.4.3 | 4.2.1.4.4 |
| 4.2.1.5.1 | 4.2.1.5.2 | 4.2.1.5.3 | 4.2.1.5.4 | 4.2.1.6.1 | 4.2.1.6.2 | 4.2.1.6.3 | 4.2.1.6.4 |
| 4.2.1.7.1 | 4.2.1.7.2 | 4.2.1.7.3 | 4.2.1.7.4 | 4.2.1.8.1 | 4.2.1.8.2 | 4.2.1.8.3 | 4.2.1.8.4 |
| 4.2.2.1.1 | 4.2.2.1.2 | 4.2.2.1.3 | 4.2.2.1.4 | 4.2.2.2.1 | 4.2.2.2.2 | 4.2.2.2.3 | 4.2.2.2.4 |
| 4.2.2.3.1 | 4.2.2.3.2 | 4.2.2.3.3 | 4.2.2.3.4 | 4.2.2.4.1 | 4.2.2.4.2 | 4.2.2.4.3 | 4.2.2.4.4 |
| 4.2.2.5.1 | 4.2.2.5.2 | 4.2.2.5.3 | 4.2.2.5.4 | 4.2.2.6.1 | 4.2.2.6.2 | 4.2.2.6.3 | 4.2.2.6.4 |
| 4.2.2.7.1 | 4.2.2.7.2 | 4.2.2.7.3 | 4.2.2.7.4 | 4.2.2.8.1 | 4.2.2.8.2 | 4.2.2.8.3 | 4.2.2.8.4 |
| 4.2.3.1.1 | 4.2.3.1.2 | 4.2.3.1.3 | 4.2.3.1.4 | 4.2.3.2.1 | 4.2.3.2.2 | 4.2.3.2.3 | 4.2.3.2.4 |
| 4.2.3.3.1 | 4.2.3.3.2 | 4.2.3.3.3 | 4.2.3.3.4 | 4.2.3.4.1 | 4.2.3.4.2 | 4.2.3.4.3 | 4.2.3.4.4 |
| 4.2.3.5.1 | 4.2.3.5.2 | 4.2.3.5.3 | 4.2.3.5.4 | 4.2.3.6.1 | 4.2.3.6.2 | 4.2.3.6.3 | 4.2.3.6.4 |
| 4.2.3.7.1 | 4.2.3.7.2 | 4.2.3.7.3 | 4.2.3.7.4 | 4.2.3.8.1 | 4.2.3.8.2 | 4.2.3.8.3 | 4.2.3.8.4 |
| 4.2.4.1.1 | 4.2.4.1.2 | 4.2.4.1.3 | 4.2.4.1.4 | 4.2.4.2.1 | 4.2.4.2.2 | 4.2.4.2.3 | 4.2.4.2.4 |
| 4.2.4.3.1 | 4.2.4.3.2 | 4.2.4.3.3 | 4.2.4.3.4 | 4.2.4.4.1 | 4.2.4.4.2 | 4.2.4.4.3 | 4.2.4.4.4 |
| 4.2.4.5.1 | 4.2.4.5.2 | 4.2.4.5.3 | 4.2.4.5.4 | 4.2.4.6.1 | 4.2.4.6.2 | 4.2.4.6.3 | 4.2.4.6.4 |
| 4.2.4.7.1 | 4.2.4.7.2 | 4.2.4.7.3 | 4.2.4.7.4 | 4.2.4.8.1 | 4.2.4.8.2 | 4.2.4.8.3 | 4.2.4.8.4 |
| 4.3.1.1.1 | 4.3.1.1.2 | 4.3.1.1.3 | 4.3.1.1.4 | 4.3.1.2.1 | 4.3.1.2.2 | 4.3.1.2.3 | 4.3.1.2.4 |
| 4.3.1.3.1 | 4.3.1.3.2 | 4.3.1.3.3 | 4.3.1.3.4 | 4.3.1.4.1 | 4.3.1.4.2 | 4.3.1.4.3 | 4.3.1.4.4 |
| 4.3.1.5.1 | 4.3.1.5.2 | 4.3.1.5.3 | 4.3.1.5.4 | 4.3.1.6.1 | 4.3.1.6.2 | 4.3.1.6.3 | 4.3.1.6.4 |
| 4.3.1.7.1 | 4.3.1.7.2 | 4.3.1.7.3 | 4.3.1.7.4 | 4.3.1.8.1 | 4.3.1.8.2 | 4.3.1.8.3 | 4.3.1.8.4 |
| 4.3.2.1.1 | 4.3.2.1.2 | 4.3.2.1.3 | 4.3.2.1.4 | 4.3.2.2.1 | 4.3.2.2.2 | 4.3.2.2.3 | 4.3.2.2.4 |
| 4.3.2.3.1 | 4.3.2.3.2 | 4.3.2.3.3 | 4.3.2.3.4 | 4.3.2.4.1 | 4.3.2.4.2 | 4.3.2.4.3 | 4.3.2.4.4 |
| 4.3.2.5.1 | 4.3.2.5.2 | 4.3.2.5.3 | 4.3.2.5.4 | 4.3.2.6.1 | 4.3.2.6.2 | 4.3.2.6.3 | 4.3.2.6.4 |
| 4.3.2.7.1 | 4.3.2.7.2 | 4.3.2.7.3 | 4.3.2.7.4 | 4.3.2.8.1 | 4.3.2.8.2 | 4.3.2.8.3 | 4.3.2.8.4 |
| 4.3.3.1.1 | 4.3.3.1.2 | 4.3.3.1.3 | 4.3.3.1.4 | 4.3.3.2.1 | 4.3.3.2.2 | 4.3.3.2.3 | 4.3.3.2.4 |
| 4.3.3.3.1 | 4.3.3.3.2 | 4.3.3.3.3 | 4.3.3.3.4 | 4.3.3.4.1 | 4.3.3.4.2 | 4.3.3.4.3 | 4.3.3.4.4 |
| 4.3.3.5.1 | 4.3.3.5.2 | 4.3.3.5.3 | 4.3.3.5.4 | 4.3.3.6.1 | 4.3.3.6.2 | 4.3.3.6.3 | 4.3.3.6.4 |
| 4.3.3.7.1 | 4.3.3.7.2 | 4.3.3.7.3 | 4.3.3.7.4 | 4.3.3.8.1 | 4.3.3.8.2 | 4.3.3.8.3 | 4.3.3.8.4 |
| 4.3.4.1.1 | 4.3.4.1.2 | 4.3.4.1.3 | 4.3.4.1.4 | 4.3.4.2.1 | 4.3.4.2.2 | 4.3.4.2.3 | 4.3.4.2.4 |
| 4.3.4.3.1 | 4.3.4.3.2 | 4.3.4.3.3 | 4.3.4.3.4 | 4.3.4.4.1 | 4.3.4.4.2 | 4.3.4.4.3 | 4.3.4.4.4 |
| 4.3.4.5.1 | 4.3.4.5.2 | 4.3.4.5.3 | 4.3.4.5.4 | 4.3.4.6.1 | 4.3.4.6.2 | 4.3.4.6.3 | 4.3.4.6.4 |
| 4.3.4.7.1 | 4.3.4.7.2 | 4.3.4.7.3 | 4.3.4.7.4 | 4.3.4.8.1 | 4.3.4.8.2 | 4.3.4.8.3 | 4.3.4.8.4 |
| 4.4.1.1.1 | 4.4.1.1.2 | 4.4.1.1.3 | 4.4.1.1.4 | 4.4.1.2.1 | 4.4.1.2.2 | 4.4.1.2.3 | 4.4.1.2.4 |

TABLE 1-continued

| | | | | | | | |
|---|---|---|---|---|---|---|---|
| 4.4.1.3.1 | 4.4.1.3.2 | 4.4.1.3.3 | 4.4.1.3.4 | 4.4.1.4.1 | 4.4.1.4.2 | 4.4.1.4.3 | 4.4.1.4.4 |
| 4.4.1.5.1 | 4.4.1.5.2 | 4.4.1.5.3 | 4.4.1.5.4 | 4.4.1.6.1 | 4.4.1.6.2 | 4.4.1.6.3 | 4.4.1.6.4 |
| 4.4.1.7.1 | 4.4.1.7.2 | 4.4.1.7.3 | 4.4.1.7.4 | 4.4.1.8.1 | 4.4.1.8.2 | 4.4.1.8.3 | 4.4.1.8.4 |
| 4.4.2.1.1 | 4.4.2.1.2 | 4.4.2.1.3 | 4.4.2.1.4 | 4.4.2.2.1 | 4.4.2.2.2 | 4.4.2.2.3 | 4.4.2.2.4 |
| 4.4.2.3.1 | 4.4.2.3.2 | 4.4.2.3.3 | 4.4.2.3.4 | 4.4.2.4.1 | 4.4.2.4.2 | 4.4.2.4.3 | 4.4.2.4.4 |
| 4.4.2.5.1 | 4.4.2.5.2 | 4.4.2.5.3 | 4.4.2.5.4 | 4.4.2.6.1 | 4.4.2.6.2 | 4.4.2.6.3 | 4.4.2.6.4 |
| 4.4.2.7.1 | 4.4.2.7.2 | 4.4.2.7.3 | 4.4.2.7.4 | 4.4.2.8.1 | 4.4.2.8.2 | 4.4.2.8.3 | 4.4.2.8.4 |
| 4.4.3.1.1 | 4.4.3.1.2 | 4.4.3.1.3 | 4.4.3.1.4 | 4.4.3.2.1 | 4.4.3.2.2 | 4.4.3.2.3 | 4.4.3.2.4 |
| 4.4.3.3.1 | 4.4.3.3.2 | 4.4.3.3.3 | 4.4.3.3.4 | 4.4.3.4.1 | 4.4.3.4.2 | 4.4.3.4.3 | 4.4.3.4.4 |
| 4.4.3.5.1 | 4.4.3.5.2 | 4.4.3.5.3 | 4.4.3.5.4 | 4.4.3.6.1 | 4.4.3.6.2 | 4.4.3.6.3 | 4.4.3.6.4 |
| 4.4.3.7.1 | 4.4.3.7.2 | 4.4.3.7.3 | 4.4.3.7.4 | 4.4.3.8.1 | 4.4.3.8.2 | 4.4.3.8.3 | 4.4.3.8.4 |
| 4.4.4.1.1 | 4.4.4.1.2 | 4.4.4.1.3 | 4.4.4.1.4 | 4.4.4.2.1 | 4.4.4.2.2 | 4.4.4.2.3 | 4.4.4.2.4 |
| 4.4.4.3.1 | 4.4.4.3.2 | 4.4.4.3.3 | 4.4.4.3.4 | 4.4.4.4.1 | 4.4.4.4.2 | 4.4.4.4.3 | 4.4.4.4.4 |
| 4.4.4.5.1 | 4.4.4.5.2 | 4.4.4.5.3 | 4.4.4.5.4 | 4.4.4.6.1 | 4.4.4.6.2 | 4.4.4.6.3 | 4.4.4.6.4 |
| 4.4.4.7.1 | 4.4.4.7.2 | 4.4.4.7.3 | 4.4.4.7.4 | 4.4.4.8.1 | 4.4.4.8.2 | 4.4.4.8.3 | 4.4.4.8.4 |
| 4.5.1.1.1 | 4.5.1.1.2 | 4.5.1.1.3 | 4.5.1.1.4 | 4.5.1.2.1 | 4.5.1.2.2 | 4.5.1.2.3 | 4.5.1.2.4 |
| 4.5.1.3.1 | 4.5.1.3.2 | 4.5.1.3.3 | 4.5.1.3.4 | 4.5.1.4.1 | 4.5.1.4.2 | 4.5.1.4.3 | 4.5.1.4.4 |
| 4.5.1.5.1 | 4.5.1.5.2 | 4.5.1.5.3 | 4.5.1.5.4 | 4.5.1.6.1 | 4.5.1.6.2 | 4.5.1.6.3 | 4.5.1.6.4 |
| 4.5.1.7.1 | 4.5.1.7.2 | 4.5.1.7.3 | 4.5.1.7.4 | 4.5.1.8.1 | 4.5.1.8.2 | 4.5.1.8.3 | 4.5.1.8.4 |
| 4.5.2.1.1 | 4.5.2.1.2 | 4.5.2.1.3 | 4.5.2.1.4 | 4.5.2.2.1 | 4.5.2.2.2 | 4.5.2.2.3 | 4.5.2.2.4 |
| 4.5.2.3.1 | 4.5.2.3.2 | 4.5.2.3.3 | 4.5.2.3.4 | 4.5.2.4.1 | 4.5.2.4.2 | 4.5.2.4.3 | 4.5.2.4.4 |
| 4.5.2.5.1 | 4.5.2.5.2 | 4.5.2.5.3 | 4.5.2.5.4 | 4.5.2.6.1 | 4.5.2.6.2 | 4.5.2.6.3 | 4.5.2.6.4 |
| 4.5.2.7.1 | 4.5.2.7.2 | 4.5.2.7.3 | 4.5.2.7.4 | 4.5.2.8.1 | 4.5.2.8.2 | 4.5.2.8.3 | 4.5.2.8.4 |
| 4.5.3.1.1 | 4.5.3.1.2 | 4.5.3.1.3 | 4.5.3.1.4 | 4.5.3.2.1 | 4.5.3.2.2 | 4.5.3.2.3 | 4.5.3.2.4 |
| 4.5.3.3.1 | 4.5.3.3.2 | 4.5.3.3.3 | 4.5.3.3.4 | 4.5.3.4.1 | 4.5.3.4.2 | 4.5.3.4.3 | 4.5.3.4.4 |
| 4.5.3.5.1 | 4.5.3.5.2 | 4.5.3.5.3 | 4.5.3.5.4 | 4.5.3.6.1 | 4.5.3.6.2 | 4.5.3.6.3 | 4.5.3.6.4 |
| 4.5.3.7.1 | 4.5.3.7.2 | 4.5.3.7.3 | 4.5.3.7.4 | 4.5.3.8.1 | 4.5.3.8.2 | 4.5.3.8.3 | 4.5.3.8.4 |
| 4.5.4.1.1 | 4.5.4.1.2 | 4.5.4.1.3 | 4.5.4.1.4 | 4.5.4.2.1 | 4.5.4.2.2 | 4.5.4.2.3 | 4.5.4.2.4 |
| 4.5.4.3.1 | 4.5.4.3.2 | 4.5.4.3.3 | 4.5.4.3.4 | 4.5.4.4.1 | 4.5.4.4.2 | 4.5.4.4.3 | 4.5.4.4.4 |
| 4.5.4.5.1 | 4.5.4.5.2 | 4.5.4.5.3 | 4.5.4.5.4 | 4.5.4.6.1 | 4.5.4.6.2 | 4.5.4.6.3 | 4.5.4.6.4 |
| 4.5.4.7.1 | 4.5.4.7.2 | 4.5.4.7.3 | 4.5.4.7.4 | 4.5.4.8.1 | 4.5.4.8.2 | 4.5.4.8.3 | 4.5.4.8.4 |
| 4.6.1.1.1 | 4.6.1.1.2 | 4.6.1.1.3 | 4.6.1.1.4 | 4.6.1.2.1 | 4.6.1.2.2 | 4.6.1.2.3 | 4.6.1.2.4 |
| 4.6.1.3.1 | 4.6.1.3.2 | 4.6.1.3.3 | 4.6.1.3.4 | 4.6.1.4.1 | 4.6.1.4.2 | 4.6.1.4.3 | 4.6.1.4.4 |
| 4.6.1.5.1 | 4.6.1.5.2 | 4.6.1.5.3 | 4.6.1.5.4 | 4.6.1.6.1 | 4.6.1.6.2 | 4.6.1.6.3 | 4.6.1.6.4 |
| 4.6.1.7.1 | 4.6.1.7.2 | 4.6.1.7.3 | 4.6.1.7.4 | 4.6.1.8.1 | 4.6.1.8.2 | 4.6.1.8.3 | 4.6.1.8.4 |
| 4.6.2.1.1 | 4.6.2.1.2 | 4.6.2.1.3 | 4.6.2.1.4 | 4.6.2.2.1 | 4.6.2.2.2 | 4.6.2.2.3 | 4.6.2.2.4 |
| 4.6.2.3.1 | 4.6.2.3.2 | 4.6.2.3.3 | 4.6.2.3.4 | 4.6.2.4.1 | 4.6.2.4.2 | 4.6.2.4.3 | 4.6.2.4.4 |
| 4.6.2.5.1 | 4.6.2.5.2 | 4.6.2.5.3 | 4.6.2.5.4 | 4.6.2.6.1 | 4.6.2.6.2 | 4.6.2.6.3 | 4.6.2.6.4 |
| 4.6.2.7.1 | 4.6.2.7.2 | 4.6.2.7.3 | 4.6.2.7.4 | 4.6.2.8.1 | 4.6.2.8.2 | 4.6.2.8.3 | 4.6.2.8.4 |
| 4.6.3.1.1 | 4.6.3.1.2 | 4.6.3.1.3 | 4.6.3.1.4 | 4.6.3.2.1 | 4.6.3.2.2 | 4.6.3.2.3 | 4.6.3.2.4 |
| 4.6.3.3.1 | 4.6.3.3.2 | 4.6.3.3.3 | 4.6.3.3.4 | 4.6.3.4.1 | 4.6.3.4.2 | 4.6.3.4.3 | 4.6.3.4.4 |
| 4.6.3.5.1 | 4.6.3.5.2 | 4.6.3.5.3 | 4.6.3.5.4 | 4.6.3.6.1 | 4.6.3.6.2 | 4.6.3.6.3 | 4.6.3.6.4 |
| 4.6.3.7.1 | 4.6.3.7.2 | 4.6.3.7.3 | 4.6.3.7.4 | 4.6.3.8.1 | 4.6.3.8.2 | 4.6.3.8.3 | 4.6.3.8.4 |
| 4.6.4.1.1 | 4.6.4.1.2 | 4.6.4.1.3 | 4.6.4.1.4 | 4.6.4.2.1 | 4.6.4.2.2 | 4.6.4.2.3 | 4.6.4.2.4 |
| 4.6.4.3.1 | 4.6.4.3.2 | 4.6.4.3.3 | 4.6.4.3.4 | 4.6.4.4.1 | 4.6.4.4.2 | 4.6.4.4.3 | 4.6.4.4.4 |
| 4.6.4.5.1 | 4.6.4.5.2 | 4.6.4.5.3 | 4.6.4.5.4 | 4.6.4.6.1 | 4.6.4.6.2 | 4.6.4.6.3 | 4.6.4.6.4 |
| 4.6.4.7.1 | 4.6.4.7.2 | 4.6.4.7.3 | 4.6.4.7.4 | 4.6.4.8.1 | 4.6.4.8.2 | 4.6.4.8.3 | 4.6.4.8.4 |
| 4.7.1.1.1 | 4.7.1.1.2 | 4.7.1.1.3 | 4.7.1.1.4 | 4.7.1.2.1 | 4.7.1.2.2 | 4.7.1.2.3 | 4.7.1.2.4 |
| 4.7.1.3.1 | 4.7.1.3.2 | 4.7.1.3.3 | 4.7.1.3.4 | 4.7.1.4.1 | 4.7.1.4.2 | 4.7.1.4.3 | 4.7.1.4.4 |
| 4.7.1.5.1 | 4.7.1.5.2 | 4.7.1.5.3 | 4.7.1.5.4 | 4.7.1.6.1 | 4.7.1.6.2 | 4.7.1.6.3 | 4.7.1.6.4 |
| 4.7.1.7.1 | 4.7.1.7.2 | 4.7.1.7.3 | 4.7.1.7.4 | 4.7.1.8.1 | 4.7.1.8.2 | 4.7.1.8.3 | 4.7.1.8.4 |
| 4.7.2.1.1 | 4.7.2.1.2 | 4.7.2.1.3 | 4.7.2.1.4 | 4.7.2.2.1 | 4.7.2.2.2 | 4.7.2.2.3 | 4.7.2.2.4 |
| 4.7.2.3.1 | 4.7.2.3.2 | 4.7.2.3.3 | 4.7.2.3.4 | 4.7.2.4.1 | 4.7.2.4.2 | 4.7.2.4.3 | 4.7.2.4.4 |
| 4.7.2.5.1 | 4.7.2.5.2 | 4.7.2.5.3 | 4.7.2.5.4 | 4.7.2.6.1 | 4.7.2.6.2 | 4.7.2.6.3 | 4.7.2.6.4 |
| 4.7.2.7.1 | 4.7.2.7.2 | 4.7.2.7.3 | 4.7.2.7.4 | 4.7.2.8.1 | 4.7.2.8.2 | 4.7.2.8.3 | 4.7.2.8.4 |
| 4.7.3.1.1 | 4.7.3.1.2 | 4.7.3.1.3 | 4.7.3.1.4 | 4.7.3.2.1 | 4.7.3.2.2 | 4.7.3.2.3 | 4.7.3.2.4 |
| 4.7.3.3.1 | 4.7.3.3.2 | 4.7.3.3.3 | 4.7.3.3.4 | 4.7.3.4.1 | 4.7.3.4.2 | 4.7.3.4.3 | 4.7.3.4.4 |
| 4.7.3.5.1 | 4.7.3.5.2 | 4.7.3.5.3 | 4.7.3.5.4 | 4.7.3.6.1 | 4.7.3.6.2 | 4.7.3.6.3 | 4.7.3.6.4 |
| 4.7.3.7.1 | 4.7.3.7.2 | 4.7.3.7.3 | 4.7.3.7.4 | 4.7.3.8.1 | 4.7.3.8.2 | 4.7.3.8.3 | 4.7.3.8.4 |
| 4.7.4.1.1 | 4.7.4.1.2 | 4.7.4.1.3 | 4.7.4.1.4 | 4.7.4.2.1 | 4.7.4.2.2 | 4.7.4.2.3 | 4.7.4.2.4 |
| 4.7.4.3.1 | 4.7.4.3.2 | 4.7.4.3.3 | 4.7.4.3.4 | 4.7.4.4.1 | 4.7.4.4.2 | 4.7.4.4.3 | 4.7.4.4.4 |
| 4.7.4.5.1 | 4.7.4.5.2 | 4.7.4.5.3 | 4.7.4.5.4 | 4.7.4.6.1 | 4.7.4.6.2 | 4.7.4.6.3 | 4.7.4.6.4 |
| 4.7.4.7.1 | 4.7.4.7.2 | 4.7.4.7.3 | 4.7.4.7.4 | 4.7.4.8.1 | 4.7.4.8.2 | 4.7.4.8.3 | 4.7.4.8.4 |
| 4.8.1.1.1 | 4.8.1.1.2 | 4.8.1.1.3 | 4.8.1.1.4 | 4.8.1.2.1 | 4.8.1.2.2 | 4.8.1.2.3 | 4.8.1.2.4 |
| 4.8.1.3.1 | 4.8.1.3.2 | 4.8.1.3.3 | 4.8.1.3.4 | 4.8.1.4.1 | 4.8.1.4.2 | 4.8.1.4.3 | 4.8.1.4.4 |
| 4.8.1.5.1 | 4.8.1.5.2 | 4.8.1.5.3 | 4.8.1.5.4 | 4.8.1.6.1 | 4.8.1.6.2 | 4.8.1.6.3 | 4.8.1.6.4 |
| 4.8.1.7.1 | 4.8.1.7.2 | 4.8.1.7.3 | 4.8.1.7.4 | 4.8.1.8.1 | 4.8.1.8.2 | 4.8.1.8.3 | 4.8.1.8.4 |
| 4.8.2.1.1 | 4.8.2.1.2 | 4.8.2.1.3 | 4.8.2.1.4 | 4.8.2.2.1 | 4.8.2.2.2 | 4.8.2.2.3 | 4.8.2.2.4 |
| 4.8.2.3.1 | 4.8.2.3.2 | 4.8.2.3.3 | 4.8.2.3.4 | 4.8.2.4.1 | 4.8.2.4.2 | 4.8.2.4.3 | 4.8.2.4.4 |
| 4.8.2.5.1 | 4.8.2.5.2 | 4.8.2.5.3 | 4.8.2.5.4 | 4.8.2.6.1 | 4.8.2.6.2 | 4.8.2.6.3 | 4.8.2.6.4 |
| 4.8.2.7.1 | 4.8.2.7.2 | 4.8.2.7.3 | 4.8.2.7.4 | 4.8.2.8.1 | 4.8.2.8.2 | 4.8.2.8.3 | 4.8.2.8.4 |
| 4.8.3.1.1 | 4.8.3.1.2 | 4.8.3.1.3 | 4.8.3.1.4 | 4.8.3.2.1 | 4.8.3.2.2 | 4.8.3.2.3 | 4.8.3.2.4 |
| 4.8.3.3.1 | 4.8.3.3.2 | 4.8.3.3.3 | 4.8.3.3.4 | 4.8.3.4.1 | 4.8.3.4.2 | 4.8.3.4.3 | 4.8.3.4.4 |
| 4.8.3.5.1 | 4.8.3.5.2 | 4.8.3.5.3 | 4.8.3.5.4 | 4.8.3.6.1 | 4.8.3.6.2 | 4.8.3.6.3 | 4.8.3.6.4 |
| 4.8.3.7.1 | 4.8.3.7.2 | 4.8.3.7.3 | 4.8.3.7.4 | 4.8.3.8.1 | 4.8.3.8.2 | 4.8.3.8.3 | 4.8.3.8.4 |
| 4.8.4.1.1 | 4.8.4.1.2 | 4.8.4.1.3 | 4.8.4.1.4 | 4.8.4.2.1 | 4.8.4.2.2 | 4.8.4.2.3 | 4.8.4.2.4 |
| 4.8.4.3.1 | 4.8.4.3.2 | 4.8.4.3.3 | 4.8.4.3.4 | 4.8.4.4.1 | 4.8.4.4.2 | 4.8.4.4.3 | 4.8.4.4.4 |
| 4.8.4.5.1 | 4.8.4.5.2 | 4.8.4.5.3 | 4.8.4.5.4 | 4.8.4.6.1 | 4.8.4.6.2 | 4.8.4.6.3 | 4.8.4.6.4 |
| 4.8.4.7.1 | 4.8.4.7.2 | 4.8.4.7.3 | 4.8.4.7.4 | 4.8.4.8.1 | 4.8.4.8.2 | 4.8.4.8.3 | 4.8.4.8.4 |

TABLE 1-continued

| | | | | | | | |
|---|---|---|---|---|---|---|---|
| 5.1.1.1.1 | 5.1.1.1.2 | 5.1.1.1.3 | 5.1.1.1.4 | 5.1.1.2.1 | 5.1.1.2.2 | 5.1.1.2.3 | 5.1.1.2.4 |
| 5.1.1.3.1 | 5.1.1.3.2 | 5.1.1.3.3 | 5.1.1.3.4 | 5.1.1.4.1 | 5.1.1.4.2 | 5.1.1.4.3 | 5.1.1.4.4 |
| 5.1.1.5.1 | 5.1.1.5.2 | 5.1.1.5.3 | 5.1.1.5.4 | 5.1.1.6.1 | 5.1.1.6.2 | 5.1.1.6.3 | 5.1.1.6.4 |
| 5.1.1.7.1 | 5.1.1.7.2 | 5.1.1.7.3 | 5.1.1.7.4 | 5.1.1.8.1 | 5.1.1.8.2 | 5.1.1.8.3 | 5.1.1.8.4 |
| 5.1.2.1.1 | 5.1.2.1.2 | 5.1.2.1.3 | 5.1.2.1.4 | 5.1.2.2.1 | 5.1.2.2.2 | 5.1.2.2.3 | 5.1.2.2.4 |
| 5.1.2.3.1 | 5.1.2.3.2 | 5.1.2.3.3 | 5.1.2.3.4 | 5.1.2.4.1 | 5.1.2.4.2 | 5.1.2.4.3 | 5.1.2.4.4 |
| 5.1.2.5.1 | 5.1.2.5.2 | 5.1.2.5.3 | 5.1.2.5.4 | 5.1.2.6.1 | 5.1.2.6.2 | 5.1.2.6.3 | 5.1.2.6.4 |
| 5.1.2.7.1 | 5.1.2.7.2 | 5.1.2.7.3 | 5.1.2.7.4 | 5.1.2.8.1 | 5.1.2.8.2 | 5.1.2.8.3 | 5.1.2.8.4 |
| 5.1.3.1.1 | 5.1.3.1.2 | 5.1.3.1.3 | 5.1.3.1.4 | 5.1.3.2.1 | 5.1.3.2.2 | 5.1.3.2.3 | 5.1.3.2.4 |
| 5.1.3.3.1 | 5.1.3.3.2 | 5.1.3.3.3 | 5.1.3.3.4 | 5.1.3.4.1 | 5.1.3.4.2 | 5.1.3.4.3 | 5.1.3.4.4 |
| 5.1.3.5.1 | 5.1.3.5.2 | 5.1.3.5.3 | 5.1.3.5.4 | 5.1.3.6.1 | 5.1.3.6.2 | 5.1.3.6.3 | 5.1.3.6.4 |
| 5.1.3.7.1 | 5.1.3.7.2 | 5.1.3.7.3 | 5.1.3.7.4 | 5.1.3.8.1 | 5.1.3.8.2 | 5.1.3.8.3 | 5.1.3.8.4 |
| 5.1.4.1.1 | 5.1.4.1.2 | 5.1.4.1.3 | 5.1.4.1.4 | 5.1.4.2.1 | 5.1.4.2.2 | 5.1.4.2.3 | 5.1.4.2.4 |
| 5.1.4.3.1 | 5.1.4.3.2 | 5.1.4.3.3 | 5.1.4.3.4 | 5.1.4.4.1 | 5.1.4.4.2 | 5.1.4.4.3 | 5.1.4.4.4 |
| 5.1.4.5.1 | 5.1.4.5.2 | 5.1.4.5.3 | 5.1.4.5.4 | 5.1.4.6.1 | 5.1.4.6.2 | 5.1.4.6.3 | 5.1.4.6.4 |
| 5.1.4.7.1 | 5.1.4.7.2 | 5.1.4.7.3 | 5.1.4.7.4 | 5.1.4.8.1 | 5.1.4.8.2 | 5.1.4.8.3 | 5.1.4.8.4 |
| 5.2.1.1.1 | 5.2.1.1.2 | 5.2.1.1.3 | 5.2.1.1.4 | 5.2.1.2.1 | 5.2.1.2.2 | 5.2.1.2.3 | 5.2.1.2.4 |
| 5.2.1.3.1 | 5.2.1.3.2 | 5.2.1.3.3 | 5.2.1.3.4 | 5.2.1.4.1 | 5.2.1.4.2 | 5.2.1.4.3 | 5.2.1.4.4 |
| 5.2.1.5.1 | 5.2.1.5.2 | 5.2.1.5.3 | 5.2.1.5.4 | 5.2.1.6.1 | 5.2.1.6.2 | 5.2.1.6.3 | 5.2.1.6.4 |
| 5.2.1.7.1 | 5.2.1.7.2 | 5.2.1.7.3 | 5.2.1.7.4 | 5.2.1.8.1 | 5.2.1.8.2 | 5.2.1.8.3 | 5.2.1.8.4 |
| 5.2.2.1.1 | 5.2.2.1.2 | 5.2.2.1.3 | 5.2.2.1.4 | 5.2.2.2.1 | 5.2.2.2.2 | 5.2.2.2.3 | 5.2.2.2.4 |
| 5.2.2.3.1 | 5.2.2.3.2 | 5.2.2.3.3 | 5.2.2.3.4 | 5.2.2.4.1 | 5.2.2.4.2 | 5.2.2.4.3 | 5.2.2.4.4 |
| 5.2.2.5.1 | 5.2.2.5.2 | 5.2.2.5.3 | 5.2.2.5.4 | 5.2.2.6.1 | 5.2.2.6.2 | 5.2.2.6.3 | 5.2.2.6.4 |
| 5.2.2.7.1 | 5.2.2.7.2 | 5.2.2.7.3 | 5.2.2.7.4 | 5.2.2.8.1 | 5.2.2.8.2 | 5.2.2.8.3 | 5.2.2.8.4 |
| 5.2.3.1.1 | 5.2.3.1.2 | 5.2.3.1.3 | 5.2.3.1.4 | 5.2.3.2.1 | 5.2.3.2.2 | 5.2.3.2.3 | 5.2.3.2.4 |
| 5.2.3.3.1 | 5.2.3.3.2 | 5.2.3.3.3 | 5.2.3.3.4 | 5.2.3.4.1 | 5.2.3.4.2 | 5.2.3.4.3 | 5.2.3.4.4 |
| 5.2.3.5.1 | 5.2.3.5.2 | 5.2.3.5.3 | 5.2.3.5.4 | 5.2.3.6.1 | 5.2.3.6.2 | 5.2.3.6.3 | 5.2.3.6.4 |
| 5.2.3.7.1 | 5.2.3.7.2 | 5.2.3.7.3 | 5.2.3.7.4 | 5.2.3.8.1 | 5.2.3.8.2 | 5.2.3.8.3 | 5.2.3.8.4 |
| 5.2.4.1.1 | 5.2.4.1.2 | 5.2.4.1.3 | 5.2.4.1.4 | 5.2.4.2.1 | 5.2.4.2.2 | 5.2.4.2.3 | 5.2.4.2.4 |
| 5.2.4.3.1 | 5.2.4.3.2 | 5.2.4.3.3 | 5.2.4.3.4 | 5.2.4.4.1 | 5.2.4.4.2 | 5.2.4.4.3 | 5.2.4.4.4 |
| 5.2.4.5.1 | 5.2.4.5.2 | 5.2.4.5.3 | 5.2.4.5.4 | 5.2.4.6.1 | 5.2.4.6.2 | 5.2.4.6.3 | 5.2.4.6.4 |
| 5.2.4.7.1 | 5.2.4.7.2 | 5.2.4.7.3 | 5.2.4.7.4 | 5.2.4.8.1 | 5.2.4.8.2 | 5.2.4.8.3 | 5.2.4.8.4 |
| 5.3.1.1.1 | 5.3.1.1.2 | 5.3.1.1.3 | 5.3.1.1.4 | 5.3.1.2.1 | 5.3.1.2.2 | 5.3.1.2.3 | 5.3.1.2.4 |
| 5.3.1.3.1 | 5.3.1.3.2 | 5.3.1.3.3 | 5.3.1.3.4 | 5.3.1.4.1 | 5.3.1.4.2 | 5.3.1.4.3 | 5.3.1.4.4 |
| 5.3.1.5.1 | 5.3.1.5.2 | 5.3.1.5.3 | 5.3.1.5.4 | 5.3.1.6.1 | 5.3.1.6.2 | 5.3.1.6.3 | 5.3.1.6.4 |
| 5.3.1.7.1 | 5.3.1.7.2 | 5.3.1.7.3 | 5.3.1.7.4 | 5.3.1.8.1 | 5.3.1.8.2 | 5.3.1.8.3 | 5.3.1.8.4 |
| 5.3.2.1.1 | 5.3.2.1.2 | 5.3.2.1.3 | 5.3.2.1.4 | 5.3.2.2.1 | 5.3.2.2.2 | 5.3.2.2.3 | 5.3.2.2.4 |
| 5.3.2.3.1 | 5.3.2.3.2 | 5.3.2.3.3 | 5.3.2.3.4 | 5.3.2.4.1 | 5.3.2.4.2 | 5.3.2.4.3 | 5.3.2.4.4 |
| 5.3.2.5.1 | 5.3.2.5.2 | 5.3.2.5.3 | 5.3.2.5.4 | 5.3.2.6.1 | 5.3.2.6.2 | 5.3.2.6.3 | 5.3.2.6.4 |
| 5.3.2.7.1 | 5.3.2.7.2 | 5.3.2.7.3 | 5.3.2.7.4 | 5.3.2.8.1 | 5.3.2.8.2 | 5.3.2.8.3 | 5.3.2.8.4 |
| 5.3.3.1.1 | 5.3.3.1.2 | 5.3.3.1.3 | 5.3.3.1.4 | 5.3.3.2.1 | 5.3.3.2.2 | 5.3.3.2.3 | 5.3.3.2.4 |
| 5.3.3.3.1 | 5.3.3.3.2 | 5.3.3.3.3 | 5.3.3.3.4 | 5.3.3.4.1 | 5.3.3.4.2 | 5.3.3.4.3 | 5.3.3.4.4 |
| 5.3.3.5.1 | 5.3.3.5.2 | 5.3.3.5.3 | 5.3.3.5.4 | 5.3.3.6.1 | 5.3.3.6.2 | 5.3.3.6.3 | 5.3.3.6.4 |
| 5.3.3.7.1 | 5.3.3.7.2 | 5.3.3.7.3 | 5.3.3.7.4 | 5.3.3.8.1 | 5.3.3.8.2 | 5.3.3.8.3 | 5.3.3.8.4 |
| 5.3.4.1.1 | 5.3.4.1.2 | 5.3.4.1.3 | 5.3.4.1.4 | 5.3.4.2.1 | 5.3.4.2.2 | 5.3.4.2.3 | 5.3.4.2.4 |
| 5.3.4.3.1 | 5.3.4.3.2 | 5.3.4.3.3 | 5.3.4.3.4 | 5.3.4.4.1 | 5.3.4.4.2 | 5.3.4.4.3 | 5.3.4.4.4 |
| 5.3.4.5.1 | 5.3.4.5.2 | 5.3.4.5.3 | 5.3.4.5.4 | 5.3.4.6.1 | 5.3.4.6.2 | 5.3.4.6.3 | 5.3.4.6.4 |
| 5.3.4.7.1 | 5.3.4.7.2 | 5.3.4.7.3 | 5.3.4.7.4 | 5.3.4.8.1 | 5.3.4.8.2 | 5.3.4.8.3 | 5.3.4.8.4 |
| 5.4.1.1.1 | 5.4.1.1.2 | 5.4.1.1.3 | 5.4.1.1.4 | 5.4.1.2.1 | 5.4.1.2.2 | 5.4.1.2.3 | 5.4.1.2.4 |
| 5.4.1.3.1 | 5.4.1.3.2 | 5.4.1.3.3 | 5.4.1.3.4 | 5.4.1.4.1 | 5.4.1.4.2 | 5.4.1.4.3 | 5.4.1.4.4 |
| 5.4.1.5.1 | 5.4.1.5.2 | 5.4.1.5.3 | 5.4.1.5.4 | 5.4.1.6.1 | 5.4.1.6.2 | 5.4.1.6.3 | 5.4.1.6.4 |
| 5.4.1.7.1 | 5.4.1.7.2 | 5.4.1.7.3 | 5.4.1.7.4 | 5.4.1.8.1 | 5.4.1.8.2 | 5.4.1.8.3 | 5.4.1.8.4 |
| 5.4.2.1.1 | 5.4.2.1.2 | 5.4.2.1.3 | 5.4.2.1.4 | 5.4.2.2.1 | 5.4.2.2.2 | 5.4.2.2.3 | 5.4.2.2.4 |
| 5.4.2.3.1 | 5.4.2.3.2 | 5.4.2.3.3 | 5.4.2.3.4 | 5.4.2.4.1 | 5.4.2.4.2 | 5.4.2.4.3 | 5.4.2.4.4 |
| 5.4.2.5.1 | 5.4.2.5.2 | 5.4.2.5.3 | 5.4.2.5.4 | 5.4.2.6.1 | 5.4.2.6.2 | 5.4.2.6.3 | 5.4.2.6.4 |
| 5.4.2.7.1 | 5.4.2.7.2 | 5.4.2.7.3 | 5.4.2.7.4 | 5.4.2.8.1 | 5.4.2.8.2 | 5.4.2.8.3 | 5.4.2.8.4 |
| 5.4.3.1.1 | 5.4.3.1.2 | 5.4.3.1.3 | 5.4.3.1.4 | 5.4.3.2.1 | 5.4.3.2.2 | 5.4.3.2.3 | 5.4.3.2.4 |
| 5.4.3.3.1 | 5.4.3.3.2 | 5.4.3.3.3 | 5.4.3.3.4 | 5.4.3.4.1 | 5.4.3.4.2 | 5.4.3.4.3 | 5.4.3.4.4 |
| 5.4.3.5.1 | 5.4.3.5.2 | 5.4.3.5.3 | 5.4.3.5.4 | 5.4.3.6.1 | 5.4.3.6.2 | 5.4.3.6.3 | 5.4.3.6.4 |
| 5.4.3.7.1 | 5.4.3.7.2 | 5.4.3.7.3 | 5.4.3.7.4 | 5.4.3.8.1 | 5.4.3.8.2 | 5.4.3.8.3 | 5.4.3.8.4 |
| 5.4.4.1.1 | 5.4.4.1.2 | 5.4.4.1.3 | 5.4.4.1.4 | 5.4.4.2.1 | 5.4.4.2.2 | 5.4.4.2.3 | 5.4.4.2.4 |
| 5.4.4.3.1 | 5.4.4.3.2 | 5.4.4.3.3 | 5.4.4.3.4 | 5.4.4.4.1 | 5.4.4.4.2 | 5.4.4.4.3 | 5.4.4.4.4 |
| 5.4.4.5.1 | 5.4.4.5.2 | 5.4.4.5.3 | 5.4.4.5.4 | 5.4.4.6.1 | 5.4.4.6.2 | 5.4.4.6.3 | 5.4.4.6.4 |
| 5.4.4.7.1 | 5.4.4.7.2 | 5.4.4.7.3 | 5.4.4.7.4 | 5.4.4.8.1 | 5.4.4.8.2 | 5.4.4.8.3 | 5.4.4.8.4 |
| 5.5.1.1.1 | 5.5.1.1.2 | 5.5.1.1.3 | 5.5.1.1.4 | 5.5.1.2.1 | 5.5.1.2.2 | 5.5.1.2.3 | 5.5.1.2.4 |
| 5.5.1.3.1 | 5.5.1.3.2 | 5.5.1.3.3 | 5.5.1.3.4 | 5.5.1.4.1 | 5.5.1.4.2 | 5.5.1.4.3 | 5.5.1.4.4 |
| 5.5.1.5.1 | 5.5.1.5.2 | 5.5.1.5.3 | 5.5.1.5.4 | 5.5.1.6.1 | 5.5.1.6.2 | 5.5.1.6.3 | 5.5.1.6.4 |
| 5.5.1.7.1 | 5.5.1.7.2 | 5.5.1.7.3 | 5.5.1.7.4 | 5.5.1.8.1 | 5.5.1.8.2 | 5.5.1.8.3 | 5.5.1.8.4 |
| 5.5.2.1.1 | 5.5.2.1.2 | 5.5.2.1.3 | 5.5.2.1.4 | 5.5.2.2.1 | 5.5.2.2.2 | 5.5.2.2.3 | 5.5.2.2.4 |
| 5.5.2.3.1 | 5.5.2.3.2 | 5.5.2.3.3 | 5.5.2.3.4 | 5.5.2.4.1 | 5.5.2.4.2 | 5.5.2.4.3 | 5.5.2.4.4 |
| 5.5.2.5.1 | 5.5.2.5.2 | 5.5.2.5.3 | 5.5.2.5.4 | 5.5.2.6.1 | 5.5.2.6.2 | 5.5.2.6.3 | 5.5.2.6.4 |
| 5.5.2.7.1 | 5.5.2.7.2 | 5.5.2.7.3 | 5.5.2.7.4 | 5.5.2.8.1 | 5.5.2.8.2 | 5.5.2.8.3 | 5.5.2.8.4 |
| 5.5.3.1.1 | 5.5.3.1.2 | 5.5.3.1.3 | 5.5.3.1.4 | 5.5.3.2.1 | 5.5.3.2.2 | 5.5.3.2.3 | 5.5.3.2.4 |
| 5.5.3.3.1 | 5.5.3.3.2 | 5.5.3.3.3 | 5.5.3.3.4 | 5.5.3.4.1 | 5.5.3.4.2 | 5.5.3.4.3 | 5.5.3.4.4 |
| 5.5.3.5.1 | 5.5.3.5.2 | 5.5.3.5.3 | 5.5.3.5.4 | 5.5.3.6.1 | 5.5.3.6.2 | 5.5.3.6.3 | 5.5.3.6.4 |
| 5.5.3.7.1 | 5.5.3.7.2 | 5.5.3.7.3 | 5.5.3.7.4 | 5.5.3.8.1 | 5.5.3.8.2 | 5.5.3.8.3 | 5.5.3.8.4 |
| 5.5.4.1.1 | 5.5.4.1.2 | 5.5.4.1.3 | 5.5.4.1.4 | 5.5.4.2.1 | 5.5.4.2.2 | 5.5.4.2.3 | 5.5.4.2.4 |
| 5.5.4.3.1 | 5.5.4.3.2 | 5.5.4.3.3 | 5.5.4.3.4 | 5.5.4.4.1 | 5.5.4.4.2 | 5.5.4.4.3 | 5.5.4.4.4 |
| 5.5.4.5.1 | 5.5.4.5.2 | 5.5.4.5.3 | 5.5.4.5.4 | 5.5.4.6.1 | 5.5.4.6.2 | 5.5.4.6.3 | 5.5.4.6.4 |

TABLE 1-continued

| | | | | | | | |
|---|---|---|---|---|---|---|---|
| 5.5.4.7.1 | 5.5.4.7.2 | 5.5.4.7.3 | 5.5.4.7.4 | 5.5.4.8.1 | 5.5.4.8.2 | 5.5.4.8.3 | 5.5.4.8.4 |
| 5.6.1.1.1 | 5.6.1.1.2 | 5.6.1.1.3 | 5.6.1.1.4 | 5.6.1.2.1 | 5.6.1.2.2 | 5.6.1.2.3 | 5.6.1.2.4 |
| 5.6.1.3.1 | 5.6.1.3.2 | 5.6.1.3.3 | 5.6.1.3.4 | 5.6.1.4.1 | 5.6.1.4.2 | 5.6.1.4.3 | 5.6.1.4.4 |
| 5.6.1.5.1 | 5.6.1.5.2 | 5.6.1.5.3 | 5.6.1.5.4 | 5.6.1.6.1 | 5.6.1.6.2 | 5.6.1.6.3 | 5.6.1.6.4 |
| 5.6.1.7.1 | 5.6.1.7.2 | 5.6.1.7.3 | 5.6.1.7.4 | 5.6.1.8.1 | 5.6.1.8.2 | 5.6.1.8.3 | 5.6.1.8.4 |
| 5.6.2.1.1 | 5.6.2.1.2 | 5.6.2.1.3 | 5.6.2.1.4 | 5.6.2.2.1 | 5.6.2.2.2 | 5.6.2.2.3 | 5.6.2.2.4 |
| 5.6.2.3.1 | 5.6.2.3.2 | 5.6.2.3.3 | 5.6.2.3.4 | 5.6.2.4.1 | 5.6.2.4.2 | 5.6.2.4.3 | 5.6.2.4.4 |
| 5.6.2.5.1 | 5.6.2.5.2 | 5.6.2.5.3 | 5.6.2.5.4 | 5.6.2.6.1 | 5.6.2.6.2 | 5.6.2.6.3 | 5.6.2.6.4 |
| 5.6.2.7.1 | 5.6.2.7.2 | 5.6.2.7.3 | 5.6.2.7.4 | 5.6.2.8.1 | 5.6.2.8.2 | 5.6.2.8.3 | 5.6.2.8.4 |
| 5.6.3.1.1 | 5.6.3.1.2 | 5.6.3.1.3 | 5.6.3.1.4 | 5.6.3.2.1 | 5.6.3.2.2 | 5.6.3.2.3 | 5.6.3.2.4 |
| 5.6.3.3.1 | 5.6.3.3.2 | 5.6.3.3.3 | 5.6.3.3.4 | 5.6.3.4.1 | 5.6.3.4.2 | 5.6.3.4.3 | 5.6.3.4.4 |
| 5.6.3.5.1 | 5.6.3.5.2 | 5.6.3.5.3 | 5.6.3.5.4 | 5.6.3.6.1 | 5.6.3.6.2 | 5.6.3.6.3 | 5.6.3.6.4 |
| 5.6.3.7.1 | 5.6.3.7.2 | 5.6.3.7.3 | 5.6.3.7.4 | 5.6.3.8.1 | 5.6.3.8.2 | 5.6.3.8.3 | 5.6.3.8.4 |
| 5.6.4.1.1 | 5.6.4.1.2 | 5.6.4.1.3 | 5.6.4.1.4 | 5.6.4.2.1 | 5.6.4.2.2 | 5.6.4.2.3 | 5.6.4.2.4 |
| 5.6.4.3.1 | 5.6.4.3.2 | 5.6.4.3.3 | 5.6.4.3.4 | 5.6.4.4.1 | 5.6.4.4.2 | 5.6.4.4.3 | 5.6.4.4.4 |
| 5.6.4.5.1 | 5.6.4.5.2 | 5.6.4.5.3 | 5.6.4.5.4 | 5.6.4.6.1 | 5.6.4.6.2 | 5.6.4.6.3 | 5.6.4.6.4 |
| 5.6.4.7.1 | 5.6.4.7.2 | 5.6.4.7.3 | 5.6.4.7.4 | 5.6.4.8.1 | 5.6.4.8.2 | 5.6.4.8.3 | 5.6.4.8.4 |
| 5.7.1.1.1 | 5.7.1.1.2 | 5.7.1.1.3 | 5.7.1.1.4 | 5.7.1.2.1 | 5.7.1.2.2 | 5.7.1.2.3 | 5.7.1.2.4 |
| 5.7.1.3.1 | 5.7.1.3.2 | 5.7.1.3.3 | 5.7.1.3.4 | 5.7.1.4.1 | 5.7.1.4.2 | 5.7.1.4.3 | 5.7.1.4.4 |
| 5.7.1.5.1 | 5.7.1.5.2 | 5.7.1.5.3 | 5.7.1.5.4 | 5.7.1.6.1 | 5.7.1.6.2 | 5.7.1.6.3 | 5.7.1.6.4 |
| 5.7.1.7.1 | 5.7.1.7.2 | 5.7.1.7.3 | 5.7.1.7.4 | 5.7.1.8.1 | 5.7.1.8.2 | 5.7.1.8.3 | 5.7.1.8.4 |
| 5.7.2.1.1 | 5.7.2.1.2 | 5.7.2.1.3 | 5.7.2.1.4 | 5.7.2.2.1 | 5.7.2.2.2 | 5.7.2.2.3 | 5.7.2.2.4 |
| 5.7.2.3.1 | 5.7.2.3.2 | 5.7.2.3.3 | 5.7.2.3.4 | 5.7.2.4.1 | 5.7.2.4.2 | 5.7.2.4.3 | 5.7.2.4.4 |
| 5.7.2.5.1 | 5.7.2.5.2 | 5.7.2.5.3 | 5.7.2.5.4 | 5.7.2.6.1 | 5.7.2.6.2 | 5.7.2.6.3 | 5.7.2.6.4 |
| 5.7.2.7.1 | 5.7.2.7.2 | 5.7.2.7.3 | 5.7.2.7.4 | 5.7.2.8.1 | 5.7.2.8.2 | 5.7.2.8.3 | 5.7.2.8.4 |
| 5.7.3.1.1 | 5.7.3.1.2 | 5.7.3.1.3 | 5.7.3.1.4 | 5.7.3.2.1 | 5.7.3.2.2 | 5.7.3.2.3 | 5.7.3.2.4 |
| 5.7.3.3.1 | 5.7.3.3.2 | 5.7.3.3.3 | 5.7.3.3.4 | 5.7.3.4.1 | 5.7.3.4.2 | 5.7.3.4.3 | 5.7.3.4.4 |
| 5.7.3.5.1 | 5.7.3.5.2 | 5.7.3.5.3 | 5.7.3.5.4 | 5.7.3.6.1 | 5.7.3.6.2 | 5.7.3.6.3 | 5.7.3.6.4 |
| 5.7.3.7.1 | 5.7.3.7.2 | 5.7.3.7.3 | 5.7.3.7.4 | 5.7.3.8.1 | 5.7.3.8.2 | 5.7.3.8.3 | 5.7.3.8.4 |
| 5.7.4.1.1 | 5.7.4.1.2 | 5.7.4.1.3 | 5.7.4.1.4 | 5.7.4.2.1 | 5.7.4.2.2 | 5.7.4.2.3 | 5.7.4.2.4 |
| 5.7.4.3.1 | 5.7.4.3.2 | 5.7.4.3.3 | 5.7.4.3.4 | 5.7.4.4.1 | 5.7.4.4.2 | 5.7.4.4.3 | 5.7.4.4.4 |
| 5.7.4.5.1 | 5.7.4.5.2 | 5.7.4.5.3 | 5.7.4.5.4 | 5.7.4.6.1 | 5.7.4.6.2 | 5.7.4.6.3 | 5.7.4.6.4 |
| 5.7.4.7.1 | 5.7.4.7.2 | 5.7.4.7.3 | 5.7.4.7.4 | 5.7.4.8.1 | 5.7.4.8.2 | 5.7.4.8.3 | 5.7.4.8.4 |
| 5.8.1.1.1 | 5.8.1.1.2 | 5.8.1.1.3 | 5.8.1.1.4 | 5.8.1.2.1 | 5.8.1.2.2 | 5.8.1.2.3 | 5.8.1.2.4 |
| 5.8.1.3.1 | 5.8.1.3.2 | 5.8.1.3.3 | 5.8.1.3.4 | 5.8.1.4.1 | 5.8.1.4.2 | 5.8.1.4.3 | 5.8.1.4.4 |
| 5.8.1.5.1 | 5.8.1.5.2 | 5.8.1.5.3 | 5.8.1.5.4 | 5.8.1.6.1 | 5.8.1.6.2 | 5.8.1.6.3 | 5.8.1.6.4 |
| 5.8.1.7.1 | 5.8.1.7.2 | 5.8.1.7.3 | 5.8.1.7.4 | 5.8.1.8.1 | 5.8.1.8.2 | 5.8.1.8.3 | 5.8.1.8.4 |
| 5.8.2.1.1 | 5.8.2.1.2 | 5.8.2.1.3 | 5.8.2.1.4 | 5.8.2.2.1 | 5.8.2.2.2 | 5.8.2.2.3 | 5.8.2.2.4 |
| 5.8.2.3.1 | 5.8.2.3.2 | 5.8.2.3.3 | 5.8.2.3.4 | 5.8.2.4.1 | 5.8.2.4.2 | 5.8.2.4.3 | 5.8.2.4.4 |
| 5.8.2.5.1 | 5.8.2.5.2 | 5.8.2.5.3 | 5.8.2.5.4 | 5.8.2.6.1 | 5.8.2.6.2 | 5.8.2.6.3 | 5.8.2.6.4 |
| 5.8.2.7.1 | 5.8.2.7.2 | 5.8.2.7.3 | 5.8.2.7.4 | 5.8.2.8.1 | 5.8.2.8.2 | 5.8.2.8.3 | 5.8.2.8.4 |
| 5.8.3.1.1 | 5.8.3.1.2 | 5.8.3.1.3 | 5.8.3.1.4 | 5.8.3.2.1 | 5.8.3.2.2 | 5.8.3.2.3 | 5.8.3.2.4 |
| 5.8.3.3.1 | 5.8.3.3.2 | 5.8.3.3.3 | 5.8.3.3.4 | 5.8.3.4.1 | 5.8.3.4.2 | 5.8.3.4.3 | 5.8.3.4.4 |
| 5.8.3.5.1 | 5.8.3.5.2 | 5.8.3.5.3 | 5.8.3.5.4 | 5.8.3.6.1 | 5.8.3.6.2 | 5.8.3.6.3 | 5.8.3.6.4 |
| 5.8.3.7.1 | 5.8.3.7.2 | 5.8.3.7.3 | 5.8.3.7.4 | 5.8.3.8.1 | 5.8.3.8.2 | 5.8.3.8.3 | 5.8.3.8.4 |
| 5.8.4.1.1 | 5.8.4.1.2 | 5.8.4.1.3 | 5.8.4.1.4 | 5.8.4.2.1 | 5.8.4.2.2 | 5.8.4.2.3 | 5.8.4.2.4 |
| 5.8.4.3.1 | 5.8.4.3.2 | 5.8.4.3.3 | 5.8.4.3.4 | 5.8.4.4.1 | 5.8.4.4.2 | 5.8.4.4.3 | 5.8.4.4.4 |
| 5.8.4.5.1 | 5.8.4.5.2 | 5.8.4.5.3 | 5.8.4.5.4 | 5.8.4.6.1 | 5.8.4.6.2 | 5.8.4.6.3 | 5.8.4.6.4 |
| 5.8.4.7.1 | 5.8.4.7.2 | 5.8.4.7.3 | 5.8.4.7.4 | 5.8.4.8.1 | 5.8.4.8.2 | 5.8.4.8.3 | 5.8.4.8.4 |
| 6.1.1.1.1 | 6.1.1.1.2 | 6.1.1.1.3 | 6.1.1.1.4 | 6.1.1.2.1 | 6.1.1.2.2 | 6.1.1.2.3 | 6.1.1.2.4 |
| 6.1.1.3.1 | 6.1.1.3.2 | 6.1.1.3.3 | 6.1.1.3.4 | 6.1.1.4.1 | 6.1.1.4.2 | 6.1.1.4.3 | 6.1.1.4.4 |
| 6.1.1.5.1 | 6.1.1.5.2 | 6.1.1.5.3 | 6.1.1.5.4 | 6.1.1.6.1 | 6.1.1.6.2 | 6.1.1.6.3 | 6.1.1.6.4 |
| 6.1.1.7.1 | 6.1.1.7.2 | 6.1.1.7.3 | 6.1.1.7.4 | 6.1.1.8.1 | 6.1.1.8.2 | 6.1.1.8.3 | 6.1.1.8.4 |
| 6.1.2.1.1 | 6.1.2.1.2 | 6.1.2.1.3 | 6.1.2.1.4 | 6.1.2.2.1 | 6.1.2.2.2 | 6.1.2.2.3 | 6.1.2.2.4 |
| 6.1.2.3.1 | 6.1.2.3.2 | 6.1.2.3.3 | 6.1.2.3.4 | 6.1.2.4.1 | 6.1.2.4.2 | 6.1.2.4.3 | 6.1.2.4.4 |
| 6.1.2.5.1 | 6.1.2.5.2 | 6.1.2.5.3 | 6.1.2.5.4 | 6.1.2.6.1 | 6.1.2.6.2 | 6.1.2.6.3 | 6.1.2.6.4 |
| 6.1.2.7.1 | 6.1.2.7.2 | 6.1.2.7.3 | 6.1.2.7.4 | 6.1.2.8.1 | 6.1.2.8.2 | 6.1.2.8.3 | 6.1.2.8.4 |
| 6.1.3.1.1 | 6.1.3.1.2 | 6.1.3.1.3 | 6.1.3.1.4 | 6.1.3.2.1 | 6.1.3.2.2 | 6.1.3.2.3 | 6.1.3.2.4 |
| 6.1.3.3.1 | 6.1.3.3.2 | 6.1.3.3.3 | 6.1.3.3.4 | 6.1.3.4.1 | 6.1.3.4.2 | 6.1.3.4.3 | 6.1.3.4.4 |
| 6.1.3.5.1 | 6.1.3.5.2 | 6.1.3.5.3 | 6.1.3.5.4 | 6.1.3.6.1 | 6.1.3.6.2 | 6.1.3.6.3 | 6.1.3.6.4 |
| 6.1.3.7.1 | 6.1.3.7.2 | 6.1.3.7.3 | 6.1.3.7.4 | 6.1.3.8.1 | 6.1.3.8.2 | 6.1.3.8.3 | 6.1.3.8.4 |
| 6.1.4.1.1 | 6.1.4.1.2 | 6.1.4.1.3 | 6.1.4.1.4 | 6.1.4.2.1 | 6.1.4.2.2 | 6.1.4.2.3 | 6.1.4.2.4 |
| 6.1.4.3.1 | 6.1.4.3.2 | 6.1.4.3.3 | 6.1.4.3.4 | 6.1.4.4.1 | 6.1.4.4.2 | 6.1.4.4.3 | 6.1.4.4.4 |
| 6.1.4.5.1 | 6.1.4.5.2 | 6.1.4.5.3 | 6.1.4.5.4 | 6.1.4.6.1 | 6.1.4.6.2 | 6.1.4.6.3 | 6.1.4.6.4 |
| 6.1.4.7.1 | 6.1.4.7.2 | 6.1.4.7.3 | 6.1.4.7.4 | 6.1.4.8.1 | 6.1.4.8.2 | 6.1.4.8.3 | 6.1.4.8.4 |
| 6.2.1.1.1 | 6.2.1.1.2 | 6.2.1.1.3 | 6.2.1.1.4 | 6.2.1.2.1 | 6.2.1.2.2 | 6.2.1.2.3 | 6.2.1.2.4 |
| 6.2.1.3.1 | 6.2.1.3.2 | 6.2.1.3.3 | 6.2.1.3.4 | 6.2.1.4.1 | 6.2.1.4.2 | 6.2.1.4.3 | 6.2.1.4.4 |
| 6.2.1.5.1 | 6.2.1.5.2 | 6.2.1.5.3 | 6.2.1.5.4 | 6.2.1.6.1 | 6.2.1.6.2 | 6.2.1.6.3 | 6.2.1.6.4 |
| 6.2.1.7.1 | 6.2.1.7.2 | 6.2.1.7.3 | 6.2.1.7.4 | 6.2.1.8.1 | 6.2.1.8.2 | 6.2.1.8.3 | 6.2.1.8.4 |
| 6.2.2.1.1 | 6.2.2.1.2 | 6.2.2.1.3 | 6.2.2.1.4 | 6.2.2.2.1 | 6.2.2.2.2 | 6.2.2.2.3 | 6.2.2.2.4 |
| 6.2.2.3.1 | 6.2.2.3.2 | 6.2.2.3.3 | 6.2.2.3.4 | 6.2.2.4.1 | 6.2.2.4.2 | 6.2.2.4.3 | 6.2.2.4.4 |
| 6.2.2.5.1 | 6.2.2.5.2 | 6.2.2.5.3 | 6.2.2.5.4 | 6.2.2.6.1 | 6.2.2.6.2 | 6.2.2.6.3 | 6.2.2.6.4 |
| 6.2.2.7.1 | 6.2.2.7.2 | 6.2.2.7.3 | 6.2.2.7.4 | 6.2.2.8.1 | 6.2.2.8.2 | 6.2.2.8.3 | 6.2.2.8.4 |
| 6.2.3.1.1 | 6.2.3.1.2 | 6.2.3.1.3 | 6.2.3.1.4 | 6.2.3.2.1 | 6.2.3.2.2 | 6.2.3.2.3 | 6.2.3.2.4 |
| 6.2.3.3.1 | 6.2.3.3.2 | 6.2.3.3.3 | 6.2.3.3.4 | 6.2.3.4.1 | 6.2.3.4.2 | 6.2.3.4.3 | 6.2.3.4.4 |
| 6.2.3.5.1 | 6.2.3.5.2 | 6.2.3.5.3 | 6.2.3.5.4 | 6.2.3.6.1 | 6.2.3.6.2 | 6.2.3.6.3 | 6.2.3.6.4 |
| 6.2.3.7.1 | 6.2.3.7.2 | 6.2.3.7.3 | 6.2.3.7.4 | 6.2.3.8.1 | 6.2.3.8.2 | 6.2.3.8.3 | 6.2.3.8.4 |
| 6.2.4.1.1 | 6.2.4.1.2 | 6.2.4.1.3 | 6.2.4.1.4 | 6.2.4.2.1 | 6.2.4.2.2 | 6.2.4.2.3 | 6.2.4.2.4 |
| 6.2.4.3.1 | 6.2.4.3.2 | 6.2.4.3.3 | 6.2.4.3.4 | 6.2.4.4.1 | 6.2.4.4.2 | 6.2.4.4.3 | 6.2.4.4.4 |

TABLE 1-continued

| | | | | | | | |
|---|---|---|---|---|---|---|---|
| 6.2.4.5.1 | 6.2.4.5.2 | 6.2.4.5.3 | 6.2.4.5.4 | 6.2.4.6.1 | 6.2.4.6.2 | 6.2.4.6.3 | 6.2.4.6.4 |
| 6.2.4.7.1 | 6.2.4.7.2 | 6.2.4.7.3 | 6.2.4.7.4 | 6.2.4.8.1 | 6.2.4.8.2 | 6.2.4.8.3 | 6.2.4.8.4 |
| 6.3.1.1.1 | 6.3.1.1.2 | 6.3.1.1.3 | 6.3.1.1.4 | 6.3.1.2.1 | 6.3.1.2.2 | 6.3.1.2.3 | 6.3.1.2.4 |
| 6.3.1.3.1 | 6.3.1.3.2 | 6.3.1.3.3 | 6.3.1.3.4 | 6.3.1.4.1 | 6.3.1.4.2 | 6.3.1.4.3 | 6.3.1.4.4 |
| 6.3.1.5.1 | 6.3.1.5.2 | 6.3.1.5.3 | 6.3.1.5.4 | 6.3.1.6.1 | 6.3.1.6.2 | 6.3.1.6.3 | 6.3.1.6.4 |
| 6.3.1.7.1 | 6.3.1.7.2 | 6.3.1.7.3 | 6.3.1.7.4 | 6.3.1.8.1 | 6.3.1.8.2 | 6.3.1.8.3 | 6.3.1.8.4 |
| 6.3.2.1.1 | 6.3.2.1.2 | 6.3.2.1.3 | 6.3.2.1.4 | 6.3.2.2.1 | 6.3.2.2.2 | 6.3.2.2.3 | 6.3.2.2.4 |
| 6.3.2.3.1 | 6.3.2.3.2 | 6.3.2.3.3 | 6.3.2.3.4 | 6.3.2.4.1 | 6.3.2.4.2 | 6.3.2.4.3 | 6.3.2.4.4 |
| 6.3.2.5.1 | 6.3.2.5.2 | 6.3.2.5.3 | 6.3.2.5.4 | 6.3.2.6.1 | 6.3.2.6.2 | 6.3.2.6.3 | 6.3.2.6.4 |
| 6.3.2.7.1 | 6.3.2.7.2 | 6.3.2.7.3 | 6.3.2.7.4 | 6.3.2.8.1 | 6.3.2.8.2 | 6.3.2.8.3 | 6.3.2.8.4 |
| 6.3.3.1.1 | 6.3.3.1.2 | 6.3.3.1.3 | 6.3.3.1.4 | 6.3.3.2.1 | 6.3.3.2.2 | 6.3.3.2.3 | 6.3.3.2.4 |
| 6.3.3.3.1 | 6.3.3.3.2 | 6.3.3.3.3 | 6.3.3.3.4 | 6.3.3.4.1 | 6.3.3.4.2 | 6.3.3.4.3 | 6.3.3.4.4 |
| 6.3.3.5.1 | 6.3.3.5.2 | 6.3.3.5.3 | 6.3.3.5.4 | 6.3.3.6.1 | 6.3.3.6.2 | 6.3.3.6.3 | 6.3.3.6.4 |
| 6.3.3.7.1 | 6.3.3.7.2 | 6.3.3.7.3 | 6.3.3.7.4 | 6.3.3.8.1 | 6.3.3.8.2 | 6.3.3.8.3 | 6.3.3.8.4 |
| 6.3.4.1.1 | 6.3.4.1.2 | 6.3.4.1.3 | 6.3.4.1.4 | 6.3.4.2.1 | 6.3.4.2.2 | 6.3.4.2.3 | 6.3.4.2.4 |
| 6.3.4.3.1 | 6.3.4.3.2 | 6.3.4.3.3 | 6.3.4.3.4 | 6.3.4.4.1 | 6.3.4.4.2 | 6.3.4.4.3 | 6.3.4.4.4 |
| 6.3.4.5.1 | 6.3.4.5.2 | 6.3.4.5.3 | 6.3.4.5.4 | 6.3.4.6.1 | 6.3.4.6.2 | 6.3.4.6.3 | 6.3.4.6.4 |
| 6.3.4.7.1 | 6.3.4.7.2 | 6.3.4.7.3 | 6.3.4.7.4 | 6.3.4.8.1 | 6.3.4.8.2 | 6.3.4.8.3 | 6.3.4.8.4 |
| 6.4.1.1.1 | 6.4.1.1.2 | 6.4.1.1.3 | 6.4.1.1.4 | 6.4.1.2.1 | 6.4.1.2.2 | 6.4.1.2.3 | 6.4.1.2.4 |
| 6.4.1.3.1 | 6.4.1.3.2 | 6.4.1.3.3 | 6.4.1.3.4 | 6.4.1.4.1 | 6.4.1.4.2 | 6.4.1.4.3 | 6.4.1.4.4 |
| 6.4.1.5.1 | 6.4.1.5.2 | 6.4.1.5.3 | 6.4.1.5.4 | 6.4.1.6.1 | 6.4.1.6.2 | 6.4.1.6.3 | 6.4.1.6.4 |
| 6.4.1.7.1 | 6.4.1.7.2 | 6.4.1.7.3 | 6.4.1.7.4 | 6.4.1.8.1 | 6.4.1.8.2 | 6.4.1.8.3 | 6.4.1.8.4 |
| 6.4.2.1.1 | 6.4.2.1.2 | 6.4.2.1.3 | 6.4.2.1.4 | 6.4.2.2.1 | 6.4.2.2.2 | 6.4.2.2.3 | 6.4.2.2.4 |
| 6.4.2.3.1 | 6.4.2.3.2 | 6.4.2.3.3 | 6.4.2.3.4 | 6.4.2.4.1 | 6.4.2.4.2 | 6.4.2.4.3 | 6.4.2.4.4 |
| 6.4.2.5.1 | 6.4.2.5.2 | 6.4.2.5.3 | 6.4.2.5.4 | 6.4.2.6.1 | 6.4.2.6.2 | 6.4.2.6.3 | 6.4.2.6.4 |
| 6.4.2.7.1 | 6.4.2.7.2 | 6.4.2.7.3 | 6.4.2.7.4 | 6.4.2.8.1 | 6.4.2.8.2 | 6.4.2.8.3 | 6.4.2.8.4 |
| 6.4.3.1.1 | 6.4.3.1.2 | 6.4.3.1.3 | 6.4.3.1.4 | 6.4.3.2.1 | 6.4.3.2.2 | 6.4.3.2.3 | 6.4.3.2.4 |
| 6.4.3.3.1 | 6.4.3.3.2 | 6.4.3.3.3 | 6.4.3.3.4 | 6.4.3.4.1 | 6.4.3.4.2 | 6.4.3.4.3 | 6.4.3.4.4 |
| 6.4.3.5.1 | 6.4.3.5.2 | 6.4.3.5.3 | 6.4.3.5.4 | 6.4.3.6.1 | 6.4.3.6.2 | 6.4.3.6.3 | 6.4.3.6.4 |
| 6.4.3.7.1 | 6.4.3.7.2 | 6.4.3.7.3 | 6.4.3.7.4 | 6.4.3.8.1 | 6.4.3.8.2 | 6.4.3.8.3 | 6.4.3.8.4 |
| 6.4.4.1.1 | 6.4.4.1.2 | 6.4.4.1.3 | 6.4.4.1.4 | 6.4.4.2.1 | 6.4.4.2.2 | 6.4.4.2.3 | 6.4.4.2.4 |
| 6.4.4.3.1 | 6.4.4.3.2 | 6.4.4.3.3 | 6.4.4.3.4 | 6.4.4.4.1 | 6.4.4.4.2 | 6.4.4.4.3 | 6.4.4.4.4 |
| 6.4.4.5.1 | 6.4.4.5.2 | 6.4.4.5.3 | 6.4.4.5.4 | 6.4.4.6.1 | 6.4.4.6.2 | 6.4.4.6.3 | 6.4.4.6.4 |
| 6.4.4.7.1 | 6.4.4.7.2 | 6.4.4.7.3 | 6.4.4.7.4 | 6.4.4.8.1 | 6.4.4.8.2 | 6.4.4.8.3 | 6.4.4.8.4 |
| 6.5.1.1.1 | 6.5.1.1.2 | 6.5.1.1.3 | 6.5.1.1.4 | 6.5.1.2.1 | 6.5.1.2.2 | 6.5.1.2.3 | 6.5.1.2.4 |
| 6.5.1.3.1 | 6.5.1.3.2 | 6.5.1.3.3 | 6.5.1.3.4 | 6.5.1.4.1 | 6.5.1.4.2 | 6.5.1.4.3 | 6.5.1.4.4 |
| 6.5.1.5.1 | 6.5.1.5.2 | 6.5.1.5.3 | 6.5.1.5.4 | 6.5.1.6.1 | 6.5.1.6.2 | 6.5.1.6.3 | 6.5.1.6.4 |
| 6.5.1.7.1 | 6.5.1.7.2 | 6.5.1.7.3 | 6.5.1.7.4 | 6.5.1.8.1 | 6.5.1.8.2 | 6.5.1.8.3 | 6.5.1.8.4 |
| 6.5.2.1.1 | 6.5.2.1.2 | 6.5.2.1.3 | 6.5.2.1.4 | 6.5.2.2.1 | 6.5.2.2.2 | 6.5.2.2.3 | 6.5.2.2.4 |
| 6.5.2.3.1 | 6.5.2.3.2 | 6.5.2.3.3 | 6.5.2.3.4 | 6.5.2.4.1 | 6.5.2.4.2 | 6.5.2.4.3 | 6.5.2.4.4 |
| 6.5.2.5.1 | 6.5.2.5.2 | 6.5.2.5.3 | 6.5.2.5.4 | 6.5.2.6.1 | 6.5.2.6.2 | 6.5.2.6.3 | 6.5.2.6.4 |
| 6.5.2.7.1 | 6.5.2.7.2 | 6.5.2.7.3 | 6.5.2.7.4 | 6.5.2.8.1 | 6.5.2.8.2 | 6.5.2.8.3 | 6.5.2.8.4 |
| 6.5.3.1.1 | 6.5.3.1.2 | 6.5.3.1.3 | 6.5.3.1.4 | 6.5.3.2.1 | 6.5.3.2.2 | 6.5.3.2.3 | 6.5.3.2.4 |
| 6.5.3.3.1 | 6.5.3.3.2 | 6.5.3.3.3 | 6.5.3.3.4 | 6.5.3.4.1 | 6.5.3.4.2 | 6.5.3.4.3 | 6.5.3.4.4 |
| 6.5.3.5.1 | 6.5.3.5.2 | 6.5.3.5.3 | 6.5.3.5.4 | 6.5.3.6.1 | 6.5.3.6.2 | 6.5.3.6.3 | 6.5.3.6.4 |
| 6.5.3.7.1 | 6.5.3.7.2 | 6.5.3.7.3 | 6.5.3.7.4 | 6.5.3.8.1 | 6.5.3.8.2 | 6.5.3.8.3 | 6.5.3.8.4 |
| 6.5.4.1.1 | 6.5.4.1.2 | 6.5.4.1.3 | 6.5.4.1.4 | 6.5.4.2.1 | 6.5.4.2.2 | 6.5.4.2.3 | 6.5.4.2.4 |
| 6.5.4.3.1 | 6.5.4.3.2 | 6.5.4.3.3 | 6.5.4.3.4 | 6.5.4.4.1 | 6.5.4.4.2 | 6.5.4.4.3 | 6.5.4.4.4 |
| 6.5.4.5.1 | 6.5.4.5.2 | 6.5.4.5.3 | 6.5.4.5.4 | 6.5.4.6.1 | 6.5.4.6.2 | 6.5.4.6.3 | 6.5.4.6.4 |
| 6.5.4.7.1 | 6.5.4.7.2 | 6.5.4.7.3 | 6.5.4.7.4 | 6.5.4.8.1 | 6.5.4.8.2 | 6.5.4.8.3 | 6.5.4.8.4 |
| 6.6.1.1.1 | 6.6.1.1.2 | 6.6.1.1.3 | 6.6.1.1.4 | 6.6.1.2.1 | 6.6.1.2.2 | 6.6.1.2.3 | 6.6.1.2.4 |
| 6.6.1.3.1 | 6.6.1.3.2 | 6.6.1.3.3 | 6.6.1.3.4 | 6.6.1.4.1 | 6.6.1.4.2 | 6.6.1.4.3 | 6.6.1.4.4 |
| 6.6.1.5.1 | 6.6.1.5.2 | 6.6.1.5.3 | 6.6.1.5.4 | 6.6.1.6.1 | 6.6.1.6.2 | 6.6.1.6.3 | 6.6.1.6.4 |
| 6.6.1.7.1 | 6.6.1.7.2 | 6.6.1.7.3 | 6.6.1.7.4 | 6.6.1.8.1 | 6.6.1.8.2 | 6.6.1.8.3 | 6.6.1.8.4 |
| 6.6.2.1.1 | 6.6.2.1.2 | 6.6.2.1.3 | 6.6.2.1.4 | 6.6.2.2.1 | 6.6.2.2.2 | 6.6.2.2.3 | 6.6.2.2.4 |
| 6.6.2.3.1 | 6.6.2.3.2 | 6.6.2.3.3 | 6.6.2.3.4 | 6.6.2.4.1 | 6.6.2.4.2 | 6.6.2.4.3 | 6.6.2.4.4 |
| 6.6.2.5.1 | 6.6.2.5.2 | 6.6.2.5.3 | 6.6.2.5.4 | 6.6.2.6.1 | 6.6.2.6.2 | 6.6.2.6.3 | 6.6.2.6.4 |
| 6.6.2.7.1 | 6.6.2.7.2 | 6.6.2.7.3 | 6.6.2.7.4 | 6.6.2.8.1 | 6.6.2.8.2 | 6.6.2.8.3 | 6.6.2.8.4 |
| 6.6.3.1.1 | 6.6.3.1.2 | 6.6.3.1.3 | 6.6.3.1.4 | 6.6.3.2.1 | 6.6.3.2.2 | 6.6.3.2.3 | 6.6.3.2.4 |
| 6.6.3.3.1 | 6.6.3.3.2 | 6.6.3.3.3 | 6.6.3.3.4 | 6.6.3.4.1 | 6.6.3.4.2 | 6.6.3.4.3 | 6.6.3.4.4 |
| 6.6.3.5.1 | 6.6.3.5.2 | 6.6.3.5.3 | 6.6.3.5.4 | 6.6.3.6.1 | 6.6.3.6.2 | 6.6.3.6.3 | 6.6.3.6.4 |
| 6.6.3.7.1 | 6.6.3.7.2 | 6.6.3.7.3 | 6.6.3.7.4 | 6.6.3.8.1 | 6.6.3.8.2 | 6.6.3.8.3 | 6.6.3.8.4 |
| 6.6.4.1.1 | 6.6.4.1.2 | 6.6.4.1.3 | 6.6.4.1.4 | 6.6.4.2.1 | 6.6.4.2.2 | 6.6.4.2.3 | 6.6.4.2.4 |
| 6.6.4.3.1 | 6.6.4.3.2 | 6.6.4.3.3 | 6.6.4.3.4 | 6.6.4.4.1 | 6.6.4.4.2 | 6.6.4.4.3 | 6.6.4.4.4 |
| 6.6.4.5.1 | 6.6.4.5.2 | 6.6.4.5.3 | 6.6.4.5.4 | 6.6.4.6.1 | 6.6.4.6.2 | 6.6.4.6.3 | 6.6.4.6.4 |
| 6.6.4.7.1 | 6.6.4.7.2 | 6.6.4.7.3 | 6.6.4.7.4 | 6.6.4.8.1 | 6.6.4.8.2 | 6.6.4.8.3 | 6.6.4.8.4 |
| 6.7.1.1.1 | 6.7.1.1.2 | 6.7.1.1.3 | 6.7.1.1.4 | 6.7.1.2.1 | 6.7.1.2.2 | 6.7.1.2.3 | 6.7.1.2.4 |
| 6.7.1.3.1 | 6.7.1.3.2 | 6.7.1.3.3 | 6.7.1.3.4 | 6.7.1.4.1 | 6.7.1.4.2 | 6.7.1.4.3 | 6.7.1.4.4 |
| 6.7.1.5.1 | 6.7.1.5.2 | 6.7.1.5.3 | 6.7.1.5.4 | 6.7.1.6.1 | 6.7.1.6.2 | 6.7.1.6.3 | 6.7.1.6.4 |
| 6.7.1.7.1 | 6.7.1.7.2 | 6.7.1.7.3 | 6.7.1.7.4 | 6.7.1.8.1 | 6.7.1.8.2 | 6.7.1.8.3 | 6.7.1.8.4 |
| 6.7.2.1.1 | 6.7.2.1.2 | 6.7.2.1.3 | 6.7.2.1.4 | 6.7.2.2.1 | 6.7.2.2.2 | 6.7.2.2.3 | 6.7.2.2.4 |
| 6.7.2.3.1 | 6.7.2.3.2 | 6.7.2.3.3 | 6.7.2.3.4 | 6.7.2.4.1 | 6.7.2.4.2 | 6.7.2.4.3 | 6.7.2.4.4 |
| 6.7.2.5.1 | 6.7.2.5.2 | 6.7.2.5.3 | 6.7.2.5.4 | 6.7.2.6.1 | 6.7.2.6.2 | 6.7.2.6.3 | 6.7.2.6.4 |
| 6.7.2.7.1 | 6.7.2.7.2 | 6.7.2.7.3 | 6.7.2.7.4 | 6.7.2.8.1 | 6.7.2.8.2 | 6.7.2.8.3 | 6.7.2.8.4 |
| 6.7.3.1.1 | 6.7.3.1.2 | 6.7.3.1.3 | 6.7.3.1.4 | 6.7.3.2.1 | 6.7.3.2.2 | 6.7.3.2.3 | 6.7.3.2.4 |
| 6.7.3.3.1 | 6.7.3.3.2 | 6.7.3.3.3 | 6.7.3.3.4 | 6.7.3.4.1 | 6.7.3.4.2 | 6.7.3.4.3 | 6.7.3.4.4 |
| 6.7.3.5.1 | 6.7.3.5.2 | 6.7.3.5.3 | 6.7.3.5.4 | 6.7.3.6.1 | 6.7.3.6.2 | 6.7.3.6.3 | 6.7.3.6.4 |
| 6.7.3.7.1 | 6.7.3.7.2 | 6.7.3.7.3 | 6.7.3.7.4 | 6.7.3.8.1 | 6.7.3.8.2 | 6.7.3.8.3 | 6.7.3.8.4 |
| 6.7.4.1.1 | 6.7.4.1.2 | 6.7.4.1.3 | 6.7.4.1.4 | 6.7.4.2.1 | 6.7.4.2.2 | 6.7.4.2.3 | 6.7.4.2.4 |

TABLE 1-continued

| | | | | | | | |
|---|---|---|---|---|---|---|---|
| 6.7.4.3.1 | 6.7.4.3.2 | 6.7.4.3.3 | 6.7.4.3.4 | 6.7.4.4.1 | 6.7.4.4.2 | 6.7.4.4.3 | 6.7.4.4.4 |
| 6.7.4.5.1 | 6.7.4.5.2 | 6.7.4.5.3 | 6.7.4.5.4 | 6.7.4.6.1 | 6.7.4.6.2 | 6.7.4.6.3 | 6.7.4.6.4 |
| 6.7.4.7.1 | 6.7.4.7.2 | 6.7.4.7.3 | 6.7.4.7.4 | 6.7.4.8.1 | 6.7.4.8.2 | 6.7.4.8.3 | 6.7.4.8.4 |
| 6.8.1.1.1 | 6.8.1.1.2 | 6.8.1.1.3 | 6.8.1.1.4 | 6.8.1.2.1 | 6.8.1.2.2 | 6.8.1.2.3 | 6.8.1.2.4 |
| 6.8.1.3.1 | 6.8.1.3.2 | 6.8.1.3.3 | 6.8.1.3.4 | 6.8.1.4.1 | 6.8.1.4.2 | 6.8.1.4.3 | 6.8.1.4.4 |
| 6.8.1.5.1 | 6.8.1.5.2 | 6.8.1.5.3 | 6.8.1.5.4 | 6.8.1.6.1 | 6.8.1.6.2 | 6.8.1.6.3 | 6.8.1.6.4 |
| 6.8.1.7.1 | 6.8.1.7.2 | 6.8.1.7.3 | 6.8.1.7.4 | 6.8.1.8.1 | 6.8.1.8.2 | 6.8.1.8.3 | 6.8.1.8.4 |
| 6.8.2.1.1 | 6.8.2.1.2 | 6.8.2.1.3 | 6.8.2.1.4 | 6.8.2.2.1 | 6.8.2.2.2 | 6.8.2.2.3 | 6.8.2.2.4 |
| 6.8.2.3.1 | 6.8.2.3.2 | 6.8.2.3.3 | 6.8.2.3.4 | 6.8.2.4.1 | 6.8.2.4.2 | 6.8.2.4.3 | 6.8.2.4.4 |
| 6.8.2.5.1 | 6.8.2.5.2 | 6.8.2.5.3 | 6.8.2.5.4 | 6.8.2.6.1 | 6.8.2.6.2 | 6.8.2.6.3 | 6.8.2.6.4 |
| 6.8.2.7.1 | 6.8.2.7.2 | 6.8.2.7.3 | 6.8.2.7.4 | 6.8.2.8.1 | 6.8.2.8.2 | 6.8.2.8.3 | 6.8.2.8.4 |
| 6.8.3.1.1 | 6.8.3.1.2 | 6.8.3.1.3 | 6.8.3.1.4 | 6.8.3.2.1 | 6.8.3.2.2 | 6.8.3.2.3 | 6.8.3.2.4 |
| 6.8.3.3.1 | 6.8.3.3.2 | 6.8.3.3.3 | 6.8.3.3.4 | 6.8.3.4.1 | 6.8.3.4.2 | 6.8.3.4.3 | 6.8.3.4.4 |
| 6.8.3.5.1 | 6.8.3.5.2 | 6.8.3.5.3 | 6.8.3.5.4 | 6.8.3.6.1 | 6.8.3.6.2 | 6.8.3.6.3 | 6.8.3.6.4 |
| 6.8.3.7.1 | 6.8.3.7.2 | 6.8.3.7.3 | 6.8.3.7.4 | 6.8.3.8.1 | 6.8.3.8.2 | 6.8.3.8.3 | 6.8.3.8.4 |
| 6.8.4.1.1 | 6.8.4.1.2 | 6.8.4.1.3 | 6.8.4.1.4 | 6.8.4.2.1 | 6.8.4.2.2 | 6.8.4.2.3 | 6.8.4.2.4 |
| 6.8.4.3.1 | 6.8.4.3.2 | 6.8.4.3.3 | 6.8.4.3.4 | 6.8.4.4.1 | 6.8.4.4.2 | 6.8.4.4.3 | 6.8.4.4.4 |
| 6.8.4.5.1 | 6.8.4.5.2 | 6.8.4.5.3 | 6.8.4.5.4 | 6.8.4.6.1 | 6.8.4.6.2 | 6.8.4.6.3 | 6.8.4.6.4 |
| 6.8.4.7.1 | 6.8.4.7.2 | 6.8.4.7.3 | 6.8.4.7.4 | 6.8.4.8.1 | 6.8.4.8.2 | 6.8.4.8.3 | 6.8.4.8.4 |
| 7.1.1.1.1 | 7.1.1.1.2 | 7.1.1.1.3 | 7.1.1.1.4 | 7.1.1.2.1 | 7.1.1.2.2 | 7.1.1.2.3 | 7.1.1.2.4 |
| 7.1.1.3.1 | 7.1.1.3.2 | 7.1.1.3.3 | 7.1.1.3.4 | 7.1.1.4.1 | 7.1.1.4.2 | 7.1.1.4.3 | 7.1.1.4.4 |
| 7.1.1.5.1 | 7.1.1.5.2 | 7.1.1.5.3 | 7.1.1.5.4 | 7.1.1.6.1 | 7.1.1.6.2 | 7.1.1.6.3 | 7.1.1.6.4 |
| 7.1.1.7.1 | 7.1.1.7.2 | 7.1.1.7.3 | 7.1.1.7.4 | 7.1.1.8.1 | 7.1.1.8.2 | 7.1.1.8.3 | 7.1.1.8.4 |
| 7.1.2.1.1 | 7.1.2.1.2 | 7.1.2.1.3 | 7.1.2.1.4 | 7.1.2.2.1 | 7.1.2.2.2 | 7.1.2.2.3 | 7.1.2.2.4 |
| 7.1.2.3.1 | 7.1.2.3.2 | 7.1.2.3.3 | 7.1.2.3.4 | 7.1.2.4.1 | 7.1.2.4.2 | 7.1.2.4.3 | 7.1.2.4.4 |
| 7.1.2.5.1 | 7.1.2.5.2 | 7.1.2.5.3 | 7.1.2.5.4 | 7.1.2.6.1 | 7.1.2.6.2 | 7.1.2.6.3 | 7.1.2.6.4 |
| 7.1.2.7.1 | 7.1.2.7.2 | 7.1.2.7.3 | 7.1.2.7.4 | 7.1.2.8.1 | 7.1.2.8.2 | 7.1.2.8.3 | 7.1.2.8.4 |
| 7.1.3.1.1 | 7.1.3.1.2 | 7.1.3.1.3 | 7.1.3.1.4 | 7.1.3.2.1 | 7.1.3.2.2 | 7.1.3.2.3 | 7.1.3.2.4 |
| 7.1.3.3.1 | 7.1.3.3.2 | 7.1.3.3.3 | 7.1.3.3.4 | 7.1.3.4.1 | 7.1.3.4.2 | 7.1.3.4.3 | 7.1.3.4.4 |
| 7.1.3.5.1 | 7.1.3.5.2 | 7.1.3.5.3 | 7.1.3.5.4 | 7.1.3.6.1 | 7.1.3.6.2 | 7.1.3.6.3 | 7.1.3.6.4 |
| 7.1.3.7.1 | 7.1.3.7.2 | 7.1.3.7.3 | 7.1.3.7.4 | 7.1.3.8.1 | 7.1.3.8.2 | 7.1.3.8.3 | 7.1.3.8.4 |
| 7.1.4.1.1 | 7.1.4.1.2 | 7.1.4.1.3 | 7.1.4.1.4 | 7.1.4.2.1 | 7.1.4.2.2 | 7.1.4.2.3 | 7.1.4.2.4 |
| 7.1.4.3.1 | 7.1.4.3.2 | 7.1.4.3.3 | 7.1.4.3.4 | 7.1.4.4.1 | 7.1.4.4.2 | 7.1.4.4.3 | 7.1.4.4.4 |
| 7.1.4.5.1 | 7.1.4.5.2 | 7.1.4.5.3 | 7.1.4.5.4 | 7.1.4.6.1 | 7.1.4.6.2 | 7.1.4.6.3 | 7.1.4.6.4 |
| 7.1.4.7.1 | 7.1.4.7.2 | 7.1.4.7.3 | 7.1.4.7.4 | 7.1.4.8.1 | 7.1.4.8.2 | 7.1.4.8.3 | 7.1.4.8.4 |
| 7.2.1.1.1 | 7.2.1.1.2 | 7.2.1.1.3 | 7.2.1.1.4 | 7.2.1.2.1 | 7.2.1.2.2 | 7.2.1.2.3 | 7.2.1.2.4 |
| 7.2.1.3.1 | 7.2.1.3.2 | 7.2.1.3.3 | 7.2.1.3.4 | 7.2.1.4.1 | 7.2.1.4.2 | 7.2.1.4.3 | 7.2.1.4.4 |
| 7.2.1.5.1 | 7.2.1.5.2 | 7.2.1.5.3 | 7.2.1.5.4 | 7.2.1.6.1 | 7.2.1.6.2 | 7.2.1.6.3 | 7.2.1.6.4 |
| 7.2.1.7.1 | 7.2.1.7.2 | 7.2.1.7.3 | 7.2.1.7.4 | 7.2.1.8.1 | 7.2.1.8.2 | 7.2.1.8.3 | 7.2.1.8.4 |
| 7.2.2.1.1 | 7.2.2.1.2 | 7.2.2.1.3 | 7.2.2.1.4 | 7.2.2.2.1 | 7.2.2.2.2 | 7.2.2.2.3 | 7.2.2.2.4 |
| 7.2.2.3.1 | 7.2.2.3.2 | 7.2.2.3.3 | 7.2.2.3.4 | 7.2.2.4.1 | 7.2.2.4.2 | 7.2.2.4.3 | 7.2.2.4.4 |
| 7.2.2.5.1 | 7.2.2.5.2 | 7.2.2.5.3 | 7.2.2.5.4 | 7.2.2.6.1 | 7.2.2.6.2 | 7.2.2.6.3 | 7.2.2.6.4 |
| 7.2.2.7.1 | 7.2.2.7.2 | 7.2.2.7.3 | 7.2.2.7.4 | 7.2.2.8.1 | 7.2.2.8.2 | 7.2.2.8.3 | 7.2.2.8.4 |
| 7.2.3.1.1 | 7.2.3.1.2 | 7.2.3.1.3 | 7.2.3.1.4 | 7.2.3.2.1 | 7.2.3.2.2 | 7.2.3.2.3 | 7.2.3.2.4 |
| 7.2.3.3.1 | 7.2.3.3.2 | 7.2.3.3.3 | 7.2.3.3.4 | 7.2.3.4.1 | 7.2.3.4.2 | 7.2.3.4.3 | 7.2.3.4.4 |
| 7.2.3.5.1 | 7.2.3.5.2 | 7.2.3.5.3 | 7.2.3.5.4 | 7.2.3.6.1 | 7.2.3.6.2 | 7.2.3.6.3 | 7.2.3.6.4 |
| 7.2.3.7.1 | 7.2.3.7.2 | 7.2.3.7.3 | 7.2.3.7.4 | 7.2.3.8.1 | 7.2.3.8.2 | 7.2.3.8.3 | 7.2.3.8.4 |
| 7.2.4.1.1 | 7.2.4.1.2 | 7.2.4.1.3 | 7.2.4.1.4 | 7.2.4.2.1 | 7.2.4.2.2 | 7.2.4.2.3 | 7.2.4.2.4 |
| 7.2.4.3.1 | 7.2.4.3.2 | 7.2.4.3.3 | 7.2.4.3.4 | 7.2.4.4.1 | 7.2.4.4.2 | 7.2.4.4.3 | 7.2.4.4.4 |
| 7.2.4.5.1 | 7.2.4.5.2 | 7.2.4.5.3 | 7.2.4.5.4 | 7.2.4.6.1 | 7.2.4.6.2 | 7.2.4.6.3 | 7.2.4.6.4 |
| 7.2.4.7.1 | 7.2.4.7.2 | 7.2.4.7.3 | 7.2.4.7.4 | 7.2.4.8.1 | 7.2.4.8.2 | 7.2.4.8.3 | 7.2.4.8.4 |
| 7.3.1.1.1 | 7.3.1.1.2 | 7.3.1.1.3 | 7.3.1.1.4 | 7.3.1.2.1 | 7.3.1.2.2 | 7.3.1.2.3 | 7.3.1.2.4 |
| 7.3.1.3.1 | 7.3.1.3.2 | 7.3.1.3.3 | 7.3.1.3.4 | 7.3.1.4.1 | 7.3.1.4.2 | 7.3.1.4.3 | 7.3.1.4.4 |
| 7.3.1.5.1 | 7.3.1.5.2 | 7.3.1.5.3 | 7.3.1.5.4 | 7.3.1.6.1 | 7.3.1.6.2 | 7.3.1.6.3 | 7.3.1.6.4 |
| 7.3.1.7.1 | 7.3.1.7.2 | 7.3.1.7.3 | 7.3.1.7.4 | 7.3.1.8.1 | 7.3.1.8.2 | 7.3.1.8.3 | 7.3.1.8.4 |
| 7.3.2.1.1 | 7.3.2.1.2 | 7.3.2.1.3 | 7.3.2.1.4 | 7.3.2.2.1 | 7.3.2.2.2 | 7.3.2.2.3 | 7.3.2.2.4 |
| 7.3.2.3.1 | 7.3.2.3.2 | 7.3.2.3.3 | 7.3.2.3.4 | 7.3.2.4.1 | 7.3.2.4.2 | 7.3.2.4.3 | 7.3.2.4.4 |
| 7.3.2.5.1 | 7.3.2.5.2 | 7.3.2.5.3 | 7.3.2.5.4 | 7.3.2.6.1 | 7.3.2.6.2 | 7.3.2.6.3 | 7.3.2.6.4 |
| 7.3.2.7.1 | 7.3.2.7.2 | 7.3.2.7.3 | 7.3.2.7.4 | 7.3.2.8.1 | 7.3.2.8.2 | 7.3.2.8.3 | 7.3.2.8.4 |
| 7.3.3.1.1 | 7.3.3.1.2 | 7.3.3.1.3 | 7.3.3.1.4 | 7.3.3.2.1 | 7.3.3.2.2 | 7.3.3.2.3 | 7.3.3.2.4 |
| 7.3.3.3.1 | 7.3.3.3.2 | 7.3.3.3.3 | 7.3.3.3.4 | 7.3.3.4.1 | 7.3.3.4.2 | 7.3.3.4.3 | 7.3.3.4.4 |
| 7.3.3.5.1 | 7.3.3.5.2 | 7.3.3.5.3 | 7.3.3.5.4 | 7.3.3.6.1 | 7.3.3.6.2 | 7.3.3.6.3 | 7.3.3.6.4 |
| 7.3.3.7.1 | 7.3.3.7.2 | 7.3.3.7.3 | 7.3.3.7.4 | 7.3.3.8.1 | 7.3.3.8.2 | 7.3.3.8.3 | 7.3.3.8.4 |
| 7.3.4.1.1 | 7.3.4.1.2 | 7.3.4.1.3 | 7.3.4.1.4 | 7.3.4.2.1 | 7.3.4.2.2 | 7.3.4.2.3 | 7.3.4.2.4 |
| 7.3.4.3.1 | 7.3.4.3.2 | 7.3.4.3.3 | 7.3.4.3.4 | 7.3.4.4.1 | 7.3.4.4.2 | 7.3.4.4.3 | 7.3.4.4.4 |
| 7.3.4.5.1 | 7.3.4.5.2 | 7.3.4.5.3 | 7.3.4.5.4 | 7.3.4.6.1 | 7.3.4.6.2 | 7.3.4.6.3 | 7.3.4.6.4 |
| 7.3.4.7.1 | 7.3.4.7.2 | 7.3.4.7.3 | 7.3.4.7.4 | 7.3.4.8.1 | 7.3.4.8.2 | 7.3.4.8.3 | 7.3.4.8.4 |
| 7.4.1.1.1 | 7.4.1.1.2 | 7.4.1.1.3 | 7.4.1.1.4 | 7.4.1.2.1 | 7.4.1.2.2 | 7.4.1.2.3 | 7.4.1.2.4 |
| 7.4.1.3.1 | 7.4.1.3.2 | 7.4.1.3.3 | 7.4.1.3.4 | 7.4.1.4.1 | 7.4.1.4.2 | 7.4.1.4.3 | 7.4.1.4.4 |
| 7.4.1.5.1 | 7.4.1.5.2 | 7.4.1.5.3 | 7.4.1.5.4 | 7.4.1.6.1 | 7.4.1.6.2 | 7.4.1.6.3 | 7.4.1.6.4 |
| 7.4.1.7.1 | 7.4.1.7.2 | 7.4.1.7.3 | 7.4.1.7.4 | 7.4.1.8.1 | 7.4.1.8.2 | 7.4.1.8.3 | 7.4.1.8.4 |
| 7.4.2.1.1 | 7.4.2.1.2 | 7.4.2.1.3 | 7.4.2.1.4 | 7.4.2.2.1 | 7.4.2.2.2 | 7.4.2.2.3 | 7.4.2.2.4 |
| 7.4.2.3.1 | 7.4.2.3.2 | 7.4.2.3.3 | 7.4.2.3.4 | 7.4.2.4.1 | 7.4.2.4.2 | 7.4.2.4.3 | 7.4.2.4.4 |
| 7.4.2.5.1 | 7.4.2.5.2 | 7.4.2.5.3 | 7.4.2.5.4 | 7.4.2.6.1 | 7.4.2.6.2 | 7.4.2.6.3 | 7.4.2.6.4 |
| 7.4.2.7.1 | 7.4.2.7.2 | 7.4.2.7.3 | 7.4.2.7.4 | 7.4.2.8.1 | 7.4.2.8.2 | 7.4.2.8.3 | 7.4.2.8.4 |
| 7.4.3.1.1 | 7.4.3.1.2 | 7.4.3.1.3 | 7.4.3.1.4 | 7.4.3.2.1 | 7.4.3.2.2 | 7.4.3.2.3 | 7.4.3.2.4 |
| 7.4.3.3.1 | 7.4.3.3.2 | 7.4.3.3.3 | 7.4.3.3.4 | 7.4.3.4.1 | 7.4.3.4.2 | 7.4.3.4.3 | 7.4.3.4.4 |
| 7.4.3.5.1 | 7.4.3.5.2 | 7.4.3.5.3 | 7.4.3.5.4 | 7.4.3.6.1 | 7.4.3.6.2 | 7.4.3.6.3 | 7.4.3.6.4 |
| 7.4.3.7.1 | 7.4.3.7.2 | 7.4.3.7.3 | 7.4.3.7.4 | 7.4.3.8.1 | 7.4.3.8.2 | 7.4.3.8.3 | 7.4.3.8.4 |

TABLE 1-continued

| | | | | | | | |
|---|---|---|---|---|---|---|---|
| 7.4.4.1.1 | 7.4.4.1.2 | 7.4.4.1.3 | 7.4.4.1.4 | 7.4.4.2.1 | 7.4.4.2.2 | 7.4.4.2.3 | 7.4.4.2.4 |
| 7.4.4.3.1 | 7.4.4.3.2 | 7.4.4.3.3 | 7.4.4.3.4 | 7.4.4.4.1 | 7.4.4.4.2 | 7.4.4.4.3 | 7.4.4.4.4 |
| 7.4.4.5.1 | 7.4.4.5.2 | 7.4.4.5.3 | 7.4.4.5.4 | 7.4.4.6.1 | 7.4.4.6.2 | 7.4.4.6.3 | 7.4.4.6.4 |
| 7.4.4.7.1 | 7.4.4.7.2 | 7.4.4.7.3 | 7.4.4.7.4 | 7.4.4.8.1 | 7.4.4.8.2 | 7.4.4.8.3 | 7.4.4.8.4 |
| 7.5.1.1.1 | 7.5.1.1.2 | 7.5.1.1.3 | 7.5.1.1.4 | 7.5.1.2.1 | 7.5.1.2.2 | 7.5.1.2.3 | 7.5.1.2.4 |
| 7.5.1.3.1 | 7.5.1.3.2 | 7.5.1.3.3 | 7.5.1.3.4 | 7.5.1.4.1 | 7.5.1.4.2 | 7.5.1.4.3 | 7.5.1.4.4 |
| 7.5.1.5.1 | 7.5.1.5.2 | 7.5.1.5.3 | 7.5.1.5.4 | 7.5.1.6.1 | 7.5.1.6.2 | 7.5.1.6.3 | 7.5.1.6.4 |
| 7.5.1.7.1 | 7.5.1.7.2 | 7.5.1.7.3 | 7.5.1.7.4 | 7.5.1.8.1 | 7.5.1.8.2 | 7.5.1.8.3 | 7.5.1.8.4 |
| 7.5.2.1.1 | 7.5.2.1.2 | 7.5.2.1.3 | 7.5.2.1.4 | 7.5.2.2.1 | 7.5.2.2.2 | 7.5.2.2.3 | 7.5.2.2.4 |
| 7.5.2.3.1 | 7.5.2.3.2 | 7.5.2.3.3 | 7.5.2.3.4 | 7.5.2.4.1 | 7.5.2.4.2 | 7.5.2.4.3 | 7.5.2.4.4 |
| 7.5.2.5.1 | 7.5.2.5.2 | 7.5.2.5.3 | 7.5.2.5.4 | 7.5.2.6.1 | 7.5.2.6.2 | 7.5.2.6.3 | 7.5.2.6.4 |
| 7.5.2.7.1 | 7.5.2.7.2 | 7.5.2.7.3 | 7.5.2.7.4 | 7.5.2.8.1 | 7.5.2.8.2 | 7.5.2.8.3 | 7.5.2.8.4 |
| 7.5.3.1.1 | 7.5.3.1.2 | 7.5.3.1.3 | 7.5.3.1.4 | 7.5.3.2.1 | 7.5.3.2.2 | 7.5.3.2.3 | 7.5.3.2.4 |
| 7.5.3.3.1 | 7.5.3.3.2 | 7.5.3.3.3 | 7.5.3.3.4 | 7.5.3.4.1 | 7.5.3.4.2 | 7.5.3.4.3 | 7.5.3.4.4 |
| 7.5.3.5.1 | 7.5.3.5.2 | 7.5.3.5.3 | 7.5.3.5.4 | 7.5.3.6.1 | 7.5.3.6.2 | 7.5.3.6.3 | 7.5.3.6.4 |
| 7.5.3.7.1 | 7.5.3.7.2 | 7.5.3.7.3 | 7.5.3.7.4 | 7.5.3.8.1 | 7.5.3.8.2 | 7.5.3.8.3 | 7.5.3.8.4 |
| 7.5.4.1.1 | 7.5.4.1.2 | 7.5.4.1.3 | 7.5.4.1.4 | 7.5.4.2.1 | 7.5.4.2.2 | 7.5.4.2.3 | 7.5.4.2.4 |
| 7.5.4.3.1 | 7.5.4.3.2 | 7.5.4.3.3 | 7.5.4.3.4 | 7.5.4.4.1 | 7.5.4.4.2 | 7.5.4.4.3 | 7.5.4.4.4 |
| 7.5.4.5.1 | 7.5.4.5.2 | 7.5.4.5.3 | 7.5.4.5.4 | 7.5.4.6.1 | 7.5.4.6.2 | 7.5.4.6.3 | 7.5.4.6.4 |
| 7.5.4.7.1 | 7.5.4.7.2 | 7.5.4.7.3 | 7.5.4.7.4 | 7.5.4.8.1 | 7.5.4.8.2 | 7.5.4.8.3 | 7.5.4.8.4 |
| 7.6.1.1.1 | 7.6.1.1.2 | 7.6.1.1.3 | 7.6.1.1.4 | 7.6.1.2.1 | 7.6.1.2.2 | 7.6.1.2.3 | 7.6.1.2.4 |
| 7.6.1.3.1 | 7.6.1.3.2 | 7.6.1.3.3 | 7.6.1.3.4 | 7.6.1.4.1 | 7.6.1.4.2 | 7.6.1.4.3 | 7.6.1.4.4 |
| 7.6.1.5.1 | 7.6.1.5.2 | 7.6.1.5.3 | 7.6.1.5.4 | 7.6.1.6.1 | 7.6.1.6.2 | 7.6.1.6.3 | 7.6.1.6.4 |
| 7.6.1.7.1 | 7.6.1.7.2 | 7.6.1.7.3 | 7.6.1.7.4 | 7.6.1.8.1 | 7.6.1.8.2 | 7.6.1.8.3 | 7.6.1.8.4 |
| 7.6.2.1.1 | 7.6.2.1.2 | 7.6.2.1.3 | 7.6.2.1.4 | 7.6.2.2.1 | 7.6.2.2.2 | 7.6.2.2.3 | 7.6.2.2.4 |
| 7.6.2.3.1 | 7.6.2.3.2 | 7.6.2.3.3 | 7.6.2.3.4 | 7.6.2.4.1 | 7.6.2.4.2 | 7.6.2.4.3 | 7.6.2.4.4 |
| 7.6.2.5.1 | 7.6.2.5.2 | 7.6.2.5.3 | 7.6.2.5.4 | 7.6.2.6.1 | 7.6.2.6.2 | 7.6.2.6.3 | 7.6.2.6.4 |
| 7.6.2.7.1 | 7.6.2.7.2 | 7.6.2.7.3 | 7.6.2.7.4 | 7.6.2.8.1 | 7.6.2.8.2 | 7.6.2.8.3 | 7.6.2.8.4 |
| 7.6.3.1.1 | 7.6.3.1.2 | 7.6.3.1.3 | 7.6.3.1.4 | 7.6.3.2.1 | 7.6.3.2.2 | 7.6.3.2.3 | 7.6.3.2.4 |
| 7.6.3.3.1 | 7.6.3.3.2 | 7.6.3.3.3 | 7.6.3.3.4 | 7.6.3.4.1 | 7.6.3.4.2 | 7.6.3.4.3 | 7.6.3.4.4 |
| 7.6.3.5.1 | 7.6.3.5.2 | 7.6.3.5.3 | 7.6.3.5.4 | 7.6.3.6.1 | 7.6.3.6.2 | 7.6.3.6.3 | 7.6.3.6.4 |
| 7.6.3.7.1 | 7.6.3.7.2 | 7.6.3.7.3 | 7.6.3.7.4 | 7.6.3.8.1 | 7.6.3.8.2 | 7.6.3.8.3 | 7.6.3.8.4 |
| 7.6.4.1.1 | 7.6.4.1.2 | 7.6.4.1.3 | 7.6.4.1.4 | 7.6.4.2.1 | 7.6.4.2.2 | 7.6.4.2.3 | 7.6.4.2.4 |
| 7.6.4.3.1 | 7.6.4.3.2 | 7.6.4.3.3 | 7.6.4.3.4 | 7.6.4.4.1 | 7.6.4.4.2 | 7.6.4.4.3 | 7.6.4.4.4 |
| 7.6.4.5.1 | 7.6.4.5.2 | 7.6.4.5.3 | 7.6.4.5.4 | 7.6.4.6.1 | 7.6.4.6.2 | 7.6.4.6.3 | 7.6.4.6.4 |
| 7.6.4.7.1 | 7.6.4.7.2 | 7.6.4.7.3 | 7.6.4.7.4 | 7.6.4.8.1 | 7.6.4.8.2 | 7.6.4.8.3 | 7.6.4.8.4 |
| 7.7.1.1.1 | 7.7.1.1.2 | 7.7.1.1.3 | 7.7.1.1.4 | 7.7.1.2.1 | 7.7.1.2.2 | 7.7.1.2.3 | 7.7.1.2.4 |
| 7.7.1.3.1 | 7.7.1.3.2 | 7.7.1.3.3 | 7.7.1.3.4 | 7.7.1.4.1 | 7.7.1.4.2 | 7.7.1.4.3 | 7.7.1.4.4 |
| 7.7.1.5.1 | 7.7.1.5.2 | 7.7.1.5.3 | 7.7.1.5.4 | 7.7.1.6.1 | 7.7.1.6.2 | 7.7.1.6.3 | 7.7.1.6.4 |
| 7.7.1.7.1 | 7.7.1.7.2 | 7.7.1.7.3 | 7.7.1.7.4 | 7.7.1.8.1 | 7.7.1.8.2 | 7.7.1.8.3 | 7.7.1.8.4 |
| 7.7.2.1.1 | 7.7.2.1.2 | 7.7.2.1.3 | 7.7.2.1.4 | 7.7.2.2.1 | 7.7.2.2.2 | 7.7.2.2.3 | 7.7.2.2.4 |
| 7.7.2.3.1 | 7.7.2.3.2 | 7.7.2.3.3 | 7.7.2.3.4 | 7.7.2.4.1 | 7.7.2.4.2 | 7.7.2.4.3 | 7.7.2.4.4 |
| 7.7.2.5.1 | 7.7.2.5.2 | 7.7.2.5.3 | 7.7.2.5.4 | 7.7.2.6.1 | 7.7.2.6.2 | 7.7.2.6.3 | 7.7.2.6.4 |
| 7.7.2.7.1 | 7.7.2.7.2 | 7.7.2.7.3 | 7.7.2.7.4 | 7.7.2.8.1 | 7.7.2.8.2 | 7.7.2.8.3 | 7.7.2.8.4 |
| 7.7.3.1.1 | 7.7.3.1.2 | 7.7.3.1.3 | 7.7.3.1.4 | 7.7.3.2.1 | 7.7.3.2.2 | 7.7.3.2.3 | 7.7.3.2.4 |
| 7.7.3.3.1 | 7.7.3.3.2 | 7.7.3.3.3 | 7.7.3.3.4 | 7.7.3.4.1 | 7.7.3.4.2 | 7.7.3.4.3 | 7.7.3.4.4 |
| 7.7.3.5.1 | 7.7.3.5.2 | 7.7.3.5.3 | 7.7.3.5.4 | 7.7.3.6.1 | 7.7.3.6.2 | 7.7.3.6.3 | 7.7.3.6.4 |
| 7.7.3.7.1 | 7.7.3.7.2 | 7.7.3.7.3 | 7.7.3.7.4 | 7.7.3.8.1 | 7.7.3.8.2 | 7.7.3.8.3 | 7.7.3.8.4 |
| 7.7.4.1.1 | 7.7.4.1.2 | 7.7.4.1.3 | 7.7.4.1.4 | 7.7.4.2.1 | 7.7.4.2.2 | 7.7.4.2.3 | 7.7.4.2.4 |
| 7.7.4.3.1 | 7.7.4.3.2 | 7.7.4.3.3 | 7.7.4.3.4 | 7.7.4.4.1 | 7.7.4.4.2 | 7.7.4.4.3 | 7.7.4.4.4 |
| 7.7.4.5.1 | 7.7.4.5.2 | 7.7.4.5.3 | 7.7.4.5.4 | 7.7.4.6.1 | 7.7.4.6.2 | 7.7.4.6.3 | 7.7.4.6.4 |
| 7.7.4.7.1 | 7.7.4.7.2 | 7.7.4.7.3 | 7.7.4.7.4 | 7.7.4.8.1 | 7.7.4.8.2 | 7.7.4.8.3 | 7.7.4.8.4 |
| 7.8.1.1.1 | 7.8.1.1.2 | 7.8.1.1.3 | 7.8.1.1.4 | 7.8.1.2.1 | 7.8.1.2.2 | 7.8.1.2.3 | 7.8.1.2.4 |
| 7.8.1.3.1 | 7.8.1.3.2 | 7.8.1.3.3 | 7.8.1.3.4 | 7.8.1.4.1 | 7.8.1.4.2 | 7.8.1.4.3 | 7.8.1.4.4 |
| 7.8.1.5.1 | 7.8.1.5.2 | 7.8.1.5.3 | 7.8.1.5.4 | 7.8.1.6.1 | 7.8.1.6.2 | 7.8.1.6.3 | 7.8.1.6.4 |
| 7.8.1.7.1 | 7.8.1.7.2 | 7.8.1.7.3 | 7.8.1.7.4 | 7.8.1.8.1 | 7.8.1.8.2 | 7.8.1.8.3 | 7.8.1.8.4 |
| 7.8.2.1.1 | 7.8.2.1.2 | 7.8.2.1.3 | 7.8.2.1.4 | 7.8.2.2.1 | 7.8.2.2.2 | 7.8.2.2.3 | 7.8.2.2.4 |
| 7.8.2.3.1 | 7.8.2.3.2 | 7.8.2.3.3 | 7.8.2.3.4 | 7.8.2.4.1 | 7.8.2.4.2 | 7.8.2.4.3 | 7.8.2.4.4 |
| 7.8.2.5.1 | 7.8.2.5.2 | 7.8.2.5.3 | 7.8.2.5.4 | 7.8.2.6.1 | 7.8.2.6.2 | 7.8.2.6.3 | 7.8.2.6.4 |
| 7.8.2.7.1 | 7.8.2.7.2 | 7.8.2.7.3 | 7.8.2.7.4 | 7.8.2.8.1 | 7.8.2.8.2 | 7.8.2.8.3 | 7.8.2.8.4 |
| 7.8.3.1.1 | 7.8.3.1.2 | 7.8.3.1.3 | 7.8.3.1.4 | 7.8.3.2.1 | 7.8.3.2.2 | 7.8.3.2.3 | 7.8.3.2.4 |
| 7.8.3.3.1 | 7.8.3.3.2 | 7.8.3.3.3 | 7.8.3.3.4 | 7.8.3.4.1 | 7.8.3.4.2 | 7.8.3.4.3 | 7.8.3.4.4 |
| 7.8.3.5.1 | 7.8.3.5.2 | 7.8.3.5.3 | 7.8.3.5.4 | 7.8.3.6.1 | 7.8.3.6.2 | 7.8.3.6.3 | 7.8.3.6.4 |
| 7.8.3.7.1 | 7.8.3.7.2 | 7.8.3.7.3 | 7.8.3.7.4 | 7.8.3.8.1 | 7.8.3.8.2 | 7.8.3.8.3 | 7.8.3.8.4 |
| 7.8.4.1.1 | 7.8.4.1.2 | 7.8.4.1.3 | 7.8.4.1.4 | 7.8.4.2.1 | 7.8.4.2.2 | 7.8.4.2.3 | 7.8.4.2.4 |
| 7.8.4.3.1 | 7.8.4.3.2 | 7.8.4.3.3 | 7.8.4.3.4 | 7.8.4.4.1 | 7.8.4.4.2 | 7.8.4.4.3 | 7.8.4.4.4 |
| 7.8.4.5.1 | 7.8.4.5.2 | 7.8.4.5.3 | 7.8.4.5.4 | 7.8.4.6.1 | 7.8.4.6.2 | 7.8.4.6.3 | 7.8.4.6.4 |
| 7.8.4.7.1 | 7.8.4.7.2 | 7.8.4.7.3 | 7.8.4.7.4 | 7.8.4.8.1 | 7.8.4.8.2 | 7.8.4.8.3 | 7.8.4.8.4 |
| 8.1.1.1.1 | 8.1.1.1.2 | 8.1.1.1.3 | 8.1.1.1.4 | 8.1.1.2.1 | 8.1.1.2.2 | 8.1.1.2.3 | 8.1.1.2.4 |
| 8.1.1.3.1 | 8.1.1.3.2 | 8.1.1.3.3 | 8.1.1.3.4 | 8.1.1.4.1 | 8.1.1.4.2 | 8.1.1.4.3 | 8.1.1.4.4 |
| 8.1.1.5.1 | 8.1.1.5.2 | 8.1.1.5.3 | 8.1.1.5.4 | 8.1.1.6.1 | 8.1.1.6.2 | 8.1.1.6.3 | 8.1.1.6.4 |
| 8.1.1.7.1 | 8.1.1.7.2 | 8.1.1.7.3 | 8.1.1.7.4 | 8.1.1.8.1 | 8.1.1.8.2 | 8.1.1.8.3 | 8.1.1.8.4 |
| 8.1.2.1.1 | 8.1.2.1.2 | 8.1.2.1.3 | 8.1.2.1.4 | 8.1.2.2.1 | 8.1.2.2.2 | 8.1.2.2.3 | 8.1.2.2.4 |
| 8.1.2.3.1 | 8.1.2.3.2 | 8.1.2.3.3 | 8.1.2.3.4 | 8.1.2.4.1 | 8.1.2.4.2 | 8.1.2.4.3 | 8.1.2.4.4 |
| 8.1.2.5.1 | 8.1.2.5.2 | 8.1.2.5.3 | 8.1.2.5.4 | 8.1.2.6.1 | 8.1.2.6.2 | 8.1.2.6.3 | 8.1.2.6.4 |
| 8.1.2.7.1 | 8.1.2.7.2 | 8.1.2.7.3 | 8.1.2.7.4 | 8.1.2.8.1 | 8.1.2.8.2 | 8.1.2.8.3 | 8.1.2.8.4 |
| 8.1.3.1.1 | 8.1.3.1.2 | 8.1.3.1.3 | 8.1.3.1.4 | 8.1.3.2.1 | 8.1.3.2.2 | 8.1.3.2.3 | 8.1.3.2.4 |
| 8.1.3.3.1 | 8.1.3.3.2 | 8.1.3.3.3 | 8.1.3.3.4 | 8.1.3.4.1 | 8.1.3.4.2 | 8.1.3.4.3 | 8.1.3.4.4 |
| 8.1.3.5.1 | 8.1.3.5.2 | 8.1.3.5.3 | 8.1.3.5.4 | 8.1.3.6.1 | 8.1.3.6.2 | 8.1.3.6.3 | 8.1.3.6.4 |

TABLE 1-continued

| | | | | | | | |
|---|---|---|---|---|---|---|---|
| 8.1.3.7.1 | 8.1.3.7.2 | 8.1.3.7.3 | 8.1.3.7.4 | 8.1.3.8.1 | 8.1.3.8.2 | 8.1.3.8.3 | 8.1.3.8.4 |
| 8.1.4.1.1 | 8.1.4.1.2 | 8.1.4.1.3 | 8.1.4.1.4 | 8.1.4.2.1 | 8.1.4.2.2 | 8.1.4.2.3 | 8.1.4.2.4 |
| 8.1.4.3.1 | 8.1.4.3.2 | 8.1.4.3.3 | 8.1.4.3.4 | 8.1.4.4.1 | 8.1.4.4.2 | 8.1.4.4.3 | 8.1.4.4.4 |
| 8.1.4.5.1 | 8.1.4.5.2 | 8.1.4.5.3 | 8.1.4.5.4 | 8.1.4.6.1 | 8.1.4.6.2 | 8.1.4.6.3 | 8.1.4.6.4 |
| 8.1.4.7.1 | 8.1.4.7.2 | 8.1.4.7.3 | 8.1.4.7.4 | 8.1.4.8.1 | 8.1.4.8.2 | 8.1.4.8.3 | 8.1.4.8.4 |
| 8.2.1.1.1 | 8.2.1.1.2 | 8.2.1.1.3 | 8.2.1.1.4 | 8.2.1.2.1 | 8.2.1.2.2 | 8.2.1.2.3 | 8.2.1.2.4 |
| 8.2.1.3.1 | 8.2.1.3.2 | 8.2.1.3.3 | 8.2.1.3.4 | 8.2.1.4.1 | 8.2.1.4.2 | 8.2.1.4.3 | 8.2.1.4.4 |
| 8.2.1.5.1 | 8.2.1.5.2 | 8.2.1.5.3 | 8.2.1.5.4 | 8.2.1.6.1 | 8.2.1.6.2 | 8.2.1.6.3 | 8.2.1.6.4 |
| 8.2.1.7.1 | 8.2.1.7.2 | 8.2.1.7.3 | 8.2.1.7.4 | 8.2.1.8.1 | 8.2.1.8.2 | 8.2.1.8.3 | 8.2.1.8.4 |
| 8.2.2.1.1 | 8.2.2.1.2 | 8.2.2.1.3 | 8.2.2.1.4 | 8.2.2.2.1 | 8.2.2.2.2 | 8.2.2.2.3 | 8.2.2.2.4 |
| 8.2.2.3.1 | 8.2.2.3.2 | 8.2.2.3.3 | 8.2.2.3.4 | 8.2.2.4.1 | 8.2.2.4.2 | 8.2.2.4.3 | 8.2.2.4.4 |
| 8.2.2.5.1 | 8.2.2.5.2 | 8.2.2.5.3 | 8.2.2.5.4 | 8.2.2.6.1 | 8.2.2.6.2 | 8.2.2.6.3 | 8.2.2.6.4 |
| 8.2.2.7.1 | 8.2.2.7.2 | 8.2.2.7.3 | 8.2.2.7.4 | 8.2.2.8.1 | 8.2.2.8.2 | 8.2.2.8.3 | 8.2.2.8.4 |
| 8.2.3.1.1 | 8.2.3.1.2 | 8.2.3.1.3 | 8.2.3.1.4 | 8.2.3.2.1 | 8.2.3.2.2 | 8.2.3.2.3 | 8.2.3.2.4 |
| 8.2.3.3.1 | 8.2.3.3.2 | 8.2.3.3.3 | 8.2.3.3.4 | 8.2.3.4.1 | 8.2.3.4.2 | 8.2.3.4.3 | 8.2.3.4.4 |
| 8.2.3.5.1 | 8.2.3.5.2 | 8.2.3.5.3 | 8.2.3.5.4 | 8.2.3.6.1 | 8.2.3.6.2 | 8.2.3.6.3 | 8.2.3.6.4 |
| 8.2.3.7.1 | 8.2.3.7.2 | 8.2.3.7.3 | 8.2.3.7.4 | 8.2.3.8.1 | 8.2.3.8.2 | 8.2.3.8.3 | 8.2.3.8.4 |
| 8.2.4.1.1 | 8.2.4.1.2 | 8.2.4.1.3 | 8.2.4.1.4 | 8.2.4.2.1 | 8.2.4.2.2 | 8.2.4.2.3 | 8.2.4.2.4 |
| 8.2.4.3.1 | 8.2.4.3.2 | 8.2.4.3.3 | 8.2.4.3.4 | 8.2.4.4.1 | 8.2.4.4.2 | 8.2.4.4.3 | 8.2.4.4.4 |
| 8.2.4.5.1 | 8.2.4.5.2 | 8.2.4.5.3 | 8.2.4.5.4 | 8.2.4.6.1 | 8.2.4.6.2 | 8.2.4.6.3 | 8.2.4.6.4 |
| 8.2.4.7.1 | 8.2.4.7.2 | 8.2.4.7.3 | 8.2.4.7.4 | 8.2.4.8.1 | 8.2.4.8.2 | 8.2.4.8.3 | 8.2.4.8.4 |
| 8.3.1.1.1 | 8.3.1.1.2 | 8.3.1.1.3 | 8.3.1.1.4 | 8.3.1.2.1 | 8.3.1.2.2 | 8.3.1.2.3 | 8.3.1.2.4 |
| 8.3.1.3.1 | 8.3.1.3.2 | 8.3.1.3.3 | 8.3.1.3.4 | 8.3.1.4.1 | 8.3.1.4.2 | 8.3.1.4.3 | 8.3.1.4.4 |
| 8.3.1.5.1 | 8.3.1.5.2 | 8.3.1.5.3 | 8.3.1.5.4 | 8.3.1.6.1 | 8.3.1.6.2 | 8.3.1.6.3 | 8.3.1.6.4 |
| 8.3.1.7.1 | 8.3.1.7.2 | 8.3.1.7.3 | 8.3.1.7.4 | 8.3.1.8.1 | 8.3.1.8.2 | 8.3.1.8.3 | 8.3.1.8.4 |
| 8.3.2.1.1 | 8.3.2.1.2 | 8.3.2.1.3 | 8.3.2.1.4 | 8.3.2.2.1 | 8.3.2.2.2 | 8.3.2.2.3 | 8.3.2.2.4 |
| 8.3.2.3.1 | 8.3.2.3.2 | 8.3.2.3.3 | 8.3.2.3.4 | 8.3.2.4.1 | 8.3.2.4.2 | 8.3.2.4.3 | 8.3.2.4.4 |
| 8.3.2.5.1 | 8.3.2.5.2 | 8.3.2.5.3 | 8.3.2.5.4 | 8.3.2.6.1 | 8.3.2.6.2 | 8.3.2.6.3 | 8.3.2.6.4 |
| 8.3.2.7.1 | 8.3.2.7.2 | 8.3.2.7.3 | 8.3.2.7.4 | 8.3.2.8.1 | 8.3.2.8.2 | 8.3.2.8.3 | 8.3.2.8.4 |
| 8.3.3.1.1 | 8.3.3.1.2 | 8.3.3.1.3 | 8.3.3.1.4 | 8.3.3.2.1 | 8.3.3.2.2 | 8.3.3.2.3 | 8.3.3.2.4 |
| 8.3.3.3.1 | 8.3.3.3.2 | 8.3.3.3.3 | 8.3.3.3.4 | 8.3.3.4.1 | 8.3.3.4.2 | 8.3.3.4.3 | 8.3.3.4.4 |
| 8.3.3.5.1 | 8.3.3.5.2 | 8.3.3.5.3 | 8.3.3.5.4 | 8.3.3.6.1 | 8.3.3.6.2 | 8.3.3.6.3 | 8.3.3.6.4 |
| 8.3.3.7.1 | 8.3.3.7.2 | 8.3.3.7.3 | 8.3.3.7.4 | 8.3.3.8.1 | 8.3.3.8.2 | 8.3.3.8.3 | 8.3.3.8.4 |
| 8.3.4.1.1 | 8.3.4.1.2 | 8.3.4.1.3 | 8.3.4.1.4 | 8.3.4.2.1 | 8.3.4.2.2 | 8.3.4.2.3 | 8.3.4.2.4 |
| 8.3.4.3.1 | 8.3.4.3.2 | 8.3.4.3.3 | 8.3.4.3.4 | 8.3.4.4.1 | 8.3.4.4.2 | 8.3.4.4.3 | 8.3.4.4.4 |
| 8.3.4.5.1 | 8.3.4.5.2 | 8.3.4.5.3 | 8.3.4.5.4 | 8.3.4.6.1 | 8.3.4.6.2 | 8.3.4.6.3 | 8.3.4.6.4 |
| 8.3.4.7.1 | 8.3.4.7.2 | 8.3.4.7.3 | 8.3.4.7.4 | 8.3.4.8.1 | 8.3.4.8.2 | 8.3.4.8.3 | 8.3.4.8.4 |
| 8.4.1.1.1 | 8.4.1.1.2 | 8.4.1.1.3 | 8.4.1.1.4 | 8.4.1.2.1 | 8.4.1.2.2 | 8.4.1.2.3 | 8.4.1.2.4 |
| 8.4.1.3.1 | 8.4.1.3.2 | 8.4.1.3.3 | 8.4.1.3.4 | 8.4.1.4.1 | 8.4.1.4.2 | 8.4.1.4.3 | 8.4.1.4.4 |
| 8.4.1.5.1 | 8.4.1.5.2 | 8.4.1.5.3 | 8.4.1.5.4 | 8.4.1.6.1 | 8.4.1.6.2 | 8.4.1.6.3 | 8.4.1.6.4 |
| 8.4.1.7.1 | 8.4.1.7.2 | 8.4.1.7.3 | 8.4.1.7.4 | 8.4.1.8.1 | 8.4.1.8.2 | 8.4.1.8.3 | 8.4.1.8.4 |
| 8.4.2.1.1 | 8.4.2.1.2 | 8.4.2.1.3 | 8.4.2.1.4 | 8.4.2.2.1 | 8.4.2.2.2 | 8.4.2.2.3 | 8.4.2.2.4 |
| 8.4.2.3.1 | 8.4.2.3.2 | 8.4.2.3.3 | 8.4.2.3.4 | 8.4.2.4.1 | 8.4.2.4.2 | 8.4.2.4.3 | 8.4.2.4.4 |
| 8.4.2.5.1 | 8.4.2.5.2 | 8.4.2.5.3 | 8.4.2.5.4 | 8.4.2.6.1 | 8.4.2.6.2 | 8.4.2.6.3 | 8.4.2.6.4 |
| 8.4.2.7.1 | 8.4.2.7.2 | 8.4.2.7.3 | 8.4.2.7.4 | 8.4.2.8.1 | 8.4.2.8.2 | 8.4.2.8.3 | 8.4.2.8.4 |
| 8.4.3.1.1 | 8.4.3.1.2 | 8.4.3.1.3 | 8.4.3.1.4 | 8.4.3.2.1 | 8.4.3.2.2 | 8.4.3.2.3 | 8.4.3.2.4 |
| 8.4.3.3.1 | 8.4.3.3.2 | 8.4.3.3.3 | 8.4.3.3.4 | 8.4.3.4.1 | 8.4.3.4.2 | 8.4.3.4.3 | 8.4.3.4.4 |
| 8.4.3.5.1 | 8.4.3.5.2 | 8.4.3.5.3 | 8.4.3.5.4 | 8.4.3.6.1 | 8.4.3.6.2 | 8.4.3.6.3 | 8.4.3.6.4 |
| 8.4.3.7.1 | 8.4.3.7.2 | 8.4.3.7.3 | 8.4.3.7.4 | 8.4.3.8.1 | 8.4.3.8.2 | 8.4.3.8.3 | 8.4.3.8.4 |
| 8.4.4.1.1 | 8.4.4.1.2 | 8.4.4.1.3 | 8.4.4.1.4 | 8.4.4.2.1 | 8.4.4.2.2 | 8.4.4.2.3 | 8.4.4.2.4 |
| 8.4.4.3.1 | 8.4.4.3.2 | 8.4.4.3.3 | 8.4.4.3.4 | 8.4.4.4.1 | 8.4.4.4.2 | 8.4.4.4.3 | 8.4.4.4.4 |
| 8.4.4.5.1 | 8.4.4.5.2 | 8.4.4.5.3 | 8.4.4.5.4 | 8.4.4.6.1 | 8.4.4.6.2 | 8.4.4.6.3 | 8.4.4.6.4 |
| 8.4.4.7.1 | 8.4.4.7.2 | 8.4.4.7.3 | 8.4.4.7.4 | 8.4.4.8.1 | 8.4.4.8.2 | 8.4.4.8.3 | 8.4.4.8.4 |
| 8.5.1.1.1 | 8.5.1.1.2 | 8.5.1.1.3 | 8.5.1.1.4 | 8.5.1.2.1 | 8.5.1.2.2 | 8.5.1.2.3 | 8.5.1.2.4 |
| 8.5.1.3.1 | 8.5.1.3.2 | 8.5.1.3.3 | 8.5.1.3.4 | 8.5.1.4.1 | 8.5.1.4.2 | 8.5.1.4.3 | 8.5.1.4.4 |
| 8.5.1.5.1 | 8.5.1.5.2 | 8.5.1.5.3 | 8.5.1.5.4 | 8.5.1.6.1 | 8.5.1.6.2 | 8.5.1.6.3 | 8.5.1.6.4 |
| 8.5.1.7.1 | 8.5.1.7.2 | 8.5.1.7.3 | 8.5.1.7.4 | 8.5.1.8.1 | 8.5.1.8.2 | 8.5.1.8.3 | 8.5.1.8.4 |
| 8.5.2.1.1 | 8.5.2.1.2 | 8.5.2.1.3 | 8.5.2.1.4 | 8.5.2.2.1 | 8.5.2.2.2 | 8.5.2.2.3 | 8.5.2.2.4 |
| 8.5.2.3.1 | 8.5.2.3.2 | 8.5.2.3.3 | 8.5.2.3.4 | 8.5.2.4.1 | 8.5.2.4.2 | 8.5.2.4.3 | 8.5.2.4.4 |
| 8.5.2.5.1 | 8.5.2.5.2 | 8.5.2.5.3 | 8.5.2.5.4 | 8.5.2.6.1 | 8.5.2.6.2 | 8.5.2.6.3 | 8.5.2.6.4 |
| 8.5.2.7.1 | 8.5.2.7.2 | 8.5.2.7.3 | 8.5.2.7.4 | 8.5.2.8.1 | 8.5.2.8.2 | 8.5.2.8.3 | 8.5.2.8.4 |
| 8.5.3.1.1 | 8.5.3.1.2 | 8.5.3.1.3 | 8.5.3.1.4 | 8.5.3.2.1 | 8.5.3.2.2 | 8.5.3.2.3 | 8.5.3.2.4 |
| 8.5.3.3.1 | 8.5.3.3.2 | 8.5.3.3.3 | 8.5.3.3.4 | 8.5.3.4.1 | 8.5.3.4.2 | 8.5.3.4.3 | 8.5.3.4.4 |
| 8.5.3.5.1 | 8.5.3.5.2 | 8.5.3.5.3 | 8.5.3.5.4 | 8.5.3.6.1 | 8.5.3.6.2 | 8.5.3.6.3 | 8.5.3.6.4 |
| 8.5.3.7.1 | 8.5.3.7.2 | 8.5.3.7.3 | 8.5.3.7.4 | 8.5.3.8.1 | 8.5.3.8.2 | 8.5.3.8.3 | 8.5.3.8.4 |
| 8.5.4.1.1 | 8.5.4.1.2 | 8.5.4.1.3 | 8.5.4.1.4 | 8.5.4.2.1 | 8.5.4.2.2 | 8.5.4.2.3 | 8.5.4.2.4 |
| 8.5.4.3.1 | 8.5.4.3.2 | 8.5.4.3.3 | 8.5.4.3.4 | 8.5.4.4.1 | 8.5.4.4.2 | 8.5.4.4.3 | 8.5.4.4.4 |
| 8.5.4.5.1 | 8.5.4.5.2 | 8.5.4.5.3 | 8.5.4.5.4 | 8.5.4.6.1 | 8.5.4.6.2 | 8.5.4.6.3 | 8.5.4.6.4 |
| 8.5.4.7.1 | 8.5.4.7.2 | 8.5.4.7.3 | 8.5.4.7.4 | 8.5.4.8.1 | 8.5.4.8.2 | 8.5.4.8.3 | 8.5.4.8.4 |
| 8.6.1.1.1 | 8.6.1.1.2 | 8.6.1.1.3 | 8.6.1.1.4 | 8.6.1.2.1 | 8.6.1.2.2 | 8.6.1.2.3 | 8.6.1.2.4 |
| 8.6.1.3.1 | 8.6.1.3.2 | 8.6.1.3.3 | 8.6.1.3.4 | 8.6.1.4.1 | 8.6.1.4.2 | 8.6.1.4.3 | 8.6.1.4.4 |
| 8.6.1.5.1 | 8.6.1.5.2 | 8.6.1.5.3 | 8.6.1.5.4 | 8.6.1.6.1 | 8.6.1.6.2 | 8.6.1.6.3 | 8.6.1.6.4 |
| 8.6.1.7.1 | 8.6.1.7.2 | 8.6.1.7.3 | 8.6.1.7.4 | 8.6.1.8.1 | 8.6.1.8.2 | 8.6.1.8.3 | 8.6.1.8.4 |
| 8.6.2.1.1 | 8.6.2.1.2 | 8.6.2.1.3 | 8.6.2.1.4 | 8.6.2.2.1 | 8.6.2.2.2 | 8.6.2.2.3 | 8.6.2.2.4 |
| 8.6.2.3.1 | 8.6.2.3.2 | 8.6.2.3.3 | 8.6.2.3.4 | 8.6.2.4.1 | 8.6.2.4.2 | 8.6.2.4.3 | 8.6.2.4.4 |
| 8.6.2.5.1 | 8.6.2.5.2 | 8.6.2.5.3 | 8.6.2.5.4 | 8.6.2.6.1 | 8.6.2.6.2 | 8.6.2.6.3 | 8.6.2.6.4 |
| 8.6.2.7.1 | 8.6.2.7.2 | 8.6.2.7.3 | 8.6.2.7.4 | 8.6.2.8.1 | 8.6.2.8.2 | 8.6.2.8.3 | 8.6.2.8.4 |
| 8.6.3.1.1 | 8.6.3.1.2 | 8.6.3.1.3 | 8.6.3.1.4 | 8.6.3.2.1 | 8.6.3.2.2 | 8.6.3.2.3 | 8.6.3.2.4 |
| 8.6.3.3.1 | 8.6.3.3.2 | 8.6.3.3.3 | 8.6.3.3.4 | 8.6.3.4.1 | 8.6.3.4.2 | 8.6.3.4.3 | 8.6.3.4.4 |

TABLE 1-continued

| | | | | | | | |
|---|---|---|---|---|---|---|---|
| 8.6.3.5.1 | 8.6.3.5.2 | 8.6.3.5.3 | 8.6.3.5.4 | 8.6.3.6.1 | 8.6.3.6.2 | 8.6.3.6.3 | 8.6.3.6.4 |
| 8.6.3.7.1 | 8.6.3.7.2 | 8.6.3.7.3 | 8.6.3.7.4 | 8.6.3.8.1 | 8.6.3.8.2 | 8.6.3.8.3 | 8.6.3.8.4 |
| 8.6.4.1.1 | 8.6.4.1.2 | 8.6.4.1.3 | 8.6.4.1.4 | 8.6.4.2.1 | 8.6.4.2.2 | 8.6.4.2.3 | 8.6.4.2.4 |
| 8.6.4.3.1 | 8.6.4.3.2 | 8.6.4.3.3 | 8.6.4.3.4 | 8.6.4.4.1 | 8.6.4.4.2 | 8.6.4.4.3 | 8.6.4.4.4 |
| 8.6.4.5.1 | 8.6.4.5.2 | 8.6.4.5.3 | 8.6.4.5.4 | 8.6.4.6.1 | 8.6.4.6.2 | 8.6.4.6.3 | 8.6.4.6.4 |
| 8.6.4.7.1 | 8.6.4.7.2 | 8.6.4.7.3 | 8.6.4.7.4 | 8.6.4.8.1 | 8.6.4.8.2 | 8.6.4.8.3 | 8.6.4.8.4 |
| 8.7.1.1.1 | 8.7.1.1.2 | 8.7.1.1.3 | 8.7.1.1.4 | 8.7.1.2.1 | 8.7.1.2.2 | 8.7.1.2.3 | 8.7.1.2.4 |
| 8.7.1.3.1 | 8.7.1.3.2 | 8.7.1.3.3 | 8.7.1.3.4 | 8.7.1.4.1 | 8.7.1.4.2 | 8.7.1.4.3 | 8.7.1.4.4 |
| 8.7.1.5.1 | 8.7.1.5.2 | 8.7.1.5.3 | 8.7.1.5.4 | 8.7.1.6.1 | 8.7.1.6.2 | 8.7.1.6.3 | 8.7.1.6.4 |
| 8.7.1.7.1 | 8.7.1.7.2 | 8.7.1.7.3 | 8.7.1.7.4 | 8.7.1.8.1 | 8.7.1.8.2 | 8.7.1.8.3 | 8.7.1.8.4 |
| 8.7.2.1.1 | 8.7.2.1.2 | 8.7.2.1.3 | 8.7.2.1.4 | 8.7.2.2.1 | 8.7.2.2.2 | 8.7.2.2.3 | 8.7.2.2.4 |
| 8.7.2.3.1 | 8.7.2.3.2 | 8.7.2.3.3 | 8.7.2.3.4 | 8.7.2.4.1 | 8.7.2.4.2 | 8.7.2.4.3 | 8.7.2.4.4 |
| 8.7.2.5.1 | 8.7.2.5.2 | 8.7.2.5.3 | 8.7.2.5.4 | 8.7.2.6.1 | 8.7.2.6.2 | 8.7.2.6.3 | 8.7.2.6.4 |
| 8.7.2.7.1 | 8.7.2.7.2 | 8.7.2.7.3 | 8.7.2.7.4 | 8.7.2.8.1 | 8.7.2.8.2 | 8.7.2.8.3 | 8.7.2.8.4 |
| 8.7.3.1.1 | 8.7.3.1.2 | 8.7.3.1.3 | 8.7.3.1.4 | 8.7.3.2.1 | 8.7.3.2.2 | 8.7.3.2.3 | 8.7.3.2.4 |
| 8.7.3.3.1 | 8.7.3.3.2 | 8.7.3.3.3 | 8.7.3.3.4 | 8.7.3.4.1 | 8.7.3.4.2 | 8.7.3.4.3 | 8.7.3.4.4 |
| 8.7.3.5.1 | 8.7.3.5.2 | 8.7.3.5.3 | 8.7.3.5.4 | 8.7.3.6.1 | 8.7.3.6.2 | 8.7.3.6.3 | 8.7.3.6.4 |
| 8.7.3.7.1 | 8.7.3.7.2 | 8.7.3.7.3 | 8.7.3.7.4 | 8.7.3.8.1 | 8.7.3.8.2 | 8.7.3.8.3 | 8.7.3.8.4 |
| 8.7.4.1.1 | 8.7.4.1.2 | 8.7.4.1.3 | 8.7.4.1.4 | 8.7.4.2.1 | 8.7.4.2.2 | 8.7.4.2.3 | 8.7.4.2.4 |
| 8.7.4.3.1 | 8.7.4.3.2 | 8.7.4.3.3 | 8.7.4.3.4 | 8.7.4.4.1 | 8.7.4.4.2 | 8.7.4.4.3 | 8.7.4.4.4 |
| 8.7.4.5.1 | 8.7.4.5.2 | 8.7.4.5.3 | 8.7.4.5.4 | 8.7.4.6.1 | 8.7.4.6.2 | 8.7.4.6.3 | 8.7.4.6.4 |
| 8.7.4.7.1 | 8.7.4.7.2 | 8.7.4.7.3 | 8.7.4.7.4 | 8.7.4.8.1 | 8.7.4.8.2 | 8.7.4.8.3 | 8.7.4.8.4 |
| 8.8.1.1.1 | 8.8.1.1.2 | 8.8.1.1.3 | 8.8.1.1.4 | 8.8.1.2.1 | 8.8.1.2.2 | 8.8.1.2.3 | 8.8.1.2.4 |
| 8.9.1.3.1 | 8.8.1.3.2 | 8.8.1.3.3 | 8.8.1.3.4 | 8.8.1.4.1 | 8.8.1.4.2 | 8.8.1.4.3 | 8.8.1.4.4 |
| 8.8.1.5.1 | 8.8.1.5.2 | 8.8.1.5.3 | 8.8.1.5.4 | 8.8.1.6.1 | 8.8.1.6.2 | 8.8.1.6.3 | 8.8.1.6.4 |
| 8.8.1.7.1 | 8.8.1.7.2 | 8.8.1.7.3 | 8.8.1.7.4 | 8.8.1.8.1 | 8.8.1.8.2 | 8.8.1.8.3 | 8.8.1.8.4 |
| 8.8.2.1.1 | 8.8.2.1.2 | 8.8.2.1.3 | 8.8.2.1.4 | 8.8.2.2.1 | 8.8.2.2.2 | 8.8.2.2.3 | 8.8.2.2.4 |
| 8.8.2.3.1 | 8.8.2.3.2 | 8.8.2.3.3 | 8.8.2.3.4 | 8.8.2.4.1 | 8.8.2.4.2 | 8.8.2.4.3 | 8.8.2.4.4 |
| 8.8.2.5.1 | 8.8.2.5.2 | 8.8.2.5.3 | 8.8.2.5.4 | 8.8.2.6.1 | 8.8.2.6.2 | 8.8.2.6.3 | 8.8.2.6.4 |
| 8.8.2.7.1 | 8.8.2.7.2 | 8.8.2.7.3 | 8.8.2.7.4 | 8.8.2.8.1 | 8.8.2.8.2 | 8.8.2.8.3 | 8.8.2.8.4 |
| 8.8.3.1.1 | 8.8.3.1.2 | 8.8.3.1.3 | 8.8.3.1.4 | 8.8.3.2.1 | 8.8.3.2.2 | 8.8.3.2.3 | 8.8.3.2.4 |
| 8.8.3.3.1 | 8.8.3.3.2 | 8.8.3.3.3 | 8.8.3.3.4 | 8.8.3.4.1 | 8.8.3.4.2 | 8.8.3.4.3 | 8.8.3.4.4 |
| 8.8.3.5.1 | 8.8.3.5.2 | 8.8.3.5.3 | 8.8.3.5.4 | 8.8.3.6.1 | 8.8.3.6.2 | 8.8.3.6.3 | 8.8.3.6.4 |
| 8.8.3.7.1 | 8.8.3.7.2 | 8.8.3.7.3 | 8.8.3.7.4 | 8.8.3.8.1 | 8.8.3.8.2 | 8.8.3.8.3 | 8.8.3.8.4 |
| 8.8.4.1.1 | 8.8.4.1.2 | 8.8.4.1.3 | 8.8.4.1.4 | 8.8.4.2.1 | 8.8.4.2.2 | 8.8.4.2.3 | 8.8.4.2.4 |
| 8.8.4.3.1 | 8.8.4.3.2 | 8.8.4.3.3 | 8.8.4.3.4 | 8.8.4.4.1 | 8.8.4.4.2 | 8.8.4.4.3 | 8.8.4.4.4 |
| 8.8.4.5.1 | 8.8.4.5.2 | 8.8.4.5.3 | 8.8.4.5.4 | 8.8.4.6.1 | 8.8.4.6.2 | 8.8.4.6.3 | 8.8.4.6.4 |
| 8.8.4.7.1 | 8.8.4.7.2 | 8.8.4.7.3 | 8.8.4.7.4 | 8.8.4.8.1 | 8.8.4.8.2 | 8.8.4.8.3 | 8.8.4.8.4 |

The best mode of practicing the invention is with Compounds of Example numbers 50.6, 50.9, 50.15, and 50.20.

Section 1

Synthesis of Compounds of Formula I

Synthesis of compounds encompassed by the present invention typically includes some or all of the following general steps: (1) preparation of a phosphonate prodrug; (2) deprotection of a phosphonate ester; (3) modification of a heterocycle; (4) coupling of a heterocycle with a phosphonate component; (5) construction of a heterocycle; (6) ring closure to construct a heterocycle with a phosphonate moiety present and (7) preparation of useful intermediates. These steps are illustrated in the following scheme for compounds of formula I wherein $R^5$ is a 5-membered heteroaromatic ring. Compounds of formula I wherein $R^5$ is a 6-member heteroaromatic ring or other heteroaromatic rings are prepared in an analogous manner.

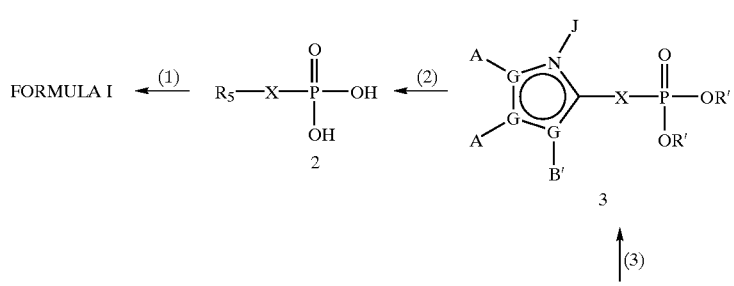

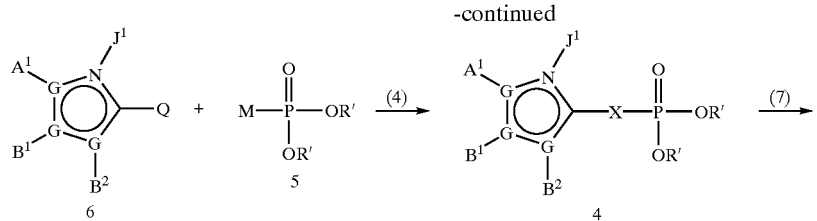

-continued

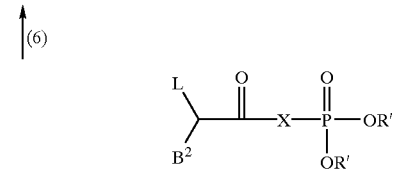

(1) Preparation of a Bisamidate Phosphonate

General synthesis of bis-phosphoroamidate prodrugs:

In general, the bis-phosphoroamidates of formula I, where both —$NR^{15}R^{16}$ and —$N(R^{18})$—$(CR^{12}R^{13})_n$—$C(O)$—$R^{14}$ are from the same amino acid residues, can be prepared from the activated phosphonates for example, dichlorophosphonate, by coupling with an amino acid ester for example, glycine ethylester with or without base for example, N-methylimidazole. The reactive dichloridates, can be prepared from the corresponding phosphonic acid and a chlorinating agent for example, thionyl chloride (Starrett, et al., *J. Med. Chem.*, 1994, 1857), oxalyl chloride (Stowell, et al, *Tetrahedron Lett.*, 1990, 31, 3261), or phosphorous pentachloride (Quast, et al., *Synthesis*, 1974, 490). These dichloridates can also be prepared from their corresponding disilyl esters (Bhongle, et al., *Synth. Commun.*, 1987, 17, 1071) and dialkyl esters (Still, et al., *Tetrahedron Lett.*, 1983, 24, 4405; Patois, et al., *Bull. Soc. Chim. Fr.*, 1993, 130, 485).

Alternatively, these bis-phosphoroamidates can be prepared by reacting the corresponding phosphonic acid with an amino acid ester for example, glycine ethylester in presence of $PPh_3$ and 2,2'-dipyridyl disulfide in pyridine as described in WO 95/07920 or Mukaiyama, T. et al, *J Am. Chem. Soc.*, 1972, 94, 8528.

Synthesis of mixed bis-phosphoroamidates of formula I, where —$NR^{15}R^{16}$ and —$N(R^{18})$—$(CR^{12}R^{13})_nC(O)$—$R^{14}$ are different amino acid esters or a combination of an amino acid ester and a substituted amine, can be prepared by direct conversion via dichloridate as described above (sequential addition) followed by purification of the desired product (e.g., by column chromatography). Alternatively, these unsymmetrical bis-phosphoroamidates can be prepared starting with an appropriate phosphonate monoester such as phenyl ester or benzyl ester to give the mixed phosphonoesteramide via the chloridate, followed by ester hydrolysis under conditions where the amide bond is stable. The resultant mono-amide can be converted to a mixed bisamide by condensation with a second amino ester or a substituted amine via the chloridate, as described above. Synthesis of such monoesters can be prepared using the reported procedure (EP 481 214).

(2) Deprotection of a Phosphonate Ester

Compounds of formula 2 may be prepared from phosphonate esters using known phosphate and phosphonate ester cleavage conditions. Silyl halides are generally used to cleave various phosphonate esters, and subsequent mild hydrolysis of the resulting silyl phosphonate esters give the desired phosphonic acids. When required, acid scavengers (e.g. 1,1,1,3,3,3-hexamethyldisilazane, 2,6-lutidine, etc.) can be used for the synthesis of acid labile compounds. Such silyl halides include chlorotrimethylsilane (Rabinowitz, *J. Org. Chem.*, 1963, 28: 2975), and bromotrimethylsilane (McKenna, et al, *Tetrahedron Lett.*, 1977, 155), and iodotrimethylsilane (Blackburn, et al, *J. Chem. Soc., Chem. Commun.*, 1978, 870). Alternately, phosphonate esters can be cleaved under strong acidic conditions (e.g. HBr or HCl: Moffatt, et al, U.S. Pat. No. 3,524,846, 1970). These esters can also be cleaved via dichlorophosphonates, prepared by treating the esters with halogenating agents (e.g. phosphorus pentachloride, thionyl chloride, $BBr_3$: Pelchowicz et al, *J. Chem. Soc.*, 1961, 238) followed by aqueous hydrolysis to give phosphonic acids. Aryl and benzyl phosphonate esters can be cleaved under hydrogenolysis conditions (Lejczak, et al, *Synthesis*, 1982, 412; Elliott, et al, *J. Med. Chem.*, 1985, 28: 1208; Baddiley, et al, *Nature*, 1953, 171: 76) or metal reduction conditions (Shafer, et al, *J. Am. Chem. Soc.*, 1977, 99: 5118). Electrochemical (Shono, et al, *J. Org. Chem.*, 1979, 44: 4508) and pyrolysis (Gupta, et al, *Synth. Commun.*, 1980, 10: 299) conditions have also been used to cleave various phosphonate esters.

(3) Modification of an Existing Heterocycle

Syntheses of the heterocycles encompassed in the disclosed compounds have been well studied and described in numerous reviews (see section 4). Although it is advantageous to have the desired substituents present in these heterocycles before synthesis of compounds of formula 4, in some cases, the desired substituents are not compatible with subsequent reactions, and therefore modifications of an existing heterocycle are required late in the synthetic scheme using conventional chemistry (Larock, *Comprehensive organic transformations*, VCH, New York, 1989; Trost, *Comprehensive organic synthesis*; Pergamon press, New York, 1991). For example, compounds of formula I wherein A, A", or B is a halo or a cyano group can be prepared from the corresponding amine group by conversion to the diazonium group and reaction with various copper (I) salts (e.g. CuI, CuBr, CuCl, CuCN). Halogens can also be introduced by direct halogenations of various heterocycles. For example, 5-unsubstituted-2-aminothiazoles can be converted to 2-amino-5-halothiazoles using various reagents (e.g. NIS, NBS, NCS). Heteroaryl halides are also useful intermediates and are often readily converted to other substituents (such as A, A", B, B", C", D, D", E and E") via transition metal assisted coupling reactions such as Suzuki, Heck or Stille reactions (Farina et al, *Organic Reactions*, Vol. 50; Wiley, New York, 1997; Mitchell, *Synthesis,* 1992, 808; Suzuki, *Pure App. Chem.,* 1991, 63, 419; Heck *Palladium Reagents in Organic Synthesis*; Academic Press: San Diego, 1985). Compounds of formula I wherein A is a carbamoyl group can be made from their corresponding alkyl carboxylate esters via aminolysis with various amines, and conventional functional group modifications of the alkyl carboxylate esters are useful for syntheses of compounds of formula I wherein A is a —CH$_2$OH group or a —CH$_2$-halo group. Substitution reactions of haloheterocycles (e.g. 2-bromothiazole, 5-bromothiazole) with various nucleophiles (e.g. HSMe, HOMe, etc.) represents still another method for introducing substituents such as A, A", B and B". For example, substitution of a 2-chlorothiazole with methanethiol gives the corresponding 2-methylthiothiazole.

It is envisioned that when necessary alkylation of nitrogen atoms in the heterocycles (e.g. imidazoles, 1,2,4-triazoles and 1,2,3,4-tetrazoles) can be readily performed using for example standard alkylation reactions (with an alkyl halide, an aralkyl halide, an alkyl sulfonate or an aralkyl sulfonate), or Mitsunobu reactions (with an alcohol).

(4) Coupling of a Heterocycle with a Phosphonate Component

When feasible compounds disclosed in the present invention are prepared via a convergent synthetic route entailing the coupling of a heterocycle with a phosphonate diester component.

Transition metal catalyzed coupling reactions such as Stille or Suzuki reactions are particularly suited for the synthesis of compounds of formula I. Coupling reactions between a heteroaryl halide or triflate (e.g. 2-bromopyridine) and a M-PO$_3$R' wherein M is a 2-(5-tributylstannyl)furanyl or a 2-(5-boronyl)furanyl group under palladium catalyzed reaction conditions (Farina et al, *Organic Reactions, Vol.* 50; Wiley, New York, 1997; Mitchell, *Synthesis,* 1992, 808; Suzuki, *Pure App. Chem.,* 1991, 63, 419) yield compounds of formula I wherein X is a furan-2,5-diyl group. It is envisioned that the nature of the coupling partners for these reactions can also be reversed (e.g. coupling of trialkylstannyl or boronyl heterocycles with a halo-X—P(O)(O-alkyl)$_2$). Other coupling reactions between organostannes and an alkenyl halide or an alkenyl triflate are also reported which may be used to prepared compounds of formula I wherein X is an alkenyl group. The Heck reaction may be used to prepare compounds of formula I wherein X is an alkenyl group (Heck *Palladium Reagents in Organic Synthesis*; Academic Press: San Diego, 1985). These reactions are particularly suited for syntheses of various heteroaromatics as R$^5$ for compounds of formula I given the availability of numerous halogenated heterocycles, and these reactions are particularly suitable for parallel synthesis (e.g. combinatorial synthesis on solid phase (Bunin, B. A., *The Combinatorial Index*; Academic Press: San Diego, 1998) or in solution phase (Flynn, D. L. et al., *Curr. Op. Drug. Disc. Dev.,* 1998, 1, 1367)) to generate large combinatorial libraries. For example, ethyl 5-iodo-2-furanylphosphonate can be coupled to Wang's resin under suitable coupling reaction conditions. The resin-coupled 5-iodo-2-[5-(O-ethyl-O-Wang's resin)phosphono]furan can then be subjected to transition metal catalyzed Suzuki and Stille reactions (as described above) with organoboranes and organotins in a parallel manner to give libraries of compounds of formula 3 wherein X is furan-2,5-diyl.

Substitution reactions are useful for the coupling of a heterocycle with a phosphonate diester component. For example, cyanuric chloride can be substituted with dialkyl mercaptoalkylphosphonates or dialkyl aminoalkylphosphonates to give compounds of formula I wherein R$^5$ is a 1,3,5-triazine, X is an alkylthio or an alkylamino group. Alkylation reactions are also used for the coupling of a heterocycle with a phosphonate diester component. For example, a heteroaromatic thiol (e.g. a 1,3,4-thiadiazole-2-thiol) can be alkylated with a dialkyl methylphosphonate derivative (e.g. ICH$_2$P(O)(OEt)$_2$, TsOCH$_2$P(O)(OEt)$_2$, TfOCH$_2$P(O)(OEt)$_2$) to lead to compounds of formula I wherein X is an alkylthio group. In another aspect, alkylation reactions of a heteroaromatic carboxylic acid (e.g. a thiazole-4-carboxylic acid) with a dialkyl methylphosphonate derivative (e.g. ICH$_2$P(O)(OEt)$_2$, TsOCH$_2$P(O)(OEt)$_2$, TfOCH$_2$P(O)(OEt)$_2$) lead to compounds of formula I wherein X is an alkoxycarbonyl group, while alkylation reactions of a heteroaromatic thiocarboxylic acid (e.g. a thiazole-4-thiocarboxylic acid) with a dialkyl methylphosphonate derivative (e.g. ICH$_2$P(O)(OEt)$_2$, TsOCH$_2$P(O)(OEt)$_2$, TfOCH$_2$P(O)(OEt)$_2$) lead to compounds of formula I wherein X is an alkylthiocarbonyl group. Substitutions of haloalkyl heterocycles (e.g. 4-haloalkylthiazole) with nucleophiles containing the phosphonate group (diethyl hydroxymethylphosphonate) are useful for the preparation of compounds of formula I wherein X is an alkoxyalkyl or an alkylthioalkyl group. For example, compounds of formula I where X is a —CH$_2$OCH$_2$— group can be prepared from 2-chloromethylpyridine or 4-chloromethylthiazole using dialkyl hydroxymethylphosphonates and a suitable base (e.g. sodium hydride). It is possible to reverse the nature of the nucleophiles and electrophiles for the substitution reactions, i.e. haloalkyl- and/or sulfonylalkylphosphonate esters can be substituted with heterocycles containing a nucleophile (e.g. a 2-hydroxyalkylpyridine, a 2-mercaptoalkylpyridine, or a 4-hydroxyalkyloxazole).

Known amide bond formation reactions (e.g. the acyl halide method, the mixed anhydride method, the carbodiimide method) can also be used to couple a heteroaromatic carboxylic acid with a phosphonate diester component leading to compounds of formula I wherein X is an alkylaminocarbonyl or an alkoxycarbonyl group. For example, couplings of a thiazole-4-carboxylic acid with a dialkyl aminoalkylphosphonate or a dialkyl hydroxyalkylphosphonate give compounds of formula I wherein R$^5$ is a thiazole, and X is an alkylaminocarbonyl or an alkoxycarbonyl group. Alternatively, the nature of the coupling partners can be reversed to give compounds of formula I wherein X is an alkylcarbonylamino group. For example, 2-aminothiazoles can be coupled with (RO)$_2$P(O)-alkyl-CO$_2$H (e.g. diethylphosphonoacetic acid) under these reaction conditions to give compounds of formula I wherein R$^5$ is a thiazole and X is an alkylcarbonylamino group. These reactions are also useful for parallel synthesis of compound libraries through combinatorial chemistry on solid phase or in solution phase. For example, HOCH$_2$P(O)(OEt)(O-resin), H$_2$NCH$_2$P(O)(OEt)(O-resin) and HOOCCH$_2$P(O)(OEt)(O-resin) (prepared using known methods) can be coupled to various heterocycles using the above described reactions to give libraries of compounds of formula 3 wherein X is a —C(O)OCH$_2$—, or a —C(O)NHCH$_2$—, or a NHC(O)CH$_2$—.

Rearrangement reactions can also be used to prepare compounds covered in the present invention. For example, the Curtius' rearrangement of a thiazole-4-carboxylic acid in the presence of a dialkyl hydroxyalkylphosphonate or a dialkyl aminoalkylphosphonate lead to compounds of formula I wherein X is an alkylaminocarbonylamino or an alkoxycarbonylamino group. These reactions can also be adopted for combinatorial synthesis of various libraries of compounds of formula 3. For example, Curtius' rearrangement reactions between a heterocyclic carboxylic acid and HOCH$_2$P(O)(OEt)(O-resin), or H$_2$NCH$_2$P(O)(OEt)(O-resin) can lead to libraries of compounds of formula I wherein X is a —NHC(O)OCH$_2$—, or a NHC(O)NHCH$_2$—.

For compounds of formula I wherein X is an alkyl group, the phosphonate group can be introduced using other common phosphonate formation methods such as Michaelis-Arbuzov reaction (Bhattacharya et al., *Chem. Rev.*, 1981, 81: 415), Michaelis-Becker reaction (Blackburn et al., *J. Organomet. Chem.*, 1988, 348: 55), and addition reactions of phosphorus to electrophiles (such as aldehydes, ketones, acyl halides, imines and other carbonyl derivatives).

Phosphonate component can also be introduced via lithiation reactions. For example, lithiation of an 2-ethynylpyridine using a suitable base followed by trapping the thus generated anion with a dialkyl chlorophosphonate lead to compounds of formula I wherein R$^5$ is a pyridyl, X is a 1-(2-phosphono)ethynyl group.

(5) Construction of a Heterocycle

Although existing heterocycles are useful for the synthesis of compounds of formula I, when required, heterocycles can also be constructed leading to compounds in the current invention. The construction of heterocycles have been well described in the literature using a variety of reaction conditions (Joule et al., *Heterocyclic Chemistry*; Chapman hall, London, 1995; Boger, Weinreb, *Hetero Diels-Alder Methodology In Organic Synthesis*; Academic press, San Diego, 1987; Padwa, *1,3-Dipolar Cycloaddition Chemistry*; Wiley, New York, 1984; Katritzsky et al., *Comprehensive Heterocyclic Chemistry*; Pergamon press, Oxford; Newkome et al., *Contemporary Heterocyclic Chemistry: Syntheses, Reaction and Applications*; Wiley, New York, 1982; *Syntheses of Heterocyclic Compounds*; Consultants Bureau, New York). Some of the methods which are useful to prepare compounds in the present invention are given as examples in the following discussion.

(i) Construction of a Thiazole Ring System

Thiazoles useful for the present invention can be readily prepared using a variety of well described ring-forming reactions (Metzger, *Thiazole and its derivatives, part 1 and part 2*; Wiley & Sons, New York, 1979). Cyclization reactions of thioamides (e.g. thioacetamide, thiourea) and alpha-halocarbonyl compounds (such as alpha-haloketones, alpha-haloaldehydes) are particularly useful for the construction of a thiazole ring system. For example, cyclization reactions between thiourea and 5-diethylphosphono-2-[(-2-bromo-1-oxo)alkyl]furans are useful for the synthesis of compounds of formula I wherein R$^5$ is a thiazole, A is an amino group and X is a furan-2,5-diyl group; cyclization reaction between thiourea and a bromopyruvate alkyl ester give a 2-amino-4-alkoxycarbonylthiazole which is useful for the preparations of compounds of formula I wherein R$^5$ is a thiazole and X is an alkylaminocarbonyl, an alkoxycarbonyl, an alkylaminocarbonylamino, or an alkoxyacarbonylamino group. Thioamides can be prepared using reactions reported in the literature (Trost, *Comprehensive organic synthesis, Vol. 6*; Pergamon press, New York, 1991, pages 419–434) and alpha-halocarbonyl compounds are readily accessible via conventional reactions (Larock, *Comprehensive organic transformations*, VCH, New York, 1989). For example, amides can be converted to thioamides using Lawesson's reagent or P$_2$S$_5$, and ketones can be halogenated using various halogenating reagents (e.g. NBS, CuBr$_2$).

(ii) Construction of an Oxazole Ring System

Oxazoles useful for the present invention can be prepared using various methods in the literature (Turchi, *Oxazoles*; Wiley & Sons, New York, 1986). Reactions between isocyanides (e.g. tosylmethylisocyanide) and carbonyl compounds (e.g. aldehydes and acyl chlorides) can be used to construct oxazole ring systems (van Leusen et al, *Tetrahedron Lett.*, 1972, 2369). Alternatively, cyclization reactions of amides (e.g. urea, carboxamides) and alpha-halocarbonyl compounds are commonly used for the construction of an oxazole ring system. For example, the reactions of urea and 5-diethylphosphono-2-[(-2-bromo-1-oxo)alkyl]furans are useful for the synthesis of compounds of formula I wherein R$^5$ is an oxazole, A is an amino group and X is a furan-2, 5-diyl group. Reactions between amines and imidates are also used to construct the oxazole ring system (Meyers et al, *J. Org. Chem.*, 1986, 51(26), 5111).

(iii) Construction of a Pyridine Ring System

Pyridines useful for the synthesis of compounds of formula I can be prepared using various known synthetic methods (Klingsberg, *Pyridine and Its Derivatives*; Interscience Publishers, New York, 1960–1984). 1,5-Dicarbonyl compounds or their equivalents can be reacted with ammonia or compounds which can generate ammonia to produce 1,4-dihydropyridines which are easily dehydrogenated to pyridines. When unsaturated 1,5-dicarbonyl compounds, or their equivalents (e.g. pyrylium ions) are used to react with ammonia, pyridines can be generated directly. 1,5-Dicarbonyl compounds or their equivalents can be prepared using conventional chemistry. For example, 1,5-diketones are accessible via a number of routes, such as Michael addition of an enolate to an enone (or precursor Mannich base (Gill et al, *J. Am. Chem. Soc.*, 1952, 74, 4923)), ozonolysis of a cyclopentene precursor, or reaction of silyl enol ethers with 3-methoxyallylic alcohols (Duhamel et al, *Tetrahedron*, 1986, 42, 4777). When one of the carbonyl carbons is at the acid oxidation state, then this type of reaction produces 2-pyridones which can be readily converted to 2-halopyridines (Isler et al, *Helv. Chim. Acta*, 1955, 38, 1033) or 2-aminopyridines (Vorbruggen et al, *Chem. Ber.*, 1984, 117, 1523). Alternatively, a pyridine can be prepared from an aldehyde, a 1,3-dicarbonyl compound and ammonia via the classical Hantzsch synthesis (Bossart et al, *Angew. Chem. Int. Ed. Engl.*, 1981, 20, 762). Reactions of 1,3-dicarbonyl compounds (or their equivalents) with 3-amino-enones or 3-amino-nitriles have also been used to produce pyridines (such as the Guareschi synthesis, Mariella, *Org. Synth., Coll, Vol. IV*, 1963, 210). 1,3-Dicarbonyl compounds can be made via oxidation reactions on corresponding 1,3-diols or aldol reaction products (Mukaiyama, *Org, Reactions*, 1982, 28, 203). Cycloaddition reactions have also been used for the synthesis of pyridines, for example cycloaddition reactions between oxazoles and alkenes (Naito et al., *Chem. Pharm. Bull.*, 1965, 13, 869), and Diels-Alder reactions between 1,2,4-triazines and enamines (Boger et al., *J. Org. Chem.*, 1981, 46, 2179).

(iv) Construction of a Pyrimidine Ring System

Pyrimidine ring systems useful for the synthesis of compounds of formula I are readily available (Brown, *The pyrimidines*; Wiley, New York, 1994). One method for pyrimidine synthesis involves the coupling of a 1,3-dicarbonyl component (or its equivalent) with an N—C—N fragment. The selection of the N—C—N component—urea (Sherman et al., *Org. Synth., Coll. Vol. IV*, 1963, 247), amidine (Kenner et al., *J. Chem. Soc.*, 1943, 125) or guanidine (Burgess, *J. Org. Chem.*, 1956, 21, 97; VanAllan, *Org. Synth., Coll. Vol. IV*, 1963, 245)—governs the substitution at C-2 in the pyrimidine products. This method is particular useful for the synthesis of compounds of formula I with various A groups. In another method, pyrimidines can be prepared via cycloaddition reactions such as aza-Diels- Alder reactions between a 1,3,5-triazine and an enamine or an ynamine (Boger et al., *J. Org. Chem.,* 1992, 57, 4331 and references cited therein).

(v) Construction of an Imidazole Ring System

Imidazoles useful for the synthesis of compounds of formula I are readily prepared using a variety of different synthetic methodologies. Various cyclization reactions are generally used to synthesize imidazoles such as reactions between amidines and alpha-haloketones (Mallick et al, *J. Am. Chem. Soc.,* 1984, 106(23), 7252) or alpha-hydroxyketones (Shi et al, *Synthetic Comm.,* 1993, 23(18), 2623), reactions between urea and alpha-haloketones, and reactions between aldehydes and 1,2-dicarbonyl compounds in the presence of amines.

(vi) Construction of an Isoxazole Ring System

Isoxazoles useful for the synthesis of compounds of formula I are readily synthesized using various methodologies (such as cycloaddition reactions between nitrile oxides and alkynes or active methylene compounds, oximation of 1,3-dicarbonyl compounds or alpha, beta-acetylenic carbonyl compounds or alpha,beta-dihalocarbonyl compounds, etc.) can be used to synthesize an isoxazole ring system (Grunanger et al., *Isoxazoles*, Wiley & Sons, New York, 1991). For example, reactions between alkynes and 5-diethylphosphono-2-chlorooximidofuran in the presence of base (e.g. triethylamine, Hunig's base, pyridine) are useful for the synthesis of compounds of formula I wherein $R^5$ is an isoxazole and X is a furan-2,5-diyl group.

(vii) Construction of a Pyrazole Ring System

Pyrazoles useful for the synthesis of compounds of formula I are readily prepared using a variety of methods (Wiley, *Pyrazoles, Pyrazolines, Pyrazolidines, Indazoles, and Condensed Rings*; Interscience Publishers, New York, 1967) such as reactions between hydrazines and 1,3-dicarbonyl compounds or 1,3-dicarbonyl equivalents (e.g. one of the carbonyl group is masked as an enamine or ketal or acetal), and additions of hydrazines to acrylonitriles followed by cyclization reactions (Dom et al, *Org. Synth.,* 1973, *Coll. Vol. V,* 39). Reaction of 2-(2-alkyl-3-N,N-dimethylamino)acryloyl-5-diethylphosphonofurans with hydrazines are useful for the synthesis of compounds of formula I wherein $R^5$ is a pyrazole, X is a furan-2,5-diyl group and B" is an alkyl group.

(viii) Construction of a 1,2,4-triazole Ring System 1,2,4-Triazoles useful for the synthesis of compounds of formula I are readily available via various methodologies (Montgomery, 1,2,4-Triazoles; Wiley, New York, 1981). For example, reactions between hydrazides and imidates or thioimidates (Sui et al., *Bioorg. Med. Chem. Lett.,* 1998, 8, 1929; Catarzi et al., *J. Med. Chem.,* 1995, 38(2), 2196), reactions between 1,3,5-triazine and hydrazines (Grundmann et al., *J. Org. Chem.,* 1956, 21, 1037), and reactions between aminoguanidine and carboxylic esters (Ried et al., *Chem. Ber.,* 1968, 101, 2117) are used to synthesize 1,2,4-triazoles.

(6) Ring Closure to Construct a Heterocycle with a Phosphonate

Compounds of formula 4 can also be prepared using a ring closure reaction to construct the heterocycle from precursors that contain the phosphonate component. For example, cyclization reactions between thiourea and 5-diethylphosphono-2-[(-2-bromo-1-oxo)alkyl]furans are useful for the synthesis of compounds of formula I wherein $R^5$ is a thiazole, A is an amino group and X is a furan-2,5-diyl group. Oxazoles of the present invention can also be prepared using a ring closure reaction. In this case, reactions of urea and 5-diethylphosphono-2-[(-2-bromo-1-oxo)alkyl]furans are useful for the synthesis of compounds of formula I wherein $R^5$ is an oxazole, A is an amino group and X is a furan-2,5-diyl group. Reactions between 5-diethylphosphono-2-furaldehyde, an alkyl amine, a 1,2-diketone and ammonium acetate are useful to synthesize compounds of formula I wherein $R^5$ is an imidazole and X is a furan-2,5-diyl group. These types of ring closure reactions can also be used for the synthesis of pyridines or pyrimidines useful in the present invention. For example, reaction of 5-diethylphosphono-2-[3-dimethylamino-2-alkyl)acryloyl]furans and cyanoacetamide in the presence of base gives 5-alkyl-3-cyano-6-[2-(5-diethylphosphono) furanyl]-2-pyridones (Jain et al., *Tetrahedron Lett.,* 1995, 36, 3307). Subsequent conversion of these 2-pyridones to the corresponding 2-halopyridines (see references cited in section 3 for the modifications of heterocycles) will lead to compounds of formula I wherein $R^5$ is a pyridine, A is a halo group, X is a furan-2,5-diyl group, and B is an alkyl group. Reactions of 5-diethylphosphono-2-[3-dimethylamino-2-alkyl)acryloyl]furans and amidines in the presence of base give 5-alkyl-6-[2-(5-diethylphosphono)-furanyl] pyrimidines which will lead to compounds of formula I wherein $R^5$ is a pyrimidine, X is a furan-2,5-diyl group and B is an alkyl group.

(7) Preparation of Various Precursors Useful for Cyclization Reactions

Intermediates required for the synthesis of compounds in the present invention are generally prepared using either an existing method in the literature or a modification of an existing method. Syntheses of some of the intermediates useful for the synthesis of compounds in the present invention are described herein.

Various aryl phosphonate dialkyl esters are particularly useful for the synthesis of compounds of formula I. For example, compounds of formula I wherein X is a furan-2, 5-diyl group can be prepared from a variety of furanyl precursors. It is envisioned that synthesis of other precursors may follow some or all of these reaction steps, and some modifications of these reactions may be required for different precursors. 5-Dialkylphosphono-2-furancarbonyl compounds (e.g. 5-diethylphosphono-2-furaldehyde, 5-diethylphosphono-2-acetylfuran) are well suited for the synthesis of compounds of formula I wherein X is a furan-2,5-diyl group. These intermediates are prepared from furan or furan derivatives using conventional chemistry such as lithiation reactions, protection of carbonyl groups and deprotection of carbonyl groups. For example, lithiation of furan using known methods (Gschwend *Org. React.,* 1979, 26: 1) followed by addition of phosphorylating agents (e.g. $CLPO_3R_2$) gives 2-dialkylphosphono-furans (e.g. 2-diethylphosphonofuran). This method can also be applied to a 2-substituted furan (e.g. 2-furoic acid) to give a 5-dialkylphosphono-2-substituted furan (e.g. 5-diethylphosphono-2-furoic acid). It is envisioned that other aryl phosphonate esters can also be prepared using this approach or a modification of this approach. Alternatively, other methods such as transition metal catalyzed reactions of aryl halides or triflates (Balthazar et al. *J. Org. Chem.,* 1980, 45: 5425; Petrakis et al. *J. Am. Chem. Soc.,* 1987, 109: 2831; Lu et al. *Synthesis,* 1987, 726) are used to prepare aryl phosphonates. Aryl phosphonate esters can also be prepared from aryl phosphates under anionic rearrangement conditions (Melvin, *Tetrahedron Lett.,* 1981, 22: 3375; Casteel et al. *Synthesis,* 1991, 691). N-Alkoxy aryl salts with alkali metal derivatives of dialkyl phosphonate provide another general synthesis for heteroaryl-2-phosphonate esters (Redmore *J. Org. Chem.,* 1970, 35: 4114).

A second lithiation step can be used to incorporate a second group on the aryl phosphonate dialkyl ester such as an aldehyde group, a trialkylstannyl or a halo group, although other methods known to generate these functionalities (e.g. aldehydes) can be envisioned as well (e.g. Vilsmeier-Hack reaction or Reimar-Teimann reaction for aldehyde synthesis). In the second lithiation step, the lithiated aromatic ring is treated with reagents that either directly generate the desired functional group (e.g. for an aldehyde using DMF, $HCO_2R$, etc.) or with reagents that lead to a group that is subsequently transformed into the desired functional group using known chemistry (e.g. alcohols, esters, nitriles, alkenes can be transformed into aldehydes). For example, lithiation of a 2-dialkylphosphonofuran (e.g. 2-diethylphosphonofuran) under normal conditions (e.g. LDA in THF) followed by trapping of the thus generated anion with an electrophile (e.g. tributyltin chloride or iodine) produces a 5-functionalized-2-dialkylphosphonofuran (e.g. 5-tributylstannyl-2-diethylphosphonofuran or 5-iodo-2-diethylphosphonofuran). It is also envisioned that the sequence of these reactions can be reversed, i.e. the aldehyde moiety can be incorporated first followed by the phosphorylation reaction. The order of the reaction will be dependent on reaction conditions and protecting groups. Prior to the phosphorylation, it is also envisioned that some of these functional groups may be protected using a number of well-known methods (e.g. protection of aldehydes as acetals, aminals; protection of ketones as ketals). The protected functional group is then unmasked after phosphorylation. (*Protective groups in Organic Synthesis*, Greene, T. W., 1991, Wiley, New York). For example, protection of 2-furaldehyde as 1,3-propanediol acetal followed by a lithiation step (using for example LDA) and trapping the anion with a dialkyl chlorophosphate (e.g. diethyl chlorophosphate), and subsequent deprotection of the acetal functionality under normal deprotection conditions produces the 5-dialkylphosphono-2-furaldehyde (e.g. 5-diethylphosphono-2-furaldehyde). Another example is the preparation of 5-keto-2-dialkylphosphonofurans which encompass the following steps: acylations of furan under Friedel-Crafts reaction conditions give 2-ketofuran, subsequent protection of the ketone as ketals (e.g. 1,3-propanediol cyclic ketal) followed by a lithiation step as described above gives the 5-dialkylphosphono-2-furanketone with the ketone being protected as a 1,3-propanediol cyclic ketal, and final deprotection of the ketal under, for example, acidic conditions gives 2-keto-5-dialkylphosphonofurans (e.g. 2-acetyl-5-diethylphosphonofuran). Alternatively, 2-ketofurans can be synthesized via a palladium catalyzed reaction between 2-trialkylstannylfurans (e.g. 2-tributylstannylfuran) and an acyl chloride (e.g. acetyl chloride, isobutyryl chloride). The phosphonate moiety may be present in the 2-trialkylstannylfurans (e.g. 2-tributylstannyl-5-diethylphosphonofuran). 2-Keto-5-dialkylphosphonofurans can also be prepared from a 5-dialkylphosphono-2-furoic acid (e.g. 5-diethylphosphono-2-furoic acid) by conversion of the acid to the corresponding acyl chloride and followed by additions of a Grignard reagent.

Some of the above described intermediates can also be used for the synthesis of other useful intermediates. For example, a 2-keto-5-dialkylphosphonofuran can be further converted to a 1,3-dicarbonyl derivative which is useful for the preparation of pyrazoles, pyridines or pyrimidines. Reaction of a 2-keto-5-dialkylphosphonofuran (e.g. 2-acetyl-5-diethylphosphonofuran) with a dialkylformamide dialkyl acetal (e.g. dimethylformamide dimethyl acetal) gives a 1,3-dicarbonyl equivalent as a 2-(3-dialkylamino-2-alkyl-acryloyl)-5-dialkylphosphonofuran (e.g. 2-(3-dimethylaminoacryloyl)-5-diethylphosphonofuran).

It is envisioned that the above described methods for the synthesis of furan derivatives can be, either directly or with some modifications, applied to syntheses of various other useful intermediates such as aryl phosphonate esters (e.g. thienyl phosphonate esters, phenyl phosphonate esters or pyridyl phosphonate esters).

It is conceivable that when applicable the above described synthetic methods can be adopted for parallel synthesis either on solid phase or in solution to provide rapid SAR (structure activity relationship) exploration of FBPase inhibitors encompassed in the current invention, provided method development for these reactions are successful.

Section 2

Synthesis of Compounds of Formula X

Synthesis of the compounds encompassed by the present invention typically includes some or all of the following general steps: (1) preparation of a phosphonate prodrug; (2) deprotection of a phosphonate ester; (3) construction of a heterocycle; (4) introduction of a phosphonate component; (5) synthesis of an aniline derivative. Step (1) and step (2) were discussed in section 1, and discussions of step (3), step (4) and step (5) are given below. These methods are also generally applicable to compounds of Formula X.

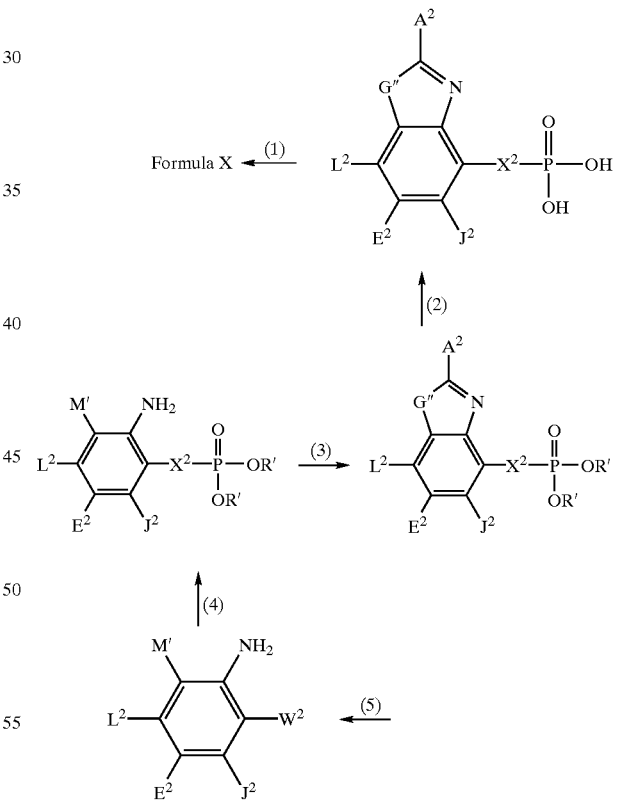

(3) Construction of a Heterocycle
(i) Benzothiazole Ring System

Compounds of formula 3 wherein G"=S, i.e. benzothiazoles, can be prepared using various synthetic methods reported in the literature. Two of these methods are given as examples as discussed below. One method is the modification of commercially available benzothiazole derivatives to give the appropriate functionality on the benzothiazole ring. Another method is the annulation of various anilines (e.g. compounds of formula 4) to construct the thiazole portion of the benzothiazole ring. For example, compounds of formula 3 wherein G"=S, $A^2$=NH$_2$, $L^2$, $E^2$, $J^2$=H, $X^2$=CH$_2$O, and R'=Et can be prepared from the commercially available 4-methoxy-2-amino thiazole via a two-step sequence: conversion 4-methoxy-2-aminobenzothiazole to 4-hydroxy-2-aminobenzothiazole with reagents such as BBr$_3$ (Node, M.; et al. *J. Org. Chem.* 45, 2243–2246, 1980) or AlCl$_3$ in presence of a thiol (e.g. EtSH) (McOmie, J. F. W.; et al. *Org. Synth., Collect. Vol. V*, 412, 1973) followed alkylation of the phenol group with diethylphosphonomethyl trifluoromethylsulfonate (Phillion, D. P.; et al. *Tetrahedron Lett.* 27, 1477–1484, 1986) in presence of a suitable base (e.g. NaH) in polar aprotic solvents (e.g. DMF) provide the required compound.

Several methods can be used to convert various anilines to benzothiazoles (Sprague, J. M.; Land, A. H. *Heterocycle. Compd.* 5, 506–13, 1957). For example, 2-aminobenzothiazoles (formula 3 wherein A=NH$_2$) can be prepared by annulation of compounds of formula 4 wherein W$_2$=H, using various common methods. One method involves the treatment of a suitably substituted aniline with a mixture of KSCN and CuSO$_4$ in methanol to give a substituted 2-aminobenzothiazole (Ismail, I. A.; Sharp, D. E; Chedekel, M. R. *J. Org. Chem.* 45, 2243–2246, 1980). Alternatively, a 2-aminobenzothiazole can also be prepared by the treatment of Br$_2$ in presence of KSCN in acetic acid (Patil, D. G.; Chedekel, M. R. *J. Org. Chem.* 49, 997–1000, 1984). This reaction can also be done in two step sequence. For example treatment of substituted phenylthioureas with Br$_2$ in CHCl$_3$ gives substituted 2-aminobenzothiazoles (Patil, D. G.; Chedekel, M. R. *J. Org. Chem.* 49, 997–1000, 1984). 2-Aminobenzothiazoles can also be made by condensation of ortho iodo anilines with thiourea in presence of Ni catalyst (NiCl$_2$(PPh$_3$)$_2$) (Takagi, K. *Chem. Lett.* 265–266, 1986).

Benzothiazoles can undergo electrophilic aromatic substitution to give 6-substituted benzothiazoles (Sprague, J. M.; Land, A. H. *Heterocycle. Compd.* 5, 606–13, 1957). For example bromination of formula 3 wherein G"=S, $A^2$=NH$_2$, $L^2$, $E^2$, $J^2$=H, $X^2$=CH$_2$O and R'=Et with bromine in polar solvents such as AcOH gave compound of formula 3 wherein $E^2$=Br.

Furthermore, compounds of formula 3 wherein A is a halo, H, alkoxy, alkylthio or an alkyl can be prepared from the corresponding amino compound (Larock, *Comprehensive organic transformations*, VCH, New York, 1989; Trost, *Comprehensive organic synthesis*; Pergamon press, New York, 1991).

(ii) Benzoxazoles

Compounds of formula 3 wherein G"=O, i.e. benzoxazoles, can be prepared by the annulation of ortho aminophenols with suitable reagent (e.g. cyanogen halide (A=NH$_2$; Alt, K. O.; et al *J. Heterocyclic Chem.* 12, 775, 1975) or acetic acid (A=CH$_3$; Saa, J. M.; *J. Org. Chem.* 57, 589–594, 1992) or trialkyl orthoformate (A=H; *Org. Prep. Proced. Int.,* 22, 613, 1990)).

(4) Introduction of a Phosphonate Component

Compounds of formula 4 (wherein $X^2$=CH$_2$O and R'=alkyl) can made in different ways (e.g. using alkylation and nucleophilic substitution reactions). Typically, compounds of formula 5 wherein M'=OH is treated with a suitable base (e.g. NaH) in polar aprotic solvent (e.g. DMF, DMSO) and the resulting phenoxide anion can be alkylated with a suitable electrophile often with a phosphonate component present (e.g. diethyl iodomethylphosphonate, diethyl trifluoromethylsulphonomethyl phosphonate, diethyl p-methyltoluenesulphonomethylphosphonate). The alkylation method can also be applied to the precursor compounds to compounds of formula 5 wherein a phenol moiety is present and it can be alkylated with a phosphonate containing component. Alternately, compounds of formula 4 can also be made from the nucleophilic substitution of the precursor compounds to compounds of formula 5, for example, wherein a halo group, e.g., such as a fluoro or a chloro, is present ortho to a nitro group. For example, a compound of formula 4 (wherein $X^2$=CH$_2$O and R'=Et) can be prepared from a 2-chloro-1-nitrobenzene derivative by treatment with NaOCH$_2$P(O)(OEt)$_2$ in DMF. Similarly, compounds of formula 4 where $X^2$=-alkyl-S— or -alkyl-N— can also be made.

(5) Synthesis of an Aniline Derivative

Numerous synthetic methods have been reported for the synthesis of aniline derivatives, these methods can be applied to the synthesis of useful intermediates which can lead to compounds of formula X. For example, various alkenyl or aryl groups can be introduced on to a benzene ring via transition metal catalyzed reactions (Kasibhatla, S. R., et al. WO 98/39343 and the references cited in); anilines can be prepared from their corresponding nitro derivatives via reduction reactions (e.g. hydrogenation reactions in presence of 10% Pd/C, or reduction reactions using SnCl$_2$ in HCl (Patil, D. G.; Chedekel, M. R. *J. Org. Chem.* 49, 997–1000, 1984)).

Section 3

Synthesis of Compounds of Formula XI

WO 98/39343 describes the synthesis of phosphonic acids and esters of the benzimidazoles of Formula XI. The bisamidate phosphonates of the present invention can be prepared by using procedures described supra for compounds of Formula I.

Formulations

Compounds of the invention are administered orally in a total daily dose in a range of about 0.01 mg/kg/dose to about 100 mg/kg/dose; and from about 0.1 mg/kg/dose to about 10 mg/kg/dose. The use of time-release preparations to control the rate of release of the active ingredient is contemplated. The dose may be administered in as many divided doses as is convenient. When other methods are used (e.g. intravenous administration), compounds are administered to the affected tissue at a rate in the range from 0.05 to 10 mg/kg/hour; and from 0.1 to 1 mg/kg/hour. Such rates are easily maintained when these compounds are intravenously administered as discussed below.

For the purposes of this invention, the compounds may be administered by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters. Oral administration is generally preferred.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions. The pharmaceutical composition can be prepared to provide easily measurable amounts for administration. For example, an aqueous solution intended for intravenous infusion should contain from about 3 to 330 $\mu$g of the active ingredient per milliliter of solution in order that infusion of a suitable volume at a rate of about 30 mL/hr can occur.

As noted above, formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste:

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile.

Tablets may optionally be provided with an enteric coating, to provide release in parts of the gut other than the stomach, especially when the active ingredient is susceptible to acid hydrolysis.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

Suitable unit dosage formulations include those containing a daily dose or unit, daily sub-dose, or an appropriate fraction thereof, of a fructose 1,6-bisphosphatase inhibitor compound.

It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

Utility

One aspect of the invention is directed to novel bisphosphoramidate prodrugs of FBPase inhibitors to increase the oral bioavailability of the parent drugs.

FBPase inhibitors and their prodrugs may be used to treat diabetes mellitus, lower blood glucose levels, and inhibit gluconeogenesis.

FBPase inhibitors and their prodrugs may also be used to treat excess glycogen storage diseases. Excessive hepatic glycogen stores are found in patients with some glycogen storage diseases. Since the indirect pathway contributes significantly to glycogen synthesis (Shulman, G. I. *Phys. Rev.* 72:1019–1035, 1992), inhibition of the indirect pathway (gluconeogenesis flux) decreases glycogen overproduction.

FBPase inhibitors and their prodrugs may also be used to treat or prevent diseases associated with increased insulin levels. Increased insulin levels are associated with an increased risk of cardiovascular complications and atherosclerosis (Folsom, et al., *Stroke*, 25:66–73, 1994; Howard, G. et al., *Circulation*, 93:1809–1817, 1996). FBPase inhibitors and their prodrugs are expected to decrease postprandial glucose levels by enhancing hepatic glucose uptake. This effect is postulated to occur in individuals that are non-diabetic (or pre-diabetic, i.e. without elevated hepatic glucose output "hereinafter HGO" or fasting blood glucose levels). Increased hepatic glucose uptake will decrease insulin secretion and thereby decrease the risk of diseases or complications that arise from elevated insulin levels.

These aspects are described in greater detail below.

EXAMPLES

1. Synthesis of Compounds of Formula IA.

Example 1

Preparation of 5-diethylnhosphono-2-furaldehyde (1)

Step A.

A solution of 2-furaldehyde diethyl acetal (1 mmole) in THF (tetrahydrofuran) was treated with nBuLi (1 mmole) at −78° C. After 1 h, diethyl chlorophosphate (1.2 mmole) was added and the reaction was stirred for 40 min. Extraction and evaporation gave a brown oil.

Step B.

The resulting brown oil was treated with 80% acetic acid at 90° C. for 4 h. Extraction and chromatography gave compound 1 as a clear yellow oil. Alternatively this aldehyde can be prepared from furan as described below.

Step C.

A solution of furan (1 mmole) in diethyl ether was treated with TMEDA (N,N,N'N'-tetramethylethylenediamine) (1 mmole) and nBuLi (2 mmole) at −78° C. for 0.5 h. Diethyl chlorophosphate (1.2 mmole) was added to the reaction mixture and stirred for another hour. Extraction and distillation gave diethyl 2-furanphosphonate as a clear oil.

Step D.

A solution of diethyl 2-furanphosphonate (1 mmole) in TBF was treated with LDA (1.12 mmole, lithium N,N-diisopropylamide) at −78° C. for 20 min. Methyl formate (1.5 mmole) was added and the reaction was stirred for 1 h. Extraction and chromatography gave compound 1 as a clear yellow oil. Preferably this aldehyde can be prepared from 2-furaldehyde as described below.

Step E.

A solution of 2-furaldehyde (1 mmole) and N,N'-dimethylethylene diamine (1 mmole) in toluene was refluxed while the resulting water being collected through a Dean-Stark trap. After 2 h the solvent was removed in vacuo and the residue was distilled to give. furan-2-(N,N'-dimethylimidazolidine) as a clear colorless oil. bp 59–61° C. (3 mm Hg).

Step F.

A solution of furan-2-(N,N'-dimethylimidazolidine) (1 mmole) and TMEDA (1 mmole) in THF was treated with nBuLi (1.3 mmole) at −40 to −48° C. The reaction was stirred at 0° C. for 1.5 h and then cooled to −55° C. and treated with a solution of diethylchlorophosphate (1.1 mmole) in THF. After stirring at 25° C. for 12 h the reaction mixture was evaporated and subjected to extraction to give 5-diethylphosphono-furan-2-(N,N'-dimethylimidazolidine) as a brown oil.

Step G.

A solution of 5-diethylphosphonofuran-2-(N,N'-dimethyl-imidazolidine) (1 mmole) in water was treated with concentrated sulfuric acid until pH=1. Extraction and chromatography gave compound 1 as a clear yellow oil.

Example 2

Preparation of 5-diethylphosphono-2-1[(1-oxo) alkyl]furans and 6-diethylphosphono-2-[(1-oxo) alkyl]pyridines Step A.

A solution of furan (1.3 mmole) in toluene was treated with 4-methyl pentanoic acid (1 mmole), trifluoroacetic anhydride (1.2 mmole) and boron trifluoride etherate (0.1 mmole) at 56° C. for 3.5 h. The cooled reaction mixture was quenched with aqueous sodium bicarbonate (1.9 mmole), filtered through a celite pad. Extraction, evaporation and distillation gave 2-[(4-methyl-1-oxo)pentyl]furan as a brown oil (bp 65–77° C., 0.1 mm Hg).

Step B.

A solution of 2-[(4-methyl-1-oxo)pentyl]furan (1 mmole) in benzene was treated with ethylene glycol (2.1 mmole) and p-toluenesulfonic acid (0.05 mmole) at reflux for 60 h while removing water via a Dean-Stark trap. Triethyl orthoformate (0.6 mmole) was added and resulting mixture was heated at reflux for an additional hour. Extraction and evaporation gave 2-(2-furanyl)-2-[(3-methyl)butyl]-1,3-dioxolane as an orange liquid.

Step C.

A solution of 2-(2-furanyl)-2-[(3-methyl)butyl]-1,3-dioxolane (1 mmole) in THF was treated with TMEDA (1 mmole) and nBuLi (1.1 mmole) at −45° C., and the resulting reaction mixture was stirred at −5 to 0° C. for 1 h. The resulting reaction mixture was cooled to −45° C., and cannulated into a solution of diethyl chlorophosphate in THF at −45° C. The reaction mixture was gradually warmed to ambient temperature over 1.25 h. Extraction and evaporation gave 2-[2-(5-diethylphosphono)furanyl]-2-[(3-methyl)butyl]-1,3-dioxolane as a dark oil.

Step D.

A solution of 2-[2-(5-diethylphosphono)furanyl]-2-[(3-methyl)butyl]-1,3-dioxolane (1 mmole) in methanol was treated with 1 N hydrochloric acid (0.2 mmole) at 60° C. for 18 h. Extraction and distillation gave 5-diethylphosphono-2-[(4-methyl-1-oxo)pentyl]furan (2.1) as a light orange oil (bp 152–156° C., 0.1 mm Hg).

The following compounds were prepared according to this procedure:

(2.2) 5-diethylphosphono-2-acetylfuran: by 125–136° C., 0.1 mm Hg.

(2.3) 5-diethylphosphono-2-[(1-oxo)butyl]furan: by 130–145° C., 0.08 mm Hg.

Alternatively these compounds can be prepared using the following procedures:

Step E.

A solution of 2-[(4-methyl-1-oxo)pentyl]furan (1 mmole, prepared as in Step A) in benzene was treated with N,N-dimethyl hydrazine (2.1 mmole) and trifluoroacetic acid (0.05 mmole) at reflux for 6 h. Extraction and evaporation gave 2-[(4-methyl-1-oxo)pentyl]furan N,N-dimethyl hydrazone as a brown liquid.

Step F.

2-[(4-Methyl-1-oxo)pentyl]furan N,N-dimethyl hydrazone was subjected to the procedures of Step C to give 2-[(4-methyl-1-oxo)pentyl]-5-diethylphosphonofuran N,N-dimethyl hydrazone as a brown liquid which was treated with copper (II) chloride (1.1 equivalent) in ethanol-water at 25° C. for 6 h. Extraction and distillation gave compound 2.1 as a light orange oil.

Some of 5-diethylphosphono-2-[(1-oxo)alkyl]furans are prepared using the following procedures:

Step G.

A solution of compound 1 (1 mmole) and 1,3-propanedithiol (1.1 mmole) in chloroform was treated with borontrifluoride etherate (0.1 mmole) at 25° C. for 24 h. Evaporation and chromatography gave 2-(2-(5-diethylphosphono)furanyl)-1,3-dithiane as a light yellow oil.

A solution of 2-(2-(5-diethylphosphono)furanyl)-1,3-dithiane (1 mmole) in THF was cooled to −78° C. and treated with nBuLi (1.2 mmole). After 1 h. at −78° C. the reaction mixture was treated with cyclopropanemethyl bromide and reaction was stirred at −78° C. for another hour. Extraction and chromatography gave 2-(2-(5-diethylphosphono)furanyl)-2-cyclopropanemethyl-1,3-dithiane as an oil.

A solution of 2-(2-(5-diethylphosphono)furanyl)-2-cyclopropanemethyl-1,3-dithiane (1 mmole) in acetonitrile—water was treated with [bis(trifluoroacetoxy)iodo]benzene (2 mmole) at 25° C. for 24 h. Extraction and chromatography gave 5-diethylphosphono-2-(2-cyclopropylacetyl)furan as a light orange oil.

The following compounds were prepared according to this procedure:

(2.4) 5-Diethylphosphono-2-(2-ethoxycarbonylacetyl)furan
(2.5) 5-Diethylphosphono-2-(2-methylthioacetyl)furan
(2.6) 6-Diethylphosphono-2-acetylpyridine

Example 3

Preparation of 4-[2-(5-phosphono)furanyl]thiazoles. 4-[2-(6-phosphono)pyridyl]thiazoles and 4-[2-(5-phosphono)furanyl]selenazoles Step A.

A solution of compound 2.1 (1 mmole) in ethanol was treated with copper (II) bromide (2.2 mmole) at reflux for 3 h. The cooled reaction mixture was filtered and the filtrate was evaporated to dryness. The resulting dark oil was purified by chromatography to give 5-diethylphosphono-2-[(2-bromo-4-methyl-1-oxo)pentyl]furan as an orange oil.

Step B.

A solution of 5-diethylphosphono-2-[(2-bromo-4-methyl-1-oxo)pentyl]furan (1 mmole) and thiourea (2 mmole) in ethanol was heated at reflux for 2 h. The cooled reaction mixture was evaporated to dryness and the resulting yellow foam was suspended in saturated sodium bicarbonate and water (pH=8). The resulting yellow solid was collected through filtration to give 2-amino-5-isobutyl-4-[2-(5-diethylphosphono)furanyl]thiazole.

Step C.

A solution of 2-amino-5-isobutyl-4-[2-(5-diethylphosphono)-furanyl]thiazole (1 mmole) in methylene chloride was treated with bromotrimethylsilane (10 mmole) at 25° C. for 8 h. The reaction mixture was evaporated to dryness and the residue was suspended in water. The resulting solid was collected through filtration to give 2-amino-5-isobutyl-4-[2-(5-phosphono)furanyl]thiazole (3.1) as an off-white solid. mp>250° C. Anal. calcd. for $C_{11}H_{15}N_2O_4PS+1.25HBr$: C: 32.75; H: 4.06; N: 6.94. Found: C: 32.39; H: 4.33; N: 7.18.

According to the above procedures or in some cases with minor modifications of these procedures using conventional chemistry the following compounds were prepared:

(3.2) 2-Methyl-5-isobutyl-4-[2-(5-phosphono)furanyl]thiazole. Anal. calcd. for $C_{12}H_{16}NO_4PS+HBr+0.1CH_2Cl_2$: C: 37.20; H: 4.44; N: 3.58. Found: C: 37.24; H: 4.56; N: 3.30.

(3.3) 4-[2-(5-Phosphono)furanyl]thiazole. Anal. calcd. for $C_7H_6NO_4PS+0.65HBr$: C: 29.63; H: 2.36; N: 4.94. Found: C: 29.92; H: 2.66; N: 4.57.

(3.4) 2-Methyl-4-[2-(5-phosphono)fiuanyl]thiazole. mp 235–236° C. Anal. calcd. for $C_8H_8NO_4PS+0.25H_2O$: C: 38.48; H: 3.43; N: 5.61. Found: C: 38.68; H: 3.33; N: 5.36.

(3.5) 2-Phenyl-5-isobutyl-4-[2-(5-phosphono)furanyl]thiazole. Anal. calcd. for $C_{17}H_{18}NO_4PS+HBr$: C: 45.96; H: 4.31; N: 3.15. Found: C: 45.56; H: 4.26; N: 2.76.

(3.6) 2-Isopropyl-4-[2-(5-phosphono)furanyl]thiazole. mp 194–197° C. Anal. calcd. for $C_{10}H_{12}NO_4PS$: C: 43.96; H: 4.43; N: 5.13. Found: C: 43.70; H: 4.35; N: 4.75.

(3.7) 5-Isobutyl-4-[2-(5-phosphono)furanyl]thiazole. mp 164–166° C. Anal. calcd. for $C_{11}H_{14}NO_4PS$: C: 45.99; H: 4.91; N: 4.88. Found: C: 45.63; H: 5.01; N: 4.73.

(3.8) 2-Aminothiocarbonyl-4-[2-(5-phosphono)furanyl]thiazole. mp 189–191° C. Anal. calcd. for $C_8H_7N_2O_4PS_2$: C: 33.10; H: 2.43; N: 9.65. Found: C: 33.14; H: 2.50; N: 9.32.

(3.9) 2-(1-Piperidyl)-5-isobutyl-4-[2-(5-phosphono)furanyl]thiazole. Anal. calcd. for $C_{16}H_{23}N_2O_4PS+1.3HBr$: C: 40.41; H: 5.15; N: 5.89. Found: C: 40.46; H: 5.36; N: 5.53.

(3.10) 2-(2-Thienyl)-5-isobutyl-4-[2-(5-phosphono)furanyl]thiazole. Anal. calcd. for $C_{15}H_{16}NO_4PS_2+0.75H_2O$: C: 47.05; H: 4.61; N: 3.66. Found: C: 47.39; H: 4.36; N: 3.28.

(3.11) 2-(3-Pyridyl)-5-isobutyl-4-[2-(5-phosphono)furanyl]thiazole. Anal. calcd. for $C_{16}H_{17}N_2O_4PS+3.75HBr$: C: 28.78; H: 3.13; N: 4.20. Found: C: 28.73; H: 2.73; N: 4.53.

(3.12) 2-Acetamido-5-isobutyl-4-[2-(5-phosphono)furanyl]thiazole. mp 179–181° C. Anal. calcd. for $C_{13}H_{17}N_2O_5PS+0.25H_2O$: C: 44:76; H: 5.06; N: 8.03. Found: C: 44.73; H: 5.07; N: 7.89.

(3.13) 2-Amino-4-[2-(5-phosphono)furanyl]thiazole. Anal. calcd. for $C_7H_7N_2O_4PS$: C: 34.15; H: 2.87; N: 11.38. Found: C: 33.88; H: 2.83; N: 11.17.

(3.14) 2-Methylamino-5-isobutyl-4-[2-(5-phosphono)furanyl]thiazole. mp 202–205° C. Anal. calcd. for $C_{12}H_{17}N_2O_4PS+0.5H_2O$: C: 44.30; H: 5.58; N: 8.60. Found: C: 44.67; H: 5.27; N: 8.43.

(3.15) 2-(N-amino-N-methyl)amino-5-isobutyl-4-[2-(5-phosphono)furanyl]thiazole. mp 179–181° C. Anal. calcd. for $C_{12}H_{18}N_3O_4PS+1.25HBr$: C: 33.33; H: 4.49; N: 9.72. Found C: 33.46; H: 4.81; N: 9.72.

(3.16) 2-Amino-5-methyl-4-[2-(5-phosphono)furanyl]thiazole. mp 200–220° C. Anal. calcd. for $C_8H_9N_2O_4PS+0.65HBr$: C: 30.72; H: 3.11; N: 8.96. Found: C: 30.86; H: 3.33; N: 8.85.

(3.17) 2,5-Dimethyl-4-[2-(5-phosphono)furanyl]thiazole. mp 195° C. (decomp). Anal. calcd. for $C_9H_{10}NO_4PS+0.7HBr$: C: 34.22; H: 3.41; N: 4.43. Found: C: 34.06; H: 3.54; N: 4.12.

(3.18) 2-Aminothiocarbonyl-5-isobutyl-4-[2-(5-phosphono)furanyl]thiazole. Anal. calcd. for $C_{12}H_{15}N_2O_4PS_2+0.1HBr+0.3EtOAc$: C: 41.62; H: 4.63; N: 7.35. Found: C: 41.72; H: 4.30; N: 7.17.

(3.19) 2-Ethoxycarbonyl-4-[2-(5-phosphono)furanyl]thiazole. mp 163–165° C. Anal. calcd. for $C_{10}H_{10}NO_6PS+0.5H_2O$: C: 38.47; H: 3.55; N: 4.49. Found: C: 38.35; H: 3.30; N: 4.42.

(3.20) 2-Amino-5-isopropyl-4-[2-(5-phosphono)furanyl]thiazole. Anal. calcd. for $C_{10}H_{13}N_2O_4PS+1HBr$: C: 32.53; H: 3.82; N: 7.59. Found: C: 32.90; H: 3.78; N: 7.65.

(3.21) 2-Amino-5-ethyl-4-[2-(5-phosphono)furanyl]thiazole. mp >250° C. Anal. calcd. for $C_9H_{11}N_2O_4PS$: C: 39.42; H: 4.04; N: 10.22. Found: C: 39.02; H: 4.15; N: 9.92.

(3.22) 2-Cyanomethyl-4-[2-(5-phosphono)furanyl]thiazole. mp 204–206° C. Anal. calcd. for $C_9H_7N_2O_4PS$: C: 40.01; H: 2.61; N: 10.37. Found: C: 39.69; H: 2.64; N: 10.03.

(3.23) 2-Aminothiocarbonylamino-5-isobutyl-4-[2-(5-phosphono)furanyl]thiazole. mp 177–182° C. Anal. calcd. for $C_{12}H_{16}N_3O_4PS_2+0.2hexane+0.3HBr$: C: 39.35; H: 4.78; N: 10.43. Found: C: 39.61; H: 4.48; N: 10.24.

(3.24) 2-Amino-5-propyl-4-[2-(5-phosphono)furanyl]thiazole. mp 235–237° C. Anal. calcd. for $C_{10}H_{13}N_2O_4PS+0.3H_2O$: C: 40.90; H: 4.67; N: 9.54. Found: C: 40.91; H: 4.44; N: 9.37.

(3.25) 2-Amino-5-ethoxycarbonyl-4-[2-(5-phosphono)furanyl]thiazole. mp 248–250° C. Anal. calcd. for $C_{10}H_{11}N_2O_6PS+0.1HBr$: C: 36.81; H: 3.43; N: 8.58. Found: C: 36.99; H: 3.35; N: 8.84.

(3.26) 2-Amino-5-methylthio-4-[2-(5-phosphono)furanyl]thiazole. mp 181–184° C. Anal. calcd. for $C_8H_9N_2O_4PS_2+0.4H_2O$: C: 32.08; H: 3.30; N: 9.35. Found: C: 32.09; H: 3.31; N: 9.15.

(3.27) 2-Amino-5-cyclopropyl-4-[2-(5-phosphono)furanyl]thiazole. Anal. calcd. for $C_{10}H_{11}N_2O_4PS+1H_2O+0.75HBr$: C: 32.91; H: 3.80; N: 7.68. Found: C: 33.10; H: 3.80; N: 7.34.

(3.28) 2-Amino-5-methanesulfinyl-4-[2-(5-phosphono)furanyl]thiazole. mp>250° C. Anal. calcd. for $C_8H_9N_2O_5PS_2+0.35NaCl$: C: 29.23; H: 2.76; N: 8.52. Found: C: 29.37; H: 2.52; N: 8.44.

(3.29) 2-Amino-5-benzyloxycarbonyl-4-[2-(5-phosphono)furanyl]thiazole. Anal. calcd. for $C_{15}H_{13}N_2O_6PS+0.2H_2O$: C: 46.93; H: 3.52; N: 7.30. Found: C: 46.64; H: 3.18; N: 7.20.

(3.30) 2-Amino-5-cyclobutyl-4-[2-(5-phosphono)furanyl]thiazole. Anal. calcd. for $C_{11}H_{13}N_2O_4PS+0.15HBr+0.15H_2O$: C: 41.93; H: 4.30; N: 8.89. Found: C: 42.18; H: 4.49; N: 8.53.

(3.31) 2-Amino-5-cyclopropyl-4-[2-(5-phosphono)furanyl]thiazole hydrobromide. Anal. calcd. for $C_{10}H_{11}N_2O_4PSBr+0.73HBr+0.15MeOH+0.5H_2O$: C: 33.95; H: 3.74; N: 7.80; S: 8.93; Br: 16.24. Found: C: 33.72; H: 3.79; N: 7.65; S: 9.26; Br: 16.03.

(3.32) 2-Amino-5-[(N,N-dimethyl)aminomethyl]-4-[2-(5-phosphono)furanyl]thiazole dihydrobromide. Anal. calcd. for $C_{10}H_{16}N_3O_4Br_2PS+0.8CH_2Cl_2$: C: 24.34; H: 3.33; N: 7.88. Found: C: 24.23; H: 3.35; N: 7.64.

(3.33) 2-Amino-5-methoxycarbonyl-4-[2-(5-phosphono)furanyl]thiazole. Mp 227° C. (decomp). Anal. calcd. for $C_9H_9N_2O_6PS+0.1H_2O+0.2HBr$: C: 33.55; H: 2.94; N: 8.69. Found: C: 33.46; H: 3.02; N: 8.49.

(3.34) 2-Amino-5-ethylthiocarbonyl-4-[2-(5-phosphono)furanyl]thiazole. Mp 245° C. (decomp). Anal. calcd. for $C_{10}H_{11}N_2O_5PS_2$: C: 35.93; H: 3.32; N: 8.38. Found: C: 35.98; H: 3.13; N: 8.17.

(3.35) 2-Amino-5-propyloxycarbonyl-4-[2-(5-phosphono)furanyl]thiazole. Mp 245° C. (decomp). Anal. calcd. for $C_{11}H_{13}N_2O_6PS$: C: 39.76; H: 3.94; N: 8.43. Found: C: 39.77; H: 3.72; N: 8.19.

(3.36) 2-Amino-5-benzyl-4-[2-(5-phosphono)furanyl]thiazole. Anal. calcd. for $C_{14}H_{13}N_2O_4PS+H_2O$: C: 47.46; H: 4.27; N: 7.91. Found: C: 47.24; H: 4.08; N: 7.85.

(3.37) 2-Amino-5-[(N,N-diethyl)aminomethyl]-4-[2-(5-phosphono)furanyl]thiazole dihydrobromide. Anal. calcd. for $C_{12}H_{20}N_3O_4Br_2PS+0.1HBr+1.4MeOH$: C: 29.47; H: 4.74; N: 7.69. Found: C: 29.41; H: 4.60; N: 7.32.

(3.38) 2-Amino-5-[(N,N-dimethyl)carbamoyl]-4-[2-(5-phosphono)furanyl]thiazole. Anal. calcd. for $C_{10}H_{12}N_3O_5PS+1.3HBr+1.0H_2O+0.3Acetone$: C: 28.59; H: 3.76; N: 9.18. Found: C: 28.40; H: 3.88; N: 9.01.

(3.39) 2-Amino-5-carboxyl-4-[2-(5-phosphono)furanyl]thiazole. Anal. calcd. for $C_8H_7N_2O_6PS+0.2HBr+0.1H_2O$: C: 31.18; H: 2.42; N: 9.09. Found: C: 31.11; H: 2.42; N: 8.83.

(3.40) 2-Amino-5-isopropyloxycarbonyl-4-[2-(5-phosphono)furanyl]thiazole. Mp 240° C. (decomp). Anal. calcd. for $C_{11}H_{13}N_2O_6PS$: C: 39.76; H: 3.94; N: 8.43. Found: C: 39.42; H: 3.67; N: 8.09.

(3.41) 2-Methyl-5-ethyl-4-[2-(5-phosphono)furanyl]thiazole. Anal. calcd. for $C_{10}H_{12}O_4PNS+0.75HBr+0.35H_2O$: C: 36.02; H: 4.13; N: 4.06. Found: C: 36.34; H: 3.86; N: 3.69.

(3.42) 2-Methyl-5-cyclopropyl-4-[2-(5-phosphono)furanyl]thiazole. Anal. calcd. for $C_{11}H_{12}NO_4PS+0.3HBr+0.5CHCl_3$: C: 37.41; H: 3.49; N: 3.79. Found: C: 37.61; H: 3.29; N: 3.41.

(3.43) 2-Methyl-5-ethoxycarbonyl-4-[2-(5-phosphono)furanyl]thiazole. Anal. calcd. for $C_{11}H_{12}NO_6PS$: C: 41.64; H: 3.81; N: 4.40. Found: C: 41.61; H: 3.78; N: 4.39.

(3.44) 2-[(N-acetyl)amino]-5-methoxymethyl-4-[2-(5-phosphono)furanyl]thiazole. Anal. calcd. for $C_{11}H_{13}N_2O_6PS+0.15HBr$: C: 38.36; H: 3.85; N: 8.13. Found: C: 38.74; H: 3.44; N: 8.13.

(3.45) 2-Amino-5-(4-morpholinyl)methyl-4-[2-(5-phosphono)furanyl]thiazole dihydrobromide. Anal. calcd. for $C_{12}H_{18}Br_2N_3O_5PS+0.25HBr$: C: 27.33; H: 3.49; N: 7.97. Found: C: 27.55; H: 3.75; N: 7.62.

(3.46) 2-Amino-5-cyclopropylmethoxycarbonyl-4-[2-(5-phosphono)furanyl]thiazole. Mp 238° C. (decom p). Anal. calcd. for $C_{12}H_{13}N_2O_6PS$: C: 41.86; H: 3.81; N: 8.14. Found: C: 41.69; H: 3.70; N: 8.01.

(3.47) 2-Amino-5-methylthio-4-[2-(5-phosphono)furanyl]thiazole N,N-dicyclohexylammonium salt. Mp>250° C. Anal. calcd. for $C_8H_9N_2O_4PS_2+1.15C_{12}H_{23}N$: C: 52.28; H: 7.13; N: 8.81. Found: C: 52.12; H: 7.17; N: 8.81.

(3.48) 2-[(N-Dansyl)amino]-5-isobutyl-4-[2-(5-phosphono)furanyl]thiazole. Anal. calcd. for $C_{23}H_{26}N_3O_6PS_2+0.5HBr$: C: 47.96; H: 4.64; N: 7.29. Found: C: 48.23; H: 4.67; N: 7.22.

(3.49) 2-Amino-5-(2,2,2-trifluoroethyl)-4-[2-(5-phosphono)furanyl]thiazole. Anal. calcd for $C_9H_8N_2F_3O_4PS$: C: 32.94, H: 2.46, N: 8.54. Found: C: 32.57, H: 2.64, N: 8.14.

(3.50) 2-Methyl-5-methylthio-4-[2-(5-phosphono)furanyl]thiazole. Anal. calcd for $C_9H_{10}NO_4PS_2$ C: 37.11; H: 3.46; N: 4.81. Found: C: 36.72; H: 3.23; N: 4.60.

(3.51) 2-Amino-5-methylthio-4-[2-(5-phosphono)furanyl]thiazole ammonium salt. Anal. calcd for $C_8H_{12}N_3O_4PS_2$: C: 31.07; H: 3.91; N: 13.59. Found: C: 31.28; H: 3.75; N: 13.60.

(3.52) 2-Cyano-5-ethyl-4-[2-(5-phosphono)furanyl]thiazole. Anal. calcd for $C_{10}H_9N_2O_4PS$: C: 42.26; H: 3.19; N: 9.86. Found: C: 41.96; H: 2.95; N: 9.76.

(3.53) 2-Amino-5-hydroxymethyl-4-[2-(5-phosphono)furanyl]thiazole. Anal. calcd for $C_8H_9N_2O_5PS$: C: 34.79; H: 3.28; N: 10.14. Found: C: 34.57; H: 3.00; N: 10.04.

(3.54) 2-Cyano-5-isobutyl-4-[2-(5-phosphono)furanyl]thiazole. Anal. calcd for $C_{12}H_{13}N_2O_4SP+0.09HBr$: C: 46.15; H: 4.20; N: 8.97. Found: C: 44.81; H: 3.91; N: 8.51.

(3.55) 2-Amino-5-isopropylthio-4-[2-(5-phosphono)furanyl]thiazole hydrobromide. Anal. calcd for $C_{10}H_{14}BrN_2O_4PS_2$: C: 29.94; H: 3.52; N: 6.98. Found: C: 30.10; H: 3.20; N: 6.70.

(3.56) 2-Amino-5-phenylthio-4-[2-(5-phosphono)furanyl]thiazole. Anal. calcd for $C_{13}H_{11}N_2O_4PS_2$: C: 44.07; H: 3.13; N: 0.91. Found: C: 43.83; H: 3.07; N: 7.74.

(3.57) 2-Amino-5-tert-butylthio-4-[2-(5-phosphono)furanyl]thiazole. Anal. calcd for $C_{11}H_{15}N_2O_4PS_2+0.6CH_2Cl_2$: C: 36.16; H: 4.24; N: 7.27. Found: C: 36.39; H: 3.86; N: 7.21.

(3.58) 2-Amino-5-propylthio-4-[2-(5-phosphono)furanyl]thiazole hydrobromide. Anal. calcd for $C_{10}H_{14}BrN_2O_4PS_2$: C: 29.94; H: 3.52; N: 6.98. Found: C: 29.58; H: 3.50; N: 6.84.

(3.59) 2-Amino-5-ethylthio-4-[2-(5-phosphono)furanyl]thiazole. Anal. calcd for $C_9H_{11}N_2O_4PS_2+0.25HBr$: C: 33.11; H: 3.47; N: 8.58. Found: C: 33.30; H: 3.42; N: 8.60.

(3.60) 2-[(N-tert-butyloxycarbonyl)amino]-5-methoxymethyl-4-[2-(5-phosphono)furanyl]thiazole. Anal. calcd for $C_{14}H_{19}N_2O_7PS$: C: 43.08; H: 4.91; N: 7.18. Found: C: 42.69; H: 4.58; N: 7.39.

(3.61) 2-Hydroxyl-4-[2-(5-phosphono)furanyl]thiazole. Anal. calcd for $C_7H_6NO_5PS$: C: 34.02; H: 2.45; N: 5.67. Found: C: 33.69; H: 2.42; N: 5.39.

(3.62) 2-Hydroxyl-5-ethyl-4-[2-(5-phosphono)furanyl]thiazole. Anal. calcd for $C_9H_{10}NO_5PS$: C: 39.28; H: 3.66; N: 5.09. Found: C: 39.04; H: 3.44; N: 4.93.

(3.63) 2-Hydroxyl-5-isopropyl-4-[2-(5-phosphono)furanyl]thiazole. Anal. calcd for $C_{10}H_{12}NO_5PS+0.1HBr$: C: 40.39; H: 4.10; N: 4.71. Found: C: 40.44; H: 4.11; N: 4.68.

(3.64) 2-Hydroxyl-5-isobutyl-4-[2-(5-phosphono)furanyl]thiazole. Anal. calcd for $C_{11}H_{14}NO_5PS$: C: 43.57; H: 4.65; N: 4.62. Found: C: 43.45; H: 4.66; N: 4.46.

(3.65) 5-Ethoxycarbonyl-4-[2-(5-phosphono)furanyl]thiazole. Anal. calcd for $C_{10}H_{10}NO_6PS$: C: 39.61; H: 3.32; N: 4.62. Found: C: 39.60; H: 3.24; N: 4.47.

(3.66) 2-Amino-5-vinyl-4-[2-(5-phosphono)furanyl]thiazole. Anal. calcd for $C_9H_9N_2O_4PS+0.28HCl$: C: 37.66; H: 3.26; N: 9.46. Found: C: 37.96; H: 3.37; N: 9.10.

(3.67) 2-Amino-4-[2-(6-phosphono)pyridyl]thiazole hydrobromide.

(3.68) 2-Methylthio-5-isobutyl-4-[2-(5-phosphono)furanyl]thiazole. Anal. calcd for $C_{12}H_{16}NO_4PS_2$: C: 43.24; H: 4.84; N: 4.20. Found: C: 43.55; H: 4.63; N: 4.46.

(3.69) 2-Amino-5-isobutyl-4-[2-(3-phosphono)furanyl]thiazole. Anal. calcd for $C_{11}H_{15}N_2O_4PS+0.1H_2O$: C: 43.45; H: 5.04; N: 9.21. Found: C: 43.68; H: 5.38; N: 8.98.

(3.70) 2-Amino-5-isobutyl-4-[2-(5-phosphono)furanyl]selenazole. Anal. calcd for $C_{11}H_{15}N_2O_4PSe+0.14HBr+0.6EtOAc$: C: 38.93; H: 4.86; N: 6.78. Found: C: 39.18; H: 4.53; N: 6.61.

(3.71) 2-Amino-5-methylthio-4-[2-(5-phosphono)furanyl]selenazole. Anal. calcd for $C_8H_9N_2O_4PSSe+0.7HBr+0.2EtOAc$: C: 25.57; H: 2.75; N: 6.78. Found: C: 25.46; H: 2.49; N: 6.74.

(3.72) 2-Amino-5-ethyl-4-[2-(5-phosphono)furanyl]selenazole. Anal. calcd for $C_9H_{11}N_2O_4PSe+HBr$: C: 26.89; H: 3.01; N: 6.97. Found: C: 26.60; H: 3.16; N: 6.81.

Example 4

Preparation of 5-halo-4-[2-(5-phosphono)furanyl]thiazoles

Step A.

A solution of 2-amino-4-[2-(5-diethylphosphono)furanyl]thiazole (prepared as in Step B of Example 3) (1 mmole) in chloroform was treated with N-bromo succinimide (NBS) (1.5 mmole) at 25° C. for 1 h. Extraction and chromatography gave 2-amino-5-bromo-4-[2-(5-diethylphosphono)furanyl]-thiazole as a brown solid.

Step B.

2-Amino-5-bromo-4-[2-(5-diethylphosphono)furanyl]thiazole was subjected to Step C of Example 3 to give 2-amino-5-bromo-4-[2-(5-phosphono)furanyl]thiazole (4.1) as a yellow solid. mp>230° C. Anal. calcd. for $C_7H_6N_2O_4PSBr$: C: 25.86; H: 1.86; N: 8.62. Found: C: 25.93; H: 1.64; N: 8.53.

The following compounds were prepared according to this procedure:

(4.2) 2-Amino-5-chloro-4-[2-(5-phosphono)furanyl]thiazole. Anal. calcd. for $C_7H_6N_2O_4PSCl$: C: 29.96; H: 2.16; N: 9.98. Found: C: 29.99; H: 1.97; N: 9.75.

(4.3) 2-Amino-5-iodo-4-[2-(5-phosphono)furanyl]thiazole. Anal. calcd. for $C_7H_6N_2O_4PSI$: C: 22.42; H: 2.28; N: 6.70. Found: C: 22.32; H: 2.10; N: 6.31.

(4.4) 2,5-Dibromo-4-[2-(5-phosphono)furanyl]thiazole. Anal. calcd. for $C_7H_4NO_4PSBr_2$: C: 21.62; H: 1.04; N: 3.60. Found: C: 21.88; H: 0.83; N: 3.66.

Example 5

Preparation of 2-halo-4-[2-(5-phosphono)furanyl]thiazoles

Step A.

A solution of 2-amino-5-isobutyl-4-[2-(5-diethylphosphono)-furanyl]thiazole (prepared as in Step B of Example 3) (1 mmole) in acetonitrile was treated with copper (II) bromide (1.2 mmole) and isoamyl nitrite (1.2 mmole) at 0° C. for 1 h. Extraction and chromatography gave 2-bromo-5-isobutyl-4-[2-(5-diethylphosphono)furanyl]thiazole as a brown solid.

Step B.

2-Bromo-5-isobutyl-4-[2-(5-diethylphosphono)furanyl]thiazole was subjected to Step C of Example 3 to give 2-bromo-5-isobutyl-4-[2-(5-phosphono)furanyl]thiazole (5.1) as a yellow hygroscopic solid. Anal. calcd. for $C_{11}H_{13}NO_4PSBr$: C: 36.08; H: 3.58; N: 3.83. Found: C: 36.47; H: 3.66; N: 3.69.

The following compounds were prepared according to this procedure:

(5.2) 2-Chloro-5-isobutyl-4-[2-(5-phosphono)furanyl]thiazole: Anal. calcd. for $C_{11}H_{13}NO_4PSCl$: C: 41.07; H: 4.07; N: 4.35. Found: C: 40.77; H: 4.31; N: 4.05.

(5.3) 2-Bromo-5-methylthio-4-[2-(5-phosphono)furanyl]thiazole: Anal. calcd. for $C_8H_7NO_4PS_2Br$: C: 26.98; H: 1.98; N: 3.93. Found: C: 27.21; H: 1.82; N: 3.84.

Example 6

Preparation of Various 2- and 5-substituted 4-[2-(5-phosphono)furanyl]thiazoles

Step A.

A solution of 2-bromo-5-isobutyl-4-[2-(5-diethylphosphono)-furanyl]thiazole (1 mmole, prepared as in the Step A of Example 5) in DMF was treated with tributyl(vinyl)tin (5 mmole) and palladium bis(triphenylphosphine) dichloride (0.05 mmole) at 100° C. under nitrogen. After 5 h the cooled reaction mixture was evaporated and the residue was subjected to chromatography to give 2-vinyl-5-isobutyl-4-[2-(5-diethylphosphono)furanyl]thiazole as a yellow solid.

Step B.

2-Vinyl-5-isobutyl-4-[2-(5-diethylphosphono)furanyl]thiazole was subjected to Step C of Example 3 to give 2-vinyl-5-isobutyl-4-[2-(5-phosphono)-furanyl]thiazole (6.1) as a yellow solid. Anal. calcd. for $C_{13}H_{16}NO_4PS+1HBr+0.1H_2O$: C: 39.43; H: 4.38; N: 3.54. Found: C: 39.18; H: 4.38; N: 3.56.

This method can also be used to prepare various 5-substituted 4-[2-(5-phosphono)furanyl]thiazoles from their corresponding halides.

Step C.

2-Amino-5-bromo-4-[2-(5-diethylphosphono)furanyl]thiazole was subjected to Step A using 2-tributylstannylfuran as the coupling partner to give 2-amino-5-(2-furanyl)-4-[2-(5-diethylphosphono)furanyl]thiazole.

Step D.

2-Amino-5-(2-furanyl)-4-[2-(5-diethylphosphono)furanyl]thiazole was subjected to Step C of Example 3 to give 2-amino-5-(2-furanyl)-4-[2-(5-phosphono)furanyl]thiazole (6.2). mp 190–210C. Anal. calcd. for $C_{11}H_9N_2O_5PS+0.25HBr$: C: 39.74; H: 2.80; N: 8.43. Found: C: 39.83; H: 2.92; N: 8.46.

The following compound was prepared according to this procedure:

(6.3) 2-Amino-5-(2-thienyl)-4-[2-(5-diethylphosphono)furanyl]thiazole. Anal. calcd. for $C_{11}H_9N_2O_4PS_2+0.3EtOAc+0.11HBr$: C: 40.77; H: 3.40; N: 7.79. Found: C: 40.87; H: 3.04; N: 7.45.

Example 7

Preparation of 2-ethyl-4-[2-(5-phosphono)furanyl]thiazoles

Step A.

A solution of 2-vinyl-5-isobutyl-4-[2-(5-diethylphosphono)furanyl]-thiazole (1 mmole, prepared as in the Step A of Example 6) in ethanol was treated with palladium on carbon (0.05 mmole) under 1 atmosphere of hydrogen for 12 h. The reaction mixture was filtered, the filtrate was evaporated and the residue was purified by chromatography to give 2-ethyl-5-isobutyl-4-[2-(5-diethylphosphono)furanyl]thiazole as a yellow foam.

Step B.

2-Ethyl-5-isobutyl-4-[2-(5-diethylphosphono)furanyl]thiazole was subjected to Step C of Example 3 to give 2-ethyl-5-isobutyl-4-[2-(5-phosphono)-furanyl]thiazole (7.1) as a yellow solid. Anal. calcd. for $C_{13}H_{18}NO_4PS+1HBr$: C: 39.41; H: 4.83; N: 3.53. Found: C: 39.65; H: 4.79; N: 3.61.

Example 8

Preparation of 4-phosphonomethoxymethylthiazoles

Step A.

A solution of diethyl hydroxymethylphosphonate (1 mmole) in DMF was treated with sodium hydride (1.2 mmole) followed by 2-methyl-4-chloromethylthiazole (1 mmole) at 0° C. and stirred at 25° C. for 12 h. Extraction and chromatography gave 2-methyl-4-(diethylphosphonomethoxymethyl)thiazole.

Step B.

2-Methyl-4-diethylphosphonomethoxymethylthiazole was subjected to Step C of Example 3 to give 2-methyl-4-phosphonomethoxymethylthiazole (8.1). Anal. calcd. for $C_6H_{10}NO_4PS+0.5HBr+0.5H_2O$: C: 26.43; H: 4.25; N: 5.14. Found: C: 26.52; H: 4.22; N: 4.84.

Step C.

2-Methyl-4-diethylphosphonomethoxymethylthiazole was subjected to Step A of Example 4 and followed by Step C of Example 3 to give 5-bromo-2-methyl-4-phosphonomethoxymethylthiazole (8.2). Anal. calcd. for $C_6H_9NO_4PSBr+0.5HBr$: C: 21.04; H: 2.80; N: 4.09. Found: C: 21.13; H: 2.69; N: 4.01.

Step D.

A solution of ethyl 2-[(N-Boc)amino]-4-thiazolecarboxylate (1 mmole) in $CH_2Cl_2$ (10 mL) was cooled to −78° C., and treated with DIBAL-H (1M, 5 mL). The reaction was stirred at −60° C. for 3 h, and quenched with a suspension of NaF/H$_2$O (1 g/1 mL). The resulting mixture was filtered and the filtrate was concentrated to give 2-[(N-Boc)amino]-4-hydroxymethylthiazole as a solid.

Step E.

A solution of 2-[(N-Boc)amino]-4-hydroxymethylthiazole (1 mmole) in DMF (10 mL) was cooled to 0° C., and treated with NaH (1.1 mmole). The mixture was stirred at room temperature for 30 min, then phosphonomethyl trifluoromethanesulfonate (1.1 mmole) was added. After stirring at room temperature for 4 h, the reaction was evaporated to dryness. Chromatography of the residue gave 2-[(N-Boc)amino]-4-diethylphosphonomethoxylmethylthiazole as a solid.

Step F.

2-[(N-Boc)amino]-4-diethylphosphonomethoxylmethylthiazole was subjected to Step C of Example 3 to give 2-amino-4-phosphonomethoxymethylthiazole (8.3) as a solid. Anal. calcd. for C$_5$H$_9$N$_2$O$_4$PS+0.16HBr+0.1MeOH: C: 25.49; H: 4.01; N: 11.66. Found: C: 25.68; H: 3.84; N: 11.33.

Example 9

Preparation of 2-carbamoyl-4-[2-(5-phosphono)furanyl]thiazoles

Step A.

A solution of 2-ethoxycarbonyl-5-isobutyl-4-[2-(5-diethylphosphono)furanyl]thiazole (1 mmole) in saturated methanolic ammonia solution at 25° C. for 12 h. Evaporation and chromatography gave 2-carbamoyl-5-isobutyl-4-[2-(5-diethylphosphono)furanyl]thiazole as a white solid.

Step B.

2-Carbamoyl-5-isobutyl-4-[2-(5-diethylphosphono)furanyl]thiazole was subjected to Step C of Example 3 to give 2-carbamoyl-5-isobutyl-4-[2-(5-phosphono)furanyl]thiazole (9.1) as a solid. mp 185–186° C. Anal. calcd. for C$_{12}$H$_{15}$N$_2$O$_5$PS: C: 43.64; H: 4.58; N: 8.48. Found: C: 43.88; H: 4.70; N: 8.17.

The following compound was prepared according to this procedure:

(9.2) 2-Carbamoyl-4-[2-(5-phosphono)furanyl]thiazole. mp 195–200° C. Anal. calcd. for C$_8$H$_7$N$_2$O$_5$PS+0.25H$_2$O: C: 34.48; H: 2.71; N: 10.05. Found: C: 34.67; H: 2.44; N: 9.84.

2-Ethoxycarbonyl-4-[2-(5-diethylphosphono)furanyl]thiazoles can also be converted to other 2-substituted 4-[2-(5-phosphono)furanyl]thiazoles.

Step C.

A solution of 2-ethoxycarbonyl-4-[2-(5-diethylphosphono)furanyl]thiazole (1 mmole) in methanol was treated with sodium borohydride (1.2 mmole) at 25° C. for 12 h. Extraction and chromatography gave 2-hydroxymethyl-4-[2-(5-diethylphosphono)furanyl]thiazole.

Step D.

2-Hydroxymethyl-4-[2-(5-diethylphosphono)furanyl]-thiazole was subjected to Step C of Example 3 to give 2-hydroxymethyl-4-[2-(5-phosphono)furanyl]thiazole (9.3). mp 205–207° C. Anal. calcd. for C$_8$H$_8$NO$_5$PS+0.25H$_2$O: C: 36.16; H: 3.22; N: 5.27. Found: C: 35.98; H: 2.84; N: 5.15.

The following compound was prepared according to this procedure:

(9.4) 2-Hydroxymethyl-5-isobutyl-4-[2-(5-phosphono)furanyl]thiazole. mp 160–170° C. Anal. calcd. for C$_{12}$H$_{16}$NO$_5$PS+0.75HBr: C: 38.13; H: 4.47; N: 3.71. Found: C: 37.90; H: 4.08; N: 3.60.

Step E.

A solution of 2-hydroxymethyl-5-isobutyl-4-[2-(5-diethylphosphono)furanyl]thiazole (1 mmole) in methylene chloride was treated with phosphorus tribromide (1.2 mmole) at 25° C. for 2 h. Extraction and chromatography gave 2-bromomethyl-5-isobutyl-4-[2-(5-diethylphosphono)furanyl]thiazole.

Step F.

2-Bromomethyl-5-isobutyl-4-[2-(5-diethylphosphono)furanyl]-thiazole was subjected to Step C of Example 3 to give 2-bromomethyl-5-isobutyl-4-[2-(5-phosphono)furanyl]thiazole (9.5). mp 161–163° C. Anal. calcd. for C$_{12}$H$_{15}$BrNO$_4$PS+0.25HBr: C: 35.99; H: 3.84; N: 3.50. Found: C: 36.01; H: 3.52; N: 3.37.

The following compound was prepared according to this procedure:

(9.6) 2-Bromomethyl-4-[2-(5-phosphono)furanyl]thiazole. mp>250° C. Anal. calcd. for C$_8$H$_7$BrNO$_4$PS: C: 29.65; H: 2.18; N: 4.32. Found: C: 29.47; H: 1.99; N: 4.16.

Step G.

A solution of 2-hydroxymethyl-5-isobutyl-4-[2-(5-diethylphosphono)furanyl]thiazole (1 mmole) in methylene chloride was treated with thionyl chloride (1.2 mmole) at 25° C. for 2 h. Extraction and chromatography gave 2-chloromethyl-5-isobutyl-4-[2-(5-diethylphosphono)furanyl]thiazole.

Step H.

2-Chloromethyl-5-isobutyl-4-[2-(5-diethylphosphono)furanyl]-thiazole was subjected to Step C of Example 3 to give 2-chloromethyl-5-isobutyl-4-[2-(5-phosphono)furanyl]thiazole (9.7). mp 160–162° C. Anal. calcd. for C$_{12}$H$_{15}$ClNO$_4$PS+0.45HBr: C: 38.73; H: 4.18; N: 3.76. Found: C: 38.78; H: 4.14; N: 3.73.

Step I.

A solution of 2-bromomethyl-5-isobutyl-4-[2-(5-diethylphosphono)furanyl]thiazole (1 mmole) in DMF was treated with potassium phthalimide (1.2 mmole) at 25° C. for 12 h. Extraction and chromatography gave 2-phthalimidomethyl-5-isobutyl-4-[2-(5-diethylphosphono)furanyl]thiazole.

Step J.

2-Phthalimidomethyl-5-isobutyl-4-[2-(5-diethylphosphono)furanyl]-thiazole (1 mmole) in ethanol was treated with hydrazine (1.5 mmole) at 25° C. for 12 h. Filtration, evaporation and chromatography gave 2-aminomethyl-5-isobutyl-4-[2-(5-diethylphosphono)furanyl]thiazole.

Step K.

2-Aminomethyl-5-isobutyl-4-[2-(5-diethylphosphono)furanyl]-thiazole was subjected to Step C of Example 3 to give 2-aminomethyl-5-isobutyl-4-[2-(5-phosphono)furanyl]thiazole (9.8). mp 235–237° C. Anal. calcd. for C$_{12}$H$_{17}$N$_2$O$_4$PS+0.205HBr: C: 43.30; H: 5.21; N: 8.41. Found: C: 43.66; H: 4.83; N: 8.02.

According to the above procedures or in some cases with some minor modifications of the above procedures, the following compounds were prepared:

(9.9) 2-Carbamoyl-5-cyclopropyl-4-[2-(5-phosphono)furanyl]thiazole. Anal. calcd for C$_{11}$H$_{11}$N$_2$O$_5$PS+0.15HBr: C: 40.48; H: 3.44; N: 8.58. Found: C: 40.28; H: 3.83; N: 8.34.

(9.10) 2-Carbamoyl-5-ethyl-4-[2-(5-phosphono)furanyl]thiazole. Anal. calcd for C$_{10}$H$_{11}$N$_2$O$_5$PS+0.75H$_2$O: C: 38.04; H: 3.99; N: 8.87. Found: C: 37.65; H: 3.93; N: 8.76.

Example 10

Preparation of 4-[12-(5-phosphono)furanyl]oxazoles and 4-[2-(5-phosphono)furanyl]imidazoles Step A.

A solution of 5-diethylphosphono-2-[(2-bromo-4-methyl-1-oxo)pentyl]furanyl (1 mmole) in t-BuOH was treated with urea (10 mmole) at reflux for 72 h. Filtration, evaporation and chromatography gave 2-amino-5-isobutyl-4-[2-(5-diethylphosphono)furanyl]oxazole, and 2-hydroxy-5-isobutyl-4-[2-(5-diethylphosphono)furanyl]imidazole.

Step B.

2-Amino-5-isobutyl-4-[2-(5-diethylphosphono)furanyl]oxazole was subjected to Step C of Example 3 to give 2-amino-5-isobutyl-4-[2-(5-phosphono)furanyl]oxazole (10.1). mp 250° C. (decomp.). Anal. calcd. for $C_{11}H_{15}N_2O_5P$: C: 46.16; H: 5.28; N: 9.79. Found: C: 45.80; H: 5.15; N: 9.55.

Step C.

2-Hydroxy-5-isobutyl-4-[2-(5-diethylphosphono)furanyl]imidazole was subjected to Step C of Example 3 to give 2-hydroxy-5-isobutyl-4-[2-(5-phosphono)furanyl]imidazole (10.14). mp 205° C. (decomp). Anal. calcd. for $C_{11}H_{15}N_2O_5P$: C: 46.16; H: 5.28; N: 9.79. Found: C: 45.80; H: 4.90; N: 9.73:

Alternatively 4-[2-(5-phosphono)furanyl]oxazoles and 4-[2-(5-phosphono)furanyl]imidazoles can be prepared as follows:

Step D.

A solution of 5-diethylphosphono-2-[(2-bromo-4-methyl-1-oxo)pentyl]furan (1 mmole) in acetic acid was treated with sodium acetate (2 mmole) and ammonium acetate (2 mmole) at 100° C. for 4 h. Evaporation and chromatography gave 2-methyl-5-isobutyl-4-[2-(5-diethylphosphono)furanyl]oxazole, 2-methyl-4-isobutyl-5-[2-(5-diethylphosphono)furanyl]oxazole and 2-methyl-5-isobutyl-4-[2-(5-diethylphosphono)furanyl]imidazole.

Step E.

2-Methyl-5-isobutyl-4-[2-(5-diethylphosphono)furanyl]oxazole, 2-methyl-4-isobutyl-5-[2-(5-diethylphosphono)furanyl]oxazole and 2-methyl-5-isobutyl-4-[2-(5-diethylphosphono)furanyl]imidazole were subjected to Step C of Example 3 to give the following compounds:

(10.18) 2-Methyl-4-isobutyl-5-[2-(5-phosphono)furanyl]oxazole hydrogen bromide. mp>230° C.; Anal. calcd. for $C_{12}H_{17}BrNO_5P+0.4H_2O$: C: 38.60; H: 4.81; N: 3.75. Found: C: 38.29; H: 4.61; N: 3.67.

(10.19) 2-Methyl-5-isobutyl-4-[2-(5-phosphono)furanyl]oxazole hydrogen bromide. Anal. Calcd. for $C_{12}H_{17}BrNO_5P$: C: 39.36; H: 4.68; N: 3.83. Found: C: 39.33; H: 4.56; N: 3.85.

(10.21) 2-Methyl-5-isobutyl-4-[2-(5-phosphono)furanyl]imidazole hydrogen bromide. Anal. Calcd. for $C_{12}H_{18}BrN_2O_4P+0.2NH_4Br$: C: 37.46; H: 4.93; N: 8.01. Found: C: 37.12; H: 5.11; N: 8.28.

Alternatively 4-[2-(5-phosphono)furanyl]imidazoles can be prepared as follows:

Step F.

A solution of 5-diethylphosphono-2-(bromoacetyl)furan (1 mmole) in ethanol was treated with trifluoroacetamidine (2 mmole) at 80° C. for 4 h. Evaporation and chromatography gave 2-trifluoromethyl-4-[2-(5-diethylphosphono)furanyl]imidazole as an oil.

Step G.

2-Trifluoromethyl-4-[2-(5-diethylphosphono)furanyl]imidazole was subjected to Step C of Example 3 to give 2-trifluoromethyl-4-[2-(5-phosphono)furanyl]imidazole (10.22). mp 188° C. (dec.); Anal. calcd. for $C_8H_6F_3N_2O_4P+0.5HBr$: C: 29.79; H: 2.03; N: 8.68. Found: C: 29.93; H: 2.27; N: 8.30.

Alternatively 4,5-dimethyl-1-isobutyl-2-[2-(5-phosphono)furanyl]-imidazole can be prepared as follows:

Step H.

A solution of 5-diethylphosphono-2-furaldehyde (1 mmole), ammonium acetate (1.4 mmole), 3,4-butanedione (3 mmole) and isobutylamine (3 mmole) in glacial acetic acid was heated at 100° C. for 24 h. Evaporation and chromatography gave 4,5-dimethyl-1-isobutyl-2-[2-(5-diethylphosphono)furanyl]imidazole as an yellow solid.

Step I.

4,5-Dimethyl-1-isobutyl-2-[2-(5-diethylphosphono)furanyl]-imidazole was subjected to Step C of Example 3 to give 4,5-dimethyl-1-isobutyl-2-[2-(5-phosphono)furanyl]imidazole (10.23); Anal. calcd. for $C_{13}H_{19}N_2O_4P+1.35HBr$: C: 38.32; H: 5.03; N: 6.87. Found: C: 38.09; H: 5.04; N: 7.20.

According to the above procedures or in some cases with some minor modifications of the above procedures, the following compounds were prepared:

(10.2) 2-Amino-5-propyl-4-[2-(5-phosphono)furanyl]oxazole. mp 250° C. (decomp.); Anal. Calcd. for $C_{10}H_{13}N_2O_5P$: C: 44.13; H: 4.81; N: 10.29. Found: C: 43.74; H: 4.69; N: 9.92.

(10.3) 2-Amino-5-ethyl-4-[2-(5-phosphono)furanyl]oxazole. Anal. calcd. for $C_9H_{11}N_2O_5P+0.4H_2O$: C: 40.73; H: 4.48; N: 10.56. Found: C: 40.85; H: 4.10; N: 10.21.

(10.4) 2-Amino-5-methyl-4-[2-(5-phosphono)furanyl]oxazole. Anal. calcd. for $C_8H_9N_2O_5P+0.1H_2O$: C: 39.07; H: 3.77; N: 11.39. Found: C: 38.96; H: 3.59; N: 11.18.

(10.5) 2-Amino-4-[2-(5-phosphono)furanyl]oxazole. Anal. calcd. for $C_7H_7N_2O_5P+0.6H_2O$: C: 34.90; H: 3.43; N: 11.63. Found: C: 34.72; H: 3.08; N: 11.35.

(10.6) 2-Amino-5-isobutyl-4-[2-(5-phosphono)furanyl]oxazole hydrogen bromide. Anal. calcd. for $C_{11}H_{16}N_2O_5BrP+0.4H_2O$: C: 35.29; H: 4.52; N: 7.48. Found: C: 35.09; H: 4.21; N: 7.34.

(10.7) 2-Amino-5-phenyl-4-[2-(5-phosphono)furanyl]oxazole. Anal. calcd. for $C_{13}H_{11}N_2O_5P$: C: 50.99; H: 3.62; N: 9.15. Found: C: 50.70; H: 3.43; N: 8.96.

(10.8) 2-Amino-5-benzyl-4-[2-(5-phosphono)furanyl]oxazole. Anal. calcd. for $C_{14}H_{13}N_2O_5P+1.1H_2O$: C: 49.45; H: 4.51; N: 8.24. Found: C: 49.35; H: 4.32; N: 8.04.

(10.9) 2-Amino-5-cyclohexylmethyl-4-[2-(5-phosphono)furanyl]oxazole. Anal. calcd. for $C_{14}H_{19}N_2O_5P+0.3H_2O$: C: 50.70; H: 5.96; N: 8.45. Found: C: 50.60; H: 5.93; N: 8.38.

(10.10) 2-Amino-5-allyl-4-[2-(5-phosphono)furanyl]oxazole. Anal. calcd. for $C_{10}H_{11}N_2O_5P+0.4HBr+0.3H_2O$: C: 39.00; H: 3.93; N: 9.10. Found: C: 39.31; H: 3.83; N: 8.76.

(10:11) 5-Isobutyl-4-[2-(5-phosphono)furanyl]oxazole. Anal. calcd. for $C_{11}H_{14}NO_5P$: C: 48.72; H: 5.20; N: 5.16. Found: C: 48.67; H: 5.02; N: 5.10.

(10.12) 2-Amino-5-butyl-4-[2-(5-phosphono)furanyl]oxazole. Anal. calcd. for $C_{11}H_{15}N_2O_5P+0.2H_2O$: C: 45.59; H: 5.36; N: 9.67. Found: C: 45.32; H: 5.29; N: 9.50.

(10.13) 5-Isobutyl-4-[2-(5-phosphono)furanyl]oxazole-2-one. Anal. calcd. for $C_{11}H_{14}NO_6P+0.39HBr$: C: 41.45; H: 4.55; N: 4.39. Found: C: 41.79; H: 4.22; N: 4.04.

(10.15) 5-Cyclohexylmethyl-2-hydroxy-4-[2-(5-phosphono)furanyl]imidazole. Anal. calcd. for $C_{14}H_{19}N_2O_5P+0.05HBr$: C: 50.90; H: 5.81; N: 8.48. Found: C: 51.06; H: 5.83; N: 8.25.

(10.16) 5-Butyl-2-hydroxy-4-[2-(5-phosphono)furanyl]. Anal. calcd. for $C_{11}H_{15}N_2O_5P+0.2H_2O$: C: 45.59; H: 5.36; N: 9.67. Found: C: 45.77; H: 5.34; N: 9.39.

(10.17) 5-Benzyl-2-hydroxy-4-[2-(5-phosphono)furanyl] imidazole. Anal. calcd. for $C_{14}H_{13}N_2O_5P$: C: 52.51; H: 4.09; N: 8.75. Found: C: 52.29; H: 4.15; N: 8.36.

(10.20) 2-Methyl-5-propyl-4-[2-(5-phosphono)furanyl] imidazole hydrogen bromide. Anal. calcd. for $C_{11}H_{16}BrN_2O_4P+0.5H_2O$: C: 36.69; H: 4.76; N: 7.78. Found: C: 36.81; H: 4.99; N: 7.42.

(10.24) 2-Amino-5-(2-thienylmethyl)-4-[2-(5-phosphono)furanyl]oxazole. Anal. calcd for $C_{12}H_{11}N_2O_5PS+0.9HBr$: C: 36.12; H: 3.01; N: 7.02. Found: C: 36.37; H: 2.72; N: 7.01.

(10.25) 2-Dimethylamino-5-isobutyl-4-[2-(5-phosphono)furanyl]oxazole hydrogen bromide. Anal. Calcd for $C_{13}H_{20}BrN_2O_5P+0.05HBr$: C: 39.11; H: 5.06; N: 7.02. Found: C: 39.17; H: 4.83; N: 6.66

(10.26) 2-Isopropyl-5-isobutyl-4-[2-(5-phosphono)furanyl]oxazole. Anal. Calcd for $C_{14}H_{20}NO_5P+0.8HBr$: C: 44.48; H: 5.55; N: 3.71. Found: C: 44.45; H: 5.57; N: 3.73.

(10.27) 2-Amino-5-ethoxycarbonyl-4-[2-(5-phosphono)furanyl]oxazole. mp 245° C. (decomp.). Anal. Calcd for $C_{10}H_{11}N_2O_7P$: C: 39.75; H: 3.67; N: 9.27. Found: C: 39.45; H: 3.71; N: 8.87

(10.28) 2-Methylamino-5-isobutyl-4-[2-(5-phosphono)furanyl]oxazole hydrogen bromide. Anal. Calcd for $C_{12}H_{18}BrN_2O_5P+0.7H_2O$: C: 36.60; H: 4.97; N: 7.11. Found: C: 36.50; H: 5.09; N: 7.04.

(10.29) 2-Ethyl-5-isobutyl-4-[2-(5-phosphono)furanyl]oxazole hydrogen bromide. Anal. Calcd for $C_{13}H_{19}BrNO_5P$: C: 41.07; H: 5.04; N: 3.68. Found: C: 41.12; H: 4.84; N: 3:62.

(10.30) 2-Ethylamino-5-isobutyl-4-[2-(5-phosphono)furanyl]oxazole hydrogen bromide. Anal. Calcd for $C_{13}H_{20}BrN_2O_5P$: C: 39.51; H: 5.10; N: 7.09. Found: C: 39.03; H: 5.48; N: 8.90.

(10.31) 2-Vinyl-5-isobutyl-4-[2-(5-phosphono)furanyl]oxazole. Anal. Calcd for $C_{13}H_{16}NO_5P+0.25HBr$: C: 49.18; H: 5.16; N: 4.41. Found: C: 48.94; H: 5.15; N: 4.40.

(10.32) 2-Amino-5-pentyl-4-[2-(5-phosphono)furanyl]oxazole. Anal. Calcd for $C_{12}H_{17}N_2O_5P+0.5H_2O$: C: 46.61; H: 5.87; N: 9.06. Found: C: 46.38; H: 5.79; N: 9.07.

(10.33) 5-Pentyl-2-hydroxy-4-[2-(5-phosphono)furanyl] imidazole. Anal. calcd. for $C_{12}H_{17}N_2O_5P$: C: 48.00; H: 5.71; N: 9.33. Found: C: 48.04; H: 5.58; N: 9.26.

(10.45) 2-Amino-5-methylthio-4-[2-(5-phosphono)furanyl]oxazole. mp 196° C. (decomp). Anal. calcd. for $C_8H_9N_2O_5PS$: C: 34.79; H: 3.28; N: 10.14. Found: C: 34.60; H: 2.97; N: 10.00.

(10.35) 2-Amino-5-benzyloxycarbonyl-4-[2-(5-phosphono)furanyl]oxazole. mp 230° C. (decomp). Anal. calcd for $C_{15}H_{13}N_2O_7P+0.7H_2O$: C: 47.81; H: 3.85; N: 7.43. Found: C: 47.85; H: 3.88; N: 7.21.

(10.36) 2-Amino-5-isopropyloxycarbonyl-4-[2-(5-phosphono)furanyl]oxazole. mp 221° C. (decomp). Anal. calcd for $C_{11}H_{13}N_2O_7P+0.9H_2O$: C: 39.75; H: 4.49; N: 8.43. Found: C: 39.72; H: 4.25; N: 8.20.

(10.37) 2-Amino-5-methoxycarbonyl-4-[2-(5-phosphono)furanyl]oxazole. mp 240° C. (decomp). Anal. calcd for $C_9H_9N_2O_7P+0.3H_2O+0.1Acetone$: C: 37.31; H: 3.43; N: 9.36. Found: C: 37.37; H: 3.19; N: 9.01.

(10.38) 2-Amino-5-[(N-methyl)carbamoyl]-4-[2-(5-phosphono)furanyl]oxazole. mp 235° C. (decomp). Anal. calcd for $C_9H_{10}N_3O_6P$: C: 37.64; H: 3.51; N: 14.63. Found: C: 37.37; H: 3.22; N: 14.44.

(10.39) 2-Amino-5-ethylthiocarbonyl-4-[2-(5-phosphono)furanyl]oxazole. mp 225° C. (decomp). Anal. calcd for $C_{10}H_{11}N_2O_6PS$: C: 37.74; H: 3.48; N: 8.80. Found: C: 37.67; H: 3.27; N: 8.46.

(10.40) 2-Amino-5-isopropylthio-4-[2-(5-phosphono)furanyl]oxazole. Anal. calcd for $C_{10}H_{13}N_2O_5PS+0.2HBr$: C: 37.48; H: 4.15; N: 8.74. Found: C: 37.39; H: 4.11; N: 8.56.

(10.41) 2-Amino-5-phenylthio-4-[2-(5-phosphono)furanyl]oxazole. Anal. calcd for $C_{13}H_{11}N_2O_5PS+0.25HBr$: C: 43.55; H: 3.16; N: 7.81. Found: C: 43.82H: 3.28; N: 7.59.

(10.42) 2-Amino-5-ethylthio-4-[2-(5-phosphono)furanyl]oxazole. Anal. calcd for $C_9H_{11}N_2O_5PS+0.85HBr$: C: 30.11; H: 3.33; N: 7.80. Found: C: 30.18; H: 3.44; N: 7.60.

(10.43) 2-Amino-5-propylthio-4-[2-(5-phosphono)furanyl]oxazole. Anal. calcd for $C_{10}H_{13}N_2O_5+H_2O$: C: 37.27; H: 4.69; N: 8.69; $H_2O$: 5.59. Found: C: 37.27; H: 4.67; N: 8.60; $H_2O$: 5.66.

(10.44) 2-Amino-5-tert-butylthio-4-[2-(5-phosphono)furanyl]oxazole. Anal. calcd for $C_{11}H_{15}N_2O_5PS+0.25HBr$: C: 39.03; H: 4.54; N: 8.28. Found: C: 39.04; H: 4.62; N: 8.06.

(10.34) 4,5-Dimethyl-2-[2-(5-phosphono)furanyl] imidazole. Anal. calcd. for $C_9H_{11}N_2O_4P+1.25H_2O$: C: 40.84; H: 5.14; N: 10.58. Found: C: 41.02; H: 5.09; N: 10.27.

Example 11

Preparation of N-alkylated 4-[12-(5-phosphono)furanyl]imidazoles and 4-[2-(5-phosphono)furanyl] oxazoles Step A.

A suspension of cesium carbonate (1.5 mmole) and 2-methyl-5-isobutyl-4-[2-(5-diethylphosphono)furanyl] imidazole (1 mmole) in DMF was treated with iodomethane (1.5 mmole) at 25° C. for 16 h. Extraction and chromatography gave 1,2-dimethyl-4-isobutyl-5-[2-(5-diethylphosphono)-fiuanyl]imidazole and 1,2-dimethyl-5-isobutyl-4-[2-(5-diethylphosphono)-furanyl]imidazole.

Step B.

1,2-Dimethyl-4-isobutyl-5-[2-(5-diethylphosphono)furanyl]-imidazole and 1,2-dimethyl-5-isobutyl-4-[2-(5-diethylphosphono)furanyl]-imidazole were subjected to Step C of Example 3 to give the following compounds:

(11.1) 1,2-Dimethyl-5-isobutyl-4-[2-(5-phosphono)furanyl] imidazole hydrogen bromide. Anal. calcd. for $C_{13}H_{20}N_2O_4PBr+0.8H_2O$: C: 39.67; H: 5.53; N: 7.12. Found: C: 39.663; H: 5.48; N: 7.16.

Example 12

Preparation of 2-[2-(6-phosphono)pyridly]pyridine

Step A.

A solution of 2,2'-bipyridyl (1 mmole) in dichloromethane was treated with m-chloroperoxybenzoic acid (2 mmole) at 0° C., and the reaction mixture was stirred at 25° C. for 2 h. Extraction and chromatography gave 2,2'-bipyridyl-N-oxide.

Step B.

(Redmore, D., *J. Org. Chem.*, 1970, 35, 4114) A solution of 2,2'-bipyridyl-N-oxide methyl ether (1 mmole, prepared from dimethyl sulfate and 2,2'-bipyridyl-N-oxide in diethyl phosphite) was added slowly at −30° C. to a solution of n-butyl lithium (1 mmole) in diethyl phosphite at −30° C. The resulting reaction mixture was stirred at 25° C. for 12 h. Extraction and chromatography gave 2-[2-(6-diethylphosphono)pyridyl]pyridine.

Step C.

2-[2-(6-Diethylphosphono)pyridyl]pyridine was subjected to Step C of Example 3 to give 2-[2-(6-phosphono)pyridyl]pyridine (12.1). mp 158–162° C. Anal. calcd. for $C_{10}H_9N_2O_3P+0.5H_2O+0.1HBr$: C: 47.42; H: 4.02; N: 11.06. Found: C: 47.03; H: 3.67; N: 10.95.

Example 13

Preparation of 4.6-dimethyl-2-(phosphonomethoxymethyl)pyridine

Step A.

A solution of 2,4,6-collidine (1 mmole) in carbon tetrachloride was treated with NBS (5 mmole) and dibenzoyl peroxide (0.25 mmole) at 80° C. for 12 h. The reaction mixture was cooled to 0° C. and the precipitate was filtered. The filtrate was concentrated under vacuum. Chromatography gave 2-bromomethyl-4,6-dimethylpyridine.

Step B.

A solution of diethyl hydroxymethylphosphonate (1 mmole) in toluene was treated with sodium hydride (1.1 mmole) at 0° C., and after 15 min 2-bromomethyl-4,6-dimethylpyridine (1 mmole) was added. After 3 h the reaction mixture was subjected to extraction and chromatography to give 2-diethylphosphonomethyl-4,6-dimethylpyridine.

Step C.

2-Diethylphosphonomethyl-4,6-dimethylpyridine was subjected to Step C of Example 3 to give 4,6-dimethyl-2-(phosphonomethoxymethyl)pyridine (13.1). mp 109–112° C. Anal. calcd. for $C_9H_{14}NO_4P+1.0H_2O+0.5HBr$: C: 37.32; H: 5.74; N: 4.84. Found: C: 37.18; H: 5.38; N: 4.67.

The following compound was prepared similarly:

(13.2) 2-Amino-4-methyl-5-propyl-6-phosphonomethoxymethylpyrimidine. mp 153–156° C. Anal. calcd. for $C_{10}H_{18}N_3O_4P+1.25H_2O+1.6HBr$: C: 28.11; H: 5.21; N: 9.84. Found: C: 28.25; H: 4.75; N: 9.74.

Example 14

Preparation of diethyl 5-tributylstannyl-2-furanphosphonate

A solution of diethyl 2-furanphosphonate (1 mmole, prepared as in Step C of Example 1) in THF was cooled at −78° C. and cannulated to a solution of lithium N-isopropyl-N-cyclohexylamide in THF at −78° C. over 15 min. The resulting mixture was stirred at −78° C. for 2 h and cannulated into a solution of tributyltin chloride (1 mmole) in THF at −78° C. over 20 min. The mixture was then stirred at −78° C. for 1 h, and at 25° C. for 12 h. Extraction and chromatography gave compound (14) as a light yellow oil.

Example 15

Preparation of 6-[2-(5-phosphono)furanyl]pyridines

Step A.

A solution of 2,6-dichloropyridine (120 mmol) in ethanol was treated with aqueous ammonia solution (28%, excess) at 160–165° C. for 60 h in a sealed tube. Extraction and chromatography gave 2-amino-6-chloropyridine as a white solid.

Step B.

A solution of 2-amino-6-chloropyridine (1 mmole) and compound 14 (1 mmole) in p-xylene was treated with tetrakis(triphenylphosphine) palladium (0.05 mmole) at reflux for 12 h. Extraction and chromatography gave 2-amino-6-[2-(5-diethylphosphono)furanyl]pyridine as a light yellow solid.

Step C.

2-Amino-6-[2-(5-diethylphosphono)furanyl]pyridine was subjected to Step C of Example 3 to give 2-amino-6-[2-(5-phosphono)furanyl]pyridine (15.1). mp 186–187° C. Anal. calcd. for $C_9H_9N_2O_4P+0.4HBr$: C: 39.67; H: 3.48; N: 10.28. Found: C: 39.95; H: 3.36; N: 10.04.

Step D.

A solution of 2-amino-6-[2-(5-diethylphosphono)furanyl] pyridine (1 mmole) in acetic acid was treated with a solution of bromine in acetic acid (1N, 1 mmole) at 25° C. for 0.5 h. Evaporation and chromatography gave 2-amino-5-bromo-6-[2-(5-diethylphosphono)furanyl]pyridine and 2-amino-3,5-dibromo-6-[2-(5-diethylphosphono)furanyl]pyridine.

Step E.

2-Amino-5-bromo-6-[2-(5-diethylphosphono)furanyl]pyridine and 2-amino-3,5-dibromo-6-[2-(5-diethylphosphono)furanyl]pyridine were subjected to Step C of Example 3 to give the following compounds:

(15.2) 6-Amino-3-bromo-2-[2-(5-phosphono)furanyl]pyridine. Anal. calcd. for $C_9H_8BrN_2O_4P+0.7H_2O+0.9HBr+0.12PhCH_3$: C: 28.44; H: 2.73; N: 6.74. Found: C: 28.64; H: 2.79; N: 6.31.

(15.3) 6-Amino-3,5-dibromo-2-[2-(5-phosphono)furanyl]pyridine. mp 233–235° C. Anal. calcd. for $C_9H_7Br_2N_2O_4P+1.2HBr$: C: 21.84; H: 1.67; N: 5.66. Found: C: 21.90; H: 1.52; N: 5.30.

Step F.

A solution of 2-amino-3,5-dibromo-6-[2-(5-diethylphosphono)-furanyl]pyridine (1 mmole) in DMF was treated with tributyl(vinyl)tin (1.2 mmole) and tetrakis(triphenylphosphine) palladium (0.2 mmole) at 85° C. for 4 h. Evaporation and chromatography gave 2-amino-3,5-bis(vinyl)-6-[2-(5-diethylphosphono)furanyl]pyridine.

Step G.

A solution of 2-amino-3,5-bis(vinyl)-6-[2-(5-diethylphosphono)-furanyl]pyridine (1 mmole) in ethyl acetate was treated with palladium on carbon (10%) at 25° C. under 1 atmosphere of hydrogen for 12 h. Filtration, evaporation and chromatography gave 2-amino-3,5-diethyl-6-[2-(5-diethylphosphono)furanyl]pyridine.

Step H.

2-Amino-3,5-diethyl-6-[2-(5-diethylphosphono)furanyl] pyridine was subjected to Step C of Example 3 to give 2-amino-3,5-diethyl-6-[2-(5-phosphono)furanyl]pyridine (15.4). mp 217–218° C. Anal. calcd. for $C_{13}H_{17}N_2O_4P+0.7H_2O+1.0HBr$: C: 40.06; H: 5.02; N: 7.19. Found: C: 40.14; H: 4.70; N: 6.87.

Step I.

A solution of 2-amino-6-picoline (1 mmole) in 48% hydrobromic acid (4.4 mmole) was treated with bromine (3 mmole) at 0° C. for 1 h. An aqueous solution of sodium nitrite (2.5 mmole) was then added and the reaction mixture was stirred at 0° C. for 0.5 h. An aqueous solution of sodium hydroxide (9.4 mmole) was then added and the reaction mixture was stirred at 25° C. for 1 h. Extraction and chromatography gave 2,3-dibromo-6-picoline and 2,3,5-tribromo-6-picoline.

Step J.

2,3-Dibromo-6-picoline was subjected to Step B of Example 15 and followed by Step C of Example 3 to give 5-bromo-2-methyl-6-[2-(5-phosphono)furanyl]pyridine (15.5). mp 207–208° C. Anal. calcd. for $C_{10}H_9BrNO_4P+0.6HBr$: C: 32.76; H: 2.64; N: 3.88. Found: C: 32.62; H: 2.95; N: 3.55.

Following compounds were prepared according to the above described procedures or with some minor modifications of these procedures using conventional chemistry.

(15.6) 2-[2-(5-Phosphono)furanyl]pyridine. mp 220–221° C. Anal. calcd. for $C_9H_8NO_4P+0.1H_2O+0.45HBr$: C: 41.05; H: 3.31; N: 5.32. Found: C: 41.06; H: 3.10; N: 5.10.

(15.7) 2-Amino-3-nitro-6-[2-(5-phosphono)furanyl]pyridine. mp 221–222° C. Anal. calcd. for $C_9H_8N_3O_6P+0.55HBr+0.02PhCH_3$: C: 33.12; H: 2.65; N: 12.68. Found: C: 33.22; H: 2:43; N: 12.26.

(15.8) 2,3-Diamino-6-[2-(5-phosphono)furanyl]pyridine. mp 150–153° C. Anal. calcd. for $C_9H_{10}N_3O_4P+1.5HBr+0.05PhCH_3$: C: 29.46; H: 3.15; N: 11.02. Found: C: 29.50; H: 3.29; N: 10.60.

(15.9) 2-Chloro-6-[2-(5-phosphono)furanyl]pyridine. mp 94–96° C. Anal. calcd. for $C_9H_7ClNO_4P+0.25HBr$: C: 38.63; H: 2.61; N: 5.01. Found: C: 38.91; H: 3.00; N: 5.07.

(15.10) 3,5-Dichloro-2-[2-(5-phosphono)furanyl]pyridine. mp 180–181° C. Anal. calcd. for $C_9H_6Cl_2NO_4P+0.7HBr$: C: 31.61; H: 2.01; N: 3.94. Found: C: 31.69; H: 2.09; N: 3.89.

(15.11) 3-Chloro-5-trifluoromethyl-2-[2-(5-phosphono)furanyl]pyridine. mp 253–254° C. Anal. calcd. for $C_{10}H_6ClF_3NO_4P$: C: 36.67; H: 1.85; N: 4.28. Found: C: 36.69; H: 1.89; N: 4.30.

(15.12) 2-Amino-6-ethyl-6-[2-(5-phosphono)furanyl]pyridine. mp 220–221° C. Anal. calcd. for $C_{11}H_{13}N_2O_4P+0.6HBr+0.2H_2O$: C: 41.24; H: 4.40; N: 8.74. Found: C: 41.02; H: 4.57; N: 8.68.

(15.13) 6-Amino-3-ethyl-2-[2-(5-phosphono)furanyl]pyridine. Anal. calcd. for $C_{11}H_{13}N_2O_4P+1.0HBr+0.3H_2O$: C: 37.27; H: 4.15; N: 7.90. Found: C: 37.27; H: 4.19; N: 7.51.

(15.14) 6-Amino-3-propyl-2-[2-(5-phosphono)furanyl]pyridine. mp 252–253° C. Anal. calcd. for $C_{12}H_{15}N_2O_4P+1.0HBr+1.0H_2O+0.32PhCH_3$: C: 41.65; H: 5.05; N: 6.82. Found: C: 41.97; H: 5.19; N: 6.83.

(15.15) 2,4-Dimethyl-3-bromo-6-[2-(5-phosphono)furanyl]pyridine. mp 232–233° C. Anal. Calcd. for $C_{11}H_{11}BrNO_4P+0.45HBr$: C: 35.85; H: 3.13; N: 3.80. Found: C: 35.98; H: 3.10; N: 3.71.

(15.16) 2-Chloro-4-amino-6-[2-(5-phosphono)furanyl]pyridine. Anal. calcd. for $C_9H_8N_2O_4PCl+HBr+0.5H_2O+MeOH$: C: 30.99; H: 3.38; N: 7.23. Found: C: 31.09; H: 3.21; N: 6.96.

(15.17) 3-Hydroxyl-2-[2-(5-phosphono)furanyl]pyridine. Anal. calcd. for $C_9H_8NO_5P+1.1HBr+0.3CH_3Ph$: C: 37.26; H: 3.24; N: 3.91. Found: C: 37.66; H: 3.55; N: 3.84.

(15.19) 2-Amino-3-cyclopropyl-6-[2-(5-phosphono)furanyl]pyridine. Anal. calcd. for $C_{12}H_{13}N_2O_4PCl+HBr+0.4H_2O$: C: 39.13; H: 4.05; N: 7.61. Found: C: 39.06; H: 3.85; N: 7.37.

(15.20) 2-Amino-5-cyclopropyl-6-[2-(5-phosphono)furanyl]pyridine. Anal. calcd. for $C_{12}H_{13}N_2O_4P+HBr+0.7CH_3Ph$: C: 47.69; H: 4.64; N: 6.58. Found: C: 47.99; H: 4.62; N: 6.91.

(15.21) 5-Amino-2-methoxy-6-[2-(5-phosphono)furanyl]pyridine. Anal. calcd. for $C_{10}H_{11}N_2O_5P+0.2H_2O$: C: 43.87; H: 4.20; N: 10.23. Found: C: 43.71; H: 3.77; N: 9.77.

(15.22) 2-Methyl-5-cyano-6-[2-(5-phosphono)furanyl]pyridine. Anal. Calcd. for $C_{11}H_9N_2O_4P+0.75HBr+0.5H_2O+0.5MePh$: C: 45.84; H: 3.91; N: 7.37. Found: C: 45.93; H: 3.56; N: 7.36.

(15.23) 2-Amino-3,5-bis(cyano)-4-methyl-6-[2-(5-phosphono)furanyl]pyridine. Anal. calcd. for $C_{12}H_9N_4O_4P+0.7H_2O$: C: 45.49; H: 3.31; N: 17.68. Found: C: 45.48; H: 3.06; N: 17.51.

(15.24) 2-Chloro-4-cyano-6-[2-(5-phosphono)furanyl]pyridine. Anal. calcd. for $C_{10}H_6N_2O_4PCl$: C: 42.20; H: 2.13; N: 9.84. Found: C: 41.95; H: 2.10; N: 9.47.

Example 16

Preparation of 2-[2-(5-phosphono)furanyl]pyrimidines and 4-[2-(5-phosphono)furanyl]pyrimidines Step A.

A solution of 5-diethylphosphono-2-[(1-oxo)pentyl]furan in N,N-dimethylformamide dimethyl acetal was heated at reflux for 12 h. Evaporation and chromatography gave diethyl 5-(2-propyl-3-N,N-dimethylamino)acryloyl-2-furanphosphonate.

Step B.

A solution of diethyl 5-(2-propyl-3-N,N-dimethylamino)acryloyl-2-furanphosphonate (1 mmole) in ethanol was treated with guanidine hydrogen chloride (1.2 mmole) and sodium ethoxide (1 mmole) at 80° C. for 12 h. The reaction mixture was evaporated, and residue was dissolved in water. The aqueous solution was neutralized with HCl (2 N), and concentrated under reduced pressure. The residue was co-evaporated with toluene to give 2-amino-5-propyl-4-[2-(5-ethylphosphono)-furanyl]pyrimidine as a yellow solid.

Step C.

2-Amino-5-propyl-4-[2-(5-ethylphosphono)furanyl]pyrimidine (1 mmole) and thionyl chloride was heated at reflux for 2 h. The reaction mixture was evaporated to dryness and the residue was dissolved in methylene chloride, and treated with excess pyridine and ethanol at 25° C. for 12 h. Evaporation and chromatography gave 2-amino-5-propyl-4-[2-(5-diethylphosphono)furanyl]pyrimidine.

Step D.

2-Amino-5-propyl-4-[2-(5-diethylphosphono)furanyl]pyrimidine was subjected to Step C of Example 3 to give 2-amino-5-propyl-4-[2-(5-phosphono)furanyl]pyrimidine (16.1). mp 258–259° C. Anal. calcd. for $C_{11}H_{14}N_3O_4P+1.33H_2O$: C: 43.01; H: 5.47; N: 13.68. Found: C: 43.18; H: 5.31; N: 13.30.

The following compound was prepared according to this procedure:

(16.2) 2-Amino-5-isobutyl-4-[2-(5-phosphono)furanyl]pyrimidine. mp 218–220° C. Anal. calcd. for $C_{12}H_{16}N_3O_4P+0.75HBr+0.3PhCH_3$: C: 43.92; H: 5.01; N: 10.90. Found: C: 44.02; H: 4.62; N: 10.69.

Alternatively other 4-[2-(5-phosphono)furanyl]pyrimidines can be prepared according to the following procedures:

Step E.

Compound 2.2 was subjected to Step A of Example 16 to give diethyl 5-(3-N,N-dimethylamino)acryloyl-2-furanphosphonate as an orange solid.

Step F.

A solution of diethyl 5-(3-N,N-dimethylamino)acryloyl-2-furanphosphonate (1 mmole), sodium ethoxide ethanol solution (2 mmole) and guanidine hydrochloride (1.1 mmole) was heated at 55° C. for 2 h. The reaction mixture was cooled in an ice bath and was neutralized with 1N HCl. Evaporation and chromatography gave 2-amino-4-[2-(5-diethylphosphono)-furanyl]pyrimidine as a yellow solid.

Step G.

2-Amino-4-[2-(5-diethylphosphono)furanyl]pyrimidine was subjected to Step C of Example 3 to give 2-amino-4-[2-(5-phosphono)furanyl]-pyrimidine (16.3). mp>230° C. Anal. calcd. for $C_8H_8N_3O_4P+0.75H_2O+0.2HBr$: C: 35.48; H: 3.61; N: 15.51. Found: C: 35.42; H: 3.80; N: 15.30.

Step H.

A solution of 2-amino-4-[2-(5-diethylphosphono)furanyl]pyrimidine (1 mmole) in methanol and chloroform was treated with NBS (1.5 mmole) at 25° C. for 1 h. Extraction and chromatography gave 2-amino-5-bromo-4-[2-(5-diethylphosphono)furanyl]pyrimidine as a yellow solid.
Step I.

2-Amino-5-bromo-4-[2-(5-diethylphosphono)furanyl]pyrimidine was subjected to Steps F and G of Example 15 followed by Step C of Example 3 to give 2-amino-5-ethyl-4-[2-(5-phosphono)furanyl]pyrimidine (16.4). mp>225° C. Anal. calcd. for $C_{10}H_{12}N_3O_4P+1.4H_2O+0.2HBr+0.25PhCH_3$: C: 42.30; H: 5.14; N: 12.59. Found: C: 42.74; H: 4.94; N: 12.13.

The following compounds were prepared according to the above described procedures or with some minor modifications using conventional chemistry:

(16.5) 2-[2-(5-Phosphono)furanyl]pyrimidine. mp 194–196° C. Anal. calcd. for $C_8H_7N_2O_4P+0.1H_2O+0.55HBr$: C: 35.27; H: 2.87; N: 10.28. Found: C: 35.26; H: 2.83; N: 9.89.

(16.6) 2-Amino-6-methyl-4-[2-(5-phosphono)furanyl]pyrimidine. mp 238–239° C. Anal. calcd. for $C_9H_{10}N_3O_4P+0.9HBr$: C: 32.96; H: 3.35; N: 12.81. Found: C: 33.25; H: 3.34; N: 12.46.

(16.7) 2-Methylthio-4-[2-(5-phosphono)furanyl]pyrimidine. mp 228–229° C. Anal. calcd. for $C_9H_9N_2O_4PS+0.5H_2O$: C: 38.44; H: 3.58; N: 9.96. Found: C: 38.19; H: 3.25; N: 9.66.

(16.8) 2-Methyl-4-[2-(5-phosphono)furanyl]pyrimidine. mp 206–212° C. Anal. calcd. for $C_9H_9N_2O_4P+0.9H_2O+0.25HBr$: C: 34.05; H: 3.30; N: 8.82. Found: C: 34.02; H: 3.06; N: 8.75.

(16.9) 4,6-Dimethyl-5-bromo-2-[2-(5-phosphono)furanyl]pyrimidine. mp 251–252° C. Anal. calcd. for $C_{10}H_{10}BrN_2O_4P$: C: 36.06; H: 3.03; N: 8.41. Found: C: 35.89; H: 2.82; N: 8.11.

(16.10) 2-Amino-5-chloro-4-[2-(5-phosphono)furanyl]pyrimidine. Anal. calcd. for $C_8H_7ClN_3O_4P+0.5H_2O$: C: 33.76; H: 2.83; N: 14.76. Found: C: 33.91; H: 2.86; N: 14.20.

(16.11) 2-Amino-6-methylthio-4-[2-(5-phosphono)furanyl]pyrimidine. Anal. calcd. for $C_9H_{10}N_3O_4PS+HBr$: C: 29.36; H: 3.01; N: 11.41. Found: C: 29.63; H: 3.02; N: 11.27.

(16.12) 2-Amino-5-bromo-6-methylthio-4-[2-(5-phosphono)furanyl]pyrimidine. Anal. calcd. for $C_9H_9N_3O_4PSBr+0.8HBr+0.2MePh$: C: 27.80; H: 2.56; N: 9.35. Found: C: 27.74; H: 2.40; N: 8.94.

(16.13) 2-Amino-(4-morpholino)-4-[2-(5-phosphono)furanyl]pyrimidine. Mp>230° C. Anal. calcd. for $C_{12}H_{15}N_4O_5P+HBr+0.05MePh$: C: 36.02; H: 4.01; N: 13.61. Found: C: 35.98; H: 4.04; N: 13.33.

(16.14) 6-Amino-4-chloro-2-[2-(5-phosphono)furanyl]pyrimidine. Mp>230° C. Anal. calcd. for $C_8H_7N_3O_4PCl+0.5H_2O$: C: 33.76; H: 2.83; N: 14.76. Found: C: 33.83; H: 2.54; N: 14.48.

Example 17

Preparation of 2-[2-(5-phosphono)furanyl]pyrazines and 2-[2-(5-phosphono)furanyl]triazines Step A.

The procedures described in Example 16 can also be applied to the synthesis of 2-[2-(5-phosphono)furanyl]pyrazine and 2-[2-(5-phosphono)furanyl]triazine analogs and in some cases with minor modifications of these procedures using conventional chemistry methods.

The following compounds were prepared accordingly:

(17.1) 2,5-Dimethyl-3-[2-(5-phosphono)furanyl]pyrazine. mp 212–213° C. Anal. calcd. for $C_{10}H_{11}N_2O_4P+0.75HBr$: C: 38.15; H: 3.76; N: 8.90. Found: C: 38.41; H: 3.93; N: 8.76.

(17.2) 2-Chloro-6-[2-(5-phosphono)furanyl]pyrazine. mp 204–205° C. Anal. calcd. for $C_8H_6ClN_2O_4P+0.3HBr+0.02PhCH_3$: C: 34.10; H: 2.27; N: 9.77. Found: C: 34.36; H: 2.07; N: 9.39.

(17.3) 2-Amino-3-propyl-6-[2-(5-phosphono)furanyl]pyrazine. mp 227–228° C. Anal. calcd. for $C_{11}H_{14}N_3O_4P+0.7HBr$: C: 38.87; H: 4.36; N: 12.36. Found: C: 39.19; H: 4.36; N: 11.92.

(17.4) 2-Amino-6-[2-(5-phosphono)furanyl]pyrazine. mp 235–236° C. Anal. calcd. for $C_8H_8N_3O_4P+1.15H_2O+0.03PhCH_3$: C: 37.26; H: 4.01; N: 15.88. Found: C: 37.09; H: 3.67; N: 15.51.

(17.5) 2-Amino-3-bromo-6-[2-(5-phosphono)furanyl]pyrazine. Anal. calcd. for $C_8H_7N_3O_4PBr+1HBr$: C: 23.97; H: 2.01; N: 10.48. Found: C: 24.00; H: 2.00; N: 10.13.

(17.6) 3-Methylthio-2-[2-(5-phosphono)furanyl]pyrazine. Anal. calcd. for $C_9H_9N_2O_4PS+0.3H_2O$: C: 38.94; H: 3.49; N: 10.09. Found: C: 38.99; H: 3.11; N: 9.67.

(17.7) 6-Amino-3-methylthio-2-[2-(5-phosphono)furanyl]pyrazine. Anal. calcd. for $C_9H_{10}N_3O_4PS+1.5H_2O+1.7HBr+0.25MePh$: C: 27.19; H: 3.54; N: 8.85. Found: C: 27.10; H: 3.85; N: 8.49.

(17.8) 6-Amino-5-methylthio-2-[2-(5-phosphono)furanyl]pyrazine. Anal. calcd. for $C_9H_{10}N_3O_4PS+1.1HBr+0.05MePh$: C: 29.49; H: 3.04; N: 11.03. Found: C: 29.23; H: 2.79; N: 10.87.

(17.9) 6-Amino-5-methoxycarbonyl-3-chloro-2-[2-(5-phosphono)furanyl]pyrazine. Anal. calcd. for $C_{10}H_9N_3O_6PCl+0.3HBr+0.04MePh$: C: 34.15; H: 2.68; N: 11.62. Found: C: 34.20; H: 2.90; N: 11.21.

(17.10) 6-Amino-3-methylthio-2-[2-(5-phosphono)furanyl]pyrazine ammonium salt. Anal. calcd. for $C_9H_{13}N_4O_4PS+0.8HBr$: C: 29.30; H: 3.77; N: 15.18. Found: C: 29.03; H: 3.88; N: 15.08.

(17.11) 2-Amino-4-phenyl-6-[2-(5-phosphono)furanyl]triazine. Anal. calcd. for $C_{13}H_{11}N_4O_4P+HBr+0.1EtOAc$: C: 39.45; H: 3.16; N: 13.73. Found: C: 39.77; H: 3.26; N: 13.48.

Example 18

Preparation of Analogs with X Being Methoxycarbonyl Methylthiocarbonyl, Methylaminocarbonyl and Methylcarbonylamino Preparations of 4-phosphonomethoxycarbonylthiazoles and 4-phosphonomethoxycarbonyloxazoles Step A.

A solution of 2-amino-4-ethoxycarbonylthiazole (1 mmole) in 1,4-dioxane (5 mL) was treated with di-tert-butyl dicarbonate (1.2 mmole), TMEDA (0.1 mmole) and DMAP (0.1 mmole) at room temperature. After the reaction was stirred for 20 h, it was evaporated to dryness. The residue was subjected to extraction to give 2-[N-Boc(amino)]-4-ethoxycarbonyl thiazole as a yellow solid.

Step B.

A solution of 2-[N-Boc(amino)]-4-ethoxycarbonylthiazole (1 mmole) in a 2:1 mixture of $EtOH:H_2O$ (10 mL) was treated with NaOH (3N, 3 mmole) and the reaction was stirred at 60° C. for 4 h. The reaction was cooled to 0° C. and neutralized to pH 5 with 3 N HCl, and the resulting solid was collected via filtration to give 2-[N-Boc(amino)]-4-carboxylthiazole as a white solid.

Step C.

A suspension of 2-[N-Boc(amino)]-4-carboxylthiazole (1 mmole) in $CH_2Cl_2$ (5 mL) was treated with thionyl chloride (4 mmole). After stirring for 4 h the reaction was evaporated to dryness. The residue was dissolved in $CH_2Cl_2$ (5 mL) and added to a solution of diethyl (hydroxymethyl)phosphonate (1.5 mmole) and pyridine (2 mmole) in $CH_2Cl_2$ (5 mL) at 0° C. The reaction was warmed to room temperature and stirred for 4 h. The reaction was quenched with water and the mixture was subjected to extraction to give 2-[N-Boc(amino)]-4-diethylphosphonomethoxycarbonylthiazole as a thick yellow oil.

Alternatively the ester linkage can be formed using a mixed anhydride method as exemplified in the following procedures:

A solution of 2-[N-Boc(amino)]-4-carboxylthiazole (1 mmole) in pyridine (5 mL) was treated with para-toluenesulfonyl chloride (2 mmole) followed by diethyl (hydroxymethyl)phosphonate (2 mmole) at room temperature for 4 h. Evaporation, extraction and chromatography gave 2-[N-Boc(amino)]-4-diethylphosphonomethoxycarbonylthiazole as a thick yellow oil.

Step D.

A solution of 2-[N-Boc(amino)]-4-diethylphosphonomethoxycarbonylthiazole (1 mmole) and anisole (0.1 mmole) in methylene chloride (5 mL) and trifluoroacetic acid (5 mL) was stirred at 0° C. for 1 h, and at room temperature for 1 h. Evaporation, extraction and chromatography gave 2-amino-4-diethyllphosphonomethoxycarbonylthiazole as a solid.

Step E.

2-Amino-4-diethyllphosphonomethoxycarbonylthiazole was subjected to Step C of Example 3 to give 2-amino-4-phosphonomethoxycarbonylthiazole (18.1) as a solid. Mp>240° C. (decomp). Anal. calcd. for $C_5H_7N_2O_5PS$: C: 25.22; H: 2.96; N: 11.76. Found: C: 25.30; H: 2.86; N: 11.77.

Step F.

A solution of 2-[N-Boc(amino)]-4-diethylphosphonomethoxycarbonylthiazole (1 mmole) in $CH_2Cl_2$ (5 mL) was treated with bromine (2 mmole) at room, temperature for 4 h. Evaporation and extraction gave 2-[N-Boc(amino)]-5-bromo-4-diethylphosphonomethoxycarbonylthiazole as an orange oil which was subjected to Step D of Example 18 followed by Step C of Example 3 to give 2-amino-5-bromo-4-phosphonomethoxycarbonylthiazole (18.2) as a solid. Mp>230° C. (decomp). Anal. calcd. for $C_5H_6N_2O_5PSBr$: C: 18.94; H: 1.91; N: 8.84. Found: C: 19.08; H: 1.76; N: 8.67.

Step G.

A solution of 2-[N-Boc(amino)]-5-bromo-4-diethylphosphonomethoxycarbonylthiazole (1 mmole) and dichlorobis(triphenylphosphine)palladium(II) (0.1 mmole) in DMF (5 mL) was treated with tributyl(vinyl)tin (2.5 mmole) and the reaction was stirred at 60° C. for 2 h. The solvent was removed and the residue taken up in EtOAc and stirred with 2 mmol NaF in 5 ml water for 1 h. Extraction and chromatography gave 2-[N-Boc(amino)]-5-vinyl-4-diethylphosphonomethoxycarbonylthiazole as a yellow solid.

Step H.

A suspension of 2-[N-Boc(amino)]-5-vinyl-4-diethylphosphonomethoxycarbonyl thiazole (1 mmole) and 10% Pd/C (0.5 mmole) in MeOH (5 mL) was stirred under an atmosphere of $H_2$ (balloon) at room temperature for 15 h. Filtration and evaporation gave 2-[N-Boc(amino)]-5-ethyl-4-diethylphosphonomethoxycarbonylthiazole as a yellow solid, which was subjected to Step D of Example 18 followed by Step C of Example 3 to give 2-amino-5-ethyl-4-phosphonomethoxycarbonylthiazole (18.3) as a solid. Mp>230° C. (decomp). Anal. Calcd. for $C_7H_{11}N_2O_5PS$: 31.58; H: 4.16; N: 10.52. Found: C: 31.80; H: 4.04; N: 10.18.

Step I.

A solution of N-[Bis(methylthio)methylene]glycine methyl ester (1 mmole) in anhydrous THF (2 mL) was added to a solution of t-BuOK (1.4 mmole) in anhydrous THF (10 mL) at −78° C. and the mixture was stirred for 30 min. Then a solution of ethyl isothiocyanate (1 mmole) in anhydrous THF (2 mL) was added and the reaction was stirred at −78° C. for 30 min and at room temperature for 2 h. The reaction was quenched with water. Extraction and chromatography gave 2-methylthio-5-(N-ethylamino)-4-methoxycarbonylthiazole as a yellow solid, which was subjected to Step B and C of Example 18 followed by Step C of Example 3 to give 2-methylthio-5-(N-ethylamino)-4-phosphonomethoxycarbonylthiazole (18.4) as a solid. Mp>200° C. (decomp). Anal. calcd. for $C_8H_{13}N_2O_5PS_2$+ 0.1HBr: C: 29.99; H: 4.12; N: 8.74. Found: C: 29.71; H: 4.10; N: 8.60.

Step J.

A solution of 1 mmol of 2-[N-Boc(amino)]-4-thiazolecarboxylate acid chloride (1 mmole) and pyridine (2 mmole) in $CH_2Cl_2$ (5 mL) was cooled to −78° C. and $H_2S(g)$ was bubbled through the solution for 10 min. The reaction was stirred at −78° C. for 30 min and then warmed to room temperature. The mixture was washed with 3 N HCl. The organic phase was separated, dried and concentrated to give 2-[N-Boc(amino)]-4-thiazolethiocarboxylic acid as a yellow solid.

Step K.

A solution of give 2-[N-Boc(amino)]-4-thiazolethiocarboxylic acid (1 mmole) in THF (5 mL) was cooled to −78° C. and treated with NaH (2 mmole) in small portions. After 10 min the reaction was treated with a solution of diethylphosphonomethyl triflate in THF (5 mL). The reaction was stirred at −78° C. for 1 h, and then quenched with $H_2O$. Extraction and chromatography gave 2-[N-Boc(amino)]-4-diethylphosphonomethylthiocarbonylthiazole as a thick oil, which was subjected to Step D of Example 18 followed by Step C of Example 3 to give 2-amino-4-phosphonomethylthiocarbonylthiazole (18.5) as a solid. Mp>230° C. (decomp). Anal. calcd. for $C_5H_7N_2O_4PS_2$: C: 23.62; H: 2.78; N: 11.02. Found: C: 23.77; H: 2.61; N: 10.73.

Preparation of 4-[(N-phosphonomethyl)carbamoyl]thiazole, 3-[N-phosphonomethyl)-carbamoyl]isothiazole and 2-[N-phosphonomethyl)carbamoyl]pyridine Step L.

A solution of 2-[N-Boc(amino)]-4-thiazolecarboxylic acid (1 mmole) in DMF (5 mL) was treated with 1-(3-dimethylaminopropyl)-3-ethylcarbodiimide hydrochloride (EDCI, 1.5 mmole) and 1-hydroxybenzotriazole hydrate (HOBt, 1.5 mmole) followed by addition of diethyl aminomethylphosphonate (1.5 mmole) at room temperature for 24 h. The reaction was subjected to evaporation, extraction and chromatography to give 2-[N-Boc(amino)]-4-[(N-diethylphosphonomethyl)carbamoyl]thiazole as a white solid, which was subjected to Step D of Example 18 followed by Step C of Example 3 to give 2-amino-4-[(N-phosphonomethyl)carbamoyl]thiazole (18.6) as a light brown solid. Mp>245° C. (decomp). Anal. calcd. for $C_5H_8N_3O_4PS+1.05HBr$: C: 18.64; H: 2.83; N: 13.04. Found: C: 18.78; H: 2.43; N: 12.97.

Preparation of 2-[(N-phosphonoacetyl)amino]thiazole and 2-[(N-phosphonoacetyl)amino]pyridine Step M.

A solution of 2-amino-4,5-dimethylthiazole hydrochloride (2 mmole) and diethyl phosphonoacetica acid (1 mmole) in DMF (5 mL) was treated with EDCI (1.5 mmole), HOBt (1.5 mmole) and triethylamine (2 mmole) at room temperature for 24 h. The reaction was subjected to evaporation, extraction and chromatography to give 2-[(N-diethylphosphonoacetyl)amino]-4,5-dimethylthiazole as a yellow solid, which was subjected to Step D of Example 18 followed by Step C of Example 3 to give 4,5-dimethyl-2-[(N-phosphonoacetyl)amino]thiazole (18.7) as a light brown solid. Mp>250° C. Anal. calcd. for $C_7H_{11}N_2O_4PS$: C: 33.60; H: 4.43; N: 11.20. Found: C: 33.62; H: 4.29; N: 10.99.

The following compounds were prepared using some of the above described procedures or some of the above procedures with some minor modifications using conventional chemistry:

(18.8) 2-[(N-phosphonomethyl)carbamoyl]pyridine. Anal. calcd. for $C_7H_9N_2O_4P+HBr+0.67H_2O$: C: 27.20; H: 3.70; N: 9.06. Found: C: 27.02; H: 3.71; N: 8.92.

(18.9) 2-[(N-phosphonoacetyl)amino]pyridine. Anal. calcd. for $C_7H_9N_2O_4P+HBr+0.67H_2O$: C: 27.20; H: 3.70; N: 9.06. Found: C: 27.05; H: 3.59; N: 8.86.

(18.10) 4-Ethoxycarbonyl-2-[(N-phosphonoacetyl)amino]thiazole. Anal. calcd. for $C_8H_{11}N_2O_6PS$: C: 32.66; H: 3.77; N: 9.52. Found: C: 32.83; H: 3.58; N: 9.20.

(18.11) 2-Amino-5-bromo-4-[(N-phosphonomethyl)carbamoyl]thiazole. Mp 232° C. (decomp). Anal. calcd. for $C_5H_7N_3O_4PSBr+0.15HBr+0.1hexane$: C: 19.97; H: 2.56; N: 12.48. Found: C: 19.90; H: 2.29; N: 12.33.

(18.12) 2-Amino-5-(2-thienyl)-4-[(N-phosphonomethyl)carbamoyl]thiazole. Mp 245° C. (decomp). Anal. calcd. for $C_9H_{10}N_3O_4PS_2+HBr+0.1EtOAc$: C: 27.60; H: 2.91; N: 10.27. Found: C: 27.20; H: 2.67; N: 9.98.

(18.13) 4,5-Dichloro-3-[(N-phosphonomethyl)carbamoyl]isothiazole. Mp 189–191° C. Anal. calcd. for $C_5H_5N_2O_4PSCl_2$: C: 20.63; H: 1.73; N: 9.62. Found: C: 20.43; H: 1.54; N: 9.51.

(18.14) 2-Amino-5-bromo-4-{[N-(1-phosphono-1-phenyl)methyl]carbamoyl}thiazole. Mp>250° C. Anal. calcd. for $C_{11}H_{11}N_3O_4PSBr$: C: 33.69; H: 2.83; N: 10.71. Found: C: 33.85; H: 2.63; N: 10.85.

(18.15) 2-Amino-5-(2-thienyl)-4-phosphonomethoxycarbonylthiazole. Mp>230° C. (decomp). Anal. calcd. for $C_9H_9N_2O_5PS_2$: C: 33.75; H: 2.83; N: 8.75. Found: C: 33.40; H: 2.74; N: 8.51.

(18.16) 2-Amino-5-benzyl-4-phosphonomethoxycarbonylthiazole. Mp>230° C. (decomp). Anal. calcd. for $C_{12}H_{13}N_2O_5PS$: C: 43.91; H: 3.99; N: 8.53. Found: C: 43.77; H: 4.03; N: 8.25.

(18.17) 2-Methylthio-5-methylamino-4-phosphonomethoxycarbonylthiazole. Anal. calcd. for $C_7H_{11}N_2O_5PS_2+0.2HBr$: C: 26.74; H: 3.59; N: 8.91. Found: C: 26.79; H: 3.89; N: 8.89.

(18.18) 2-Amino-5-ethyl-4-[(N-phosphonomethyl)carbamoyl]thiazole. Mp 180° C. (decomp). Anal. calcd. for $C_7H_{12}N_3O_4PS+HBr+0.4CH_2Cl_2$: C: 23.49; H: 3.67; N: 11.18. Found: C: 23.73; H: 3.29; N: 11.42.

(18.19) 2-Amino-5-isopropyl-4-[(N-phosphonomethyl)carbamoyl]thiazole. Mp 247–250° C. Anal. calcd. for $C_8H_{14}N_3O_4PS$: C: 34.41; H: 5.05; N: 15.05. Found: C: 34.46; H: 4.80; N: 14.68.

(18.20) 2-Amino-5-isopropyl-4-phosphonomethoxycarbonylthiazole. Mp>230° C. Anal. calcd. for $C_8H_{13}N_2O_5PS$: C: 34.29; H: 4.68; N: 10.00. Found: C: 33.97; H: 4.49; N: 9.70.

(18.21) 2-Amino-5-phenyl-4-phosphonomethoxycarbonylthiazole. Mp>230° C. Anal. calcd. for $C_{11}H_{11}N_2O_5PS$: C: 42.04; H: 3.53; N: 8.91. Found: C: 42.04; H: 3.40; N: 8.72.

(18.22) 2-Amino-4-phosphonomethoxycarbonyloxazole. Anal. calcd. for $C_5H_7N_2O_6P+0.09HBr$: C: 26.18; H: 3.12; N: 12.21. Found: C: 26.29; H: 3.04; N: 11.90.

(18.23) 2-Amino-6-[(N-phosphonoacetyl)amino]pyridine. Anal. calcd. for $C_7H_{10}N_3O_4P+1.1HBr+0.25MeOH$: C: 26.54; H: 3.72; N: 12.80. Found: C: 26.79; H: 3.63; N: 12.44.

(18.24) 2-Amino-5-methyl-4-[(N-phosphonomethyl)carbamoyl]thiazole. Mp>250° C. Anal. calcd. for $C_6H_{10}N_3O_4PS+0.06EtOAc$: C: 29.22; H: 4.12; N: 16.38. Found: C: 29.03; H: 3.84; N: 16.01.

(18.25) 2-Amino-3-bromo-6-[(N-phosphonoacetyl)amino]pyridine. Anal. calcd. for $C_7H_9N_3O_4PBr+1.25HBr+0.8EtOAc$: C: 25.43; H: 3.48; N: 8.72. Found: C: 25.58; H: 3.71; N: 8.56.

(18.26) 2-Amino-3,5-dibromo-6-[(N-phosphonoacetyl)amino]pyridine. Anal. calcd. for $C_7H_8N_3O_4PBr_2+HBr+0.5EtOAc$: C: 21.03; H: 2.55; N: 8.18. Found: C: 21.28; H: 2.55; N: 7.91.

(18.27) 2-Amino-5-methyl-4-phosphonomethoxycarbonylthiazole. Mp 230° C. (decomp). Anal. calcd. for $C_6H_9N_2O_5PS$: C: 28.58; H: 3.60; N: 11.11. Found: C: 28.38; H: 3.49; N: 11.10.

(18.28) 2-Amino-3,5-diethyl-6-[(N-phosphonoacetyl)amino]pyridine. MS calcd. for $C_{11}H_{18}N_3O_4P+H$: 288, found 288.

(18.29) 2-Amino-3,5-dibromo-6-{[N-(2,2-dibromo-2-phosphono)acetyl]amino}pyridine. Anal. calcd. for $C_7H_6N_3O_4PBr_4+0.5HBr+EtOAc$: C: 19.56; H: 2.16; N: 6.22. Found: C: 19.26; H: 2.29; N: 5.91.

(18.30) 2-Amino-5-isopropyl-4-phosphonomethoxycarbonyloxazole. Anal. calcd. for $C_8H_{13}N_2O_6P+0.2HBr$: C: 34.27; H: 4.75; N: 9.99. Found: C: 34.47; H: 4.84; N: 9.83.

(18.31) 2-Amino-5-[1-(2-cyclohexylmethyl)ethynyl]-4-phosphonomethoxycarbonylthiazole. Mp 230° C. (decomp). Anal. calcd. for $C_{14}H_{19}N_2O_5PS+0.1HBr$: C: 45.89; H: 5.25; N: 7.64. Found: C: 45.85; H: 4.96; N: 7.44.

(18.32) 2-Amino-5-[1-(4-cyano)butynyl]-4-phosphonomethoxycarbonylthiazole. Mp 230° C. (decomp). Anal. calcd. for $C_{10}H_{10}N_3O_5PS+0.25HBr$: C: 35.80; H: 3.08; N: 12.53. Found: C: 35.92; H: 2.99; N: 12.20.

(18.33) 2-Amino-5-methyl-4-phosphonomethoxycarbonyloxazole. Anal. calcd. for $C_6H_9N_2O_6P+0.15HBr$: C: 29.03; H: 3.71; N: 11.28. Found: C: 28.98; H: 3.66; N: 11.21.

(18.34) 2-Amino-5-[1-(4-cyano)butyl]-4-phosphonomethoxycarbonylthiazole. Mp 230° C. (decomp). Anal. calcd. for $C_{10}H_{14}N_3O_5PS$: C: 37.62; H: 4.42; N: 13.16. Found: C: 37.23; H: 4.18; N: 12.79.

(18.35) 2-Amino-5-pentyl-4-phosphonomethoxycarbonyloxazole. Anal. calcd. for $C_{10}H_{17}N_2O_6P$: C: 41.10; H: 5.86; N: 9.59. Found: C: 41.16; H: 5.75; N: 9.50.

(18.36) 2-[N-Boc(amino)]-4-[(2-phosphono)ethoxycarbonyl]thiazole. Anal. calcd. for $C_{11}H_{17}N_2O_7PS$: C: 37.50; H: 4.86; N: 7.95. Found: C: 37.10; H: 4.59; N: 7.84.

(18.37) 2-Amino-4-[(2-phosphono)ethoxycarbonyl]thiazole hydrobromide. Anal. calcd. for $C_6H_9N_2O_5PS+HBr$: C: 21.63; H: 3.03; N: 8.41. Found: C: 22.01; H: 2.99; N: 8.15.

(18.38) 2-Amino-5-butyl-4-phosphonomethoxycarbonyloxazole. Anal. calcd. for $C_9H_{15}N_2O_6P$: C: 38.86; H: 5.43; N: 10.07. Found: C: 38.59; H: 5.43; N: 9.96.

(18.39) 2-Amino-5-[1-(1-oxo-2,2-dimethyl)propyl]-4-phosphonomethoxycarbonylthiazole. Anal. Calcd. for $C_{10}H_{15}N_2O_6PS$: C: 37.27; H: 4.69; N: 8.69. Found: C: 37.03; H: 4.69; N: 8.39.

(18.40) 2-Amino-5-propyl-4-phosphonomethoxycarbonyloxazole. Anal. calcd. for $C_8H_{13}N_2O_6P+0.35EtOAc+0.05HBr$: C: 37.75; H: 5.34; N: 9.37. Found: C: 37.69; H: 5.21; N: 9.03.

(18.41) 2-Amino-5-propyl-4-phosphonomethoxycarbonylthiazole. Mp 134° C. (decomp). Anal. calcd. for $C_8H_{13}N_2O_5PS$: C: 34.29; H: 4.68; N: 10.00. Found: C: 33.90; H: 4.30; N: 9.61.

(18.42) 2-Amino-5-pentyl-4-phosphonomethoxycarbonylthiazole. Mp 130° C. (decomp). Anal. calcd. for $C_{10}H_{17}N_2O_5PS$: C: 38.96; H: 5.56; N: 9.09. Found: C: 38.69; H: 5.25; N: 8.85.

(18.43) 2-Amino-5-bromo-4-phosphonomethylthiocarbonylthiazole. Mp 230° C. (decomp). Anal. calcd. for $C_5H_6N_2O_5PS_2Br$: C: 18.03; H: 1.82; N: 8.41. Found: C: 18.40; H: 1.93; N: 8.18.

(18.44) 2-Amino-5-(2-furanyl)-4-phosphonomethoxycarbonylthiazole. Mp 230° C. (decomp). Anal. calcd. for $C_9H_9N_2O_6PS$: C: 35.53; H: 2.98; N: 9.21. Found: C: 35.78; H: 3.05; N: 8.11.

(18.45) 2-Amino-5-ethyl-4-phosphonomethoxycarbonyloxazole. Mp 141° C. (decomp). Anal. calcd. for $C_7H_{11}N_2O_6P$: C: 33.61; H: 4.43; N: 11.20. Found: C: 33.79; H: 4.47; N: 11.09.

(18.46) 5-Methyl-4-[(N-phosphonomethyl)carbamoyl]imidazole. Anal. calcd. for $C_6H_{10}N_3O_4P$: C: 32.89; H: 4.60; N: 19.18. Found: C: 33.04; H: 4.65; N: 18.84.

Example 19

Preparation of 3-[2-(5-phosphono)furanyl]pyrazoles
Step A.

A solution of diethyl 5-(2-isobutyl-3-N,N-dimethylamino)acryloyl-2-furanphosphonate (1 mmole, prepared according to Step A of Example 17) in ethanol was treated with hydrazine (1.2 mmole) 80° C. for 12 h. Evaporation and chromatography gave 4-isobutyl-3-[2-(5-diethylphosphono)furanyl]pyrazole.
Step B.

4-Isobutyl-3-[2-(5-diethylphosphono)furanyl]pyrazole was subjected to Step C of Example 3 to give 4-isobutyl-3-[2-(5-phosphono)furanyl]pyrazole (19.1). mp 210–215° C. Anal. calcd. for $C_{11}H_{15}N_2O_4P$: C: 48.89; H: 5.60; N: 10.37. Found: C: 48.67; H: 5.55; N: 10.20.
Step C.

4-Isobutyl-3-[2-(5-diethylphosphono)furanyl]pyrazole was subjected to Step A of Example 11 to give 1-methyl-4-isobutyl-3-[2-(5-diethylphosphono)furanyl]pyrazole.
Step D.

1-Methyl-4-isobutyl-3-[2-(5-diethylphosphono)furanyl]pyrazole was subjected to Step C of Example 3 to give 1-methyl-4-isobutyl-3-[2-(5-phosphono)furanyl]pyrazole (19.2). Anal. calcd. for $C_{12}H_{17}N_2O_4P+0.85HBr+0.75H_2O$: C: 39.32; H: 5.32; N: 7.64. Found: C: 39.59; H: 5.30; N: 7.47.

Example 20

Preparation of 3-[2-(5-phosphono)furanyl]isoxazoles
Step A.

A solution of 5-diethylphosphono-2-furaldehyde (1 mmole) in ethanol was treated with hydroxylamine (1.1 mmole) and sodium acetate (2.2 mmole) at 25° C. for 12 h. Extraction and chromatography gave 5-diethylphosphono-2-furaldehyde oxime.
Step B.

A solution of 5-diethylphosphono-2-furaldehyde oxime (1 mmole) in DMF was treated with N-chlorosuccinimide (1.1 mmole) at 25° C. for 12 h. Extraction gave 5-diethylphosphono-2-chlorooximidofuran.
Step C.

A solution of 5-diethylphosphono-2-chlorooximidofuran (1 mmole) and ethyl propiolate (5 mmole) in diethyl ether was treated with triethylamine (2 mmole) at 25° C. for 12 h. Extraction and chromatography gave 5-ethoxycarbonyl-3-{2-(5-diethylphosphono)furanyl}isoxazole.
Step D.

5-Ethoxycarbonyl-3-{2-(5-diethylphosphono)furanyl}isoxazole was subjected to Step A of Example 9 followed by Step C of Example 3 to give 5-carbamoyl-3-[2-(5-phosphono)furanyl]isoxazole (20.1). mp 221–225° C. Anal. calcd. for $C_8H_7N_2O_6P+0.25EtOH$: C: 37.86; H: 3.18; N: 10.39. Found: C: 37.90; H: 3.02; N: 10.05.

The following compound was prepared according to this procedure:

(20.2) 5-Ethoxycarbonyl-4-methyl-3-[2-(5-phosphono)furanyl]isoxazole. mp 150–152° C. Anal. calcd. for $C_{11}H_{12}NO_7P+0.25H_2O+0.15HBr$: C: 41.57; H: 4.01; N: 4.41. Found: C: 41.57; H: 4.20; N: 4.54.

(20.3) 4,5-Bis(ethoxycarbonyl)-3-[2-(5-phosphono)furanyl]isoxazole. Anal. calcd for $C_{13}H_{14}NO_9P$: C: 43.47; H: 3.93; N: 3.90. Found: C: 43.26; H: 3.92; N: 3.97.

(20.4) 5-Amino-4-ethoxycarbonyl-3-[2-(5-phosphono)furanyl]isoxazole. mp 190° C. (decomp). Anal. calcd for $C_{10}H_{11}N_2O_7P+0.25HBr$: C: 37.25; H: 3.52; N: 8.69. Found: C: 37.56; H: 3.50; N: 8.85.

(20.5) 4,5-bis(carbamoyl)-3-[2-(5-phosphono)furanyl]isoxazole. mp>220° C. Anal. calcd for $C_9H_8N_3O_7P$: C: 35.90; H: 2.68; N: 13.95. Found: C: 35.67; H: 2.55; N: 13.62.

(20.6) 4-Ethoxycarbonyl-5-trifluoromethyl-3-[2-(5-phosphono)furanyl]isoxazole. Anal. calcd for $C_{11}H_9F_3NO_7P+0.25HBr$: C: 35.20; H: 2.48; N: 3.73. Found: C: 35.25; H: 2.34; N: 3.98.

(20.7) 5-Amino-4-(2-furyl)-3-[2-(5-phosphono)furanyl]isoxazole. mp>220° C. Anal. calcd for $C_{12}H_9N_2O_7P+0.1AcOEt$: C: 44.73; H: 2.97; N: 8.41. Found: C: 45.10; H: 2.58; N: 8.73.

(20.8) 4-Amino-5-cyano-3-[2-(5-phosphono)furanyl]isoxazole. Anal. calcd for $C_8H_6N_3O_5P+0.1H_2O+0.2HBr$: C: 35.18; H: 2.36; N: 15.39. Found: C: 35.34; H: 2.50; N: 15.08.

(20.9) 4-Cyano-5-phenyl-3-[2-(5-phosphono)furanyl]isoxazole. Anal. calcd for $C_{14}H_9N_2O_5P+0.15HBr$: C: 51.21; H: 2.81; N: 8.53. Found: C: 51.24; H: 3.09; N: 8.33.

Example 21

Preparation of 2-[2-(5-phosphono)furanyl]thiazoles
Step A.

Diethyl 5-tributylstannyl-2-furanphosphonate (14) and 2-bromo-4-ethoxycarbonylthiazole was subjected to Step A of Example 6 to give 4-ethoxycarbonyl-2-[2-(5-diethylphosphono)furanyl]thiazole.

Step B.

4-Ethoxycarbonyl-2-[2-(5-diethylphosphono)furanyl]thiazole was subjected to Step A of Example 9 followed by Step C of Example 3 to give 4-carbamoyl-2-[2-(5-phosphono)furanyl]thiazole (21.1). mp 239–240° C. Anal. calcd. for $C_8H_7N_2O_5PS+0.2H_2O$: C: 34.59; H: 2.68; N: 10.08. Found: C: 34.65; H: 2.69; N: 9.84.

Example 22

Preparation of 4-(3.3-difluoro-3-phosphono-1-propyl)thiazoles

Step A.

A solution of 3-(tert-butyl-diphenylsilyloxy)-1-propanol (1 mmole) in methylene chloride (7 mL) was treated with powder molecular sieves (4 A, 0.5 equiv. wt/wt) and pyridinium chlorochromate (1.5 mmole) at 0° C. The resulting mixture was stirred at room temperature for 2 h, and diluted with diethyl ether (7 mL) and stirred at room temperature for another 30 min. Filtration, evaporation and chromatography gave 3-(tert-butyldiphenylsilyloxy)-1-propanal as a clear oil.

Step B.

A solution of LDA (1.06 mmole) in THF was treated with a solution of diethyl difluoromethylphosphonate (1 mmole) at −78° C. for 45 min. The reaction was then treated with a THF solution of 3-(tert-butyldiphenylsilyloxy)-1-propanal (1.07 mmole) and the resulting solution was stirred at −78° C. for another 4 h. The reaction was quenched with phenyl chlorothioformate (2.14 mmoles), and the reaction mixture was subjected to extraction and chromatography to give diethyl 4-(tert-butyldiphenylsilyloxy)-3-phenoxythiocarbonyloxy-2,2-difluorobutylphosphonate as a clear oil.

Step C.

A solution of diethyl 4-(tert-butyldiphenylsilyloxy)-3-phenoxythiocarbonyloxy-2,2-difluorobutylphosphonate (1 mmole) in toluene (1 mL) was treated with tri-n-butyltin hydride (1.5 mmole) and AIBN (0.1 mmole), and the resulting reaction mixture was heated to reflux for 2 h. Evaporation and chromatography gave diethyl 4-(tert-butyldiphenylsilyloxy)-2,2-difluorobutylphosphonate as a clear oil.

Step D.

A solution of diethyl 4-(tert-butyldiphenylsilyloxy)-2,2-difluorobutylphosphonate (1 mmole) in methanol (1 mL) was treated with hydrochloric acid (4 N, 4 mmole) at 0° C., and the resulting reaction was stirred at room temperature for 2 h. Evaporation and chromatography gave diethyl 4-hydroxy-2,2-difluorobutylphosphonate as a clear oil.

Step E.

A solution of gave diethyl 4-hydroxy-2,2-difluorobutylphosphonate (1 mmole) in acetone (10 mL) was treated with Jones's reagent (10 mmole) at 0° C. for 30 min. The reaction was quenched with 2-propanol (10 mL), and the resulting mixture was filtered through a Celite pad. Evaporation of the filtrate followed by extraction gave diethyl 3-carboxyl-2,3-difluoropropylphosphonate as an oil.

Step F.

A solution of diethyl 3-carboxyl-2,3-difluoropropylphosphonate (1 mmole) in thionyl chloride (3 mL) was heated to reflux for 2 h. The reaction was evaporated to dryness, and the residue was dissolved in diethyl ether (1 mL) was treated with an etheral solution of diazomethane (10 mmole) at 0° C. for 30 min. A solution of HBr in acetic acid (30%, 1 mL) was added to the reaction, and the resulting solution was stirred at room temperature for 1 h. The reaction was evaporated to dryness and the residue was dissolved in THF-EtOH (1:1, 5 mL) and treated with thiourea (1 mmole). The resulting reaction mixture was heated to 75° C. for 1 h. Evaporation followed by extraction and chromatography gave 2-amino-4-[1-(3-diethylphosphono-3,3-difluoro)propyl]thiazole as a solid, which was subjected to Step C of Example 3 to give gave 2-amino-4-[1-(3-phosphono-3,3-difluoro)propyl]thiazole (22.1) as a solid. Anal. calcd. for $C_6H_9N_2O_3PSF_2+HBr$: C: 21.25; H: 2.97; N: 8.26. Found: C: 21.24; H: 3.25; N: 8.21.

The following compound was prepared in a similar manner: 2-Amino-5-methylthio-4-[1-(3-phosphono-3,3-difluoro)propyl]thiazole (22.2). MS m/e 305 (M+H).

Example 23

Preparation of 2-methylthio-5-phosphonomethylthio-1,3,4-thiadiazole and 2-phosphonomethylthiopyridine Step A.

A solution of 2-methylthio-1,3,4-thiadiazole-5-thiol (1 mmole) in THF (5 mL) was treated with sodium hydride (60%, 1.1 mmole) at 0° C. and the resulting mixture was stirred at room temperature for 30 min. The reaction was then cooled to 0° C. and treated with diethylphosphonomethyl trifluoromethanesulfonate (1.1 mmole). After stirring at room temperature for 12 h, the reaction was quenched with saturated ammonium chloride. Extraction and chromatography gave 2-methylthio-5-diethylphosphonomethylthio-1,3,4-thiadiazole as an oil.

Step B.

2-Methylthio-5-diethylphosphonomethylthio-1,3,4-thiadiazole was subjected to Step C of Example 3 to give 2-methylthio-5-phosphonomethylthio-1,3,4-thiadiazole (23.1) as a yellow solid. Anal. calcd. for $C_4H_7N_2O_3PS_3+0.2HBr$: C: 17.50; H: 2.64; N: 10.21. Found: C: 17.64; H: 2.56; N: 10.00.

Alternatively, phosphonomethylthio substituted heteroaromatics are made using the following method as exemplified by the synthesis of 2-phosphonomethylthiopyridine:

Step C.

A solution of 2,2'-dipyridyl disulfide (1 mmole) in THF was treated with tri-n-butylphosphine (1 mmole) and diethyl hydroxymethylphosphonate at 0° C. The resulting reaction solution was stirred at room temperature for 18 h. Extraction and chromatography gave 2-diethylphosphonomethylthiopyridine as a yellow oil.

Step D.

2-Diethylphosphonomethylthiopyridine was subjected to Step C of Example 3 to give 2-phosphonomethylthiopyridine (23.2) as a yellow solid. Anal. calcd. for $C_6H_8NO_3PS+0.62HBr$: C: 28.22; H: 3.40; N: 5.49. Found: C: 28.48; H: 3.75; N: 5.14.

Example 24

Preparation of 2-[(2-phosphono)ethynyl]pyridine

Step A.

A solution of 2-ethynylpyridine (1 mmole) in THF (5 mL) was treated with LDA (1.2 mmole) at 0° C. for 40 min. Diethyl chlorophosphate (1.2 mmole) was added to the reaction and the resulting reaction solution was stirred at room temperature for 16 h. The reaction was quenched with saturated ammonium chloride followed by extraction and chromatography to give 2-[(2-diethylphosphono)ethynyl]pyridine as a yellow oil.

Step B.

2-[(2-Diethylphosphono)ethynyl]pyridine was subjected to Step C of Example 3 to give 2-[1-(2-phosphono)ethynyl] pyridine (24.1) as a brown solid. Mp 160° C. (decomp). MS m/e 184 (M+H).

Example 25

Preparation of 5-[2-(5-phosphono)furanyl]tetrazole

Step A.

To a mixture of tetrazole (1 mmole) and powdered $K_2CO_3$ (1.5 mmole) in 1 mL DMF cooled to 0° C. was added benzyl chloromethyl ether (1.2 mmole) and the resulting mixture stirred for 30 min at 0° C. and then for 16 h at rt. The mixture was diluted with water and ether. Extraction and chromatography provided 2-benzyloxymethyltetrazole as a colorless oil.

Step B.

To a solution of 2-benzyloxymethyltetrazole (1 mmole) and TMEDA (2 mmole) in 3 mL diethyl ether at −78° C. was added n-BuLi in hexanes (1 mmole). This was let stir for 5 min at −78° C. and then it was added to a precooled (−78° C.) solution of $(n-Bu)_3SnCl$ (1 mmole) in 2 mL of diethyl ether. After stirring at −78° C. for 30 min it was diluted with water and diethyl ether. Extraction and chromatography provided 2-benzyloxymethyl-5-(tributylstannyl)tetrazole as a colorless oil.

Step C.

A mixture of 5-iodo-2-diethylphosphonofuran (1 mmole), 2-benzyloxymethyl-5-(tributylstannyl)tetrazole (1.05 mmole), tetrakis(triphenylphosphine) palladium(0) (0.03 mmole) and copper(I) iodide (0.07 mmole) in 3 mL of toluene was refluxed at 110° C. for 20 h. Evaporation and chromatography provided 2-benzyloxymethyl-5-[2-(5-diethylphosphono)furanyl]tetrazole as an oil.

Step D.

A mixture of 2-benzyloxymethyl-5-[2-(5-diethylphosphono)furanyl]tetrazole (1 mmole) and 6 M HCl (1 mL) in 10 mL ethanol was heated at 70° C. for 20 h and then the solvent concentrated by evaporation, made basic with 1 N NaOH and extracted with EtOAc. The aqueous layer was made acidic and extracted with EtOAc. This EtOAc extract was evaporated to provide 5-[2-(5-diethylphosphono)furanyl]tetrazole as a solid, which was subjected to Step C of Example 3 to give 5-[2-(5-phosphono)furanyl]tetrazole (25.1) as a solid: mp 186–188° C. Anal. calcd. for $C_5H_5N_4O_4P+1.5H_2O$: C, 24.70; H, 3.32; N: 23.05. Found: C, 24.57; H, 2.57; N: 23.05.

Step E.

Step 1.

A mixture of 5-[2-(5-diethylphosphono)furanyl]tetrazole (1 mmole), 1-iodo-2-methylpropane (2 mmole) and powdered $K_2CO_3$ (2 mmole) in 5 mL DMF was stirred at 80° C. for 48 h and then diluted with $CH_2Cl_2$ and water and the layers separated. The $CH_2O_2$ layer was evaporated and combined with the product of the following reaction for chromatography.

Step 2.

The aqueous layer of Step 1 was made acidic and extracted with EtOAc. This extract was evaporated and the residue heated at 80° C. in 2 mL of $SOCl_2$ for 3 h and then the solvent evaporated. The residue was dissolved in 5 mL $CH_2Cl_2$ and 0.3 mL $NEt_3$ and 0.5 mL of EtOH was added. After stirring for 1 h at rt the mixture was diluted with $CH_2Cl_2$ and water. This organic extract was combined with that kept from Step 1 and chromatography provided 1-isobutyl-5-[2-(5-diethylphosphono)furanyl]tetrazole and 2-isobutyl-5-[2-(5-diethylphosphono)furanyl]tetrazole each as an oil.

Step 3.

1-Isobutyl-5-[2-(5-diethylphosphono)furanyl]tetrazole was subjected to Step C of Example 3 to give 1-isobutyl-5-[2-(5-phosphono)furanyl]tetrazole (25.2) as a solid: mp 200–202° C. Anal. calcd. for $C_9H_{13}N_4O_4P$: C: 39.71; H: 4.81; N: 20.58. Found: C: 39.64; H: 4.63; N: 20.21.

Step F.

A mixture of 2-isobutyl-5-[2-(5-diethylphosphono) furanyl]tetrazole (1 mmole) and TMSBr (10 mmole) in 10 mL of $CH_2Cl_2$ was stirred at room temperature for 16 h. The solvent was evaporated and the residue dissolved in 10:1 $CH_3CN$:water, the solvent evaporated and the residue precipitated from acetone by addition of dicyclohexylamine (2 mmole) to provide 2-isobutyl-5-[2-(5-phosphono)furanyl] tetrazole N,N-dicyclohexyl ammonium salt.

(25.3) as a solid: mp 226–228° C. Anal. calcd. for $C_9H_{13}N_4O_4P+C_{12}H_{23}N$: C: 55.62; H: 8.00; N: 15.44. Found: C: 55.55; H: 8.03; N: 15.07.

Example 26

High Throughput Synthesis of Various 2-(5-phosphono)furanyl Substituted Heteroaromatic Compounds Step A.

Various 2-(5-diethylphosphono)furanyl substituted heteroaromatic compounds were prepared in a similar manner as Step B of Example 15, and some of these compounds were used for the high throughput synthesis of compounds listed in Table 26.1 and Table 26.2.

Step B.

A mixture of 2-chloro-6-[2-(5-diethylphosphono)furanyl] pyridine (0.01 mmole) and TMSBr (0.1 mL) in $CH_2Cl_2$ (0.5 mL) was stirred at room temperature for 16 h and then evaporated and diluted with 0.5 mL of 9:1 $CH_3CN$:water. Evaporation provided 2-chloro-6-[2-(5-phosphono)furanyl] pyridine.

Step C.

A mixture of 2-chloro-6-[2-(5-diethylphosphono)furanyl] pyridine (0.01 mmole) and a solution of freshly prepared sodium propoxide in propanol (0.25 M, 0.4 mL) was let sit at 85° C. for 14 h. The reaction mixture was evaporated and the residue was subjected to Step B of Example 26 to give 2-propyloxy-6-[2-(5-phosphono)furanyl]pyridine.

Step D.

A mixture of 2-chloro-6-[2-(5-diethylphosphono)furanyl] pyridine (0.01 mmol) and 1-methylpiperazine (0.2 mL) in ethylene glycol (0.2 mL) was heated at 145° C. for 24 h. The mixture was further diluted with 0.5 mL of $CH_3CN$ and 0.1 mL of water and then 150 mg of Dowex 1 2-100 formate resin was added. After stirring this mixture 30 min it was filtered and the resin washed with DMF (2×10 mL), $CH_3CN$ (2×10 mL) and then 9:1 $CH_3CN$:water (1×10 mL). Finally the resin was stirred with 9:1 TFA:water for 30 min, filtered and the filtrate evaporated. The residue obtained subjected to Step B of Example 26 to give 2-[1-(4-methyl)piperazinyl]-6-[2-(5-phosphono)furanyl]pyridine.

Step E.

A mixture of 3-chloro-5-[2-(5-diethylphosphono)furanyl] pyrazine (0.01 mmole), 5-tributylstannylthiophene (0.04 mmole), $Pd(PPh_3)_4$ (0.001 mmole) and CuI (0.002 mmole) in dioxane (0.5 mL) was heated at 85° C. for 16 h then the solvent was evaporated. The resulting residue and TMSBr (0.1 mL) in 0.5 mL $CH_2Cl_2$ was stirred at rt for 16 h and then evaporated and diluted with 0.5 mL of 9:1 $CH_3CN$:water. To this solution 150 mg of Dowex 1 2-100 formate resin was added and after stirring 30 min it was filtered and the resin washed with DMF (2×10 mL), $CH_3CN$ (2×10 mL) and then 9:1 CH$_3$CN:water (1×10 mL). Finally the resin was stirred with 9:1 TFA:water for 30 min, filtered and the filtrate evaporated to give 3-(2-thienyl)-5-[2-(5-phosphono) furanyl]pyrazine.

Step F.

A mixture of 3-chloro-5-[2-(5-diethylphosphono)furanyl] pyrazine (0.01 mmole), 1-hexyne (0.04 mmole), diisopropylethylamine (0.1 mmole), Pd(PPh$_3$)$_4$ (0.001 mmole) and CuI (0.002 mmole) in dioxane (0.5 mL) was heated at 85° C. for 16 h then the solvent was evaporated. The resulting residue was subjected to Step B of Example 26 to give 3-(1-hexyn-1-yl)-5-[2-(5-phosphono)furanyl]pyrazine.

Preparation of the Carboxymethylphosphonate Resin

Step G.

A solution of trimethylphosphonoacetate (30.9 mmol), 2-(trimethylsiyl) ethanol (10.4 mmol) and DMAP (3.1 mmol) in toluene (25 mL) was refluxed for 48 h under N$_2$. After cooling, the solution was diluted with EtOAc and washed with 1N HCl followed by water. The organic solution was dried over sodium sulfate and concentrated under vacuum to give an oil. The residue was treated with LiI (10.4 mmol) in 2-butanone (30 mL), and refluxed overnight under N$_2$. The solution was diluted with EtOAc, washed with 1N HCl, dried over Na$_2$SO$_4$ and concentrated under vacuum to afford the SEM protected carboxy monomethylphosphonate as a colorless oil.

Step H.

Hydroxymethylpolystyrene (2.35 mmol) was prepared for coupling by combining with anhydrous THF (40 mL), gently shaking for 20 min. and then removing the excess solvent by cannula. This procedure was repeated 3 times. The swollen resin was then suspended in THF (40 mL) and DIPEA (21.2 mmol). To this mixture was added, by cannula, a solution of the SEM protected carboxy monomethylphosphonate (prepared in Step G) (7.1 mmol), DIAD (7.1 mmol) and tris(4-chlorophenyl)phosphine (7.1 mmol) in THF (15 mL) which had been stirred for 15 min. prior to addition. After shaking the mixture overnight under a blanket of N$_2$, the resin was filtered, rinsed with THF (3×40 mL), DMF (3×40 mL), and THF again (3×40 mL) before drying under vacuum to afford 3.8 g of the coupled phosphonate resin.

Step I.

To coupled phosphonate resin (2.41 mmol) in THF (100 mL) was added 1M TBAF in THF solution (12 mL). The mixture was shaken overnight before being filtered and the resin rinsed with THF (3×40 mL) to afford the desired carboxymethylphosphonate resin as the tetrabutylammonium salt.

Coupling of the Carboxymethylphosphonate Resin to a Heteroaromatic Amine

Step J.

In a 2 mL well, a heteroaromatic amine (0.14 mmol), resin (0.014 mmol), PyBOP (0.14 mmol) and TEA (0.36 mmol) in DMF (1.45 mL) were combined and shaken for 48 h at room temperature. The treated resin was then filtered, washed with DMF (3×) and CH$_2$Cl$_2$ (3×). The isolated resin was resuspended in CH$_2$Cl$_2$ (900 µL), combined with TMSBr (100 µL) and mixed for 6 h. The mixture was filtered, the resin washed with anhydrous CH$_2$Cl$_2$ (500 µL) and the filtrate concentrated under vacuum. To the isolated residue was added a solution of CH$_3$CN/H$_2$O (9:1, 300 µL). After shaking for 30 min. the solvents were removed to provide the desired [{N-(phosphono)acetyl]amino} substituted heteroaromatic analogs. Compounds 26.97–26.119 and 26.146–26.164 were synthesized according to these procedures and they are listed in Table 26.1 and Table 26.2.

Preparation of the Aminomethylphosphonate Resin

Step K.

To a solution of dimethyl phthalimidomethylphosphonate (37 mmole) in 2-butanone (150 mL) was added LiI (38.9 mmol). After refluxing overnight under N$_2$, the solution was diluted with EtOAc, washed with 1N HCl, dried over MgSO$_4$ and concentrated under vacuum to afford monomethyl phthalimidomethylphosphonate as a white solid.

Step L.

As described above in Step H, monomethyl phthalimidomethyl-phosphonate was coupled to hydroxymethylpolystyrene to give the resin-coupled phthalimidomethylphosphonate monomethyl ester.

Step M.

To the resin-coupled phthalimidomethylphosphonate monomethyl ester (6.8 mmol) in DMF (7 mL) was added anhydrous hydrazine (3 mL). After shaking at room temperature for 24 h the resin was filtered, rinsed with DMF (3×10 mL), CH$_2$Cl$_2$ (3×10 mL) and then dried under vacuum to afford 832 mg the desired resin-coupled aminomethylphosphonate monomethyl ester.

Coupling of Various Heteroaromatic Carboxylic Acids to the Resin-coupled Aminomethylphosphonate Monomethyl Ester.

Step N.

In a 2 mL well, a heteroaromatic carboxylic acid (0.2 mmol), resin (0.02 mmol), EDC (0.2 mmol) and HOBT (0.2 mmol) in DMF (0.5 mL) were combined and shaken for 24 h at room temperature. The treated resin was then filtered, washed with DMF (3×) and CH$_2$Cl$_2$ (3×). The isolated resin was resuspended in CH$_2$Cl$_2$ (500 µL), combined with TMSBr (50 µL) and mixed for 6 h. The mixture was filtered, the resin washed with anhydrous CH$_2$Cl$_2$ (500 µL) and the filtrate concentrated under vacuum. To the isolated residue was added a solution of CH$_3$CN/H$_2$O (9:1, 300 µL). After shaking for 30 min the solvents were evaporated to provide the desired (N-phosphonomethyl)carbamoyl substituted heteroaromatic analogs. Compounds 26.120–26.145 were synthesized according to these procedures and they are listed in Table 26.2.

The following compounds were prepared according to some or all of the above described procedures. These compounds were characterized by HPLC (as described below) and mass spectroscopy (APCI negative ion), and these characterization data are listed in Table 26.1 and Table 26.2.

HPLC was performed using a YMC ODS-Aq, Aq-303-5, 250 4.6 mm ID, S-5 µm, 120 A column with the UV detector set at 280 nm.

| HPLC Elution Program: 1.5 mL/min flow rate | | |
|---|---|---|
| Time (min) | % Acetonitrile (A) | % Buffered[a] (B) |
| 0 | 10 | 90 |
| 7.5 | 90 | 10 |
| 12.4 | 90 | 10 |
| 12.5 | 10 | 90 |
| 15 | 10 | 90 |

[a]Buffer = 95:5:0.1 water:methanol:acetic acid

TABLE 26.1

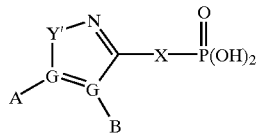

| synthetic example number | A | B | X | Y' | HPLC Rt (min.) | M-1 found |
|---|---|---|---|---|---|---|
| 26.146 | H | Br | NHC(O)CH₂ | S | 6.58 | 299/301 |
| 26.147 | H | Ph | NHC(O)CH₂ | S | 6.57 | 297 |
| 26.148 | Ph | H | NHC(O)CH₂ | S | 6.06 | 297 |
| 26.149 | Ph | Et | NHC(O)CH₂ | O | | 309 |
| 26.150 | H | H | NHC(O)CH₂ | S | 4.22 | 221 |
| 26.151 | adamantyl | Me | NHC(O)CH₂ | S | 6.59 | 369 |
| 26.152 | Bu-t | Br | NHC(O)CH₂ | S | 6.62 | 355/357 |
| 26.153 | H | Ph(-4-Br) | NHC(O)CH₂ | S | 6.62 | 375/377 |

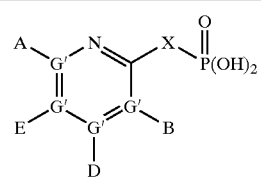

| synthetic example number | A* | B* | X | Y' | HPLC Rt (min.) | M-1 found |
|---|---|---|---|---|---|---|
| 26.154 | H | H | NHC(O)NH₂ | O | 6.68 | 205 |
| 26.155 | null | NH₂ | NHC(O)CH₂ | O | 6.6 | 221 |
| 26.156 | NHMe | null | NHC(O)CH₂ | S | 3.82 | 251 |
| 26.157 | Me | H | NHC(O)CH₂ | NH | | |
| 26.158 | H | H | NHC(O)CH₂ | NH | | |
| 26.159 | OH | H | NHC(O)CH₂ | NH | | |
| 26.160 | Bu-t | H | NHC(O)NH₂ | O | 6.62 | 261 |
| 26.161 | null | 3-pyridyl | NHC(O)CH₂ | O | 6.58 | 283 |
| 26.162 | CH₂—Ph-(2,6-dichloro) | null | NHC(O)CH₂ | O | | |
| 26.163 | Br | null | furan-2,5-diyl | NH | 4.46 | 292/294 |
| 26.164 | Br | null | furan-2,5-diyl | S | 5.96 | 309/311 |

*when A or B is null, then the corresponding G is N.

TABLE 26.2

| synthetic example number | A* | B* | C | D* | E* | HPLC Rt M-1 (min.) | found |
|---|---|---|---|---|---|---|---|
| 26.1 | NH₂ | Cl | furan-2,5-diyl | Me | | 11.06 | 288 |
| 26.2 | H | OC(O)(Ph-2,6-dichloro) | furan-2,5-diyl | H | H | 3.99 | 413 |
| 26.3 | OMe | H | furan-2,5-diyl | CH₂OH | H | 8.34 | 284 |
| 26.4 | OMe | H | furan-2,5-diyl | C(O)NH₂ | H | 8.23 | 297 |
| 26.5 | OMe | H | furan-2,5-diyl | CO₂H | H | 9.54 | 298 |
| 26.6 | OH | H | furan-2,5-diyl | CF₃ | C(O)NH₂ | 3.91 | 351 |
| 26.7 | OMe | H | furan-2,5-diyl | CF₃ | C(O)NH₂ | 9.14 | 365 |
| 26.8 | null | H | furan-2,5-diyl | H | OMe | 9.72 | 255 |
| 26.9 | null | H | furan-2,5-diyl | H | OH | 4.52 | 241 |
| 26.10 | OH | H | furan-2,5-diyl | Me | null | 3.79 | 255 |
| 26.11 | OMe | H | furan-2,5-diyl | Me | null | 6.44 | 269 |
| 26.12 | NH₂ | null | furan-2,5-diyl | OH | H | 3.96 | 256 |
| 26.13 | NH₂ | null | furan-2,5-diyl | OMe | H | 8.02 | 270 |
| 26.14 | H | OMe | furan-2,5-diyl | null | H | 7.22 | 255 |
| 26.15 | H | OH | furan-2,5-diyl | null | H | 4.82 | 241 |

TABLE 26.2-continued

| synthetic example number | A* | B* | C | D* | E* | HPLC Rt M-1 (min.) | found |
|---|---|---|---|---|---|---|---|
| 26.16 | OMe | H | furan-2,5-diyl | null | H | 7.48 | 255 |
| 26.17 | OEt | H | furan-2,5-diyl | H | H | 9.72 | 268 |
| 26.18 | OEt | H | furan-2,5-diyl | $CH_2OH$ | H | 5.26 | 298 |
| 26.19 | null | H | furan-2,5-diyl | Me | OEt | 7.80 | 283 |
| 26.20 | null | H | furan-2,5-diyl | Me | OH | 3.80 | 255 |
| 26.21 | OH | H | furan-2,5-diyl | Me | null | 3.77 | 255 |
| 26.22 | OEt | H | furan-2,5-diyl | Me | null | 7.33 | 283 |
| 26.23 | $NH_2$ | null | furan-2,5-diyl | OH | H | 3.94 | 256 |
| 26.24 | $NH_2$ | null | furan-2,5-diyl | OEt | H | 5.66 | 284 |
| 26.25 | $NH_2$ | H | furan-2,5-diyl | OEt | null | 5.90 | 284 |
| 26.26 | $NH_2$ | H | furan-2,5-diyl | OH | null | 3.78 | 256 |
| 26.27 | H | OEt | furan-2,5-diyl | null | H | 9.74 | 269 |
| 26.28 | H | OH | furan-2,5-diyl | null | H | 4.81 | 241 |
| 26.29 | OEt | H | furan-2,5-diyl | null | H | 9.78 | 269 |
| 26.30 | Br | H | furan-2,5-diyl | H | $NO_2$ | 7.78 | 347/349 |
| 26.31 | Cl | H | furan-2,5-diyl | H | C(O)OEt | 9.69 | 330 |
| 26.32 | Br | H | furan-2,5-diyl | H | C(O)OEt | 9.69 | 374/376 |
| 26.33 | Cl | H | furan-2,5-diyl | Me | $C(O)NH_2$ | 3.72 | 315 |
| 26.34 | Cl | $CF_3$ | furan-2,5-diyl | H | $CF_3$ | 9.04 | 394 |
| 26.35 | Cl | H | furan-2,5-diyl | $NH_2$ | H | 4.89 | 273 |
| 26.36 | Cl | H | furan-2,5-diyl | CN | H | 7.93 | 283 |
| 26.37 | Cl | H | furan-2,5-diyl | $CH_2OH$ | H | 5.38 | 288 |
| 26.38 | Cl | H | furan-2,5-diyl | $C(O)NH_2$ | H | 5.57 | 301 |
| 26.39 | Cl | H | furan-2,5-diyl | C(O)OEt | H | 8.54 | 330 |
| 26.40 | Cl | 1-triazinyl-(3-amino-5-methyl-thio) | furan-2,5-diyl | H | H | 8.91 | 398 |
| 26.41 | Cl | H | furan-2,5-diyl | Me | CN | 8.22 | 297 |
| 26.42 | Cl | H | furan-2,5-diyl | $CF_3$ | $NH_2$ | 8.60 | 341 |
| 26.43 | Cl | H | furan-2,5-diyl | $CF_3$ | CN | 8.66 | 351 |
| 26.44 | null | $CH_3$ | furan-2,5-diyl | Me | Br | 9.25 | 331/333 |
| 26.45 | null | $CH_3$ | furan-2,5-diyl | Me | Cl | 9.25 | 287 |
| 26.46 | Br | $CH_3$ | furan-2,5-diyl | H | null | 5.62 | 317/319 |
| 26.47 | Br | Br | furan-2,5-diyl | H | null | 3.54 | 381/383/385 |
| 26.48 | Br | H | furan-2,5-diyl | Me | null | 5.55 | 317/319 |
| 26.49 | H | $NH_2$ | furan-2,5-diyl | Br | null | 4.78 | 318/320 |
| 26.50 | Br | Cl | furan-2,5-diyl | Br | null | 8.38 | 417/419 |
| 26.51 | SMe | Ph | furan-2,5-diyl | Br | null | 9.26 | 425/427 |
| 26.52 | $NH_2$ | H | furan-2,5-diyl | Br | null | 4.87 | 318/320 |
| 26.53 | $NH_2$ | H | furan-2,5-diyl | OH | null | 3.70 | 256 |
| 26.54 | Br | H | furan-2,5-diyl | Br | null | 9.64 | 381/383/385 |
| 26.55 | Br | H | furan-2,5-diyl | Cl | null | 9.64 | 337/339 |
| 26.56 | H | Br | furan-2,5-diyl | null | H | 5.08 | 303/305 |
| 26.57 | $NH_2$ | Cl | furan-2,5-diyl | null | C(O)OMe | 3.34 | 332 |
| 26.58 | OPr-n | H | furan-2,5-diyl | Me | null | 8.14 | 297 |
| 26.59 | H | OPr-n | furan-2,5-diyl | null | H | 8.45 | 283 |
| 26.60 | H | $O(CH_2)_2$—OEt | furan-2,5-diyl | null | H | 7.82 | 313 |
| 26.61 | $NH_2$ | null | furan-2,5-diyl | OH | H | 3.97 | 256 |
| 26.62 | $NH_2$ | null | furan-2,5-diyl | OPr-n | H | 7.84 | 298 |
| 26.63 | OPr-n | H | furan-2,5-diyl | $CH_2OH$ | H | 4.36 | 312 |
| 26.64 | OBu-n | H | furan-2,5-diyl | $CH_2OH$ | H | 8.58 | 326 |
| 26.65 | O—$(CH_2)_2$—OEt | H | furan-2,5-diyl | $CH_2OH$ | H | 4.13 | 342 |
| 26.66 | $NH_2$ | H | furan-2,5-diyl | OPr-n | null | 7.96 | 298 |
| 26.67 | $NH_2$ | H | furan-2,5-diyl | OBu-n | null | 3.86 | 312 |
| 26.68 | H | OBu-i | furan-2,5-diyl | null | H | 8.80 | 297 |
| 26.69 | H | $O(CH_2)_2$—OEt | furan-2,5-diyl | null | H | 7.14 | 299 |
| 26.70 | H | $O(CH_2)_2$—$NMe_2$ | furan-2,5-diyl | null | H | 4.57 | 312 |
| 26.71 | $NH_2$ | null | furan-2,5-diyl | OBu-i | H | 8.06 | 312 |
| 26.72 | $NH_2$ | null | furan-2,5-diyl | $O(CH_2)_2OMe$ | H | 4.84 | 314 |
| 26.73 | $NH_2$ | H | furan-2,5-diyl | OBu-i | null | 8.70 | 312 |

TABLE 26.2-continued

| synthetic example number | A* | B* | C | D* | E* | HPLC Rt M-1 (min.) | found |
|---|---|---|---|---|---|---|---|
| 26.74 | Br | H | furan-2,5-diyl | C(O)NH$_2$ | H | 7.68 | 346/348 |
| 26.75 | NH$_2$ | null | furan-2,5-diyl | Cl | H | 4.77 | 274 |
| 26.76 | NH—(CH$_2$)$_2$—OH | H | furan-2,5-diyl | Me | null | 4.56 | 298 |
| 26.77 | H | NH(CH$_2$)$_2$OH | furan-2,5-diyl | null | H | 4.55 | 284 |
| 26.78 | NH$_2$ | null | furan-2,5-diyl | NH—(CH)$_2$OH | H | 4.58 | 299 |
| 26.79 | NH—(CH$_2$)$_2$—OH | H | furan-2,5-diyl | NH$_2$ | null | 4.58 | 299 |
| 26.80 | NH—(CH$_2$)$_2$—OH | H | furan-2,5-diyl | CH$_2$OH | H | 4.44 | 313 |
| 26.81 | NH$_2$ | H | furan-2,5-diyl | NH—(CH$_2$)$_2$OH | null | 4.33 | 299 |
| 26.82 | NH—CH—CH—(OH)—Me | H | furan-2,5-diyl | CH | null | 4.65 | 312 |
| 26.83 | NH$_2$ | null | furan-2,5-diyl | NHCH$_2$—CH(OH)—Me | H | 4.63 | 313 |
| 26.84 | NH—CH$_2$—CH—(OH)—Me | H | furan-2,5-diyl | NH$_2$ | null | 4.63 | 313 |
| 26.85 | NH—CH$_2$—CH—(OH)—Me | H | furan-2,5-diyl | CH$_2$OH | H | 4.52 | 327 |
| 26.86 | NH$_2$ | H | furan-2,5-diyl | NHCH$_2$—CH(OH)—Me | null | 4.65 | 313 |
| 26.87 | NH—(CH$_2$)$_3$—OH | H | furan-2,5-diyl | Me | null | 4.62 | 312 |
| 26.88 | NH$_2$ | null | furan-2,5-diyl | NH—(CH$_2$)$_3$OH | H | 4.48 | 313 |
| 26.89 | NH—(CH$_2$)$_3$—OH | H | furan-2,5-diyl | NH$_2$ | null | 4.48 | 313 |
| 26.90 | NH$_2$ | NH—(CH$_2$)$_3$OH | furan-2,5-diyl | null | C(O)NH—(CH$_2$)$_3$OH | 4.76 | 414 |
| 26.91 | H | 4-morpholinyl | furan-2,5-diyl | null | H | 6.46 | 310 |
| 26.92 | 4-morpholinyl | H | furan-2,5-diyl | Me | null | 6.53 | 324 |
| 26.93 | NH$_2$ | null | furan-2,5-diyl | 4-morpholinyl | H | 6.15 | 325 |
| 26.94 | 4-morpholinyl | H | furan-2,5-diyl | NH$_2$ | null | 4.84 | 325 |
| 26.95 | NH$_2$ | 4-morpholinyl | furan-2,5-diyl | null | C(O)-(4-morpholinyl) | 7.47 | 438 |
| 26.96 | NH$_2$ | H | furan-2,5-diyl | 4-morpholinyl | null | 5.30 | 325 |
| 26.97 | Me | H | NHC(O)CH$_2$ | H | H | 6.58 | 229 |
| 26.98 | H | Me | NHC(O)CH$_2$ | H | H | 6.60 | 229 |
| 26.99 | NH$_2$ | H | NHC(O)CH$_2$ | H | Cl | 6.63 | 264 |
| 26.100 | NH$_2$ | Cl | NHC(O)CH$_2$ | H | H | 6.63 | 264 |
| 26.101 | H | OH | NHC(O)CH$_2$ | H | H | 6.54 | 231 |
| 26.102 | Me | H | NHC(O)CH$_2$ | Me | H | 6.59 | 243 |
| 26.103 | H | H | NHC(O)CH$_2$ | H | Cl | 7.02 | 249 |
| 26.104 | H | H | NHC(O)CH$_2$ | H | Br | 8.01 | 293/295 |
| 26.105 | Me | H | NHC(O)CH$_2$ | H | Br | 6.64 | 307/309 |
| 26.106 | H | H | NHC(O)CH$_2$ | H | H | 6.72 | 215 |
| 26.107 | H | H | NHC(O)CH$_2$ | H | Me | 6.54 | 229 |
| 26.108 | H | H | NHC(O)CH$_2$ | Me | H | 6.53 | 229 |
| 26.109 | Me | Cl | NHC(O)CH$_2$ | Me | null | 3.93 | 279 |
| 26.110 | Cl | H | NHC(O)CH$_2$ | null | H | 4.20 | 251 |
| 26.111 | H | Br | NHC(O)CH$_2$ | H | Me | 6.44 | 307/309 |
| 26.112 | NH$_2$ | H | NHC(O)CH$_2$ | NH-(Ph-4-Br) | null | 4.42 | 401/403 |
| 26.113 | NH$_2$ | Bn | NHC(O)CH$_2$ | H | Bn | 6.49 | 410 |
| 26.114 | H | H | NHC(O)CH$_2$ | Et | H | 6.57 | 243 |
| 26.115 | Me | Et | NHC(O)CH$_2$ | H | H | 6.54 | 257 |
| 26.116 | Me | H | NHC(O)CH$_2$ | H | Br | 6.55 | 307/309 |
| 26.117 | H | Br | NHC(O)CH$_2$ | H | Me | 6.51 | 307/309 |
| 26.118 | H | Me | NHC(O)CH$_2$ | H | Br | 6.52 | 307/309 |
| 26.119 | Me | Br | NHC(O)CH$_2$ | H | Br | 6.19 | 385/387/389 |
| 26.120 | H | H | C(O)NHCH$_2$ | H | H | 3.74 | 215 |
| 26.121 | Me | H | C(O)NHCH$_2$ | H | H |  | 229 |
| 26.122 | OH | H | C(O)NHCH$_2$ | H | H | 3.72 | 231 |
| 26.123 | Br | H | C(O)NHCH$_2$ | H | H | 5.02 | 293/295 |
| 26.124 | Cl | H | C(O)NHCH$_2$ | H | H | 4.60 | 249/251 |
| 26.125 | H | H | C(O)NHCH$_2$ | Cl | H | 5.18 | 249/251 |
| 26.126 | H | Br | C(O)NHCH$_2$ | OH | H | 3.60 | 310/312 |

TABLE 26.2-continued $$A\diagdown_{G'}N\diagup^{X}\diagdown P(OH)_2$$
(structure: 6-membered ring with positions A, B, D, E and G' nitrogens; X-P(OH)₂ with =O on P)

| synthetic example number | A* | B* | C | D* | E* | HPLC Rt M-1 (min.) | found |
|---|---|---|---|---|---|---|---|
| 26.127 | H | H | C(O)NHCH₂ | null | H | 3.70 | 216 |
| 26.128 | H | H | C(O)NHCH₂ | NO₂ | H | 5.00 | 260 |
| 26.129 | H | H | C(O)NHCH₂ | H | Bu-n | 8.35 | 271 |
| 26.130 | H | OPr-n | C(O)NHCH₂ | H | H | 7.46 | 273 |
| 26.131 | Cl | Cl | C(O)NHCH₂ | H | H | 4.23 | 283/285/287 |
| 26.132 | Cl | CF₃ | C(O)NHCH₂ | H | H | 8.05 | 317/319 |
| 26.133 | H | Cl | C(O)NHCH₂ | H | CF₃ | 6.49 | 317/319 |
| 26.134 | H | Cl | C(O)NHCH₂ | Cl | Cl | 7.20 | 318/320/322 |
| 26.135 | H | C(O)Ph | C(O)NHCH₂ | H | H | 7.00 | 319 |
| 26.136 | H | OEt | C(O)NHCH₂ | H | CF₃ | 6.65 | 327 |
| 26.137 | SMe | Cl | C(O)NHCH₂ | H | null | 5.82 | 296/298 |
| 26.138 | SMe | Br | C(O)NHCH₂ | H | null | 5.40 | 340/342 |
| 26.139 | H | O(Ph-3-CF₃) | C(O)NHCH₃ | null | H |  | 376 |
| 26.140 | H | H | C(O)NHCH₂ | null | Me | 3.75 | 230 |
| 26.141 | H | Me | C(O)NHCH₂ | H | H | 4.96 | 229 |
| 26.142 | Cl | Cl | C(O)NHCH₂ | Cl | Cl | 9.18 | 351/353/355/357 |
| 26.143 | H | F | C(O)NHCH₂ | OH | null |  | 250 |
| 26.144 | Me | F | C(O)NHCH₂ | OH | null |  | 264 |
| 26.145 | OH | F | C(O)NHCH₂ | OH | null | 3.93 | 266 |

*When A, B, D or E is null, then the corresonpding G' is N.

Section 2

Synthesis of Compounds of Formula X

Example 27

Preparation of 2-amino-4-phosphonomethyloxy-6-bromobenzothiazole

Step A.

A solution of AlCl₃ (5 mmole) in EtSH (10 mL) was cooled to 0° C. and treated with 2-amino-4-methoxybenzothiazole (1 mmole). The mixture was stirred at 0–5° C. for 2 h. Evaporation and extraction gave 2-amino-4-hydroxybenzothiazole as white solid.

Step B.

A mixture of 2-amino-4-hydroxybenzothiazole (1 mmole) and NaH (1.3 mmole) in DMF (5 mL) was stirred at 0° C. for 10 min, and then treated with diethylphosphonomethyl trifluoromethylsulfonate (1.2 mmole). After being stirred at room temperature for 8 h, the reaction was subjected to extraction and chromatography to give 2-amino-4-diethylphosphonomethyloxybenzothiazole as an oil.

Step C.

A solution of 2-amino-4-(diethylphosphonomethyloxy) benzothiazole (1 mmole) in AcOH (6 mL) was cooled to 10° C. and treated with bromine (1.5 mmole) in AcOH (2 mL). After 5 min the mixture was stirred at room temperature for 2.5 h. The yellow precipitate was collected via filtration and washed with CH₂Cl₂ to give 2-amino-4-diethylphosphonomethyloxy-6-bromobenzothiazole.

Step D.

A solution of 2-amino-4-diethylphosphonomethyloxy-6-bromobenzothiazole (1 mmole) in CH₂Cl₂ (4 mL) was treated with TMSBr (10 mmole) at 0° C. After stirred for 8 h at room temperature the reaction was evaporated to dryness and the residue was taken into water (5 mL). The resulting precipitate was collected via filtration and washed with water to give 2-amino-4-phosphonomethyloxy-6-bromobenzothiazole (27.1) as white solid. mp>220° C. (dec.). Anal. calcd. for C₈H₈N₂O₄PSBr: C: 28.34; H: 2.38; N: 8.26. Found: C: 28.32; H: 2.24; N: 8.06.

Similarly, the following compounds were prepared according to the above described procedures:
(27.2) 2-Amino-4-phosphonomethyloxybenzothiozole. mp>250° C. Anal. calcd. for C₈H₉N₂O₄PS+0.4H₂O: C: 35.93; H: 3.69; N: 10.48. Found: C: 35.90; H: 3.37; N: 10.37.

Example 28

Preparation of 2-amino-4-phosphonomethyloxy-6-bromo-7-chlorobenzothiazole

Step A.

A solution of 1-(2-methoxy-5-chlorophenyl)-2-thiourea (1 mmole) in chloroform (10 mL) was cooled to 10° C. and treated with bromine (2.2 mmole) in chloroform (10 mL). The reaction was stirred at 10° C. for 20 min and at room temperature for 0.5 h. The resulting suspension was heated at reflux for 0.5 h. The precipitate was collected via filtration (washed with CH₂Cl₂) to give 2-amino-4-methoxy-7-chlorobenzothiazole which was subjected to Steps A, B, C and D of Example 27 to give 2-amino-4-phosphonomethoxy-6-bromo-7-chloro benzothiazole (28.1). mp>220° C.(dec.). Anal. calcd. for $C_8H_7N_2O_4PSClBr$: C: 25.72; H: 1.89; N: 7.50. Found: C: 25.66; H: 1.67; N: 7.23.

Similarly, the following compounds were prepared according to the above described procedures:

(28.2) 2-Amino-4-phosphonomethoxy-6-bromo-7-methyl benzothiazole. mp>220° C. (dec.). Anal. calcd. for $C_9H_{10}N_2O_4PSBr$: C: 30.61; H: 2.85; N: 7.93 Found: C: 30.25; H: 2.50; N: 7.77.

(28.3) 2-Amino-4-phosphonomethoxy-7-methylbenzothiazole. mp>220° C. (dec.). Anal: calcd. for $C_9H_{11}N_2O_4PS+1.0H_2O$: C: 36.99; H: 4.48; N: 9.59. Found: C: 36.73; H: 4.23; N: 9.38.

(28.4) 2-Amino-4-phosphonomethoxy-7-chlorobenzothiazole. mp>220° C.(dec.). Anal. calcd. for $C_8H_8N_2O_4PSCl+0.1H_2O$: C: 32.41; H: 2.79; N: 9.45. Found: C: 32.21; H: 2.74; N: 9.22.

Example 29

Preparation of 2-Amino-4-phosphonomethoxy-5,6,7,8-tetrahydronaphtho[1,2-d]thiazole Step A.

3-Amino-2-hydroxy-5,6,7,8-tetrahydronaphthalene was subjected to Step B of Example 27 to give 3-amino-2-diethylphosphonomethyloxy-5,6,7,8-tetrahydronaphthlene.

Step B.

A solution of KSCN (16 mmole) and $CuSO_4$ (7.7 mmole) in MeOH (10 mL) was treated with a solution of 3-amino-2-diethylphosphonomethyloxy-5,6,7,8-tetrahydronaphthalene (1 mmole) in MeOH (5 mL) at room temperature. The mixture was heated at reflux for 2 h. Filtration, extraction and chromatography provided 2-amino-4-diethylphosphonomethyloxy-5,6,7,8-tetrahydronaphtho[1,2-d]thiazole as light brown solid.

Step C.

2-Amino-4-diethylphosphonomethyloxy-5,6,7,8-tetrahydronaphtho[1,2-d]thiazole was subjected to Step D of Example 27 to give 2-Amino-4-phosphonomethoxy-5,6,7,8-tetrahydronaphtho[1,2-d]thiazole (29.1). mp>220° C. (dec.). Anal. calcd. for $C_{12}H_{15}N_2O_4PS+0.5H_2O$: C: 45.86; H: 4.81; N: 8.91 Found: C: 44.68; H: 4.77; N: 8.73.

The following compounds were also prepared according to above procedures:

(29.2) 2-Amino-4-phosphonomethoxy-[1,2-d]naphthothiazole. mp>240° C.(dec.). Anal. calcd. for $C_{12}H_{11}N_2O_4PS+0.2HBr$: C: 44.15; H: 3.46; N: 8.58. Found: C: 44.13; H: 3.46; N: 8.59.

(29.3) 2-Amino-5,7-dimethyl-6-thiocyanato-4-phosphonomethoxybenzothiazole. mp>240° C.(dec.). Anal. calcd. for $C_{11}H_{12}N_3O_4PS_2+0.2CH_2Cl_2$: C: 37.13; H: 3.45; N: 11.60. Found: C: 37.03; H: 3.25; N: 11.65.

(29.4) Starting with 2-hydroxy-5-phenyl aniline and using the same reaction sequence as above gave 2-Amino-7-phenyl-6-thiocyanato-4-phosphonomethoxybenzothiazole. mp.>250° C.(dec.). Anal. calcd. for $C_{15}H_{12}N_3O_4PS_2+0.2H_2O$: C: 45.38; H: 3.15; N: 10.58. Found: C: 45.25; H: 3.21; N: 10.53.

(29.5) Starting with 2-hydroxy-3,5-dichloro-4-methyl aniline and using the same reaction sequence as above (except the cyclization step was done using $B_2$, AcOH method i.e. Step A of Example 33) gave 2-Amino-5,7-dichloro-6-methyl-4-phosphonomethoxybenzothiazole. mp.>230° C.(dec.). Anal. calcd. for $C_9H_9N_2O_4PSCl_2$: C: 31.50; H: 2.64; N: 8.16. Found: C: 31.61; H: 2.66; N: 8.08.

(29.6) Starting with 2-hydroxy-4-methoxycarbonyl aniline and using the same reaction sequence as above gave 2-Amino-4-phosphonomethoxy-6-carboxybenzothiazole. mp.>230° C.(dec.). Anal. calcd. for $C_9H_9N_2O_6PS$: C: 35.53; H: 2.98; N: 9.21. Found: C: 35.56; H: 3.26; N: 9.03.

Example 30

Preparation of 2-Amino-7-methoxy-6-thiocyanato-4-phosphonomethoxy-benzothiazole

Step A.

2-Hydroxy-5-methoxynitrobenzene was subjected to Step B of Example 27 to give 2-diethylphosphonomethyloxy-5-methoxynitrobenzene.

Step B.

A solution of $SnCl_2$ (4 mmole) in freshly prepared methonolic HCl (10 mL) was added to a cold (0° C.) solution of 2-diethylphosphonomethyloxy-5-methoxynitrobenzene (1 mmole) in MeOH (5 mL). The mixture was warmed to room temperature and stirred for 3 h. Evaporation, extraction and chromatography provided 2-diethylphosphonomethyloxy-5-methoxyaniline.

Step C.

2-Diethylphosphonomethyloxy-5-methoxyaniline was subjected to Step B of Example 29 to give 2-amino-4-diethylphosphonomethyloxy-6-thiocyano-7-methoxybenzothiazole, which was subjected to Step D of Example 27 to give 2-amino-7-methoxy-6-thiocyanato-4-phosphonomethoxybenzothiazole (30.1). mp>170° C.(dec.). Anal. calcd. for $C_{10}H_{10}N_3O_5PS_2$: C: 34.58; H: 2.90; N: 12.10. Found: C: 34.23; H: 2.68; N: 11.77.

Similarly, the following compounds were prepared according to above procedures:

(30.2) 2-Amino-5,6-difluoro-4-phosphonomethoxybenzothiazole. mp>240° C.(dec.). Anal. calcd. for $C_8H_7N_2O_4PSF_2$: C: 32.44; H: 2.38; N: 9.46. Found: C: 32.30; H: 2.26; N: 9.17.

(30.3) 2-Amino-5-fluoro-7-bromo-4-phosphonomethoxybenzothiazole. mp>190° C.(dec.). Anal. calcd. for $C_8H_7N_2O_4PSBrF$: C: 26.91; H: 1.98; N: 7.84. Found: C: 27.25; H: 1.92; N: 7.54.

(30.4) 2-Amino-7-ethoxycarbonyl-4-phosphonomethoxybenzothiazole. mp>240° C.(dec.). Anal. calcd. for $C_{11}H_{13}N_2O_6PS+0.2HBr+0.1DMF$: C: 38.15; H: 3.94; N: 8.27. Found: C: 38.51; H: 3.57; N: 8.66.

Example 31

Preparation of 2-Amino-7-bromo-6-thiocyanato-4-phosphonomethoxy benzothiazole

Step A.

A solution of 2-fluoro-5-bromonitrobenzene (1 mmole) in DMF (5 mL) was cooled to 0° C., and treated with a solution of freshly prepared sodium salt of diethylhydroxymethylphosphonate (1.2 mmole) in DMF (5 mL). The mixture was stirred at room, temperature for 16 h. Evaporation, extraction and chromatography provided 2-diethylphosphonomethyloxy-5-bromonitrobenzene.

Step B.

2-Diethylphosphonomethyloxy-5-bromonitrobenzene was subjected to Step B of Example 30, Step B of Example 29, and Step D of Example 27 to give 2-amino-7-bromo-6-thiocyanato-4-phosphonomethoxybenzothiazole (31.1). mp>250° C.(dec.). Anal. calcd. for $C_9H_7N_3O_4PS_2Br$: C: 27.29; H: 1.78; N: 10.61. Found: C: 26.90; H: 1.58; N: 10.54.

Similarly, the following compounds were prepared according to above procedures:

(31.2) 2-Amino-7-fluoro-6-thiocyanato-4-phosphonomethoxybenzothiazole. mp>136° C.(dec.). Anal. calcd. for $C_9H_7N_3O_4PFS_2$+0.3HBr: C: 30.07; H: 2.05; N: 11.69. Found: C: 30.27; H: 2.01; N: 11:38.

(31.3) Starting with 2-fluoro-4-chloro nitrobenzene and using the same reaction sequence as above gave 2-Amino-6-chloro-4-phosphonomethoxybenzothiazole. mp.>250° C.(dec.). Anal. calcd. for $C_8H_8N_2O_4PSCl$: C: 32.61; H: 2.74; N: 9.51. Found: C: 32.27; H: 2.67; N: 9.18.

(31.4) Starting with 2-fluoro-4,5-dichloro nitrobenzene and using the same reaction sequence as above gave 2-Amino-6,7-dichloro-4-phosphonomethoxybenzothiazole. mp.>250° C.(dec.). Anal. calcd. for $C_8H_7N_2O_4PSCl_2$: C: 29.20; H: 2.14; N: 8.51. Found: C: 29.11; H: 2.11; N: 8.36.

Example 32

Preparation of 2-Amino-7-hydroxymethyl-6-thiocyano-4-phosphonomethoxy benzothiazole Step A.

2-Chloro-5-formylnitrobenzene was subjected to Step A of Example 31 to give 2-diethylphosphonomethyloxy-5-formylnitrobenzene.

Step B.

A solution of 2-diethylphosphonomethyloxy-5-formylnitrobenzene (1 mmole) in methanol (5 mL) was treated with 10% palladium on carbon (0.05 mmole) under 1 atmosphere of hydrogen at room temperature for 12 h. Filtration followed by evaporation gave 2-diethylphosphonomethyloxy-5-hydroxymethylaniline which was subjected to Step B of Example 29 followed by Step D of Example 27 to give 2-amino-7-hydroxymethyl-6-thiocyanato-4-phosphonomethoxybenzothiazole (32.1). mp 181–184° C. Anal. calcd. for $C_{10}H_{10}N_3O_5PS_2$+ $0.35H_2O$: C: 33.97; 11:3.05; N: 11.88. Found: C: 33.76; 11:2.66; N: 11.61.

A similar procedure was used to prepare the following compounds:

(32.2) Starting with 2-fluoro-4-methyl nitrobenzene and using the same reaction sequence as above gave 2-Amino-6-methyl-4-phosphonomethoxybenzothiazole. mp.>250° C.(dec.). Anal. calcd. for $C_9H_{11}N_2O_4PS$+$0.2CH_2Cl_2$: C: 37.94; H: 3.95; N: 9.62. Found: C: 38.16; H: 4.18; N: 9.39.

(32.3) Starting with 2-chloro-5-cyano nitrobenzene and using the same reaction sequence as above gave 2-Amino-7-cyano-4-phosphonomethoxybenzothiazole. mp.>250° C.(dec.). Anal. calcd. for $C_9H_8N_3O_4PS$+$0.9H_2O$: C: 35.86; H: 3.28; N: 13.94. Found: C: 35.07; H: 2.88; N: 13.58.

Example 33

Preparation of 2-Amino-6-bromo-7-fluoro-4-phosphonomethoxybenzothiazole

Step A.

A solution of 2-diethylphosphonomethyloxy-4-bromo-5-fluoroaniline (1 mmole, prepared as in Example 4, Step B) and KSCN (2 mmole) in AcOH (8 mL) was cooled to 10° C., and treated with a solution of bromine (2 mmole) in AcOH (5 mL). After being stirred at room temperature for 0.5 h, the reaction mixture was evaporated to dryness and the residue was purified by chromatography to provide 2-amino-7-fluoro1-6-bromo-4-diethylphosphonomethyloxybenzothiazole which was subjected to Step D of Example 27 to give 2-amino-6-bromo-7-fluoro-4-phosphonomethoxybenzothiazole (33.1). Anal. calcd. for $C_8H_7N_2O_4PSBrF$+0.1HBr: 0:26.31; 11:1.96; N: 7.67. Found: 0:25.96; 11:1.94; N: 7.37.

Example 34

Preparation of 2-Amino-7-ethyl-6-thiocyano-4-phosphonomethoxybenzothiazole

Step A.

A solution of 2-diethylphosphonomethyloxy-5-bromonitrobenzene (1 mmole, prepared as in Example 31, Step A from 2-fluoro-5-bromonitrobenzene) in DMF (5 mL) was treated with tributyl(vinyl)tin (1.2 mmole) and palladium bis(triphenylphosphine) dichloride (0.1 mmole), and the mixture was heated at 60° C. under nitrogen for 6 h. Evaporation and chromatography gave 2-diethylphosphonomethyloxy-5-vinylnitrobenzene as an oil which was subjected to Step B of Example 31, Step B of Example 29, and Step D of Example 27 to give 2-amino-7-ethyl-6-thiocyano-4-phosphonomethoxybenzothiazole (34.1). mp>167° C.(dec.). Anal. calcd. for $C_{11}H_{12}N_3O_4PS_2$: C: 38.26; H: 3.50; N: 12.17. Found: C: 37.87; H: 3.47; N: 11.93.

A similar procedure was used to prepare the following compounds:

(34.2) 2-Amino-7-propyl-6-thiocyanato-4-phosphonomethoxybenzothiazole. mp.>250° C.(dec.). Anal. calcd. for $C_{12}H_{14}N_3O_4PS_2$: C: 40.11; H: 3.93; N: 11.69. Found: C: 39.72; H: 3.82; N: 11.50. Using allyl tributyltin.

(34.3) 2-Amino-7-(2-furyl)-6-thiocyanato-4-phosphonomethoxybenzothiazole. Anal. calcd. for $C_{14}H_{11}N_3O_5BrPS_2$+0.6MeOH: C: 33.79; H: 2.79; N: 8.69. Found: C: 34.10; H: 2.83; N: 8.35. Using 2-furanyl tributyltin.

(34.4) 2-Amino-6-thiocyanato-7-(2-thienyl)-4-phosphonomethoxybenzothiazole. mp.>250° C.(dec.). Anal. calcd. for $C_{13}H_{10}N_3O_4PS_3$: C: 39.09; H: 2.52; N: 10.52. Found: C: 38.91; H: 2.41; N: 10.34. Using 2-thienyl tributyltin.

(34.5) 2,5-Difluoro-4-bromo nitrobenzene was treated the same way to give 2-Amino-6-ethyl-7-fluoro-4-phosphonomethoxybenzothiazole. mp.>250° C.(dec.). Anal. calcd. for $C_{10}H_{12}N_2O_4PSF$: C: 39.22; H: 3.95; N: 9.15. Found: C: 38.83; H: 3.55; N: 9.02.

(34.6) 2,5-Difluoro-4-bromo nitrobenzene was treated with 2-thienyl tributyltin in the second step to give 2-Amino-7-fluoro-6-[2-(5-thiocyanato)thienyl]-4-phosphonomethoxybenzothiazole. mp.>250° C.(dec.). Anal. calcd. for $C_{13}H_9N_3O_4PS_3F$+$0.6H_2O$: C: 36.46; H: 2.40; N: 9.81. Found: C: 36.16; H: 2.10; N: 9.68.

Example 35

Preparation of 2-Amino-7-cyclopropyl-6-thiocyanato-4-phosphonomethoxy benzothiazole Step A.

A suspension of 2-diethylphosphonomethyloxy-5-vinylnitrobenzene (1 mmole, prepared as in Step A of Example 33) and $Pd(OAc)_2$ (0.1 mmole) in ether (8 mL) was treated with a solution of diazomethane (generated from 3.0 g of 1-methyl-3-nitro-1-nitrosoguanidine) in ether at 0° C. After being stirred at room temperature for 20 h the reaction was evaporated to dryness and the residue was chromatographed to give 2-diethylphosphonomethyloxy-5-cyclopropylnitrobenzene which was subjected to Step B of Example 30, Step B of Example 29, and Step D of Example 27 to give 2-amino-7-cyclopropyl-6-thiocyanato-4- phosphonomethoxybenzothiazole hydrogen bromide (35.1). Anal. calcd. for $C_{12}H_{13}N_3O_4PS_2Br+0.1HBr$: C: 27.76; H: 2.72; N: 8.09. Found: C: 27.54; H: 3.05; N: 7.83.

Example 36

Preparation of 2-Amino-4-phosphonomethoxy-6-chloro-7-methyl benzothiazole

Step A.

2-Methoxy-4-chloro-5-methylaniline was subjected to Steps A and B of Example 27, Step B of Example 29, and Step D of Example 27 to give 2-amino-4-phosphonomethoxy-6-chloro-7-methyl benzothiazole (36.1). mp>250° C.(dec.). Anal. calcd. for $C_9H_{10}N_2O_4PS_2Cl+0.3H_2O+0.4HBr$: C: 31.20; H: 3.20; N: 8.09. Found: C: 31.37; H: 2.87; N: 7.89.

Similarly, the following compounds were prepared according to above procedures:

(36.2) 2-Amino-7-phenyl-6-thiocyanato-4-phosphonomethoxybenzothiazole. mp>250° C. (dec.). Anal. calcd. for $C_{15}H_{12}N_3O_4PS_2+0.2H_2O$: C: 45.38; H: 3.15; N: 10.58. Found: C: 45.25; H: 3.21; N: 10.53.

Example 37

Preparation of 2-bromo-4-diethylphosphonomethoxy-5,6,7,8-tetrahydronaphtho[1,2-d]thiazole Step A.

A solution of 2-amino-4-diethylphosphonomethoxy-5,6,7,8-tetrahydronaphtho[1,2-d]thiazole (1 mmole) in $CH_3CN$ (4 mL) was cooled to 0° C., and treated with $CuBr_2$ (1.2 mmole) followed by isoamylnitrite (1.5 mmole) in a dropwise fashion. The resulting dark mixture was stirred for 3.5 h. Evaporation and chromatography gave 2-bromo-4-diethylphosphonomethoxy-5,6,7,8-tetrahydronaphtho[1,2-d]thiazole as an oil.

Step B.

2-Bromo-4-diethylphosphonomethoxy-5,6,7,8-tetrahydronaphtho[1,2-d]thiazole was subjected to Step D of Example 27 to give 2-bromo-4-phosphonomethoxy-5,6,7,8-tetrahydronaphtho[1,2-d]thiazole (37.1) as a solid. Mp 220–230° C. Anal. calcd. for $C_{12}H_{13}NO_4PSBr$: C: 38.11; H: 3.46; N: 3.70. Found: C: 37.75; H: 3.26; N: 3.69.

(37.2) The same procedure was used to react 2-amino-4-diethylphosphonomethoxy-6-chloro-7-methyl benzothiazole with $CuCl_2$ to give 2-Chloro-4-phosphonomethoxy-6-chloro-7-methyl benzothiazole. mp.>250° C.(dec.). Anal. calcd. for $C_9H_8NO_4PSCl_2+0.7HBr$: C: 28.10; H: 2.28; N: 3.64. Found: C: 28.23; H: 2.20; N: 3.79.

Example 38

Preparation of 4-diethylphosphonomethoxy-5,6,7,8-tetrahydronaphtho[1.2-d]thiazole Step A.

A solution of isoamylnitrite (1.5 mmole) in DMF (1 mL) at 65° C. was treated with 2-amino-4-diethylphosphonomethoxy-5,6,7,8-tetrahydronaphtho[1,2-d]thiazole (1 mmole) in DMF (3 mL). After 30 min, the cooled reaction solution was subjected to evaporation and chromatography to provide 4-diethylphosphonomethoxy-5,6,7,8-tetrahydronaphtho[1,2-d]thiazole as an oil, which was subjected to Step D of Example 27 to give 4-phosphonomethoxy-5,6,7,8-tetrahydronaphtho[1,2-d]thiazole (38.1) as a solid. Mp 215–220° C. Anal. calcd. for $C_{12}H_{14}NO_4PS+1.3HBr$: C: 35.63; H: 3.81; N: 3.46. Found: C: 35.53; H: 3.46; N: 3.40.

(38.2) The same reaction sequence was used to transform 2-amino-4-diethylphosphonomethoxy-6-chloro-7-methyl benzothiazole to 4-Phosphonomethoxy-6-chloro-7-methyl benzothiazole. mp. 195–198° C. Anal. calcd. for $C_9H_9NO_4PSCl+0.5H_2O$: C: 35.71; H: 3.33; N: 4.63. Found: C: 35.49; H: 3.19; N: 4.65.

Example 39

Preparation of 2-Amino-4-phosphonomethythio benzothiazole

Step A.

2-Diethylphosphonomethylthioaniline, prepared according to Step B of Example 27, was subjected to Step B of Example 29 to give 2-amino-4-diethylphosphonomethythiobenzothiazole.

Step B.

2-Amino-4-diethylphosphonomethythiobenzothiazole was subjected to Step D of Example 34 to give 2-amino-4-phosphonomethythiobenzothiazole (39.1) as a foam. Anal. calcd. for $C_8H_{10}N_2O_3PS_2+0.4H_2O$: C: 35.63; H: 3.81; N: 3.46. Found: C: 35.53; H: 3.36; N: 3.40.

Example 40

Preparation of 2-Amino-7-hexyl-6-thiocyano-4-phosphonomethoxy benzothiazole Step A.

A solution of 1 mmole of 2-diethylphosphonomethoxy-5-bromonitrobenzene (prepared as in Example 30, step A) in diethyl amine (5 mL) was treated with 1-hexyne (1.2 mmole), CuI (0.1 mmole) and palladium bis (triphenylphosphine) dichloride (0.1 mmole), and the mixture was heated at 60° C. under nitrogen for 14 h. Evaporation and chromatography gave 2-diethylphosphonomethoxy-5-(1-hexyn) benzene as an oil, which was subjected to Step B of Example 32, Step B of Example 29, and Step D of Example 27 to give 2-amino-7-hexyl-6-thiocyano-4-phosphonomethoxybenzothiazole.

(40.1) 2-Amino-6-thiocyanato-7-(n-hexyl)-4-phosphonomethoxybenzothiazole. mp.>250° C.(dec.). Anal. calcd. for $C_{15}H_{20}N_3O_4PS_2$: C: 44.88; H: 5.02; N: 10.47. Found: C: 44.54; H: 4.75; N: 10.37.

Similarly, the following compounds were prepared:

(40.2) A solution of 1 mmole of 2-diethylphosphonomethoxy-5-bromonitrobenzene (prepared as in Example 30, step A) was subjected to Step C of Example 27, followed a similar sequence as compound 40.1 to give 2-Amino-6-methyl-7-(n-hexyl)-4-phosphonomethoxybenzothiazole. mp.>250° C.(dec.). Anal. calcd. for $C_{15}H_{23}N_2O_4PS+0.25HBr$: C: 47.58; H: 6.19; N: 7.40. Found: C: 47.40; H: 6.07; N: 7.54.

Example 41

Preparation of 2-Amino-6-methoxy-7-methyl-4-phosphonomethoxybenzothiazole

Step A.

A solution of 2-chloro-4-floro-5-methylnitrobenzene (1 mmole) in DMF (5 mL) was treated with fresh sodium methoxy (1.1 mmole), and the mixture was stirred for 6 h. Evaporation and chromatography gave 2-chloro-4-methoxy-5-methylnitrobenzene.

Step B.

2-chloro-4-methoxy-5-methylnitrobenzene was subjected to Step A of Example 31, Step B of Example 32, Step A of Example 33, and Step D of Example 27 to give 2-Amino-6-methoxy-7-methyl-4-phosphonomethoxybenzothiazole 41.1. mp.>250° C.(dec.). Anal. calcd. for $C_{10}H_{13}N_2O_4PS$: C: 39.48; H: 4.31; N: 9.21. Found: C: 39.39; H: 4.17; N: 8.98.

Similarly, the following compounds were prepared:
(41.2) 2-Amino-7-methyl-6-methylthio-4-phosphonomethoxybenzothiazole. mp.>250° C.(dec.). Anal. calcd. for $C_{10}H_{13}N_2O_4PS_2$+0.45HBr: C: 33.67; H: 3.80; N: 7.85. Found: C: 33.62; H: 3.86; N: 7.76.
(41.3) 2-Amino-6-ethoxy-7-methyl-4-phosphonomethoxybenzothiazole. mp.>250° C.(dec.). Anal. calcd. for $C_{11}H_{15}N_2O_5PS$: C: 41.51; H: 4.75; N: 8.80. Found: C: 41.80; H: 4.59; N: 8.95.
(41.4) 2-Amino-6-isobutoxy-7-methyl-4-phosphonomethoxybenzothiazole. mp.>250° C.(dec.). Anal. calcd. for $C_{13}H_{19}N_2O_5PS$+0.15HBr: C: 43.56; H: 5.38; N: 7.81. Found: C: 43.59; H: 5.38; N: 7.86.

Example 42

Preparation of 2-Amino-6-ethyl-4-phosphonomethoxybenzothiazole

Step A.

To a solution of 1 mmol of 3-bromo chlorobenzene in 2 mL of con. $H_2SO_4$ was added 1.5 mmol of 79% $HNO_3$ at −10° C. After it was stirred for 30 min. the mixture was poured onto ice/water mixture. The yellow precipitate was filtered and dried to give a mixture of 2-chloro-4-bromo nitrobenzene (desired) and 4-chloro-2-bromo nitrobenzene.

Step B.

2-Chloro-4-bromo nitrobenzene was subjected to Step A of Example 34, Step B of Example 32, Step B of Example 29, and Step D of Example 27 to give 2-Amino-6-ethyl-4-phosphonomethoxybenzothiazole (42.1) mp.>220° C.(dec.). Anal. calcd. for $C_{10}H_{13}N_2O_4PS$+0.3HBr: C: 38.43; H: 4.29; N: 8.96. Found: C: 38.35; H: 4.44; N: 8.75.

Similarly, the following compound was prepared:
(42.2) 2-Amino-6-propyl-4-phosphonomethoxybenzothiazole. mp.>220° C.(dec.). Anal. calcd. for $C_{11}H_{15}N_2O_4PS$+0.2HBr: C: 41.49; H: 4.81; N: 8.80. Found: C: 41.85; H: 4.12; N: 8.31.

Example 43

Preparation of 2-Amino-6-thio-7-ethyl-4-phosphonomethoxybenzothiazole

Step A.

A solution of 1 mmol of 2-Amino-6-thio-7-ethyl-4-diethylphosphonomethoxybenzothiazole (for preparation see Example 34) in 3 mL of 48% HBr in AcOH was heated at 90° C. for 16 h. Solvent was removed and the residue was washed with water to give 2-Amino-6-thio-7-ethyl-4-phosphonomethoxybenzothiazole (43.1). mp.>220° C.(dec.). Anal. calcd. for $C_{10}H_{13}N_2O_4PS_2$+0.2HBr: C: 35.69; H: 3.95; N: 8.33. Found: C: 35.49; H: 3.74; N: 8.33.

Example 44

Preparation of 2-Amino-7-propyloxy-6-thiocyano-4-phosphonomethoxybenzothiazole

Step A.

To a solution of 1 mmol of 2-chloro-5-hydroxy nitrobenzene in 5 mL of DMF was added 1.2 mmol of NaH at 0° C. After 30 min, allyl bromide was added and the mixture was stirred at rt for 16 h. Solvent was removed and the residue was washed with water and extracted with EtOAc to give 2-chloro-5-propenyloxy nitrobenzene.

Step B.

2-Chloro-5-propenyloxy nitrobenzene was subjected to Step A of Example 31, Step B of Example 32, Step A of Example 33, and Step D of Example 27 to give 2-Amino-7-propyloxy-6-thiocyano-4-phosphonomethoxy benzothiazole. (44.1). mp.>220° C.(dec.). Anal. calcd. for $C_{12}H_{14}N_3O_5PS_2$+0.15HBr+0.08$H_2O$: C: 37.06; H: 3.71; N: 10.8. Found: C: 37.46; H: 3.48; N: 10.38.

Example 45

Preparation of 2-Amino-6-methoxy-4-phosphonomethoxybenzothiazole

Step A.

2-Hydroxy-4-methoxy nitrobenzene was subjected to Step B of Example 32, Step B of Example 27, Step B of Example 29, Step D of Example 27 to give 2-Amino-6-methoxy-4-phosphonomethoxybenzothiazole (45.1) mp.>230° C.(dec.). Anal. calcd. for $C_9H_{11}N_2O_5PS$+0.5$H_2O$: C: 36.12; H: 4.04; N: 9.36. Found: C: 36.18; H: 3.81; N: 9.47.

Example 46

2-Amino-7-ethyl-6-methyl-4-phosphonomethoxybenzothiazole

Step A.

2-Fluoro-4-methyl nitrobenzene was subjected to Step A of Example 31, Step C of Example 27, Step A of Example 34, Step B of Example 32, Step B of Example 29, Step D of Example 27 to give (46.1) 2-Amino-7-ethyl-6-methyl-4-phosphonomethoxybenzothiazole. mp.>250° C.(dec.). Anal. calcd. for $C_{11}H_{15}N_2O_4PS$+0.1HBr: C: 42.57; H: 4.90; N: 9.03. Found: C: 42.32; H: 4.71; N: 8.87.

Example 47

2-Amino-7-bromo-6-methyl-4-phosphonomethoxybenzothiazole

Step A.

2-Fluoro-4-methyl nitrobenzene was subjected to Step A of Example 31, Step C of Example 27, Step B of Example 30, Step A of Example 33, Step D of Example 27 to give 2-Amino-7-bromo-6-methyl-4-phosphonomethoxybenzothiazole. (47.1) mp.>250° C.(dec.). Anal. calcd. for $C_9H_{10}N_2O_4PSBr$+0.3HBr: C: 28.64; H: 2.75; N: 7.42. Found: C: 28.62; H: 2.60; N: 7.42.

Example 48

2-Amino-7-fluoro-6-methyl-4-phosphonomethoxybenzothiazole

Step A.

2-Hydroxy-4-methyl-5-fluoro nitrobenzene was subjected to Step B of Example 27, Step B of Example 32, Step A of Example 33, Step D of Example 27 to give
(48.1) 2-Amino-7-fluoro-6-methyl-4-phosphonomethoxybenzothiazole. mp.>250° C.(dec.). Anal. calcd. for $C_9H_{10}N_2O_4PSF$+0.1HBr: C: 35.99; H: 3.39; N: 9.33. Found: C: 35.84; H: 3.32; N: 9.31.
(48.2) Starting with 2-hydroxy-5-chloro-4-methyl aniline and using the same reaction sequence as above (except the reduction of $NO_2$ step was done using $SnCl_2$ method i.e. Step B of Example 30) gave 2-Amino-7-chloro-6-methyl-4-phosphonomethoxybenzothiazole. (48.2) mp.>250° C.(dec.). Anal. calcd. for $C_9H_{10}N_2O_4PSCl$+0.6$H_2O$: C: 34.62; H: 3.36; N: 8.97. Found: C: 34.48; H: 3.40; N: 8.72.

Example 49

2-Amino-6-bromo-7-methoxy-4-phosphonomethoxybenzothiazole

Step A.

2-Amino-4,7-dimethoxy benzothiazole [prepared from 1-(2,5-dimethoxyphenyl)-2-thiourea using the procedure Step A of Example 28] was subjected to Step C to give 2-Amino-4,7-dimethoxy-6-bromo benzothiazole.

Step B.

To a solution of 1 mmol of 2-Amino-4,7-dimethoxy-6-bromo benzothiazole in $CH_2Cl_2$ was added 2.2 mmol of $BBr_3$ in $CH_2Cl_2$ at 0° C. for 16 h. Aqueous work-up and chromatography gave 2-amino-4-hydroxy-6-bromo-7-methoxy benzothiazole.

Step C.

2-amino-4-hydroxy-6-bromo-7-methoxy benzothiazole was subjected to Step B of Example 27, Step D of Example 27 to give (49.1) 2-Amino-6-bromo-7-methoxy-4-phosphonomethoxybenzothiazole. mp.>250° C.(dec.). Anal. calcd. for $C_9H_{10}N_2O_5PSBr$: C: 29.28; H: 2.73; N: 7.59. Found: C: 28.90; H: 3.05; N: 7.20.

Example 50

General Procedure for Bis-phosphoroamide Prodrugs: Dichloridate Formation

To a suspension of 1 mmol of phosphonic acid in 5 mL of dichloroethane was added 0.1 mmol of pyridine (or 0.1 mmol of DMF) followed by 6 mmol of thionyl chloride and was heated to reflux for 2.5 h. Solvent and excess thionyl chloride were removed under reduced pressure and dried to give the dichloridate.

Coupling Reaction:

Method A: The crude dichloridate was taken into 5 mL of dry $CH_2Cl_2$, and was added 8 mmol of amino acid ester at 0° C. The resultant mixture was allowed to come to rt where it was stirred for 16 h. The reaction mixture was subjected to aq. work up and chromatography.

Method B: The crude dichloridate was taken into 5 mL of dry $CH_2Cl_2$, and was added a mixture of 4 mmol of amino acid ester and 4 mmol of N-methylimidazole at 0° C. The resultant mixture was allowed to come to rt where it was stirred for 16 h. The reaction mixture was subjected to aq. work up and chromatography.

The following compounds were prepared in this manner.

(50.1) 2-Amino-5-isobutyl-4-[2-(5-N,N-bis(L-glutamic acid diethylester)phosphonoamido)furanyl]thiazole. Anal. calcd. for $C_{29}H_{45}N_4O_{10}PS$: C: 51:78; H: 6.74; N: 8.33. Found: C: 51.70; H: 6.64; N: 8.15.

(50.2) 2-Amino-5-isobutyl-4-[2-(5-N,N-bis(L-alanine acid dibenzyl ester)phosphonoamido)furanyl]thiazole. Anal. calcd. for $C_{31}H_{37}N_4O_6PS$: C: 59.60; H: 5.97; N: 8.97. Found: C: 59.27; H: 5.63; N: 8.74.

(50.3) 2-Amino-5-isobutyl-4-{2-[5-(N,N-bis(benzyloxycarbonylmethyl)phosphonodiamido]furanyl}thiazole. Anal. calcd. for $C_{19}H_{25}N_4O_6PS$+ $0.3CH_2Cl_2$: C: 46.93; H: 5.22; N: 11.34. Found: C: 46.92; H: 5.00; N: 11.22.

(50.4) 2-Amino-5-isobutyl-4-{2-[5-(N,N-bis(benzyloxycarbonylmethyl)phosphonodiamido]furanyl}thiazole. Anal. calcd. for $C_{29}H_{33}N_4O_6PS$: C: 58.38; H: 5.57; N: 9.39. Found: C: 58.20; H: 5.26; N: 9.25.

(50.5) 2-Amino-5-isobutyl-4-{2-[5-(N,N'-bis((R)-1-methoxycarbonyl)ethyl)phosphonamido]furanyl}thiazole. Anal. calcd. for $C_{19}H_{29}N_4O_6PS$+ $0.6CH_2Cl_2$: C: 44.97; H: 5.82; N: 10.70. Found: C: 44.79; H: 5.46; N: 10.48.

(50.6) 2-Amino-5-isobutyl-4-{2-[5-(N,N'-bis((S)-1-ethoxycarbonyl)ethyl)phosphonamido]furanyl}thiazole. mp. 164–165° C.: Anal. calcd. for $C_{21}H_{33}N_4O_6PS$+ $0.61CH_2Cl_2$: C: 46.99; H: 6.24; N: 10.14. Found: C: 47.35; H: 5.85; N: 9.85.

(50.7) 2-Amino-5-isobutyl-4-{2-[5-(N,N'-bis((t-butoxycarbonyl)methyl)phosphonamido]furanyl}thiazole. Anal. calcd. for $C_{23}H_{37}N_4O_6PS$+ $0.15CH_2Cl_2$: C: 51.36; H: 6.94; N: 10.35. Found: C: 51.34; H: 6.96; N: 10.06.

(50.8) 2-Amino-5-isobutyl-4-{2-[5-(N,N'-bis(ethoxycarbonyl)methyl)phosphonamido)]furanyl}thiazole. Anal. calcd. for $C_{19}H_{29}N_4O_6PS$+ $0.1EtOAc+0.47CH_2Cl_2$: C: 45.79; H: 5.94; N: 10.75. Found: C: 46.00; H: 5.96; N: 10.46.

(50.9) 2-Amino-5-isobutyl-4-{2-[5-(O-(2-bis(N-(1-methyl-1-ethoxycarbonyl)ethyl)phosphonamido]furanyl}thiazole. mp. 142–145° C.: Anal. calcd. for $C_{23}H_{37}N_4O_6PS$: C: 52.26; 7.06; 10.60. Found: C: 52.21; 6.93; 10.62.

(50.10) 2-Amino-5-isobutyl-4-{2-[5-(N,N'-bis(ethoxycarbonylmethyl)-N,N'-dimethylphosphonamido)]furanyl}thiazole. Anal. calcd. for $C_{21}H_{33}N_4O_6PS$: C: 50.39; H: 6.65; N: 11.19. Found: C: 50.57; H: 6.56; N: 11.06.

(50.11) 2-Amino-5-isobutyl-4-{2-[5-(N,N'-bis((S)-1-benzyloxycarbonyl-2-methyl)propyl)phosphonamido]furanyl}thiazole. Anal. calcd. for $C_{35}H_{45}N_4O_6PS$+ $0.5H_2O$: C: 60.94; H: 6.72; N: 8.12. Found: C: 61.01:H: 6.48; N: 7.82.

(50.12) 2-Amino-5-isobutyl-4-{2-[5-(N,N'-bis((S)-1-methoxycarbonyl-3-methyl)butyl)phosphonamido]furanyl}thiazole. Anal. calcd. for $C_{25}H_{41}N_4O_6PS$: C: 53.94; H: 7.42; N: 10.06. Found: C: 54.12; H: 7.62; N: 9.82.

(50.13) 2-Amino-5-isobutyl-4-{2-[5-(N,N'-bis((R)-1-ethoxycarbonyl-2-(S-benzyl))ethyl)phosphonamido]furanyl)thiazole. Anal. calcd. for $C_{35}H_{45}N_4O_6PS_3$+0.4 toluene: C: 58.07; H: 6.21; N: 7.17. Found: C: 57.87; H: 6.14; N: 6.81.

(50.14) 2-Amino-5-isobutyl-4-{2-[5-(N,N'-bis((S)-1-ethoxycarbonyl-3-(S-methyl))butyl)phosphonamido]furanyl}thiazole. Anal. calcd. for $C_{23}H_{37}N_4O_6PS_3$: C: 46.61; H: 6.92; N: 9.45. Found: C: 46.26; H: 6.55; N: 9.06.

(50.15) 2-Amino-5-propylthio-4-{2-[5-(N,N'-(1-(S)ethoxycarbonyl)ethyl)phosphonamido]furanyl}thiazole. Anal. calcd. for $C_{20}H_{31}N_4O_6PS_2$: C: 46.32; H: 6.03; N: 10.80. Found: C: 46.52; H: 6.18; H: 10.44.

(50.16) 2-Amino-5-isobutyl-4-{2-[5-(N,N'-bis((S)-1-benzyloxycarbonyl-2-methyl)isobutyl)phosphonamido]furanyl}thiazole. Anal. calcd. for $C_{37}H_{49}N_4O_6PS$: C: 62.69; H: 6.97; H: 7.90. Found: C: 62.85; h 7.06, 7.81.

(50.17) 2-Amino-5-isobutyl-4-{2-[5-(N,N'-bis((S)-1-ethoxycarbonyl-3-methyl)butyl)phosphonamido]furanyl}thiazole. Anal. calcd. for $C_{27}H_{45}N_4O_6PS$: C: 55.46; H: 7.76; N: 9.58. Found: C: 55.35; H: 7.94; N: 9.41.

(50.18) 2-Amino-5-isobutyl-4-{2-[5-(N,N'-bis((S)-1-ethoxycarbonyl-2-methyl)propyl)phosphonamido]furanyl}thiazole. Anal. calcd. for $C_{25}H_{41}N_4O_6PS$: C: 53.94; H: 7.42; N: 10.06. Found: C: 54.01; H: 7.58; N: 9.94.

(50.19) 2-Amino-5-isobutyl-4-{2-[5-(N,N'-bis((S)-1-ethoxycarbonyl-2-phenyl)ethyl)phosphonamido]

furanyl}thiazole. Anal. calcd. for $C_{33}H_{41}N_4O_6PS+0.15CH_2Cl_2$: C: 59.83; H: 6.26; H: 8.42. Found: C: 59.88; H: 6.28; H: 8.32.

(50.20) 2-Amino-5-propylthio-4-{2-[5-(N,N'-(1-methyl-ethoxycarbonyl)ethyl)phosphonamido]furanyl}thiazole. mp. 110–115° C.: Anal. calcd. for $C_{22}H_{35}N_4O_6PS_2+0.4HCl+0.5Et_2O$: C: 48.18; H: 6.81; N: 9.36. Found: C: 48.38; H: 6.60; H: 8.98.

(50.21) 2-Amino-5-methylthio-4-{2-[5-(N,N'-bis(1-methyl-1-ethoxycarbonyl)ethyl)phosphonamido]furanyl}thiazole. Anal. calcd. for $C_{20}H_{31}N_4O_6PS_2+0.5H_2O$: C: 45.53; H: 6.11; N: 10.62. Found: C: 45.28; H: 5.85; N: 10.56.

Example 51

General Procedure For Mixed Bis-phosphoroamidate Prodrugs

To a solution of crude dichloridate (1 mmol, prepared as described in Example 50) in 5 mL of dry $CH_2Cl_2$ was added amine (1 mmol) followed by 4-dimethylaminopyridine (3 mmol) at 0° C. The resulting mixture was allowed to warm to room temperature and stirred for 1 h. The reaction was cooled back to 0° C. before adding amino acid ester (2 mmol) and left at room temperature for 16 h. The reaction mixture was subjected to aq. work up and the mixed bis-phosphoroamidate prodrug was purified by column chromatography.

The following compounds were prepared in this manner.

(51.1) 2-Amino-5-isobutyl-4-{2-[5-(N-morpholino-N'-(1-methyl-1-ethoxycarbonyl)ethyl)phosphonamido]furanyl}thiazole. mp. 182–183° C.: Anal. calcd. for $C_{21}H_{33}N_4O_5PS$: C: 52.05; H: 6.86; N: 11.56. Found: C: 51.66; H: 6.68; N: 11.31.

(51.2) 2-Amino-5-isobutyl-4-{2-[5-(N-pyrrolidino-N'-(1-methyl-1-ethoxycarbonyl)ethyl)phosphonamido]furanyl}thiazole. mp. 189–190° C.: Anal. calcd. for $C_{21}H_{33}N_4O_4PS$: C: 53.83; H: 7.10; N: 11.96. Found: C: 54.15; H: 7.48; N: 12.04.

Example 52

Bis-phosphoroamide Prodrug Synthesis Using Mukaiyama's Method with Some Modifications

*J. Am. Chem. Soc.* 1972, 94, 8528.

To a suspension of 1.0 mmol. phosphonic acid and 2.0 mmol of amino acid ester salt (for example alanine ethyl ester HCl salt) in 9 mL of pyridine, $Et_3N$ and 1,3-dimethyl-3,4,5,6-tetrahydro-2(1H)-pyrimidione (DMPU) (1:1:1) was added a premixed solution of 4 mmol of aldrithiol and 4 mmol of $PPh_3$ in 3 mL of pyridine. After 16 h at 90° C., the solvents pyridine and $Et_3N$ were removed under reduced pressure. The remaining solution upon dilution with hexane (100 mL) the crude product was oiled out and was subjected to chromatography purification.

The following compounds were prepared using this method.

(52.1) 2-Amino-4-[(N,N'-(1-(S)-ethoxycarbonyl)ethyl)phosphonodiamidomethoxy]-5,6,7,8-tetrahydronaphtho[1,2-d]thiazole. Mp. 153–156° C.: Anal. calcd. for $C_{22}H_{33}N_4O_6PS$: C: 51.55; H: 6.49; N: 10.93. Found: C: 51.39; H: 6.24; N: 10.96.

(52.2) 2-Amino-5-isopropyl-4-[(N,N'-(1-(S)-ethoxycarbonyl)methyl)phosphonodiamidomethoxycarbonyl]-thiazole. Anal. calcd. for $C_{18}H_{31}N_4O_7PS$: C: 45.18; H: 6.53; N: 11.71. Found: C: 45.33; H: 6.56; N: 11.46.

(52.3) 4-Amino-7-ethyl-5-fluoro-1-isobutyl-2-[5-({N,N'-(1-(S)ethoxycarbonyl)ethyl}phosphonodiamido)furanyl]benzimidazole. Anal. calcd. for $C_{27}H_{39}N_5O_6PF$: C: 55.95; H: 6.78; N: 12.08. Found: C: 55.73; H: 6.65; N: 11.72.

(52.4) 2-Amino-5-ethoxycarbonyl-4-[2-(5-({N,N'-(1-(S)ethoxycarbonyl)ethyl}phosphono)furanyl]thiazole. Anal. calcd. for $C_{20}H_{29}N_4O_8PS+0.3CH_2Cl_2$: C: 44.99; H: 5.50; N: 10.34. Found: C: 44.68; H: 5.30; N: 10.37.

(52.5) 2-Amino-4-[(N,N'-(1-(S)-ethoxycarbonyl)methyl)phosphonodiamidomethoxy]-5,6,7,8-tetrahydronaphtho[1,2-d]thiazole. Mp. 177–178° C.: Anal. calcd. for $C_{20}H_{29}N_4O_6PS$: C: 49.58; H: 6.03; N: 11.56. Found: C: 49.20; H: 5.95; N: 11.51.

(52.6) 2-Amino-5-isopropyl-4-[(N,N'-(1-(S)-ethoxycarbonyl)methyl)phosphonodiamidomethoxycarbonyl]-thiazole. Mp. 122–125° C.: Anal. calcd. for $C_{16}H_{27}N_4O_7PS$: C: 42.66; H: 6.04; N: 12.44. Found: C: 42.60; H: 6.08; N: 12.43.

(52.7) 2-Amino-4-{N,N'-(1-(S)-ethoxycarbonyl)ethyl}phosphonomethoxy-6-bromo-7-chloro-benzothiazole. Mp. 210–212° C.: Anal. calcd. for $C_{18}H_{25}N_4O_6PSBrCl$: C: 37.81; H: 4.41; N: 9.80. Found: C: 37.88; H: 4.35; N: 9.84.

(52.8) 2-Amino-5-propylthio-4-{2-[5-(N,N'-bis(S)-1-methoxycarbonyl-2-(t-butoxy)ethyl)phosphonamido]furanyl}thiazole. Anal. calcd. for $C_{26}H_{43}N_4O_8PS_2$: C: 49.20; H: 6.83; N: 8.83. Found: C: 49.38; H: 6.68; N: 8.65.

(52.9) 2-Amino-5-propylthio-4-{2-[5-(N,N'-bis(S)-1-ethoxycarbonyl-2-methylbutyl)phosphonamido]furanyl}thiazole. Anal. calcd. for $C_{26}H_{43}N_4O_6PS_2$: C: 51.81; H: 7.19; N: 9.30. Found: C: 52.03; H: 6.78; N: 9.04.

(52.10) 2-Amino-5-propylthio-4-[2-{5-(N,N'-bis(S)-1-ethoxycarbonyl-2-methylpropyl)phosphonamido}furanyl]thiazole. Anal. calcd for $C_{24}H_{39}N_4O_6PS_2$: C: 50.16; H: 6.84; N: 9.75. Found: C: 50.01; H: 6.76; N: 9.66.

(52.11) 2-Amino-5-propylthio-4-[2-{5-(N,N'-bis(S)-1-methoxycarbonyl-2-(t-butoxy)propyl)phosphonamido}furanyl]thiazole. Anal. calcd. for $C_{28}H_{47}N_4O_8PS_2$: C: 50.74; H: 7.15; N: 8.45. Found: C: 51.08; H: 7.33; N: 8.25.

(52.12) 2-Amino-propylthio-4-[2-{5-(N,N'-bis(1-ethoxycarbonyl)cyclopentyl)phosphonamido}furanyl]thiazole. Anal. calcd. for $C_{26}H_{39}N_4O_6PS_2$: C: 52.16; H: 6.57; N: 9.36. Found: C: 52.55; H: 6.53; N: 9.31.

(52.13) 2-Amino-5-propylthio-4-[2-{5-(N,N'-bis(S)-1-ethoxycarbonyl)propylphosphonamido}furanyl]thiazole. Anal. calcd. for $C_{22}H_{35}N_4O_6PS_2$: C: 48.34; H: 6.45; N: 10.25. Found: C: 48.65; H: 6.29; N: 10.23.

(52.14) 2-Amino-4-{N,N'-(1-(S)-ethoxycarbonyl)ethyl}phosphonomethoxy-6-chloro-7-methyl-benzothiazole. Mp. 178–180° C.: Anal. calcd. for $C_{19}H_{28}N_4O_6PSCl$: C: 45.02; H: 5.57; N: 11.05. Found: C: 45.12; H: 5.49; N: 10.92.

(52.15) 2-Amino-5-methylthio-4-{2-[5-(N,N'-bis((S)-1-ethoxycarbonyl)ethyl)phosphonamido]furanyl}thiazole. Mp. 94–95° C.: Anal. calcd. for $C_{18}H_{27}N_4O_6PS_2$: C: 44.07; H: 5.55; N: 11.42. Found: C: 44.42; H: 5.44; N: 11.29.

(52.16) 2-Amino-propylthio-4-[2-{5-(N,N'-bis((S)1-ethoxycarbonyl)butyl)phosphonamido)}furanyl]thiazole.: Anal. calcd. for $C_{24}H_{39}N_4O_6PS_2$: C: 50.16; H: 6.84; N: 9.75. Found: C: 49.96; H: 6.91; N: 9.68.

(52.17) 2-Amino-propylthio-4-[2-{5-(N,N'-bis((S)1-ethoxycarbonyl)cyclohexanylmethyl)phosphonamido)

(52.18) 2-Amino-4-{N,N'-(1-(S)-ethoxycarbonyl)ethyl}phosphonomethoxy-6-methoxy-benzothiazole. Mp. 144–146° C.: Anal. calcd. for $C_{19}H_{29}N_4O_7PS$: C: 46.72; H: 5.98; N: 11.47. Found: C: 46.76; H: 5.72; N: 11.33.

(52.19) 2-Amino-4-{N,N'-(ethoxycarbonyl)methyl}phosphonomethoxy-6-methoxy-benzothiazole. Mp. 150–152° C.: Anal. calcd. for $C_{17}H_{25}N_4O_7PS$: C: 44.35; H: 5.47; N: 12.17. Found: C: 44.74; H: 5.45; N: 11.99.

(52.20) 2-Amino-7-ethyl-4-{N,N'-(1-(S)-ethoxycarbonyl)ethyl}phosphonomethoxy-6-methylbenzothiazole. Anal. calcd. for $C_{21}H_{33}N_4O_6PS$: C: 50.39; H: 6.65; N: 11.19. Found: C: 50.22; H: 6.34; N: 11.30.

(52.21) 2-Amino-4-{N,N'-(1-(S)-ethoxycarbonyl)ethyl}phosphonomethoxy-6-methyl-benzothiazole. Anal. calcd. for $C_{19}H_{29}N_4O_6PS$: C: 48.30; H: 6.19; N: 11.86. Found: C: 48.67; H: 5.90; N: 11.86.

(52.22) 2-Amino-4-{N,N'-(1-methyl-1-ethoxycarbonyl)ethyl}phosphonomethoxy-6-chloro-7-methyl-benzothiazole. Mp. 170–172° C.: Anal. calcd. for $C_{21}H_{32}N_4O_6PSCl$: C: 47.15; H: 6.03; N: 10.47. Found: C: 47.22; H: 5.87; N: 10.08.

(52.23) 2-Amino-7-ethyl-4-{N,N'-bis(ethoxycarbonylmethyl)}phosphonomethoxy-6-methyl-benzothiazole. Anal. calcd. for $C_{19}H_{29}N_4O_6PS$: C: 48.30; H: 6.19; N: 11.86. Found: C: 47.98; H: 6.36; N: 11.88.

(52.24) 2-Amino-4-{N,N'-bis(ethoxycarbonylmethyl)}phosphonomethoxy-6-methyl-benzothiazole. Anal. calcd. for $C_{17}H_{25}N_4O_6PS+0.5H_2O$: C: 45.03; H: 5.78; N: 12.36. Found: C: 44.80; H: 6.10; N: 12.40.

(52.25) 2-Amino-5-propylthio-4-[2-{5-(N,N'-bis((S)1-t-butoxycarbonyl)ethyl)phosphonamido)}furanyl]thiazole. Anal. calcd. for $C_{24}H_{39}N_4O_6PS_2$: C: 50.16; H: 6.84; N: 9.75. Found: C: 50.26; H: 6.71; N: 9.51.

(52.26) 2-Amino-5-propylthio-4-[2-{5-(N,N'-bis((S)1-n-butoxycarbonyl)ethyl)phosphonamido)}furanyl]thiazole. Anal. calcd. for $C_{24}H_{39}N_4O_6PS_2$: C: 50.16; H: 6.84; N: 9.75. Found: C: 50.38; H: 6.64; N: 9.64.

(52.27) 2-Amino-5-ethoxycarbonyl-4-[2-(5-({N,N'-(1-(S)-ethoxycarbonyl)propyl}phosphono)furanyl]thiazole. Anal. calcd. for $C_{22}H_{33}N_4O_8PS$: C: 48.52; H: 6.11; N: 10.29. Found: C: 48.62; H: 6.02; N: 10.26.

(52.28) 2-Amino-5-ethoxycarbonyl-4-[2-(5-({N,N'-(1-(S)-ethoxycarbonyl)butyl}phosphono)furanyl]thiazole. Anal. calcd. for $C_{24}H_{37}N_4O_8PS$: C: 50.34; H: 6.51; N: 9.78. Found: C: 50.34; H: 6.57; N: 9.65.

(52.29) 2-Amino-5-ethoxycarbonyl-4-[2-(5-({N,N'-(1-ethoxycarbonyl)cyclopentyl}phosphono)furanyl]thiazole. Anal. calcd. for $C_{26}H_{37}N_4O_8PS$: C: 52.34; H: 6.25; N: 9.39. Found: C: 52.02; H: 6.20; N: 9.34.

(52.30) 2-Amino-5-ethoxycarbonyl-4-[2-(5-(N,N'-bis(S)-1-ethoxycarbonyl-2-methylpropyl)phosphonamido}furanyl]thiazole. Anal. calcd. for $C_{24}H_{37}N_4O_8PS$: C: 50.34; H: 6.51; N: 9.78. Found: C: 50.56; H: 6.40; N: 9.65.

(52.31) 2-Amino-5-propylthio-4-[2-{5-(N,N'-bis-coumarin)phosphonamido}furanyl]thiazole. Anal. calcd. for $C_{28}H_{23}N_4O_6PS_2$: C: 55.44; H: 3.82; N: 9.24. Found: C: 55.52; H: 3.66; N: 9.01.

(52.32) 2-Amino-5-propylthio-4-[2-{5-(N,N'-bis((S)1-isopropoxycarbonyl)ethyl)phosphonamido)}furanyl]thiazole. Anal. calcd. For $C_{22}H_{35}N_4O_6PS_2$: C: 48.34; H: 6.45; N: 10.25. Found: C: 48.03; H: 6.45; N: 10.09.

(52.33) 2-Amino-5-propylthio-4-[2-{5-(N,N'-bis((S)1-n-propoxycarbonyl)ethyl)phosphonamido}furanyl]thiazole. Anal. calcd. for $C_{22}H_{35}N_4O_6PS_2$: C: 48.34; H: 6.45; N: 10.25. Found: C: 48.39; H: 6.27; N: 10.20.

(52.34) 2-Amino-5-propylthio-4-[2-{5-(N,N'-bis((S)1-cycloheptoxycarbonyl)ethyl)phosphonamido)}furanyl]thiazole. Anal. calcd. for $C_{26}H_{39}N_4O_6PS_2$: C: 52.16; H: 6.57; N: 9.36. Found: C: 52.07; H: 6.51; N: 9.10.

(52.35) 2-Amino-6-ethyl-7-fluoro-4-{N,N'-(1-(S)-ethoxycarbonyl)ethyl}phosphonomethoxy-benzothiazole. Anal. calcd. for $C_{20}H_{30}N_4O_6PSF$: C: 47.61; H: 5.99; N: 11.10. Found: C: 47.59; H: 5.79; N: 10.90.

(52.36) 2-Amino-6-ethyl-7-fluoro-4-{N,N'-(1-ethoxycarbonyl)methyl}phosphonomethoxy-benzothiazole. Anal. calcd. for $C_{18}H_{26}N_4O_6PSF$: C: 45.38; H: 5.50; N: 11.76. Found: C: 45.07; H: 5.25; N: 11.49.

(52.37) 2-Amino-7-bromo-4-{N,N'-(1-(S)-ethoxycarbonyl)ethyl}phosphonomethoxy-6-methylbenzothiazole. Anal. calcd. for $C_{19}H_{28}N_4O_6PSBr$: C: 41.39; H: 5.12; N: 10.16. Found: C: 41.40; H: 5.05; N: 9.94.

(52.38) 2-Amino-4-{N,N'-(1-ethoxycarbonyl)methylethyl}phosphonomethoxy-6-methylbenzothiazole. Anal. calcd. for $C_{21}H_{33}N_4O_6PS+0.5H_2O$: C: 49.50; H: 6.73; N: 11.00. Found: C: 49.18; H: 6.61; N: 11.39.

(52.39) 2-Amino-5-isobutyl-4-[2-{5-(N,N'-bis((S)-1-(1-ethoxycarbonyl)propyl)phosphonamido)}furanyl]thiazole. Anal. calcd. for $C_{23}H_{37}N_4O_6PS$: C: 52.26; H: 7.06; N: 10.60. Found: C: 52.47; H: 7.29; N: 10.77.

(52.40) 2-Amino-5-propylthio-4-[2-{5-(N,N'-bis((S)-1-cyclohexylmethoxycarbonyl)ethyl)phosphonamido)}furanyl]thiazole. Anal. calcd. for $C_{30}H_{47}N_4O_6PS_2$: C: 55.03; H: 7.23; N: 8.56. Found: C: 55.08; H: 7.35; N: 8.39.

(52.41) 2-Amino-5-isobutyl-4-[2-{5-(1-ethoxycarbonyl)cyclopentyl)phosphonamido)}furanyl]thiazole. Anal. calcd. for $C_{27}H_{41}N_4O_6PS$: C: 55.85; H: 7.12; N: 9.65. Found: C: 55.62; H: 6.81; N: 9.66.

(52.42) 2-Amino-4-{N,N'-(1-ethoxycarbonyl)cyclopentyl}phosphonomethoxy-7-fluoro-6-methyl benzothiazole. Anal. calcd. for $C_{26}H_{38}N_4O_6PSF+0.15Et_2O$: C: 53.63; H: 6.68; N: 9.40. Found: C: 53.93; H: 6.39; N: 9.50.

(52.43) 2-Amino-5-isobutyl-4-[2-{5-(N,N'-bis((S)-1-(1-neopentoxycarbonyl)ethyl)phosphonamido)}furanyl]thiazole. Anal. calcd. for $C_{27}H_{45}N_4O_6PS+0.1H_2O$: C: 55.29; H: 7.77; N: 9.55. Found: C: 54.90; H: 7.68; N: 9.44.

(52.44) 2-Amino-5-isobutyl-4-{2-[5-(N,N'-bis((R,S)-1-(1-ethoxycarbonyl)ethyl)phosphonamido)]furanyl}thiazole. Mp. 143–146° C.: Anal. calcd. for $C_{21}H_{33}N_4O_6PS$: C: 50.39; H: 6.65; N: 11.19. Found: C: 50.33; H: 6.58; N: 11.00.

(52.45) 2-Amino-5-isobutyl-4-[2-{5-(N,N'-bis((S)-1-(1-isopropoxycarbonyl)ethyl)phosphonamido)}furanyl]thiazole. Anal. calcd. for $C_{23}H_{37}N_4O_6PS$: C: 52.26; H: 7.06; N: 10.60. Found: C: 52.34; H: 7.02; N: 10.50.

(52.46) 2-Amino-5-isobutyl-4-[2-{5-(N,N'-bis((S)-1-(1-propoxycarbonyl)ethyl)phosphonamido)}furanyl]thiazole. Anal. calcd. for $C_{23}H_{37}N_4O_6PS+0.1CH_2Cl_2$: C: 51.66; H: 6.98; N: 10.43. Found: C: 51.50; H: 7.01; N: 10.63.

(52.47) 2-Amino-5-isobutyl-4-[2-{5-(N,N'-bis((S)-1-(1-isobutoxycarbonyl)ethyl)phosphonamido)}furanyl]thiazole. Anal. calcd. for $C_{25}H_{41}N_4O_6PS$: C: 53.94; H: 7.42; N: 10.06. Found: C: 53.59; H: 7.64; N: 9.98.

(52.48) 2-Amino-5-propylthio-4-{2-[5-(N,N'-bis((S)-1-ethoxycarbonyl)ethyl)phosphonamido]furanyl}oxazole. Anal. calcd. for $C_{20}H_{31}N_4O_7PS$: C: 47.80; H: 6.22; N: 11.15. Found: C: 47.90; H: 6.17; N: 10.92.

(52.49) 2-Amino-5-propylthio-4-{2-[5-(N,N'-bis-1-ethoxycarbonyl)methyl)phosphonamido]furanyl}oxazole. Anal. calcd. for $C_{18}H_{27}N_4O_7PS$: C: 45.57; H: 5.74; N: 11.81. Found: C: 45.87; H: 5.68; N: 11.68.

(52.50) 2-Amino-5-(isobutyl-$d_9$)-4-[2-{5-(N,N'-bis(S)-1-(1-ethoxycarbonyl)ethylphosphonamido}furanyl]thiazole. Anal. calcd. for $C_{21}H_{24}D_9N_4O_6SP$: C: 49.50; H: 4,75; N: 10.99. Found: C: 49.89; H: 6.55; N: 10.97.

Examples of use of the method of the invention include the following. It will be understood that these examples are exemplary and that the method of the invention is not limited solely to these examples.

For the purposes of clarity and brevity, chemical compounds are referred to by synthetic Example number in the biological examples below.

Compound A is 4-Amino-5-fluoro-7-ethyl-1-isobutyl-2-(2-phosphono-5-furanyl)benzimidazole;

Compound B is 4-Amino-5-fluoro-1-cyclopropylmethyl-2-(2-phosphono-5-furanyl)benzimidazole.

Compound C is 2-Amino-5-isobutyl-4-{2-[N-(1-methyl-1-carboxy)ethylmonophosphonamido]furanyl}thiazole Besides the following Examples, assays that may be useful for identifying compounds which inhibit gluconeogenesis include the following animal models of diabetes:

i. Animals with pancreatic b-cells destroyed by specific chemical cytotoxins such as Alloxan or Streptozotocin (e.g. the Streptozotocin-treated mouse, rat, dog, and monkey). Kodama, H., Fujita, M., Yamaguchi, I., *Japanese Journal of Pharmacology* 66, 331–336 (1994) (mouse); Youn, J. H., Kim, J. K., Buchanan, T. A., *Diabetes* 43, 564–571 (1994) (rat); Le Marchand, Y., Loten, E. G., Assimacopoulos-Jannet, F., et al., *Diabetes* 27, 1182–88 (1978) (dog); and Pitkin, R. M., Reynolds, W. A., *Diabetes* 19, 70–85 (1970) (monkey).

ii. Mutant mice such as the C57BL/Ks db/db, C57BL/Ks ob/ob, and C57BL/6J ob/ob strains from Jackson Laboratory, Bar Harbor, and others such as Yellow Obese, T-KK, and New Zealand Obese. Coleman, D. L., Hummel, K. P., *Diabetologia* 3, 238–248 (1967) (C57BL/Ks db/db); Coleman, D. L., *Diabetologia* 14, 141–148 (1978) (C57BL/6J ob/ob); Wolff, G. L., Pitot, H. C., *Genetics* 73, 109–123 (1973) (Yellow Obese); Dulin, W. E., Wyse, B. M., *Diabetologia* 6, 317–323 (1970) (T-KK); and Bielschowsky, M., Bielschowsky, F. Proceedings of the University of Otago Medical School 31, 29–31 (1953) (New Zealand Obese).

iii. Mutant rats such as the Zucker fa/fa Rat rendered diabetic with Streptozotocin or Dexamethasone, the Zucker Diabetic Fatty Rat, and the Wistar Kyoto Fatty Rat. Stolz, K. J., Martin, R. J. *Journal of Nutrition* 112, 997–1002 (1982) (Streptozotocin); Ogawa, A., Johnson, J. H., Ohnbeda, M., McAllister, C. T., Inman, L., Alam, T., Unger, R. H., *The Journal of Clinical Investigation* 90, 497–504 (1992) (Dexamethasone); Clark, J. B., Palmer, C. J., Shaw, W N., *Proceedings of the Society for Experimental Biology and Medicine* 173, 68–75 (1983) (Zucker Diabetic Fatty Rat); and Idida, H., Shino, A., Matsuo, T., et al., *Diabetes* 30, 1045–1050 (1981) (Wistar Kyoto Fatty Rat).

iv. Animals with spontaneous diabetes such as the Chinese Hamster, the Guinea Pig, the New Zealand White Rabbit, and non-human primates such as the Rhesus monkey and Squirrel monkey. Gerritsen, G. C., Connel, M. A., Blanks, M. C., *Proceedings of the Nutrition Society* 40, 237 245 (1981) (Chinese Hamster); Lang, C. M., Munger, B. L., *Diabetes* 25, 434–443 (1976) (Guinea Pig); Conaway, H. H., Brown, C. J., Sanders, L. L. et al., *Journal of Heredity* 71, 179–186 (1980) (New Zealand White Rabbit); Hansen, B. C., Bodkin, M. L., *Diabetologia* 29, 713–719 (1986) (Rhesus monkey); and Davidson, I. W., Lang, C. M., Blackwell, W. L., *Diabetes* 16, 395–401 (1967) (Squirrel monkey).

v. Animals with nutritionally induced diabetes such as the Sand Rat, the Spiny Mouse, the Mongolian Gerbil, and the Cohen Sucrose-Induced Diabetic Rat. Schmidt-Nielsen, K., Hainess, H. B., Hackel, D. B., *Science* 143, 689–690 (1964) (Sand Rat); Gonet, A. E., Stauffacher, W., Pictet, R., et al., *Diabetologia* 1, 162–171 (1965) (Spiny Mouse); Boquist, L., *Diabetologia* 8, 274–282 (1972) (Mongolian Gerbil); and Cohen, A. M., Teitebaum, A., Saliternik, R., *Metabolism* 21, 235–240 (1972) (Cohen Sucrose-Induced Diabetic Rat).

vi. Any other animal with one of the following or a combination of the following characteristics resulting from a genetic predisposition, genetic engineering, selective breeding, or chemical or nutritional induction: impaired glucose tolerance, insulin resistance, hyperglycemia, obesity, accelerated gluconeogenesis, increased hepatic glucose output.

Example A

Inhibition of Human Liver FBPase

*E. coli* strain BL21 transformed with a human liver FBPase-encoding plasmid was obtained from Dr. M. R. El-Maghrabi at the State University of New York at Stony Brook. The enzyme was typically purified from 10 liters of recombinant *E. coli* culture as described (M. Gidh-Jain et al., 1994, *The Journal of Biological Chemistry* 269, pp 27732–27738). Enzymatic activity was measured spectrophotometrically in reactions that coupled the formation of product (fructose 6-phosphate) to the reduction of dimethylthiazoldiphenyltetrazolium bromide (MTT) via $NADP^+$ and phenazine methosulfate (PMS), using phosphoglucose isomerase and glucose 6-phosphate dehydrogenase as the coupling enzymes. Reaction mixtures (200 $\mu$l) were made up in 96-well microtitre plates, and consisted of 50 mM Tris-HCl, pH 7.4, 100 mM KCl, 5 mM EGTA, 2 mM $MgCl_2$, 0.2 mM NADP, 1 mg/ml BSA, 1 mM MTT, 0.6 mM PMS, 1 unit/ml phosphoglucose isomerase, 2 units/ml glucose 6-phosphate dehydrogenase, and 0.150 mM substrate (fructose 1,6-bisphosphate). Inhibitor concentrations were varied from 0.01 $\mu$M to 10 $\mu$M. Reactions were started by the addition of 0.002 units of pure hlFBPase, and were monitored for 7 minutes at 590 nm in a Molecular Devices Plate Reader (37° C.).

The table below provides the $IC_{50}$ values for several compounds prepared. The $IC_{50}$ for AMP is 1 $\mu$LM.

| Compound # | $IC_{50}$ (hlFBPase), $\mu$M |
|---|---|
| 3.1 | 0.025 |
| 3.2 | 0.1 |
| 3.25 | 0.014 |
| 3.26 | 0.015 |
| 3.58* | 0.018 (*non-HBr salt) |
| 3.67 | 2 |
| 3.69 | 1 |
| 3.70 | 0.04 |
| 6.3 | 0.044 |
| 10.1 | 0.12 |

-continued

| Compound # | IC$_{50}$ (hlFBPase), μM |
| --- | --- |
| 10.27 | 0.038 |
| 10.43 | 0.07 |
| 15.20 | 0.04 |
| 15.14 | 0.032 |
| 16.1 | 0.06 |
| 17.6 | 0.62 |
| 17.11 | 0.78 |
| 18.3 | 0.05 |
| 18.11 | 0.33 |
| 18.20 | 0.039 |
| 18.25 | 2 |
| 19.2 | 0.4 |
| 22.2 | 2.8 |
| 34.1 | 0.022 |
| A | 0.055 |
| B | 0.055 |

Inhibition of Rat Liver FBPase

E. coli strain BL21 transformed with a rat liver FBPase-encoding plasmid was obtained from Dr. M. R. El-Maghrabi at the State University of New York at Stony Brook. Recombinant FBPase was purified as described (El-Maghrabi, M. R., and Pilkis, S. J. (1991) BioChem. Biophys. Res. Commun. 176, 137–144) The enzyme assay was identical to that described above for human liver FBPase.

The table below provides the IC$_{50}$ values for several compounds prepared. The IC$_{50}$ for AMP is 20 μM.

| Compound # | IC$_{50}$ (rlFBPase), μM |
| --- | --- |
| 3.1 | 0.18 |
| 3.2 | 2.5 |
| 3.25 | 0.5 |
| 3.26 | 0.25 |
| 3.58* | 0.05 (*non-HBr salt) |
| 3.70 | 0.15 |
| 6.3 | 0.5 |
| 10.1 | 2 |
| 10.2 | 2.5 |
| 10.27 | 2.9 |
| 10.43 | 0.8 |
| 15.2 | 1.3 |
| 15.4 | 4.1 |
| 15.6 | 7 |
| 15.20 | 0.6 |
| 15.14 | 0.68 |
| 16.1 | 1.8 |
| 18.20 | 0.28 |
| 18.3 | 0.49 |
| 34.1 | 0.16 |
| A | 0.55 |
| B | 2.1 |

Example B

AMP Site Binding

To assess whether compounds bind to the allosteric AMP binding site of hlFBPase, the enzyme is incubated with radio-labeled AMP in the presence of a range of test compound concentrations. The reaction mixtures consist of 25 mM $^3$H-AMP (54 mCi/mmole) and 0–1000 mM test compound in 25 mM Tris-HCl, pH 7.4, 100 mM KCl and 1 mM MgCl$_2$ 1.45 mg of homogeneous FBPase (±nmole) is added last. After a 1 minute incubation, AMP bound to FBPase is separated from unbound AMP by means of a centrifugal ultrafiltration unit ("Ultrafree-MC", Millipore) used according to the instructions of the manufacturer. The radioactivity in aliquots (100 μl) of the upper compartment of the unit (the retentate, which contains enzyme and label) and the lower compartment (the filtrate, which contains unbound label) is quantified using a Beckman liquid scintillation counter. The amount of AMP bound to the enzyme is estimated by comparing the counts in the filtrate (the unbound label) to the total counts in the retentate.

Example C

Inhibition of Gluconeogenesis in Rat Hepatocytes

Hepatocytes were prepared from overnight fasted Sprague-Dawley rats (250–300 g) according to the procedure of Berry and Friend (Berry, M. N., Friend, D. S., 1969, J. Cell. Biol. 43, 506–520) as modified by Groen (Groen, A. K., Sips, H. J., Vervoorn, R. C., Tager, J. M., 1982, Eur. J. BioChem. 122, 87–93). Hepatocytes (75 mg wet weight/ml) were incubated in 1 ml Krebs-bicarbonate buffer containing 10 mM Lactate, 1 mM pyruvate, 1 mg/ml BSA, and test compound concentrations from 1 to 500 μM. Incubations were carried out in a 95% oxygen, 5% carbon dioxide atmosphere in closed, 50-ml Falcon tubes submerged in a rapidly shaking water bath (37° C.). After 1 hour, an aliquot (0.25 ml) was removed, transferred to an Eppendorf tube and centrifuged. 50 μl of supernatant was then assayed for glucose content using a Sigma Glucose Oxidase kit as per the manufacturer's instructions.

IC$_{50}$'s for select compounds in this assay are shown in the table below.

| Compound | IC$_{50}$ Glucose Production, μM |
| --- | --- |
| 3.1 | 2.5 |
| 3.2 | 26 |
| 3.26 | 10 |
| 3.58* | 2.0 (*non-HBr salt) |
| 10.1 | 15 |
| 10.2 | 16 |
| 16.1 | 10 |
| 50.6 | 2.0 |
| 50.9 | 2.2 |
| 50.2 | 2.1 |

Example D

Glucose Production Inhibition and Fructose-1.6-bisphosphate Accumulation in Rat Hepatocytes Isolated rat hepatocytes are prepared as described in Example C and incubated under the identical conditions described. Reactions are terminated by removing an aliquot (250 μL) of cell suspension and spinning it through a layer of oil (0.8 ml silicone/mineral oil, 4/1) into a 10% perchloric acid layer (100 μL). After removal of the oil layer, the acidic cell extract layer is neutralized by addition of ⅓rd volume of 3 M KOH/3 M KHCO$_3$. After thorough mixing and centrifugation, the supernatant is analyzed for glucose content as described in Example C, and also for fructose-1,6-bisphosphate. Fructose 1,6-bisphosphate is assayed spectrophotometrically by coupling its enzymatic conversion to glycerol 3-phosphate to the oxidation of NADH, which is monitored at 340 nm. Reaction mixtures (1 mL) consist of 200 mM Tris-HCl, pH 7.4, 0.3 mM NADH, 2 units/ml glycerol 3-phosphate dehydrogenase, 2 units/ml triosephosphate isomerase, and 50–100 μL cell extract. After a 30 minute preincubation at 37° C., 1 unit/ml of aldolase is added and the change in absorbance measured until a stable value is obtained. 2 moles of NADH are oxidized in this reaction per mole of fructose-1,6-bisphosphate present in the cell extract.

A dose-dependent inhibition of glucose production accompanied by a dose-dependent accumulation of fructose-1,6-bisphosphate (the substrate of FBPase) is an indication that the target enzyme in the gluconeogenic pathway, FBPase, is inhibited.

Example E

Chemical Stability

Aim: To assess the stability of prodrugs 50.6, 50.9, 50.15, and 50.20 in a phosphate buffered, aqueous solution at neutral pH.

Methods: A 50 or 100 µg/mL solution of prodrug in potassium phosphate buffer at pH 7 (room temperature) was sampled daily for up to 10 days. Samples were analyzed by reverse phase HPLC with use of a Beckman Ultrasphere C18 column (4.6×250 mm). The column was equilibrated and eluted with a gradient from 50 mM sodium phosphate pH 5.5 to 70% acetonitrile at a flow rate of 1.5 mL/min. Detection was at 300 or 315 nm, column temperature at 40° C. Under these conditions, the prodrugs were well separated from parent compound standards; the retention time for the prodrugs was between 16 and 18 minutes, whereas the parent compounds, 3.1 and 3.58 (non-HBr salt), eluted at 9 and 10 minutes, respectively.

Results: The prodrugs evaluated exhibited good stability at neutral pH. Less than 10% decomposition of the prodrugs was noted over a 4 day incubation period. The t90's for 50.6, 50.9, 50.15, and 50.20 at pH 7 were thus >96 hours.

Example F

Estimation of Oral Bioavailability in the Rat

Aim: To estimate the oral bioavailability of prodrugs by means of the urinary parent compound excretion method in the rat.

Methods: Prodrugs were dissolved in 10% ethanol/90% polyethylene glycol (mw 400) and administered by oral gavage at doses of 10 to 40 mg/kg parent compound equivalents to 6-hour fasted, Sprague Dawley rats (220–240 g). Parent compounds were typically dissolved in deionized water, neutralized with sodium hydroxide, and then administered via the tail vein at ~10 mg/kg to rats that were briefly anesthetized with halothane. The rats were subsequently placed in metabolic cages and urine was collected for 24 hours. The quantity of parent compound excreted into urine was determined by HPLC analysis. Analysis was performed as described in Example E. The percentage oral bioavailability was estimated by comparison of the recovery in urine of the parent compound generated from the prodrug administered orally, to that recovered in urine following intravenous administration of unsubstituted parent compound.

Results: The estimated % oral bioavailability of select prodrugs is shown below.

| Prodrug | Parent compound | Oral Bioavailability, % |
|---|---|---|
| 50.2 | 3.1 | 11 |
| 50.3 | 3.1 | 7 |
| 50.4 | 3.1 | 17 |
| 50.5 | 3.1 | 22 |
| 50.6 | 3.1 | 21.5 |
| 50.8 | 3.1 | 26 |
| 50.9 | 3.1 | 40 |
| 50.15 | 3.8 | 22 |
| 50.20 | 3.8 | 42 |
| 50.17 | 3.1 | 7 |
| 50.21 | 3.26 | 45 |
| 51.2 | 3.1 | 37 |
| 52.1 | 29.1 | 16 |
| 52.4 | 3.25 | 30 |
| 52.15 | 3.26 | 23 |
| 52.18 | 45.1 | 22 |
| 52.21 | 32.2 | 24 |
| 52.22 | 36.1 | 18 |
| 52.32 | 3.58 | 17 |
| 52.33 | 3.58 | 19 |
| 52.38 | 32.2 | 30 |
| 52.41 | 3.1 | 27 |
| 52.43 | 3.1 | 18 |
| 52.44 | 3.1 | 28 |
| 52.45 | 3.1 | 31 |
| 52.46 | 3.1 | 16 |

Example G

Oral Pharmacokinetics in the Rat

Aim: To determine the pharmacokinetic parameters of 50.6 and 50.9 (prodrugs of 3.1), and of 50.2 (prodrug of 3.58) following oral administration in the rat.

Methods: Prodrugs were administered orally at 10 mg/kg to fed rats instrumented with tail artery catheters. At appropriate time points following drug administration, blood samples were removed via the tail vein catheters. Plasma was prepared from the samples by centrifugation and plasma protein subsequently precipitated by addition of methanol to 60%. The methanolic extracts were clarified by centrifugation and then analyzed for prodrug and parent compound content by HPLC as described in Example E. Pharmacokinetic parameters were calculated from the parent compound plasma concentration-time profiles using non-compartmental analysis (WinNonLin v. 1.1 software).

Results: Prodrugs were not detected in plasma indicating rapid in vivo conversion to their respective parent compounds. Pharmacokinetic parameters are summarized below.

| | Parent Compound | | | |
|---|---|---|---|---|
| Compound | Cmax (µg/ml) | Tmax (h) | Clearance (L/kg/h) | Half-life (h) |
| 50.6 | 0.78 | 1.5 | 1.31 | 5.1 |
| 50.9 | 0.99 | 1.1 | 1.6 | 2.5 |
| 50.2 | 1 | 3.1 | 0.54 | 7.0 |

Example H

Acute Oral Efficacy in the ZDF Rat

Aim: To determine the blood glucose lowering effect of acute 50.6, 50.9 and 50.2 administration in the Zucker Diabetic Fatty (ZDF rat).

Methods: ZDF rats were purchased from Genetics Inc (Indianapolis, Ind.) at 8 weeks of age. Animals were maintained under standard vivarium conditions and provided with Purina 5008 chow and water ad libitum. At 10–12 weeks of age, rats with blood glucose levels>500 mg/dl were selected and dosed orally either with vehicle (PEG 400), or prodrug (60 mg/kg). Blood glucose levels were monitored at regular intervals for 6 hours following dosing. Blood samples were taken from tail vein nicks and analyzed by means of a HemoCue glucose analyzer (Hemocue, Mission Viejo, Calif.). Statistical analysis was performed using the Student's t test. Means±standard error of the means are shown.

Results: The three prodrugs were orally efficacious as indicated by the significant blood glucose lowering effects observed (see table below).

| Treatment | Blood Glucose, mg/dl | | % Change |
|---|---|---|---|
| | Tbaseline | T6h | |
| Vehicle (n = 8) | 562 ± 38 | 528 ± 29 | −6% |
| 50.6 (n = 8) | 544 ± 25 | 406 ± 12* | −25% |
| 50.9 (n = 8) | 602 ± 26 | 410 ± 18* | −32% |
| 50.2 (n = 8) | 591 ± 35 | 415 ± 15* | −30% |

*P < 0.005 versus vehicle

Example I

Chronic Oral Efficacy in the ZDF Rat

Aim: To determine the glucose lowering effects of 50.6 in the ZDF rat during 3 weeks of chronic, oral treatment.

Methods: ZDF rats (10 weeks of age) were maintained either on powdered Purina 5008 rat chow (n=10) or the same powdered chow supplemented with 0.4% 50.6 (n=8). Blood glucose measurements were made as described in Example E at baseline and at weekly intervals thereafter for a total of 3 weeks. Statistical analysis was performed using the Student's t test. Means±standard error of the means are shown.

Results: As illustrated in the table below, efficacy was maintained throughout the 3-week treatment period, with 45% blood glucose lowering evident in the drug treated group (relative to vehicle) at the end of the study.

| Treatment | Blood glucose, mg/dl, | |
|---|---|---|
| | tbaseline | t21 days |
| Vehicle | 678 ± 19 | 776 ± 28 |
| 50.6 | 674 ± 20 | 436 ± 41* |

*p < 0.0001 versus vehicle

Example J

Identification of the Intermediate Formed During Activation 50.6

The metabolism of 50.6 was evaluated in rat, monkey, and human plasma by reverse phase HPLC with use of a Beckman Ultrasphere ODS column (4.6×150 mm) equipped with an Alltech All-Guard column. The column was equilibrated with 20 mM potassium phosphate, pH 6.2 and eluted with a linear gradient of 0–60% acetonitrile over 20 minutes at a flow rate of 1.5 mL/min and at a temperature of 40° C. UV absorbance was monitored at 300 nM. Exposure of 50.6 (100 $\mu$M) to the plasma samples resulted in the formation of a single metabolite. This metabolite had the same retention time and UV spectrum as a product formed following incubation of the prodrug with pig liver esterase (Sigma Chemical Co, Mo.), suggesting that it was a product of an esterase-catalyzed reaction. The metabolite formed in rat plasma was collected and subjected to mass spectrum analysis at Mass Consortium Corporation (San Diego, Calif.). The sample yielded a negative ion peak at 372, indicating that the metabolite formed had a molecular weight of 373. This molecular weight is consistent with that of a monophosphoramidate intermediate. This intermediate is likely formed via a reaction mechanism in which the prodrug first undergoes full de-esterification followed by intramolecular, hydrolytic cleavage of one of the amino acyl substituents. Formation of the postulated monophosphoramidate intermediate was confirmed following the synthesis of a synthetic standard, Compound C. The standard had the identical HPLC and UV profile as the metabolite formed in plasma samples.

Example K

Metabolism of 50.6 in Human Hepatocytes

Cryopreserved human hepatocytes were obtained from In Vitro Technologies and thawed according to the vendor's recommendations. Cells were incubated at 37° C. in a Krebs-bicarbonate based buffer containing 50.6 at 10 $\mu$M. At various time points over the course of 4 hours, aliquots of cells were removed and extracted by addition of methanol to 60%. Cell extracts were clarified by centrifugation and analyzed by reverse phase HPLC with use of a Beckman Ultrasphere ODS column (4.6×150 mm) equipped with an Alltech All-Guard column. The column was equilibrated with 20 mM potassium phosphate, pH 6.2 and eluted with a linear gradient of 0–60% acetonitrile over 20 minutes at a flow rate of 1.5 mL/min and at a temperature of 40° C. UV absorbance was monitored at 300 nM. 50.6, Compound C, and 3.1 were quantified by comparison to authentic standards. Disappearance of 50.6 was rapid and essentially complete within 60 minutes of incubation. Two metabolites of 50.6 were detected: Compound C and 3.1. The initial rate of 3.1 formation was 24 pmol/million cells/minute. This study indicates that 50.6 is converted to the active FBPase inhibitor, 3.1, in intact human hepatocytes.

Example L

Structure Activity Relationship of Human Liver Phosphoramidase

Human liver, purchased from the Anatomic Gift Foundation (Laurel, Md.), was homogenized in Krebs-bicarbonate buffer and clarified by a slow-speed centrifugation. Prodrug metabolism was evaluated in reaction mixtures containing human liver homogenate (4 mgs protein), 50 mM Tris-HCl, pH 7.4, 10 mM MgCl2, and 10 mM dithiothreitol. At various time intervals over the course of 2 hours, aliquots were removed from the reaction mixtures and deproteinated by addition of methanol to 60%. Following clarification by centrifugation, metabolites were analyzed by reverse phase HPLC with use of a Beckman Ultrasphere ODS column (4.6×150 mm) equipped with an Alltech All-Guard column. The column was equilibrated with 20 mM potassium phosphate, pH 6.2 and eluted with a linear gradient of 0–60% acetonitrile over 20 minutes at a flow rate of 1.5 mL/min and at a temperature of 40° C. UV absorbance was monitored at 300 nM. Most of the prodrugs evaluated were metabolized via a non-rate limiting, esterase-catalyzed step to their monophosphoramidate form within 5 minutes of incubation. The rate of phosphonic acid appearance was therefore essentially a reflection of the rate of the final phosphoramidate-catalyzed cleavage step. Results for representative prodrugs for which the esterase-catalyzed step was non-rate limiting are shown below:

| Prodrug | Phosphoramidase Activity (Rate of 3.1 or 3.58 production, nmoles/mn/mg liver protein) |
| --- | --- |
| 50.6 | 0.022 |
| 50.8 | 0.019 |
| 50.10 | 0.005 |
| 50.12 | 0.022 |
| 50.20 | 0.085 |
| 50.19 | 0.029 |
| 52.8 | 0.025 |
| 52.12 | 0.032 |
| 52.16 | 0.033 |

The results indicate that human liver phosphoramidase readily cleaves the phosphorus-nitrogen bond of a variety of phosphonic acid-monoamidate substrates, thereby liberating the free phosphonic acid FBPase inhibitor. The lowest P-N cleavage rate was observed with a secondary amine substrate, the monophosphoramidate of 50.10. The first step in prodrug activation, esterase-catalyzed de-esterification, was not rate-limiting for the majority of substrates evaluated.

While in accordance with the patent statutes, description of the various embodiments and processing conditions have been provided, the scope of the invention is not to be limited thereto or thereby. Modifications and alterations of the present invention will be apparent to those skilled in the art without departing from the scope and spirit of the present invention. Therefore, it will be appreciated that the scope of this invention is to be defined by the appended claims, rather than by the specific examples which have been presented by way of example.

We claim:

1. A compound of formula IA:

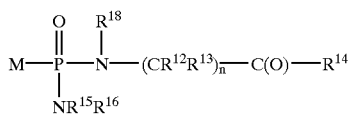

(IA)

wherein M is $R^5$—X—,
wherein:
$R^5$ is represented by the formula

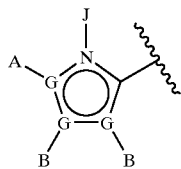

wherein:
each G is independently selected from the group consisting of C, N, O, S, and Se, and wherein only one G may be O, S, or Se, and at most one G is N;
A is selected from the group consisting of —H, —NR$^4_2$, —CONR$^4_2$, —CO$_2$R$^3$, halo, —S(O)R$^3$, —SO$_2$R$^3$, alkyl, alkenyl, alkynyl, perhaloalkyl, haloalkyl, aryl, —CH$_2$OH, —CH$_2$NR$^4_2$, —CH$_2$CN, —CN, —C(S)NH$_2$, —OR$^2$, —SR$^2$, —N$_3$, —NHC(S)NR$^4_2$, —NHAc, and null;
each B is independently selected from the group consisting of —H, alkyl, alkenyl, alkynyl, aryl, alicyclic, aralkyl, alkoxyalkyl, —C(O)R$^{11}$, —C(O)SR$^3$, —SO$_2$R$^{11}$, —S(O)R$^3$, —CN, —NR$^9_2$, —OR$^3$, —SR$^3$, perhaloalkyl, halo, —NO$_2$, and null, all except —H, —CN, perhaloalkyl, —NO$_2$, and halo are optionally substituted;
J is selected from the group consisting of —H and null;
X is an optionally substituted linking group that links $R^5$ to the phosphorus atom via 2–4 atoms, including 0–1 heteroatoms selected from N, O, and S, except that if X is urea or carbamate there are 2 heteroatoms, measured by the shortest path between $R^5$ and the phosphorus atom, and wherein the atom attached to the phosphorus is a carbon atom, and wherein X is selected from the group consisting of -alkyl(hydroxy)-, -alkynyl-, -heteroaryl-, -carbonylalkyl-, -1,1-dihaloalkyl-, -alkoxyalkyl-, -alkyloxy-, -alkylthioalkyl-, -alkylthio-, -alkylaminocarbonyl-, -alkylcarbonylamino-, -alkoxycarbonyl-, -carbonyloxyalkyl-, -alkoxycarbonylamino-, and -alkylaminocarbonylamino-, all optionally substituted; with the proviso that X is not substituted with —COOR$^2$, —SO$_3$H, or —PO$_3$R$^2_2$;
$R^2$ is selected from the group consisting of $R^3$ and —H;
$R^3$ is selected from the group consisting of alkyl, aryl, alicyclic, and aralkyl;
each $R^4$ is independently selected from the group consisting of —H and alkyl or, together, $R^4$ and $R^4$ form a cyclic alkyl group;
each $R^9$ is independently selected from the group consisting of —H, alkyl, aryl, aralkyl, and alicyclic or, together, $R^9$ and $R^9$ form a cyclic alkyl group;
$R^{11}$ is selected from the group consisting of alkyl, aryl, —NR$^2_2$, and —OR$^2$;
each $R^{12}$ and $R^{13}$ is independently selected from the group consisting of H, lower alkyl, lower aryl, lower aralkyl, all optionally substituted, or $R^{12}$ and $R^{13}$ together are connected via 2–6 atoms, optionally including 1–2 heteroatoms selected from the group consisting of O, N and S, to form a cyclic group;
each $R^{14}$ is independently selected from the group consisting of —OR$^{17}$, —N(R$^{17}$)$_2$, —NHR$^{17}$, —NR$^2$OR$^{19}$ and —SR$^{17}$;
$R^{15}$ is selected from the group consisting of —H, lower alkyl, lower aryl, lower aralkyl, or together with $R^{16}$ is connected via 2–6 atoms, optionally including 1 heteroatom selected from the group consisting of O, N, and S;
$R^{16}$ is selected from the group consisting of —(CR$^{12}$R$^{13}$)$_n$—C(O)—R$^{14}$, —H, lower alkyl, lower aryl, lower aralkyl, or together with $R^{15}$ is connected via 2–6 atoms, optionally including 1 heteroatom selected from the group consisting of O, N, and S;
each $R^{17}$ is independently selected from the group consisting of lower alkyl, lower aryl, and lower aralkyl, all optionally substituted, or together $R^{17}$ and $R^{17}$ on N are connected via 2–6 atoms, optionally including 1 heteroatom selected from the group consisting of O, N, and S;
$R^{18}$ is independently selected from the group consisting of H, lower alkyl, aryl, aralkyl, or together with $R^{12}$ is connected via 1–4 carbon atoms to form a cyclic group;

each $R^{19}$ is independently selected from the group consisting of —H, lower alkyl, lower aryl, lower alicyclic, lower aralkyl, and $COR^3$;

and with the proviso that:
1) at least one of A and B, is not —H or null;
2) when G is N, then the respective A or B is not halogen or a group directly bonded to G via a heteroatom;

or a pharmaceutically acceptable salt thereof.

2. The compounds of claim 1 wherein $R^5$ is selected from the group consisting of pyrrolyl, imidazolyl, oxazolyl, thiazolyl, isothiazolyl, 1,2,4-thiadiazolyl, pyrazolyl, isoxazolyl, 1,2,3-oxadiazolyl, 1,2,4-oxadiazolyl, 1,2,5-oxadiazolyl, 1,3,4-oxadiazolyl, 1,2,4-thiadiazolyl, 1,3,4-thiadiazolyl, and 1,3-selenazolyl, all of which contain at least one substituent.

3. The compounds of claim 1 wherein

A is selected from the group consisting of —H, —$NR^4_2$, —$CONR^4_2$, —$CO_2R^3$, halo, C1–C6 alkyl, C2–C6 alkenyl, C2–C6 alkynyl, C1–C6 perhaloalkyl, C1–C6 haloalkyl, aryl, —$CH_2OH$, —$CH_2NR^4_2$, $CH_2CN$, —CN, —$C(S)NH_2$, —$OR^2$, —$SR^2$, —$N_3$, —$NHC(S)NR^4_2$, —NHAc, and null;

each B and D is independently selected from the group consisting of —H, alkyl, alkenyl, alkynyl, aryl, heteroaryl, alicyclic, aralkyl, alkoxyalkyl, —$C(O)R^{11}$, —$C(O)SR^3$, —$SO_2R^{11}$, —$S(O)R^3$, —CN, —$NR^9_2$, —$OR^3$, —$SR^3$, perhaloalkyl, halo, and null, all except —H, —CN, perhaloalkyl, and halo are optionally substituted;

E is selected from the group consisting of —H, C1–C6 alkyl, C2–C6 alkenyl, C2–C6 alkynyl, aryl, C4–C6 alicyclic, alkoxyalkyl, —$C(O)OR^3$, —$CONR^4_2$, —CN, —$NR^9_2$, —$OR^3$, —$SR^3$, C1–C6 perhaloalkyl, halo, and null, all except —H, —CN, perhaloalkyl, and halo are optionally substituted; and each $R^4$ is independently selected from the group consisting of —H and C1–C2 alkyl.

4. The compounds of claim 1 wherein $R^5$ is selected from the group consisting of:

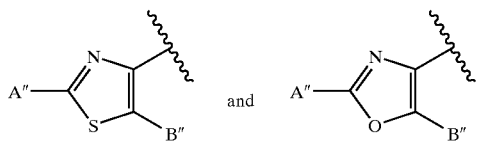

wherein

A" is selected from the group consisting of —H, —$NR^4_2$, —$CONR^4_2$, —$CO_2R^3$, halo, C1–C6 alkyl, C2–C6 alkenyl, C2–C6 alkynyl, C1–C6 perhaloalkyl, C1–C6 haloalkyl, aryl, —$CH_2OH$, —$CH_2NR^4_2$, —$CH_2CN$, —CN, —$C(S)NH_2$, —$OR^2$, —$SR^2$, —$N_3$, —$NHC(S)NR^4_2$, and —NHAc;

B" is independently selected from the group consisting of —H, alkyl, alkenyl, alkynyl, aryl, heteroaryl, alicyclic, aralkyl, alkoxyalkyl, —$C(O)R^{11}$, —$C(O)SR^3$, —$SO_2R^{11}$, —$S(O)R^3$, —CN, —$NR^9_2$, —$OR^3$, —$SR^3$, perhaloalkyl, and halo, all except —H, —CN, perhaloalkyl, and halo are optionally substituted; and each $R^4$ is independently selected from the group consisting of —H and C1–C2 alkyl.

5. The compounds of claim 1 wherein X is selected from the group consisting of -heteroaryl-, -alkylcarbanylamino-, -alkylaminocarbonyl-, and -alkoxycarbonyl-.

6. The compounds of claim 1 wherein said compound is a compound of formulae II, III, or IV:

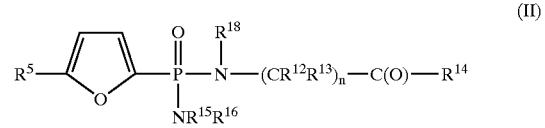

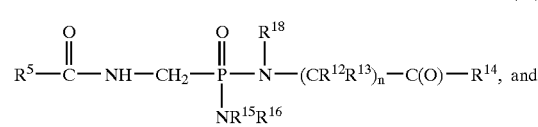

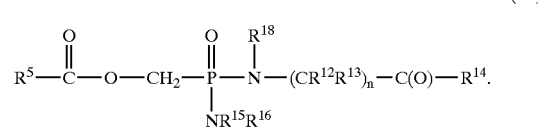

7. The compounds of claim 4 wherein X is selected from the group consisting of -heteroaryl-, -alkoxyalkyl-, -alkylcarbonylamino-, -alkylaminocarbonyl-, and -alkoxycarbonyl-.

8. The compounds of claim 1 wherein n is 1;

$R^{12}$ and $R^{13}$ are independently selected from the group consisting of —H, lower alkyl, lower perhaloalkyl, and lower aryl, optionally substituted with —$OR^{19}$, —$NR^{19}_2$, —$SR^{19}$, —$C(O)NR^2R^3$, halo, —$CO_2R^2$, 3-indolyl, 4-imidazolyl, or guanidinyl, or $R^{12}$ and $R^{13}$ are connected via 2–5 carbon atoms to form a cycloalkyl group;

$R^{14}$ is selected from the group consisting of —$OR^{17}$, —$SR^{17}$, and —$NR^2OR^{19}$ $R^{15}$ and $R^{16}$ are independently selected from the group consisting of —H and C1–C6 alkyl, or together $R^{15}$ and $R^{16}$ are connected via 2–6 atoms, optionally including 1 heteroatom selected from the group consisting of O, N and S;

$R^{17}$ is selected from the group consisting of C1–C7 alkyl, phenyl, indolyl, 3,4-(methylenedioxy)phenyl and benzyl, wherein said phenyl, indolyl, 3,4-(methylenedioxy)phenyl and benzyl may be optionally substituted with 1–3 groups selected from the group of —$CO_2R^2$, —$OR^2$, —$NHC(O)R^3$, halo and lower alkyl; and $R^{18}$ is selected from the group consisting of —H, C1–C6 alkyl and benzyl.

9. The compounds of claim 1 wherein $R^{18}$ is selected from the group consisting of —H and C1–C6 alkyl.

10. The compounds of claim 9 wherein $R^{18}$ is selected from the group consisting of —H and methyl.

11. The compounds of claim 10 wherein $R^{18}$ is —H.

12. The compounds of claim 1 wherein each $R^{12}$ and $R^{13}$ is independently selected from the group consisting of —H, lower alkyl, lower perhaloalkyl, lower aralkyl, and lower aryl, all optionally substituted with —$OR^{19}$, —$NR^{19}_2$, —$SR^{19}$, —$C(O)NR^2R^3$, halo, —$CO_2R^2$, 3-indolyl, 4-imidazolyl, or guanidinyl or, together, $R^{12}$ and $R^{13}$ are connected via 2–5 carbon atoms to form a cycloalkyl group.

13. The compounds of claim 12 wherein each $R^{12}$ and $R^{13}$ is independently selected from the group consisting of —H, C1–C4 alkyl, —$CH_2$—O—$C(CH_3)_3$, phenyl, and benzyl or, together, $R^{12}$ and $R^{13}$ are connected via 2 or 4 carbon atoms to form a cyclopropyl or cyclopentyl group.

14. The compounds of claim 13 wherein each $R^{12}$ and $R^{13}$ is independently selected from the group consisting of —H, and methyl or, together, $R^{12}$ and $R^{13}$ are connected via 4 carbon atoms to form a cyclopentyl group.

15. The compounds of claim 13 wherein $R^{12}$ and $R^{13}$ are both —H, both methyl, or $R^{12}$ is H and $R^{13}$ is selected from the group consisting of methyl, i-propyl, and benzyl.

16. The compounds of claim 15 wherein n is 1, and $R^{12}$ is —H, then the carbon attached to $R^{12}$ and $R^{13}$ has S stereochemistry.

17. The compounds of claim 1 wherein n is an integer of from 1–2.

18. The compounds of claim 17 wherein n is 1.

19. The compounds of claim 1 wherein each $R^{14}$ is independently selected from the group consisting of —$OR^{17}$, —$SR^{17}$, and —$NR^2OR^{19}$, and $R^{17}$ is selected from the group consisting of C1–C7 alkyl, phenyl, indolyl, 3,4-(methylenedioxy)phenyl and benzyl, wherein said phenyl, indolyl, 3,4-(methylenedioxy)phenyl and benzyl may be optionally substituted with 1–3 groups selected from the group consisting of —$CO_2R^2$, —$OR^2$, —$NHC(O)R^3$, halo, and lower alkyl.

20. The compounds of claim 19 wherein $R^{14}$ is —$OR^{17}$.

21. The compounds of claim 20, wherein $R^{17}$ is selected from the group consisting of methyl, ethyl, i-propyl, n-propyl, t-butyl, isobutyl, neopentyl, cyclopentyl, and unsubstituted benzyl.

22. The compounds of claim 1 wherein $R^{15}$ and $R^{16}$ are independently selected from the group consisting of —H and C1–C6 alkyl or, together, $R^{15}$ and $R^{16}$ are connected via 2–6 atoms, optionally including 1 heteroatom selected from the group consisting of O, N, and S.

23. The compounds of claim 22 wherein —$NR^{15}R^{16}$ is selected from the group consisting of morpholinyl and pyrrolidinyl.

24. The compounds of claim 1 wherein $R^{16}$ is —$(CR^{12}R^{13})_n$—C(O)—$R^{14}$, and each n is 1.

25. The compounds of claim 1 wherein n is 1;

$R^{12}$ and $R^{13}$ are independently selected from the group consisting of —H, lower alkyl, lower perhaloalkyl, and lower aryl, optionally substituted with —$OR^{19}$, —$NR^{19}_2$, —$SR^{19}$, —$C(O)NR^2R^3$, halo, —$CO_2R^2$, 3-indolyl, 4-imidazolyl, and guanidinyl, or $R^{12}$ and $R^{13}$ are connected via 2–5 carbon atoms to form a cycloalkyl group;

$R^{14}$ is selected from the group consisting of —$OR^{17}$, —$SR^{17}$, and —$NR^2OR^{19}$;

$R^{15}$ is selected from the group consisting of —H and C1–C6 alkyl;

$R^{16}$ is selected from the group consisting of —H, C1–C6 alkyl, and —$(CR^{12}R^{13})_n$—C(O)—$R^{14}$ or, together, $R^{15}$ and $R^{16}$ are connected via 2–6 atoms, optionally including 1 heteroatom selected from the group consisting of N, O and S;

$R^{17}$ is selected from the group consisting of C1–C7 alkyl, phenyl, indolyl, 3,4-(methylenedioxy)phenyl, and benzyl, wherein said phenyl, indolyl, 3,4-(methylenedioxy)phenyl, and benzyl may be optionally substituted with 1–3 groups selected from the group of —$CO_2R^2$, —$OR^3$, —$NHC(O)R^3$, halo, and lower alkyl; and $R^{18}$ is selected from the consisting of —H, C1–C6 alkyl, and benzyl.

26. The compounds of claim 25 that are of the formula:

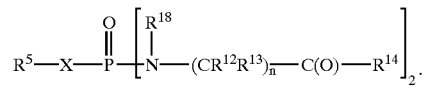

27. The compounds of claim 26 wherein n is 1.

28. The compounds of claim 27 wherein when $R^{12}$ and $R^{13}$ are not the same, then $R^{18}HN$—$CR^{12}R^{13}$—C(O)—$R^{14}$ is an ester or thioester of a naturally occurring amino acid; and $R^{14}$ is selected from the group consisting of —$OR^{17}$ and —$SR^{17}$.

29. The compounds of claim 4 wherein

A″ is selected from the group consisting of —$NH_2$, —$CONH_2$, halo, —$CH_3$, —$CF_3$, —$CH_2$-halo, —CN, —$OCH_3$, —$SCH_3$, and —H;

B″ is selected from the group consisting of —H, —C(O)$R^{11}$, —C(O)$SR^3$, alkyl, aryl, alicyclic, halo, —CN, —$SR^3$, $OR^3$, and —$NR^2$;

X is selected from the group consisting of -heteroaryl-, -alkoxycarbonyl-, and -alkylaminocarbonyl-, all optionally substituted;

$R^2$ is selected from the group consisting of $R^3$ and —H;

$R^3$ is selected from the group consisting of C1–C4 alkyl, C4–C6 aryl, C2–C7 alicyclic, and C5–C7 aralkyl, wherein said aryl, alicyclic, and aralkyl may be optionally substituted with 1–2 heteroatoms;

each $R^{12}$ and $R^{13}$ is independently selected from the group consisting of —H, C1–C4 alkyl, —$CH_2$—O—$C(CH_3)_3$, phenyl, and benzyl or, together, $R^{12}$ and $R^{13}$ are connected via 2 or 4 carbon atoms to form a cyclopropyl or cyclopentyl group;

n is 1;

each $R^{14}$ is independently selected from the group consisting of —$OR^{17}$, —$SR^{17}$, and —$NR^2OR^{19}$;

$R^{15}$ is selected from the group consisting of —H, methyl, ethyl, and propyl;

$R^{16}$ is —$(CR^{12}R^{13})_n$—C(O)—$R^{14}$;

$R^{17}$ is selected from the group consisting of C1–C7 alkyl, phenyl, indolyl, and benzyl, wherein said phenyl, indolyl, and benzyl may be optionally substituted with 1–3 groups selected from the group consisting of —$CO_2R^2$, —$OR^3$, —$NHC(O)R^3$, halo, and lower alkyl;

$R^{18}$ is selected from the group consisting of —H and methyl; and $R^{19}$ is selected from the group of —H, C1–C4 alkyl, C4–C6 aryl, C2–C7 alicyclic, C5–C7 aralkyl, and —$COR^3$.

30. The compounds of claim 29 wherein

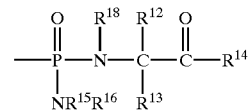

is selected from the group consisting of

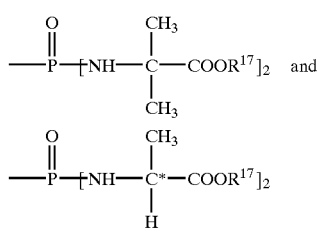 and wherein $R^{17}$ is selected from group consisting of ethyl, i-propyl, n-propyl, and neopentyl.

31. The compounds of claim 30 wherein C* has S stereochemistry.

32. The compounds of claim 29 wherein $R^5$ is

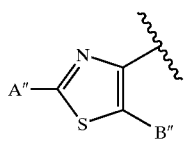

X is selected from the group consisting of methylenoxycarbonyl, and furan-2,5-diyl, or a pharmaceutically acceptable salt thereof.

33. The compounds of claim 32 wherein A" is —NH$_2$, X is furan-2,5-diyl, and B" is —S(CH$_2$)$_2$CH$_3$.

34. The compounds of claim 32 wherein A" is —NH$_2$, X is furan-2,5-diyl, and B" is —CH$_2$—CH(CH$_3$)$_2$.

35. The compounds of claim 32 wherein A" is —NH$_2$, X is furan-2,5-diyl, and B" is —COOEt.

36. The compounds of claim 32 wherein A" is —NH$_2$, X is furan-2,5-diyl, and B" is —SMe.

37. The compounds of claim 32 wherein A" is —NH$_2$, X is methyleneoxycarbonyl, and B" is —CH(CH$_3$)$_2$.

38. The compounds of claim 33 wherein

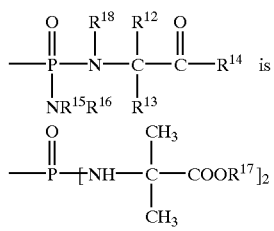

wherein $R^{17}$ is selected from the group consisting of ethyl, i-propyl, n-propyl, and neopentyl.

39. The compounds of claim 33 wherein

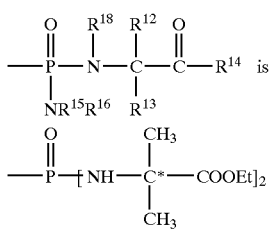

and wherein C* has S stereochemistry and wherein $R^{17}$ is selected from the group consisting of ethyl, i-propyl, n-propyl, and neopentyl.

40. The compounds of claim 34 wherein

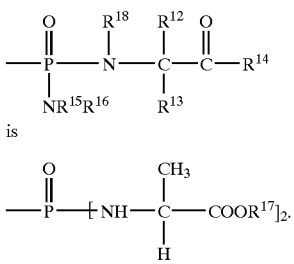

41. The compounds of claim 34 wherein

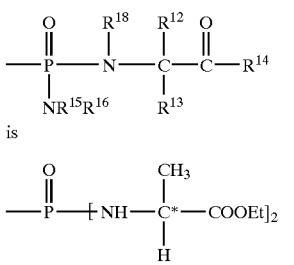

wherein C* has S stereochemistry.

42. The compounds of claim 41 that are selected from the group consisting of a hydrochloride salt, a hydrobromide salt, an acetic acid salt, a trifluoroacetic acid salt, a methanesulfonic acid salt, a p-toluenesulfonic acid salt, and maleic acid salt.

43. The compounds of claim 34 wherein

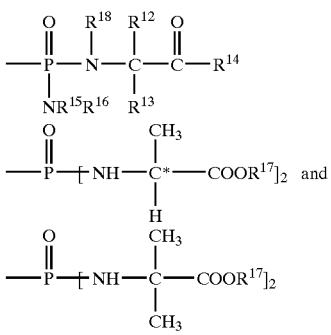

wherein $R^{17}$ is ethyl, n-propyl, i-propyl, and neopentyl and wherein C* has S stereochemistry.

44. The compounds of claim 43 that are selected from the group consisting of a hydrochloride salt, a hydrobromide salt, an acetic acid salt, a trifluoroacetic acid salt, a methanesulfonic acid salt, a p-toluenesulfonic acid salt, and a maleic acid salt.

45. The compounds of claim 34 wherein

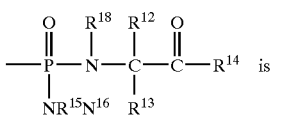

-continued

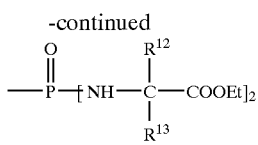

wherein $R^{12}$ and $R^{13}$ together form a cyclopentyl group.

46. The compounds of claim 45 that are selected from the group consisting of a hydrochloride salt, a hydrobromide salt, an acetic acid salt, a trifluoroacetic acid salt, a methanesulfonic acid salt, a p-toluenesulfonic acid salt, and a maleic acid salt.

47. The compounds of claim 36 wherein

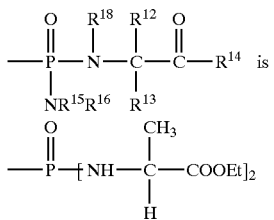

is wherein C* has S sterochemistry.

48. The compounds of claim 47 that are selected from the group consisting of a hydrochloride salt, a hydrobromide salt, an acetic acid salt, a trifluoroacetic acid salt, a methanesulfonic acid salt, a p-toluenesulfonic acid salt, and a maleic acid salt.

49. The compounds of claim 29 wherein $R^5$ is

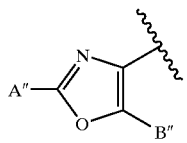

X is selected from the group consisting of furan-2,5-diyl, and methyleneoxycarbonyl, A″ is —NH₂, and pharmaceutically acceptable salts thereof.

50. The compounds of claim 49 wherein X is furan-2,5-diyl and B″ is —SCH₂CH₂CH₃.

51. A method of treating diabetes comprising administering to an animal a pharmaceutically effective amount of a compound of formula (I):

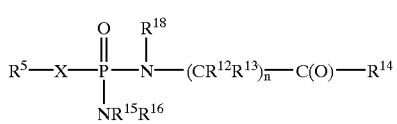

(I)

wherein $R^5$ is represented by the formula:

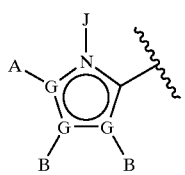

wherein:

each G is independently selected from the group consisting of C, N, O, S, and Se, and wherein only one G may be O, S, or Se, and at most one G is N;

A is selected from the group consisting of —H, —NR⁴₂, —CONR⁴₂, —CO₂R³, halo, —S(O)R³, —SO₂R³, alkyl, alkenyl, alkynyl, perhaloalkyl, haloalkyl, aryl, —CH₂OH, —CH₂NR⁴₂, —CH₂CN, —CN, —C(S)NH₂, —OR², —SR², —N₃, —NHC(S)NR⁴₂, —NHAc, and null;

each B is independently selected from the group consisting of —H, alkyl, alkenyl, alkynyl, aryl, alicyclic, aralkyl, alkoxyalkyl, —C(O)R¹¹, —C(O)SR³, —SO₂R¹¹, —S(O)R³, —CN, —NR⁹₂, —OR³, —SR³, perhaloalkyl, halo, —NO₂, and null, all except —H, —CN, perhaloalkyl, —NO₂, and halo are optionally substituted;

J is selected from the group consisting of —H and null;

X is an optionally substituted linking group that links $R^5$ to the phosphorus atom via 2–4 atoms, including 0–1 heteroatoms selected from N, O, and S, except that if X is urea or carbamate there are 2 heteroatoms, measured by the shortest path between $R^3$ and the phosphorus atom, and wherein the atom attached to the phosphorus is a carbon atom, and wherein X is selected from the group consisting of -alkyl(hydroxy)-, -alkynyl-, -heteroaryl-, -carbonylalkyl-, -1,1-dihaloalkyl-, -alkoxyalkyl-, -alkyloxy-, -alkylthioalkyl-, -alkylthio-, -alkylaminocarbonyl-, -alkylcarbonylamino-, -alkoxycarbonyl-, -carbonyloxyalkyl-, -alkoxycarbonylamino-, and -alkylaminocarbonylamino-, all optionally substituted; with the proviso that X is not substituted with —COOR², —SO₃H, or —PO₃R²₂;

n is an integer from 1 to 3;

$R^2$ is selected from the group consisting of $R^3$ and —H;

$R^3$ is selected from the group consisting of alkyl, aryl, alicyclic, and aralkyl;

each $R^4$ is independently selected from the group consisting of —H and alkyl or, together, $R^4$ and $R^4$ form a cyclic alkyl group;

each $R^9$ is independently selected from the group consisting of —H, alkyl, aralkyl, and alicyclic or, together, $R^9$ and $R^9$ form a cyclic alkyl group;

$R^{11}$ is selected from the group consisting of alkyl, aryl, —NR²₂, and —OR²;

each $R^{12}$ and $R^{13}$ is independently selected from the group consisting of H, lower alkyl, lower aryl, lower aralkyl, all optionally substituted, or $R^{12}$ and $R^{13}$ together are connected via 2–6 atoms, optionally including 1–2 heteroatoms selected from the group consisting of O, N and S, to form a cyclic group;

each $R^{14}$ is independently selected from the group consisting of —OR¹⁷, —N(R¹⁷)₂, —NHR¹⁷, —NR²OR¹⁹ and —SR¹⁷;

$R^{15}$ is selected from the group consisting of —H, lower alkyl, lower aryl, and lower aralkyl or, together, with $R^{16}$ is connected via 2–6 atoms, optionally including 1 heteroatom selected from the group consisting of O, N, and S;

$R^{16}$ is selected from the group consisting of —(CR¹²R¹³)ₙ—C(O)—R¹⁴, —H, lower alkyl, lower aryl, and lower aralkyl or, together, with $R^{15}$ is connected via 2–6 atoms, optionally including 1 heteroatom selected from the group consisting of O, N, and S;

each $R^{17}$ is independently selected from the group consisting of lower alkyl, lower aryl, and lower aralkyl, all optionally substituted, or together $R^{17}$ and $R^{17}$ on N are connected via 2–6 atoms, optionally including 1 heteroatom selected from the group consisting of O, N, and S;

$R^{18}$ is independently selected from the group consisting of H, lower alkyl, aryl, and aralkyl or, together, with $R^{12}$ is connected via 1–4 carbon atoms to form a cyclic group;

each $R^{19}$ is independently selected from the group consisting of —H, lower alkyl, lower aryl, lower alicyclic, lower aralkyl, and $COR^3$;

and with the provisos that:

1) at least one of A and B is not selected from the group consisting of —H or null;
2) when G is N, then the respective A or B is not halogen or a group directly bonded to G via a heteroatom;

or a pharmaceutically acceptable salt thereof.

52. A method of treating complications of diabetes or cardiovascular diseases in an animal comprising administering to said animal a pharmaceutically effective amount of a compound of formula (I):

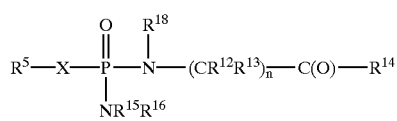

(I)

wherein $R^5$ represented by the formula:

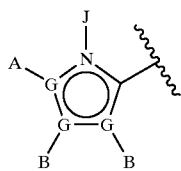

wherein:
 each G is independently selected from the group consisting of C, N, O, S, and Se, and wherein only one G may be O, S, or Se, and at most one G is N;
 A is selected from the group consisting of —H, —$NR^4_2$, —$CONR^4_2$, —$CO_2R^3$, halo, —$S(O)R^3$, —$SO_2R^3$, alkyl, alkenyl, alkynyl, perhaloalkyl, haloalkyl, aryl, —$CH_2OH$, —$CH_2NR^4_2$, —$CH_2CN$, —CN, —C(S)$NH_2$, —$OR^2$, —$SR^2$, —$N_3$, —$NHC(S)NR^4_2$, —NHAc, and null;
 each B is independently selected from the group consisting of —H, alkyl, alkenyl, alkynyl, aryl, alicyclic, aralkyl, alkoxyalkyl, —$C(O)R^{11}$, —$C(O)SR^3$, —$SO_2R^{11}$, —$S(O)R^3$, —CN, —$NR^9_2$, —$OR^3$, —$SR^3$, perhaloalkyl, halo, —$NO_2$, and null, all except —H, —CN, perhaloalkyl, —$NO_2$, and halo are optionally substituted;
 J is selected from the group consisting of —H and null;
 X is an optionally substituted linking group that links $R^5$ to the phosphorus atom via 2–4 atoms, including 0–1 heteroatoms selected from N, O, and S, except that if X is urea or carbamate there is 2 heteroatoms, measured by the shortest path between $R^5$ and the phosphorus atom, and wherein the atom attached to the phosphorus is a carbon atom, and wherein X is selected from the group consisting of -alkyl(hydroxy)-, -alkynyl-, -heteroaryl-, -carbonylalkyl-, -1,1-dihaloalkyl-, -alkoxyalkyl-, -alkyloxy-, -alkylthioalkyl-, -alkylthio-, -alkylaminocarbonyl-, -alkylcarbonylamino-, -alkoxycarbonyl-, -carbonyloxyalkyl-, -alkoxycarbonylamino-, and -alkylaminocarbonylamino-, all optionally substituted; with the proviso that X is not substituted with —$COOR^2$, —$SO_3H$, or —$PO_3R^2_2$;

n is an integer from 1 to 3;

$R^2$ is selected from the group consisting of $R^3$ and —H;

$R^3$ is selected from the group consisting of alkyl, aryl, alicyclic, and aralkyl;

each $R^4$ is independently selected from the group consisting of —H, and alkyl, or together $R^4$ and $R^4$ form a cyclic alkyl group;

each $R^9$ is independently selected from the group consisting of —H, alkyl, aralkyl, and alicyclic, or together $R^9$ and $R^9$ form a cyclic alkyl group;

$R^{11}$ is selected from the group consisting of alkyl, aryl, —$NR^2_2$, and —$OR^2$;

each $R^{12}$ and $R^{13}$ is independently selected from the group consisting of H, lower alkyl, lower aryl, lower aralkyl, all optionally substituted, or $R^{12}$ and $R^{13}$ together are connected via 2–6 atoms, optionally including 1–2 heteroatoms selected from the group consisting of O, N and S, to form a cyclic group;

each $R^{14}$ is independently selected from the group consisting of —$OR^{17}$, —$N(R^{17})_2$, —$NHR^{17}$, —$NR^2OR^{19}$ and —$SR^{17}$;

$R^{15}$ is selected from the group consisting of —H, lower alkyl, lower aryl, lower aralkyl, or together with $R^{16}$ is connected via 2–6 atoms, optionally including 1 heteroatom selected from the group consisting of O, N, and S;

$R^{16}$ is selected from the group consisting of —$(CR^{12}R^{13})_n$—$C(O)$—$R^{14}$, —H, lower alkyl, lower aryl, lower aralkyl, or together with $R^{15}$ is connected via 2–6 atoms, optionally including 1 heteroatom selected from the group consisting of O, N, and S;

each $R^{17}$ is independently selected from the group consisting of lower alkyl, lower aryl, and lower aralkyl, all optionally substituted, or together $R^{17}$ and $R^{17}$ on N is connected via 2–6 atoms, optionally including 1 heteroatom selected from group consisting of O, N, and S;

$R^{18}$ is independently selected, from the group consisting of H, lower alkyl, aryl, aralkyl, or together with $R^{12}$ is connected via 1–4 carbon atoms to form a cyclic group;

each $R^{19}$ is independently selected from the group consisting of —H, lower alkyl, lower aryl, lower alicyclic, lower aralkyl, and $COR^3$;

and with the proviso that:

1) at least one of A and B is not selected from the group consisting of —H or null;
2) when G is N, then the respective A or B is not halogen or a group directly bonded to G via a heteroatom;

or a pharmaceutically acceptable salt thereof.

53. A method of lowering blood glucose comprising administering to an animal a pharmaceutically effective amount of compound of formula (I):

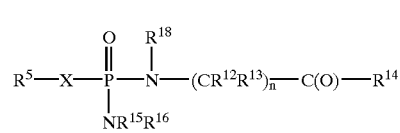

(I)

wherein $R^5$ represented by the formula:

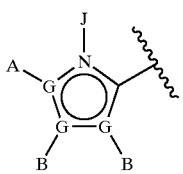

wherein:
- each G is independently selected from the group consisting of C, N, O, S, and Se, and wherein only one G may be O, S, or Se, and at most one G is N;
- A is selected from the group consisting of —H, —NR$^4_2$, —CONR$^4_2$, —CO$_2$R$^3$, halo, —S(O)R$^3$, —SO$_2$R$^3$, alkyl, alkenyl, alkynyl, perhaloalkyl, haloalkyl, aryl, —CH$_2$OH, —CH$_2$NR$^4_2$, —CH$_2$CN, —CN, —C(S)NH$_2$, —OR$^2$, —SR$^2$, —N$_3$, —NHC(S)NR$^4_2$, —NHAc, and null;
- each B is independently selected from the group consisting of —H, alkyl, alkenyl, alkynyl, aryl, alicyclic, aralkyl, alkoxyalkyl, —C(O)R$^{11}$, —C(O)SR$^3$, —SO$_2$R$^{11}$, —S(O)R$^3$, —CN, —NR$^9_2$, —OR$^3$, —SR$^3$, perhaloalkyl, halo, —NO$_2$, and null, all except —H, —CN, perhaloalkyl, —NO$_2$, and halo are optionally substituted;
- J is selected from the group consisting of —H and null;
- X is an optionally substituted linking group that links R$^5$ to the phosphorus atom via 2–4 atoms, including 0–1 heteroatoms selected from N, O, and S, except that if X is urea or carbamate there is 2 heteroatoms, measured by the shortest path between R$^5$ and the phosphorus atom, and wherein the atom attached to the phosphorus is a carbon atom, and wherein X is selected from the group consisting of -alkyl(hydroxy)-, -alkynyl-, -heteroaryl-, -carbonylalkyl-, -1,1-dihaloalkyl-, -alkoxyalkyl-, -alkyloxy-, -alkylthioalkyl-, -alkylthio-, -alkylaminocarbonyl-, -alkylcarbonylamino-, -alkoxycarbonyl-, -carbonyloxyalkyl-, -alkoxycarbonylamino-, and -alkylaminocarbonylamino-, all optionally substituted; with the proviso that X is not substituted with —COOR$^2$, —SO$_3$H, or —PO$_3$R$^2_2$;
- n is an integer from 1 to 3;
- R$^2$ is selected from the group consisting of R$^3$ and —H;
- R$^3$ is selected from the group consisting of alkyl, aryl, alicyclic, and aralkyl;
- each R$^4$ is independently selected from the group consisting of —H, and alkyl, or together R$^4$ and R$^4$ form a cyclic alkyl group;
- each R$^9$ is independently selected from the group consisting of —H, alkyl, aralkyl, and alicyclic, or together R$^9$ and R$^9$ form a cyclic alkyl group;
- R$^{11}$ is selected from the group consisting of alkyl, aryl, —NR$^2_2$, and —OR$^2$;
- each R$^{12}$ and R$^{13}$ is independently selected from the group consisting of H, lower alkyl, lower aryl, lower aralkyl, all optionally substituted, or R$^{12}$ and R$^{13}$ together are connected via 2–6 atoms, optionally including 1–2 heteroatoms selected from the group consisting of O, N and S, to form a cyclic group;
- each R$^{14}$ is independently selected from the group consisting of —OR$^{17}$, —N(R$^{17}$)$_2$, —NHR$^{17}$, —NR$^2$OR$^{19}$ and —SR$^{17}$;
- R$^{15}$ is selected from the group consisting of —H, lower alkyl, lower aryl, lower aralkyl, or together with R$^{16}$ is connected via 2–6 atoms, optionally including 1 heteroatom selected from the group consisting of O, N, and S;
- R$^{16}$ is selected from the group consisting of —(CR$^{12}$R$^{13}$)$_n$—C(O)—R$^{14}$, —H, lower alkyl, lower aryl, lower aralkyl, or together with R$^{15}$ is connected via 2–6 atoms, optionally including 1 heteroatom selected from the group consisting of O, N, and S;
- each R$^{17}$ is independently selected from the group consisting of lower alkyl, lower aryl, and lower aralkyl, all optionally substituted, or together R$^{17}$ and R$^{17}$ on N is connected via 2–6 atoms, optionally including 1 heteroatom selected from the group consisting of O, N, and S;
- R$^{18}$ is independently selected, from the group consisting of H, lower alkyl, aryl, aralkyl, or together with R$^{12}$ is connected via 1–4 carbon atoms to form a cyclic group;
- each R$^{19}$ is independently selected from the group consisting of —H, lower alkyl, lower aryl, lower alicyclic, lower aralkyl, and COR$^3$;

and with the proviso that:
1) at least one of A and B is not selected from the group consisting of —H or null;
2) when G is N, then the respective A or B is not halogen or a group directly bonded to G via a heteroatom;

and pharmaceutically acceptable salts thereof.

54. A method of treating glycogen storage diseases, by administering to a patient a pharmaceutically effective amount of a compound of formula (I):

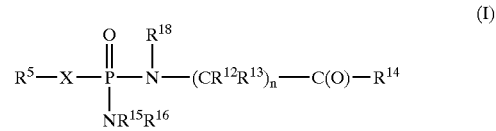

(I)

wherein R$^5$ is selected from the group consisting of:

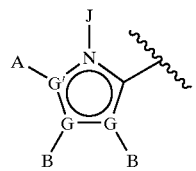

wherein
- each G is independently selected from the group consisting of C, N, O, S, and Se, and wherein only one G may be O, S, or Se, and at most one G is N;
- A is selected from the group consisting of —H, —NR$^4_2$, —CONR$^4_2$, —CO$_2$R$^3$, halo, —S(O)R$^3$, —SO$_2$R$^3$, alkyl, alkenyl, alkynyl, perhaloalkyl, haloalkyl, aryl, —CH$_2$OH, —CH$_2$NR$^4_2$, —CH$_2$CN, —CN, —C(S)NH$_2$, —OR$^2$, —SR$^2$, —N$_3$, —NHC(S)NR$^4_2$, —NHAc, and null;
- each B is independently selected from the group consisting of —H, alkyl, alkenyl, alkynyl, aryl, alicyclic, aralkyl, alkoxyalkyl, —C(O)R$^{11}$, —C(O)SR$^3$, —SO$_2$R$^{11}$, —S(O)R$^3$, —CN, —NR$^9_2$, —OR$^3$, —SR$^3$, perhaloalkyl, halo, —NO$_2$, and null, all except —H, —CN, perhaloalkyl, —NO$_2$, and halo are optionally substituted;
- J is selected from the group consisting of —H and null;
- X is an optionally substituted linking group that links R$^5$ to the phosphorus atom via 2–4 atoms, including 0–1 heteroatoms selected from N, O, and S, except that if X is urea or carbamate there is 2 heteroatoms, measured by the shortest path between $R^5$ and the phosphorus atom, and wherein the atom attached to the phosphorus is a carbon atom, and wherein X is selected from the group consisting of -alkyl(hydroxy)-, -alkynyl-, -heteroaryl-, -carbonylalkyl-, -1,1-dihaloalkyl-, -alkoxyalkyl-, -alkyloxy-, -alkylthioalkyl-, -alkylthio-, -alkylaminocarbonyl-, -alkylcarbonylamino-, -alkoxycarbonyl-, -carbonyloxyalkyl-, -alkoxycarbonylamino-, and -alkylaminocarbonylamino-, all optionally substituted; with the proviso that X is not substituted with —$COOR^2$, —$SO_3H$, or —$PO_3R^2_2$;

n is an integer from 1 to 3;

$R^2$ is selected from the group consisting of $R^3$ and —H;

$R^3$ is selected from the group consisting of alkyl, aryl, alicyclic, and aralkyl;

each $R^4$ is independently selected from the group consisting of —H, and alkyl, or together $R^4$ and $R^4$ form a cyclic alkyl group;

each $R^9$ is independently selected from the group consisting of —H, alkyl, aralkyl, and alicyclic, or together $R^9$ and $R^9$ form a cyclic alkyl group;

$R^{11}$ is selected from the group consisting of alkyl, aryl, —$NR^2_2$, and —$OR^2$;

each $R^{12}$ and $R^{13}$ is independently selected from the group consisting of H, lower alkyl, lower aryl, lower aralkyl, all optionally substituted, or $R^{12}$ and $R^{13}$ together are connected via 2–6 atoms, optionally including 1–2 heteroatoms selected from the group consisting of O, N and S, to form a cyclic group;

each $R^{14}$ is independently selected from the group consisting of —$OR^{17}$, —$N(R^{17})_2$, —$NHR^{17}$, —$NR^2OR^{19}$ and —$SR^{17}$;

$R^{15}$ is selected from the group consisting of —H, lower alkyl, lower aryl, lower aralkyl, or together with $R^{16}$ is connected via 2–6 atoms, optionally including 1 heteroatom selected from the group consisting of O, N, and S;

$R^{16}$ is selected from the group consisting of —$(CR^{12}R^{13})_n$—C(O)—$R^{14}$, —H, lower alkyl, lower aryl, lower aralkyl, or together with $R^{15}$ is connected via 2–6 atoms, optionally including 1 heteroatom selected from the group consisting of O, N, and S;

each $R^{17}$ is independently selected from the group consisting of lower alkyl, lower aryl, and lower aralkyl, all optionally substituted, or together $R^{17}$ and $R^{17}$ on N is connected via 2–6 atoms, optionally including 1 heteroatom selected from the group consisting of O, N, and S;

$R^{18}$ is independently selected, from the group consisting of H, lower alkyl, aryl, aralkyl, or together with $R^{12}$ is connected via 1–4 carbon atoms to form a cyclic group;

each $R^{19}$ is independently selected from the group consisting of —H, lower alkyl, lower aryl, lower alicyclic, lower aralkyl, and $COR^3$;

and with the proviso that:

1) at least one of A and B is not selected from the group consisting of —H or null;

2) when G is N, then the respective A or B is not halogen or a group directly bonded to G via a heteroatom;

and pharmaceutically acceptable salts thereof.

55. A method of inhibiting gluconeogenesis in an animal comprising administering to said animal a pharmaceutically effective amount of a compound of claim 1.

* * * * *

UNITED STATES PATENT AND TRADEMARK OFFICE
CERTIFICATE OF CORRECTION

PATENT NO. : 6,965,033 B2  Page 1 of 1
APPLICATION NO. : 09/747182
DATED : November 15, 2005
INVENTOR(S) : Tao Jiang, Srinivas Kasibhatla and K. R. Reddy It is certified that error appears in the above-identified patent and that said Letters Patent is hereby corrected as shown below:

Column 142,
Lines 27-28:  "—COOR$^2$, —SO$_3$H, or —PO$_3$R$^2_2$;
R$^2$ is selected from the group consisting of R$^3$ and —H;"

should read

-- —COOR$^2$, —SO$_3$H, or —PO$_3$R$^2_2$;
n is an integer from 1 to 3;
R$^2$ is selected from the group consisting of R$^3$ and —H;--.

Column 148,
Lines 40-45:

"  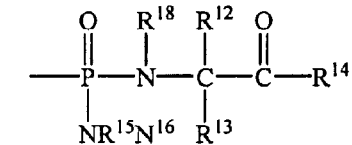  should read --  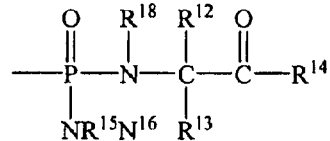

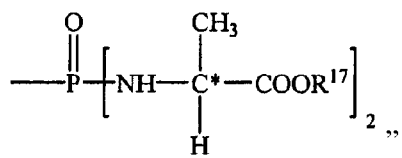  is selected from the group consisting of

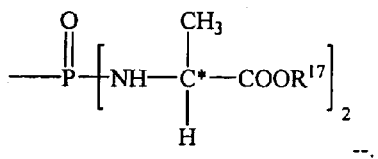

  --.

Signed and Sealed this

Fifth Day of February, 2008

UNITED STATES PATENT AND TRADEMARK OFFICE
CERTIFICATE OF CORRECTION

PATENT NO. : 6,965,033 B2  Page 1 of 7
APPLICATION NO. : 09/747182
DATED : November 15, 2005
INVENTOR(S) : Tao Jiang, Srinivas Kasibhatla and K. R. Reddy It is certified that error appears in the above-identified patent and that said Letters Patent is hereby corrected as shown below:

Column 5,
Line 43, "norbomyl" should read --norbornyl--.

Column 15,
Line 8-11, Table A, Row $R^2$, Markush Group B, "—H, lower alkyl, lower alkyl, lower alicyclic and lower aralkyl" should read -- —H, lower alkyl, lower aryl, lower alicyclic and lower aralkyl--.

Column 17,
Lines 3-5, Table A,

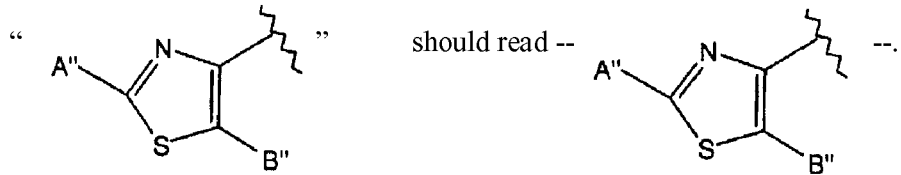

Column 18,
Table A, Markush Group D,

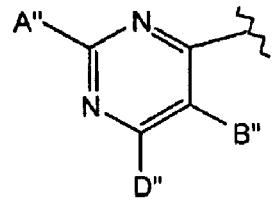

UNITED STATES PATENT AND TRADEMARK OFFICE
CERTIFICATE OF CORRECTION

| | |
|---|---|
| PATENT NO. | : 6,965,033 B2 |
| APPLICATION NO. | : 09/747182 |
| DATED | : November 15, 2005 |
| INVENTOR(S) | : Tao Jiang, Srinivas Kasibhatla and K. R. Reddy |

Page 2 of 7

It is certified that error appears in the above-identified patent and that said Letters Patent is hereby corrected as shown below:

Column 19,
Table A, Row $R^{12}$, Markush Group A, "—H, lower alkyl, lower perhaloalkyl, lower aryl, optionally substituted with —$OR^{19}$, -$NR_2^{19}$, -$SR^{19}$, -$C(O)$-$NR^{21}R^3$, halo, -$CO_2R^2$, 3-indolyl, 4-imidazolyl, or guandinyl; or" should read -- —H, lower alkyl, lower perhaloalkyl, lower aralkyl, lower aryl, optionally substituted with —$OR^{19}$, -$NR^{19}_2$, -$SR^{19}$, -$C(O)$-$NR^2R^3$, halo, -$CO_2R^2$, 3-indolyl, 4-imidazolyl, or guandinyl; or--.

Table A, Row $R^{12}$, Markush Group C,

" " should read -- --.

| –H, C1-C4 alkyl, and benzyl; or | –H, lower alkyl, lower perhaloalkyl optionally substituted with -$OR^{19}$, -$NR^{19}_2$, -$SR^{19}$, -$C(O)$-$NR^2R^3$, halogen, -$CO_2R^2$, 3-indolyl, 4-imidazolyl, or guanidinyl; or |
|---|---|

| –H, C1-C4 alkyl, phenyl, and benzyl; or | –H, lower alkyl, lower perhaloalkyl, and lower aryl, optionally substituted with -$OR^{19}$, -$NR^{19}_2$, -$SR^{19}$, -$C(O)$-$NR^2R^3$, halogen, -$CO_2R^2$, 3-indolyl, 4-imidazolyl, or guanidinyl; or |
|---|---|

Column 20,
Table A, Row $R^{12}$, Markush Group D,
"—H, C1-C4 alkyl, —$CH_2$—O—$C(CH_3)_3$, phenyl, aryl, and benzyl; or" should read -- —H, C1-C4 alkyl, —$CH_2$—O—$C(CH_3)_3$, phenyl, and benzyl; or--.

Column 21,
Table A, Row $R^{16}$, Markush Group A,
"—H, lower alkyl, lower aryl, and lower arylalkyl, or" should read
-- —H, lower alkyl, lower aryl, and lower aralkyl, or--.

UNITED STATES PATENT AND TRADEMARK OFFICE
CERTIFICATE OF CORRECTION

PATENT NO. : 6,965,033 B2  
APPLICATION NO. : 09/747182  
DATED : November 15, 2005  
INVENTOR(S) : Tao Jiang, Srinivas Kasibhatla and K. R. Reddy Page 3 of 7

It is certified that error appears in the above-identified patent and that said Letters Patent is hereby corrected as shown below:

Column 62,  
Formula I, Structure 3,

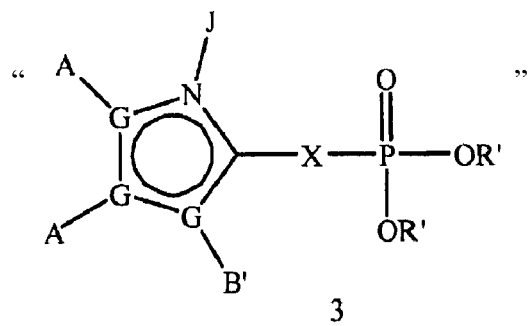

should read

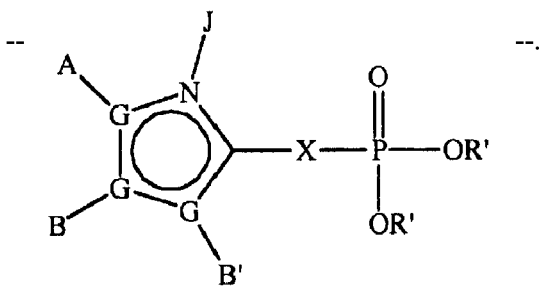

Column 73,  
Line 61, "can made" should read --can be made--.

Column 78,  
Line 16, "5-diethylnhosphono-2-furaldehyde" should read  
--5-diethylphosphono-2-furaldehyde--.  
Lines 50-51, "to give.furan-2- (N,N'-dimethylimidazolidine)" should read  
--to give furan-2- (N,N'-dimethylimidazolidine)--.

Column 80,  
Line 64, "fiuanyl]" should read --furanyl]--.

UNITED STATES PATENT AND TRADEMARK OFFICE
CERTIFICATE OF CORRECTION

PATENT NO. : 6,965,033 B2
APPLICATION NO. : 09/747182
DATED : November 15, 2005
INVENTOR(S) : Tao Jiang, Srinivas Kasibhatla and K. R. Reddy It is certified that error appears in the above-identified patent and that said Letters Patent is hereby corrected as shown below:

Column 83,
Line 26, "(decom p)" should read --(decomp)--.

Column 89,
Line 2, "Preparation of 4-[12-(5-phosphono)" should read
    --Preparation of 4-[2-(5-phosphono)--.

Column 92,
Line 29, "N-alkylated 4-[12-(5-phosphono)" should read
    --N-alkylated 4-[2-(5-phosphono)--.
Line 48, "39.663" should read --39.63--.

Column 99,
Line 32, "diethyllphosphonomethoxycarbonylthiazole" should read
    --diethylphosphonomethoxycarbonylthiazole--.
Line 34, "diethyllphosphonomethoxycarbonylthiazole" should read
    --diethylphosphonomethoxycarbonylthiazole--.
Line 44, "room, temperature" should read --room temperature--.

Column 102,
Line 32, "MS calcd" should read --Anal. calcd.--.

Column 106,
Line 8, "to give gave 2" should read --to give 2--.

Column 107,
Lines 45-46, "C, 24.70; H, 3.32; N: 23.05. Found: C, 24.57; H, 2.57; N: 23.05."
should read --C: 24.70; H, 3.32; N: 23.05. Found: C: 24.57; H: 2.57; N: 23.05.--.

Column 111,
Table 26.1, Column X, Row 26.154, "NHC(O)NH$_2$" should read --NHC(O)CH$_2$--.

UNITED STATES PATENT AND TRADEMARK OFFICE
CERTIFICATE OF CORRECTION

PATENT NO. : 6,965,033 B2
APPLICATION NO. : 09/747182
DATED : November 15, 2005
INVENTOR(S) : Tao Jiang, Srinivas Kasibhatla and K. R. Reddy It is certified that error appears in the above-identified patent and that said Letters Patent is hereby corrected as shown below:

Columns 111-112,
Table 26.2, Row synthetic example number,
"A*   B*   C   D*   E*   HPLC found"
                              Rt M-1
                              (min)

should read

--A*   B*   X   D*   E*   HPLC   M-1--.
                          Rt     found
                          (min)

Column 112,
Table 26.2, Row 26.1, Column E*, "[blank]" should read --null--.

Column 120,
Line 57, "room, temperature" should read --room temperature--.

Column 121,
Line 37, "11:3.05" should read --H: 3.05--.
Line 38, "11:2.66" should read --H: 2.66--.

Column 122,
Lines 2-3, "0: 26.31; 11: 1.96; N: 7.67. Found: 0: 25.96; 11: 1.94;" should read
    --C: 26.31; H: 1.96; N: 7.67. Found: C: 25.96; H: 1.94;--.

Column 124,
Line 22, "H: 3.36" should read --H: 3.46--.

Column 128,
Lines 21-22, "C: 52.26; 7.06; 10.60. Found: C: 52.21; 6.93; 10.62." should read
    --C: 52.26; H: 7.06; N: 10.60. Found: C: 52.21; H: 6.93; N: 10.62.--.
Line 31, "61.01:H:" should read --61.01; H:--.
Line 51, "H: 10.44" should read --N: 10.44--.

UNITED STATES PATENT AND TRADEMARK OFFICE
CERTIFICATE OF CORRECTION

| | | |
|---|---|---|
| PATENT NO. | : 6,965,033 B2 | Page 6 of 7 |
| APPLICATION NO. | : 09/747182 | |
| DATED | : November 15, 2005 | |
| INVENTOR(S) | : Tao Jiang, Srinivas Kasibhatla and K. R. Reddy | |

It is certified that error appears in the above-identified patent and that said Letters Patent is hereby corrected as shown below:

<u>Column 128,</u>
Line 55, "H: 6.97; H: 7.90. Found: C: 62.85; h 7.06, 7.81" should read
--H: 6.97; N: 7.90. Found: C: 62.85; H: 7.06, N: 7.81--.

<u>Column 129,</u>
Lines 2-3, "H: 8.42. Found: C: 59.88; H: 6.28; H: 8.32." should read
--N: 8.42. Found: C: 59.88; H: 6.28; N: 8.32.--.
Line 8, "H: 8.98" should read --N: 8.98--.

<u>Column 133,</u>
Line 12, "H: 4,75" should read --N: 4.75--.
Line 67, "237 245" should read --237-245--.

<u>Column 140,</u>
Line 54, "MgCl2" should read --$MgCl_2$--.

<u>Column 143,</u>
Line 64, "-alkylcarbanylamino-" should read -- -alkylcarbonylamino- --.

<u>Column 144,</u>
Line 33, "—$NR^2OR^{19}$" should read -- —$NR^2OR^{19}$;--.

<u>Column 145,</u>
Line 50, "$_{SR}{}^{17}$" should read --$SR^{17}$--.
Line 66, "the consisting" should be --the group consisting--.

<u>Column 146,</u>
Line 22, "—$NR^2$" should read -- —$NR^9{}_2$--.

UNITED STATES PATENT AND TRADEMARK OFFICE
CERTIFICATE OF CORRECTION

PATENT NO.         : 6,965,033 B2
APPLICATION NO. : 09/747182
DATED              : November 15, 2005
INVENTOR(S)       : Tao Jiang, Srinivas Kasibhatla and K. R. Reddy It is certified that error appears in the above-identified patent and that said Letters Patent is hereby corrected as shown below:

Column 150,
Line 18, "between $R^3$ and" should read --between $R^5$ and--.
Line 59, "with $R^{13}$ is" should read --with $R^{15}$ is--.

Signed and Sealed this

Twenty-sixth Day of August, 2008

JON W. DUDAS
*Director of the United States Patent and Trademark Office*